United States Patent
Bryan et al.

(10) Patent No.: US 7,109,315 B2
(45) Date of Patent: *Sep. 19, 2006

(54) RENILLA RENIFORMIS FLUORESCENT PROTEINS, NUCLEIC ACIDS ENCODING THE FLUORESCENT PROTEINS AND THE USE THEREOF IN DIAGNOSTICS, HIGH THROUGHPUT SCREENING AND NOVELTY ITEMS

(75) Inventors: Bruce Bryan, Beverly Hills, CA (US); Christopher Szent-Gyorgyi, Pittsburgh, PA (US); William Szczepaniak, Pittsburgh, PA (US)

(73) Assignees: Bruce J. Bryan, Beverly Hills, CA (US); Prolone, Ltd., Pinetop, AR (US)

( * ) Notice: Subject to any disclaimer, the term of this patent is extended or adjusted under 35 U.S.C. 154(b) by 78 days.

This patent is subject to a terminal disclaimer.

(21) Appl. No.: 09/808,898

(22) Filed: Mar. 15, 2001

(65) Prior Publication Data

US 2003/0092098 A1 May 15, 2003

Related U.S. Application Data

(60) Provisional application No. 60/189,691, filed on Mar. 15, 2000.

(51) Int. Cl.
C07K 21/04 (2006.01)

(52) U.S. Cl. .................. 536/23.1; 435/69.1; 435/320.1; 435/252.3; 435/325

(58) Field of Classification Search ................ 536/23.1; 435/69.1, 325, 252.3, 320.1
See application file for complete search history.

(56) References Cited

U.S. PATENT DOCUMENTS

| 2,541,851 A | 2/1951 | Wright | 260/37 |
|---|---|---|---|
| 3,384,498 A | 5/1968 | Ahrabi | 106/38.5 |

(Continued)

FOREIGN PATENT DOCUMENTS

| DE | 3935974 A1 | 5/1991 |
|---|---|---|
| EP | 0025350 A2 | 9/1980 |
| EP | 0226979 A2 | 7/1987 |
| EP | 0245093 B1 | 11/1987 |
| EP | 0245093 A1 | 11/1987 |
| EP | 0246174 A1 | 11/1987 |
| EP | 0386691 A3 | 9/1990 |
| EP | 0387355 A1 | 9/1990 |
| EP | 0194102 B1 | 10/1991 |
| EP | 0540064 A1 | 5/1993 |
| EP | 0713089 A2 | 5/1996 |
| FR | 2292595 | 6/1976 |
| GB | 2288232 | 10/1995 |
| JP | 633177079 | 12/1988 |
| JP | 3030678 | 2/1991 |
| JP | 4258288 | 9/1992 |
| JP | 5064583 | 3/1993 |
| JP | 7222590 | 8/1995 |
| JP | 7241192 A | 9/1995 |
| WO | 8603840 | 7/1986 |
| WO | 8703304 | 6/1987 |
| WO | 9001542 | 2/1990 |
| WO | 9201225 | 1/1992 |
| WO | 9204577 | 3/1992 |
| WO | 9215673 | 9/1992 |
| WO | 9313395 | 7/1993 |
| WO | 9418342 | 8/1994 |
| WO | 9425855 | 11/1994 |
| WO | 9507463 | 3/1995 |
| WO | 9518853 | 7/1995 |
| WO | 9521191 | 8/1995 |
| WO | 9525798 | 9/1995 |
| WO | 9607100 | 3/1996 |
| WO | 9607917 | 3/1996 |
| WO | 9623810 | 8/1996 |
| WO | 9627675 | 9/1996 |
| WO | 9711094 | 3/1997 |
| WO | 9726333 | 7/1997 |
| WO | 9728261 | 8/1997 |
| WO | 9729319 | 8/1997 |
| WO | 9741228 | 11/1997 |
| WO | 9802571 | 1/1998 |
| WO | 9814605 | 4/1998 |
| WO | 9826277 | 6/1998 |
| WO | 9949019 | 9/1999 |
| WO | 9966324 | 12/1999 |

OTHER PUBLICATIONS

Baldwin et al., Active Center Studies on Bacterial Luciferase: Modification of the Enzyme with 2,4–Dinitrofluorobenzene, *Biochemistry* 20:512–517 (1981).

Baldwin et al., Cloning of the luciferase structural genes from *Vibro harveyi* and expression of bioluminescene in *Escherichia coli*, *Biochemistry* 23: 3663–3667 (1984).

Belas et al., Bacterial bioluminescene: Isolation and expression of the luciferase genes from *Vibrio harveyi*, *Science* 218: 791–793 (1982).

Blinks et al., Multiple forms of the calcium–sensitive bioluminescent protein aequorin, *Fed. Proc. 1435*: 474 (1975).

Casper et al. Expression of the green fluorescent protein–encoding gene from a tobacco mosaic virus–based vector *Gene 173*: 69–73 (1996).

Chalfie, Green fluorescent protein, *Photochemistry and Photobiology*, 62(4):651–656 (1995).

(Continued)

*Primary Examiner*—Karen Cochrane Carlson
*Assistant Examiner*—Samuel W. Liu
(74) *Attorney, Agent, or Firm*—Alan G. Yosner, Esq.; Lara A. Northrop, Esq.; Pletragallo, Bosick & Gordon LLP

(57) ABSTRACT

Isolated and purified nucleic acids encoding green fluorescent proteins from *Renilla reniformis* and the green fluorescent protein encoded thereby are also provided. Mutants of the nucleic acid molecules and the modified encoded proteins are also provided. Compositions and combinations comprising the green fluorescent proteins and/or the luciferase are further provided.

29 Claims, 6 Drawing Sheets

U.S. PATENT DOCUMENTS

| | | | |
|---|---|---|---|
| 3,511,612 A | 5/1970 | Kennerly et al. | 23/252 |
| 3,565,815 A | 2/1971 | Christy | 252/301.3 |
| 3,584,211 A | 6/1971 | Rauhut | 240/2.25 |
| 3,634,280 A | 1/1972 | Dean et al. | 252/301.3 R |
| 3,649,029 A | 3/1972 | Worrell | 273/186 |
| 3,661,790 A | 5/1972 | Dean et al. | 252/301.3 R |
| 3,669,891 A | 6/1972 | Greenwood et al. | 252/90 |
| 3,727,236 A | 4/1973 | Lloyd et al. | 2/51 |
| 3,873,485 A | 3/1975 | Fichera | 260/29.2 |
| 4,021,364 A | 5/1977 | Speiser | 252/316 |
| 4,044,126 A | 8/1977 | Cook et al. | 424/243 |
| 4,175,183 A | 11/1979 | Ayers | 536/57 |
| 4,177,038 A | 12/1979 | Biebricher et al. | 8/192 |
| 4,225,581 A | 9/1980 | Kreuter et al. | 424/88 |
| 4,229,790 A | 10/1980 | Gilliland et al. | 364/200 |
| 4,269,821 A | 5/1981 | Kreuter | 424/19 |
| 4,281,645 A | 8/1981 | Jöbsis | 128/633 |
| 4,282,287 A | 8/1981 | Giese | 428/407 |
| 4,313,843 A | 2/1982 | Bollyky et al. | 252/188.3 |
| 4,324,683 A | 4/1982 | Lim et al. | 252/316 |
| 4,364,923 A | 12/1982 | Cook et al. | 424/46 |
| 4,414,209 A | 11/1983 | Cook et al. | 424/243 |
| 4,478,817 A | 10/1984 | Campbell et al. | 424/7.1 |
| 4,528,180 A | 7/1985 | Schaeffer | 424/52 |
| 4,534,317 A | 8/1985 | Walsh | 119/51 R |
| 4,542,102 A | 9/1985 | Dattagupta et al. | 435/6 |
| 4,562,157 A | 12/1985 | Lowe et al. | 435/291 |
| 4,563,726 A | 1/1986 | Newcomb et al. | 362/34 |
| 4,581,335 A | 4/1986 | Baldwin | 435/172.3 |
| 4,676,406 A | 6/1987 | Frischmann et al. | 222/136 |
| 4,681,870 A | 7/1987 | Balint et al. | 502/403 |
| 4,714,682 A | 12/1987 | Schwartz | 436/10 |
| 4,717,158 A | 1/1988 | Pennisi | 273/58 A |
| 4,735,660 A | 4/1988 | Cane | 106/203 |
| 4,745,051 A | 5/1988 | Smith et al. | 435/68 |
| 4,762,881 A | 8/1988 | Kauer | 525/54.11 |
| 4,765,510 A | 8/1988 | Rende | 222/79 |
| 4,767,206 A | 8/1988 | Schwartz | 356/73 |
| 4,774,189 A | 9/1988 | Schwartz | 436/10 |
| 4,777,128 A | 10/1988 | Lippa | 435/5 |
| 4,781,647 A | 11/1988 | Doane, Jr. | 446/219 |
| 4,789,633 A | 12/1988 | Huang | 435/240.2 |
| 4,853,327 A | 8/1989 | Dattagupta | 435/6 |
| 4,861,709 A | 8/1989 | Ulitzur et al. | 435/6 |
| 4,867,908 A | 9/1989 | Recktenwald et al. | 252/408.1 |
| 4,870,009 A | 9/1989 | Evans et al. | 435/70 |
| 4,882,165 A | 11/1989 | Hunt et al. | 424/450 |
| 4,891,043 A | 1/1990 | Zeimer et al. | 604/20 |
| 4,908,405 A | 3/1990 | Bayer et al. | 525/61 |
| 4,921,757 A | 5/1990 | Wheatley et al. | 428/402.2 |
| 4,924,358 A | 5/1990 | Von Heck | 362/32 |
| 4,927,923 A | 5/1990 | Mathis et al. | 540/456 |
| 4,950,588 A | 8/1990 | Dattagupta | 435/6 |
| 4,952,496 A | 8/1990 | Studier et al. | 435/91 |
| 4,963,117 A | 10/1990 | Gualdoni | 446/219 |
| 4,968,613 A | 11/1990 | Masuda et al. | 435/172.3 |
| 5,004,565 A | 4/1991 | Schaap | 252/700 |
| 5,023,181 A | 6/1991 | Inouye | 435/189 |
| 5,093,240 A | 3/1992 | Inouye et al. | 435/69.1 |
| 5,096,807 A | 3/1992 | Leaback | 435/6 |
| 5,098,828 A | 3/1992 | Geiger et al. | 435/7.72 |
| 5,128,256 A | 7/1992 | Huse et al. | 435/172.3 |
| 5,139,937 A | 8/1992 | Inouye et al. | 435/69.1 |
| 5,158,349 A | 10/1992 | Holland et al. | 362/34 |
| 5,162,227 A | 11/1992 | Cormier | 435/252.33 |
| 5,162,508 A | 11/1992 | Lehn et al. | 401/4 |
| 5,169,784 A | 12/1992 | Summers et al. | 435/320.1 |
| 5,171,081 A | 12/1992 | Pita et al. | 362/34 |
| 5,182,202 A | 1/1993 | Kajiyama et al. | 435/189 |
| 5,189,029 A | 2/1993 | Boyer et al. | 514/64 |
| 5,196,318 A | 3/1993 | Baldwin et al. | 435/69.1 |
| 5,196,524 A | 3/1993 | Gustafson et al. | 536/23.2 |
| 5,215,899 A | 6/1993 | Dattagupta | 435/6 |
| 5,219,737 A | 6/1993 | Kajiyama et al. | 435/69.1 |
| 5,221,623 A | 6/1993 | Legocki et al. | 435/252.3 |
| 5,222,797 A | 6/1993 | Holland | 362/34 |
| 5,229,285 A | 7/1993 | Kajiyama et al. | 435/189 |
| 5,243,041 A | 9/1993 | Fernandez-Pol | 536/23.5 |
| 5,246,834 A | 9/1993 | Tsuji et al. | 435/7.91 |
| 5,266,317 A | 11/1993 | Tomalski et al. | 424/93 T |
| 5,268,463 A | 12/1993 | Jefferson | 536/23.7 |
| 5,277,913 A | 1/1994 | Thompson et al. | 424/450 |
| 5,279,943 A | 1/1994 | Mathis et al. | 435/7.32 |
| 5,288,623 A | 2/1994 | Zenno et al. | 435/69.7 |
| 5,292,658 A | 3/1994 | Cormier et al. | 435/252.33 |
| 5,310,421 A | 5/1994 | Shapero et al. | 106/208 |
| 5,323,492 A | 6/1994 | DeMars | 2/203.13 |
| 5,330,906 A | 7/1994 | Kajiyama et al. | 435/189 |
| 5,337,745 A | 8/1994 | Benaron | 128/633 |
| 5,352,598 A | 10/1994 | Kajiyama et al. | 435/189 |
| 5,360,726 A | 11/1994 | Raikhel | 435/172.3 |
| 5,360,728 A | 11/1994 | Prasher | 435/189 |
| 5,362,865 A | 11/1994 | Austin | 536/24.1 |
| 5,364,797 A | 11/1994 | Olson et al. | 436/501 |
| 5,366,881 A | 11/1994 | Singh et al. | 435/177 |
| 5,374,534 A | 12/1994 | Zomer et al. | 435/8 |
| 5,383,100 A | 1/1995 | Kikos | 362/34 |
| 5,387,526 A | 2/1995 | Garner et al. | 436/169 |
| 5,405,905 A | 4/1995 | Darr | 524/420 |
| 5,405,958 A | 4/1995 | VanGemert | 544/71 |
| 5,412,085 A | 5/1995 | Allen et al. | 536/24.1 |
| 5,413,098 A | 5/1995 | Benaron | 128/633 |
| 5,413,332 A | 5/1995 | Montgomery | 273/58 |
| 5,415,151 A | 5/1995 | Fusi et al. | 124/56 |
| 5,418,155 A | 5/1995 | Cormier et al. | 435/189 |
| 5,422,075 A | 6/1995 | Saito et al. | 422/52 |
| 5,422,266 A | 6/1995 | Cormier et al. | 435/252.3 |
| 5,424,216 A | 6/1995 | Nagano et al. | 436/116 |
| 5,432,081 A | 7/1995 | Jefferson | 435/252.3 |
| 5,433,896 A | 7/1995 | Kang et al. | 252/700 |
| 5,435,937 A | 7/1995 | Bell et al. | 252/301.18 |
| 5,439,797 A | 8/1995 | Tsien et al. | 435/7.21 |
| 5,451,347 A | 9/1995 | Akhavan-Tafti et al. | 252/700 |
| 5,455,357 A | 10/1995 | Herrmann et al. | 548/147 |
| 5,464,758 A | 11/1995 | Gossen et al. | 435/69.1 |
| 5,484,723 A | 1/1996 | Zenno et al. | 435/189 |
| 5,486,455 A | 1/1996 | Stults | 435/6 |
| 5,491,084 A | 2/1996 | Chalfie et al. | 435/189 |
| 5,496,934 A | 3/1996 | Shoseyov et al. | 536/23.7 |
| 5,604,123 A | 2/1997 | Kazami et al. | 435/189 |
| 5,605,662 A | 2/1997 | Heller et al. | 422/68.1 |
| 5,624,711 A | 4/1997 | Sundberg et al. | 427/261 |
| 5,625,048 A | 4/1997 | Tsien et al. | 536/23.4 |
| 5,632,957 A | 5/1997 | Heller et al. | 422/68.1 |
| 5,670,623 A | 9/1997 | Shoseyov et al. | 530/350 |
| 5,671,998 A | 9/1997 | Collet | 362/101 |
| 5,719,044 A | 2/1998 | Shoseyov et al. | 435/69.7 |
| 5,730,321 A | 3/1998 | McAllister et al. | 222/1 |
| 5,738,984 A | 4/1998 | Shoseyov | 435/4 |
| 5,741,668 A | 4/1998 | Ward et al. | 435/69.1 |
| 5,776,681 A | 7/1998 | Virta et al. | 435/6 |
| 5,777,079 A | 7/1998 | Tsien et al. | 530/350 |
| 5,804,387 A | 9/1998 | Cormack et al. | 435/6 |
| 5,874,304 A | 2/1999 | Zolotukhin et al. | 435/366 |
| 5,876,995 A | 3/1999 | Bryan | 435/189 |
| 5,891,646 A | 4/1999 | Barak et al. | 435/7.2 |
| 5,912,137 A | 6/1999 | Tsien et al. | 435/15 |
| 6,020,538 A | 2/2000 | Han et al. | 800/293 |
| 6,113,886 A | 9/2000 | Bryan | 424/49 |
| 6,152,358 A | 11/2000 | Bryan | 229/87.19 |
| 6,232,107 B1 * | 5/2001 | Bryan et al. | 435/189 |

OTHER PUBLICATIONS

Charbonneau et al., "Amino acid sequence of the calcium–dependent photoprotein aequorin," *Biochem.* 24:6762–6771 (1985).

Chemical Abstract #115(5)43510b (citing, Japanese Patent Application No. JP 3–30678 Osaka).

Cohn et al., Nucleotide Sequence of the luxA Gene of *Vibrio harveyi* and the Complete Amino Acid Sequence of the–Subunit of Bacterial Luciferase, *J. Biol. Chem.*, 260(*10*) : 6139–6146; (1985).

Cohn *et al.* "Cloning of the *Vibrio harveyi* luciferase genes: use of a synthetic oligonucleotide probe", *Proc. Natl. Acad. Sci. U.S.A.* 80(*1*): 102–123 (1983).

Database Derwent # 007778737 WPI Acc. No. 89–043849/198906 (citing, Japanese Patent Application No. JP. 63317079, published Dec. 26, 1988).

Database Derwent #008196500 (citing WO 9001542, Recombinant luciferase, fragments from it, and gene coding for it—the luciferase having increased stability and quantum yield).

Database Derwent #010423635 WPI Acc. No. 95–324955/199542 (citing, Japanese Patent Application No. JP 7222590, published Aug. 22, 1995).

Database Derwent #008580311 WPI Acc. No. 91–084343/199112 (citing, Japanese Patent Application No. JP 3030678 published Feb. 8, 1991).

Database EMBL Nucleotide and Protein Sequences, AC=AF025844, Co–reporter vector pRL–Null, complete sequence, abstract, (1997).

Database Derwent #009227258 WPI Acc. No. 92–354680/199243 (citing, Japanese Patent Application No. JP 4258288, published Sep. 14, 1993).

de Wet et al., "Cloning and expression of the firefly luciferase gene in mammalian cells," *Bioluminescence and Chemlluminescence. Basic Chemistry and Analytical Applications*, DeLuca et al., eds. pp. 368–371, Academic Press (1981).

de Wet et al., "Cloning firefly luciferase", *Meth. Enzymol.* 133:3–14 (1986).

de Wet et al., "Cloning of firefly luciferase cDNA and the expression of active luciferase in *Escherichia coli,*" *Proc. Natl. Acad. Sci. USA* 82:7870–7873 (1985).

Delagrave et al., Red–shifted excitation mutants of the green fluorescent protein, *Bio/Technology* 13(2):151–154 (1995).

Ehrig et al., Green–fluorescent protein mutants with altered fluorence excitationspectra, *FEBS Letters* 367:163–166 (1995).

Engebrecht et al., "Techniques for cloning and analyzing bioluminescence genes from marine bacteria," *Meth. Enzymol.* 133:83–99, 234 (1986).

Engebrecht et al., Bacterial bioluminescence: Isolation and genetic analysis of functions from *Vibrio fischeri*, *Cell* 32: 773–781 (1983).

Engebrecht et al., Identification of genes and gene products necessary for bacterial bioluminescene, *Proc. Natl. Acad. Sci. USA 81*: 4154–4158 (1984).

Gast et al., Separation of a blue fluorescence protein from bacterial luciferase. Biochem. Biophys. Res. Commun. 80(1): 14–21 (1978).

Goto et al., Preliminary report on the pink–colored Cypridina luciferase, a natural model of the luciferin–luciferase complex, in *Bioluminescence and Chemiluminescence. Basic Chemistry and Analytical Applications*, DeLuca et al., eds., pp. 203–207, Academic Press (1981).

Hastings et al., The Red Absorbing Flavin Species in the Reaction of Bacterial Luciferase with $FMNH_2$ and $O_2$[,], *Bioluminescence and Chemiluminescence* pp. 403–408 (1981).

Hastings et al., Fluorescence Properties of Luciferase Peroxyflavins Prepared with ISO–FMN and 2–THIO FMN[1,] *Bioluminescence and Chemiluminescence* pp. 97–102 (1981).

Hastings, Bioluminescence, in *Cell Physiol.: Source Book*, Sperelakis, ed., pp. 665–681, Academic Press (1995).

Hill et al., *Bioluminescence and Chemiluminescence. Basic Chemistry and Analytical Applications*, DeLuca et al., eds., pp. 396–399, Academic Press (1981).

Hori et al., Structure of native *Renilla reniformis* luciferin, *Proc. Natl. Acad. Sci. USA 74*: 4285–4287 (1977).

Illarionov et al., Sequence of the cDNA encoding the $Ca^{2+}$–activated photoprotein obelin from the hydroid poly *Obelia longissima, Gene 153*:273–274 (1995).

Inouye et al., "Overexpression and purification of the recombinant $ca^{2+}$ —binding protein, apoaequorin," *J. Biochem. 105*(*3*):473–477 (1989).

Inouye et al., Cloning and sequence analysis of cDNA for the luminescent protein aequorin, *Proc. Natl. Acad. Sci. USA* 82:3154–3158 (1985).

Inouye et al., Squid bioluminescence II. Isolation from *Watasenia scintillans* and synthesis of 2–(p–hydroxybenzyl)–6–(p–hydroxyphenyl)–3,7–dihydroimidazo[1,2–a]pyrazin–3–one, *Jap. Soc. Chem. Lett.* pp. 141–144 (1975).

Inouye et al., Expression of Apoaequorin Complementary DNA in *Escherichia coli, Biochemistry* 25:8425–8429 (1986).

Johnson et al., Introduction to the *Cypridina* system, *Methods in Enzymology. Bioluminescence and Chemiluminescence*. 57:331–349 (1978).

Johnson, *Luminescence, Narcosis, and Life in the Deep Sea*, pp. 50–56, Vantage Press.

Johnson et al., "Compartmentalization of algal bioluminescence: autofluorescence of bioluminescent particles in the dinoflagellate Gonyoulax as studied with image–intensified video microscopy and flow cytometry", *J. Cell. Biol. 100*(5):1435–1446 (1985).

Karatani et al., A blue fluorescent protein from a yellow–emitting luminous bacterium, *Photochem. Photobiol.* 55(*2*): 293–299 (1992).

Kohama et al., Molecular weight of the photoprotein aequorin, *Biochemistry 10*: 4149–4152 (1971).

Kurose et al., Bioluminescence of the $Ca^{2+}$–binding photoprotein aequorin after cysteine modification, *Proc. Natl. Acad. Sci. USA 86*(*1*): 80–84 (1989).

Lee et al., "Purification of a Blue–fluorescent Protein from the Bioluminescent Bacterium *Photobacterium phosphoreum,*" *Methods Enzymol.*, (Biolumin. Chemilumin.), *57*:226–234 (1978).

Lorenz et al., Isolation and expression of a cDNA encoding *Renilla reniformis* luciferase, *Proc. Natl. Acad. Sci. USA* 88: 4438–4442 (1991).

Matthews et al., Purification and properties of *Renilla reniformis* luciferase, *Biochemistry, 16*: 85–91 (1977).

Matz et al., "Fluorescent proteins from nonbioluminescent Anthozoa species", *Nature Biotechnol., 17*:969–973; (1999).

McElroy et al., The colors of bioluminescence: Role of enzyme and substrate structure, in *Molecular Architecture in Cell Physiology*, pp. 63–80, Hayashi et al., eds., Prentice–Hall, Inc., Englewood Cliffs, NJ (1966).

Miyamoto et al., Cloning and expression of the genes from the bioluminescent system of marine bacteria, *Meth. Enzymol. 133*:70–81 (1986).

Morise et al., Intermolecular Energy Transfer in the Bioluminescent System of Aequorea *Biochemistry 13*:2656–2662 (1974).

Ormo et al. Crystal Structure of the Aequorea victoria Green Fluorescent Protein *Science 273*:1392–1395 (1996).

Prasher et al., Cloning expression of the cDNA coding for aequorin, a bioluminescent calcium–binding protein, *Biochem. Biophys. Res. Commun. 126(3)*:1259–1268 (1985).

Prasher et al., *Bioluminescence and Chemiluminescence. Basic Chemistry and Analytical Applications*, DeLuca et al., eds., pp. 365–367, Academic Press (1981).

Prasher et al., Isolation and expression of a cDNA coding for aequorin, the $Ca^{2+}$ —activated photoprotein from *Aequorea victoria, Meth. Enzymol. 133*:288–297 (1986).

Prasher et al., Sequence comparisons of complementary DNAs encoding aequorin isotypes, *Biochem. 26*:1326–1332 (1987).

Prasher et al., Primary structure of the *Aequorea victoria* green–fluorescent protein, *Gene 111*:229–233 (1992).

Prendergast et al., "Chemical and Physical Properties of Aequorin and the Green Fluorescent Protein Isolated from *Aequorea forskàlea*", *Biochem., 17*: 3448–3453; (1978).

Sandalova, Some notions about structure of bacterial luciferase, obtained by analysis of amino acid sequence, and study of monoclonal antibodies binding, In *Biological Luminescence, Proceedings of International School*, 1st, ed., Jezowska–Trzebiatowska et al., World Science (1990).

*SeaLite Sciences Technical Report No. 3*, "The Recombinant Photoprotein, AquaLite™", SeaLite Sciences, Inc., pp. 1–6; (1994).

Sherf et al., Dual–luciferase reporter assay: an advanced co–reporter technology integrating firefly and *Renilla* luciferase assays, *Promega Notes 57*:2–5 (1996).

Shimomura et al., Semi–synthetic aequorin. An improved tool for the measurement of calcium ion concentration, *Biochem. J. 251(2)*:405–10 (1988).

Shimomura et al. Structure of Light–Emitting Moiety of Aequorin *Biochemistry 11*:1602–1608 (1972).

Shimomura et al., Recombinant aequorin and recombinant semi–synthetic aequorins. Cellular $Ca^{2+}$ ion indicators, *Biochem. J. 270(2)*: 309–12 (1990).

Shimomura et al. The Structure of *Latia* Luciferin *Biochemistry 7*:1734–1738 (1968).

Shimomura, Structure of the Chromophore of Aequorea Green Fluorescent Protein *FEBS Letters 104*:220–222 (1979).

Shimomura et al., Extraction, purification and properties of a aequorin, a bioluminescent protein from the luminous hydromedusan, *Aequorea, J. Cell. Comp. Physiol. 59*: 223–238 (1962).

Shimomura et al., Properties and reaction mechanism of the bioluminescence system of the deep–sea shrimp Oplophorus gracilorostris, *Biochem 17(6)*: 994–998 (1978).

Shimomura et al., Properties of the bioluminescent protein aequorin, *Biochemistry 8*: 3991–3997 (1969).

Shimomura et al. Reactions Involved in Bioluminescence of Limpet (*Latia neritoides*) and Luminous Bacteria *Proc. Natl. Acad. Sci. U.S.A. 69*:2086–2089 (1972).

Spurlok et al., A fine structure study of the anthocodium in *Renilla mulleri, J. of Cell Biology 64*:15–28 (1975).

Thompson et al., Cloning and expression of cDNA for th eluciferase from the marine ostracod *Vargula hilgendorfi xi, Proc. Natl. Acad. Sci. USA 86*: 6567–6571 (1989).

Tsien, The Green Fluorescent Protein *Annu. Rev. Biochem. 67*:509–544 (1998).

Tsuji et al., Some properties of luciferase from the bioluminescent crustacean, *Cypridina hilgendorfii, Biochem. 13(25)*:5204–5209 (1974).

Tsuji, "*Cypridina* luciferin and luciferase", *Meth. Enzymol. 57*:364–372; (1978).

Tsuji et al., Site–specific mutagenesis of the calcium–binding photoprotein aequorin, *Proc. Natl. Acad. Sci. USA 83*:8107–8111 (1986).

Wampler et al. Similarities in the Bioluminescence from the Pennatulacea *Biochimicia et a Biophysica Acta 314*:104–109 (1973).

Ward et al., Energy Transfer Via Protein–Protein Interaction in *Renilla* Bioluminescence, *Photochemistry and Photobiology* 27:389–396 (1978).

Ward et al., Sequence and Chemical Structure of the Hexapeptide Chromophore of Aequorea Green–Fluorescent Protein, *Photochemistry and Photobiology* 49:62S (1989).

Ward et al., Extraction of *Renilla*–type luciferin from the calcium–activated photoproteins aequorin, mnemiopsin, and berovin, *Proc. Natl. Acad. Sci. USA 72*: 2530–2534 (1975).

"AquaLite®. A calcium–triggered photoprotein," *SeaLite Sciences Technical Report No. 3* (1994).

Amsterdam, et al. The Aequorea victoria Green Fluorescent Protein Can Be Used as a Reporter in Live Zebrafish Embryos *Developmental Biology 171*:123–129 (1995).

Anctil et al., Mechanism of photoinactivation and re–activatioon in the bioluminescence system of the ctenophore Mnemiopsis, *Biochem. J. 22(1)*: 269–272 (1984).

Badminton et al., nucleoplasmin–targeted aequorin provides evidence for a nuclear calcium barrier, *Expt. Cell Research 216(1)*: 236–243 (1995).

Baldwin et al., "Applications of the cloned bacterial luciferase genes LUXA and LUXB to the study of transcriptional promoters and terminators," *Bioluminescence and Chemiluminescence: Basic Chemistry and Analytical Applications*, DeLuca and McElroy, Eds., Academic Press (1981).

Becvar et al., A thermodymanic explanation for the kinetic differences observed using different chain length aldehydes in the in vitro bacterial bioluminescent reaction, in *Bioluminescence and Chemiluminescence*, pp. 147–155, 180–185, Proc. of the IV Int. Bioluminescence and Chemiluminescence Symp., Freiburg, Sep. 1986.

Button et al., Aequorin–expressing mammalian cell lines used to report $Ca^{2+}$ mobilization, *Cell Calcium 14(9)*:663–671 (1993).

Chalfie et al. Green Fluorescent Protein as a marker for Gene Expression *Science 263*: 802–805 (1994).

Charbonneau et al. $Ca^{2+}$–induced Bioluminescence in *Renilla reniformis* Purification and Characterization of a Calcium–Triggered Luciferin–Binding Protein *J. Biol. Chem. 254*:769–780 (1979).

Cody et al. Chemical Structure of the Hexapeptide Chromophore of the Aequorea Green–Fluorescent Protein *Biochemistry 32*:1212–1218 (1993).

Cormack et al. Yeast–enhanced green fluorescent protein (yEGFP): a reporter of gene expression in Candida albicans *Microbiology 143*:303–311 (1997).

Cormier et al., Evidence for similar biochemical requirements for bioluminescence among the coelenterates, *J. Cell Physiol. 81*: 291–298 (1972).

Cormier "Renilla and Aequorea bioluminescence" pp 225–233 in *Bioluminescence and Chemiluminescence. Basic Chemistry and Analytical Applications*. DeLuca et al eds, Academic Press 1981.

Dabiri et al. Myofibrillogenesis visualized in living embryonic cardiomyocytes *Pro. Natl. Acad. Sci. USA 94*:9493–9498 (1997).

Database Derwent #009443237 WPI Acc. No. 93–136754/199317 (citing Japanese Patent Application No. JP 5064583, published Mar. 19, 1993).

Fey et al. Green Fluorescent protein production in the cellular slime molds Polysphondylium pallidum and Dictyostelium discoideum *Gene 165*:127–130 (1995).

Fratamico et al., Construction and characterization of *Escherichia coli* 0157:H7 strains expressing firefly luciferase and green fluorescent protein and their use in survival studies, *J of Food Protection* 60(10):1167–1173 (1997).

Giuliano et al. Fluorescent–protein biosensors: new tools for drug discovery *TiBech 16*: 135–140 (1998).

Grentzmann et al., A dual–luciferase system for studying recoding signals, *RNA* 479–486 (1998).

Hart et al. "*Renilla reniformis* bioluminescence: Luciferase–catalyzed production of nonradiating excited states from luciferin analogues and elucidation of the excited state species involved in energy transfer to *Renilla* green fluorescent protein", (1979) *Biochemistry 18*:2204–2210 (1979).

Heim et al., Engineering green fluorescent protein for improved brightness, longer wavelengths and fluorescence resonance energy transfer, *Current Biology* 6(2):178–182 (1996).

Heinlein et al. Interaction of Tobamovirus Movement Proteins with the Plant Cytoskeleton *Science 270*:1983–1985 (1995).

Hori et al., *Renilla* luciferin as the substrate for calcium induced photoprotein bioluminescence. Assignment of luciferin plutomers in aequorin and mnemiopsin, *Biochemistry 14*: 2371–2376, (1975).

Ikawa et al. A rapid and non–invasive selection of transgenic embryos before implantation using green fluorescent protein (GFP) *FEBS Letters 375*:125–128 (1995).

Inouye et al., Electroporation as a new technique for producing transgenic fish, *Cell Differ. Devel. 29*:123–128 (1990).

Inouye et al., Monitoring gene expression in Chinese hamster ovary cells using secreted apoaequorin, *Analyt. Biochem. 201(1)*: 114–118 (1992).

Inouye et al., "Imaging of luciferase secretion from transformed Chinese hamster ovary cells," *Proc. Natl. Acad. Sci. USA 89*:9584–9587 (1992).

Inouye et al., "Expression of apoaequorin complementary DNA in *Escherichia coli*," *Biochem. 25*:8425–8429 (1986).

Kain et al., Green Fluorescent Protein as a reporter of Gene Expression and Protein Localization *BioTechniques 19*:650–655 (1995).

Karp et al., *Bioluminescence and Chemiluminescence. Basic Chemistry and Analytical Applications*, DeLuca et al., eds., pp. 360–363, Academic Press (1981).

Kendall et al., Changes in free calcium in the endoplasmic reticulum of living cells detected using targeted aequorin, *Anal. Biochem. 22(1)*:173–81 (1994).

Knight et al., Imaging calcium dynamics in living plants using semi–synthetic recombinant aequorins, *J. Cell Biol. 121(1)*:83–90 (1993).

Knight et al., Transgenic plant aequorin reports the effects of touch and cold–shock and elicitors on cytoplasmic calcium, *Nature 352(6335)*: 524–526 (1991).

Leach et al., Commercially available firefly luciferase reagents, in *Methods in Enzymology. Bioluminescence and Chemiluminescence Part B 133*:51–69, Academic Press (1986).

Legocki et al., Bioluminescence in soybean root nodules: Demonstration of a general approach to assay gene expression in vivo by using bacterial luciferase, *Proc. Natl. Acad. Sci. USA 81*: 9080–9084 (1986).

McElroy, et al., The Chemistry and Applications of Firefly Luminescence, *Bioluminescence and Chemiluminescence*, 179–185, Academic Press, Inc. (1981).

Miller et al. An improved GFP cloning cassette designed for prokaryotic transcriptional fusions *Gene 191*:149–153 (1997).

Mitra et al., Fluorescence resonance energy tranfer between blue–emitting and red–shifted excitation derivatives of the green fluorescent protein, *Gene* 73(1):13–17 (1996).

Miyawaki et al. Fluorescent indicators for $CA^{2+}$ based on green fluorescent proteins and calmodulin *Nature 388*:882–887 (1997).

Morin, Energy in a Bioluminescent System, *J. Cell Physiol., 77*:313–318 (1971).

Nakajima–Shimada et al., Monitoring of intracellular calcium in *Saccharomyces cerevisiae* with an apoaequorin cDNA expression system, *Proc. Natl. Acad. Sci. USA 88(15)*: 6878–6882 (1991).

Plautz et al., Green Fluorescent protein and its derivatives as versatile markers for gene expression in living Drosophila melanogaster, plant and mamalian cells *Gene 173*:83–87 (1996).

Rivera et al., AquaLite® Streptavidin for supersentive TSH assays in microtiter plates and coated tubes, *SeaLite Sciences Technical Report No. 6*.

Rizzuto et al., Rapid changes of mitochondrial $Ca^{2+}$ revealed by specifically targeted recombinant aequorin, *Nature 358(6384)*: 325–327 (1992).

Romoser et al., Detection in living cells of Ca2+–dependent changes in the fluorescence emission of an indicator composed of two green fluorescent protein variants liked by a calmodulin–binding sequence, *J. of Biolog. Chem.* 272(20):13270–13274 (1997).

Rutter et al., Involvement of MAP kinase in insulin signalling revealed by non–invasive imaging of luciferase gene expression in single living cells, *Current Biology* 5(8): 890–9 (1995).

Saran et al., Intracellular free calcium level and its response to cAMP stimulation in developing Dictyostelium cells transformed with jellyfish apoaequorin cDNA, *FEBS Lett.* 337(1): 43–7 (1994).

Sedlak et al., Bioluminescent Technology for Reagents, Diagnostics and Toxicology, *Genetic Engineering News*, Sep. 15, 1995.

Sgoutas et al., AquaLite® bioluminescence assay of thyrotropin in serum evaluated, *Clin. Chem. 41(11)*:1637–1643 (1995).

Sheu et al., Measurement of intracellular calcium using bioluminescent aequorin exposed in human cells, *Analyt. Biochem.* 209(2): 343–347 (1993).

Straight et al. GFP tagging of budding yeast chromosomes reveals that protein–protein interations can mediate sister chromatid cohesion *Current Biology* 12:1599–1608 (1996).

Stults et al. Use of Recombinant Biotinylated Apoaequorin in Microtiter and Membrane–Based Assays: Purification of Recombinant Apoaequorin from *Escherichia coli Biochemistry* 31:1433–1442 (1992).

Terry et al. Molecular characterisation of recombinant green fluorescent protein by fluorescence correlation microscopy *Biochemical and Biophysical Research Communication* 217:21–27 (1995).

Thompson et al., *Vargula hilgendorfii* luciferase: a secreted reporter enzyme for monitoring gene expression in mammalian cells, *Gene* 96:257–262 (1990).

Travis, J. Following the Inner Light, Glow Genes provide revealing pictures of infections *Science News* 150:220–221 (1996).

Xu et al. A bioluminescence resonance energy transfer (BRET) system: Application to interacting circadian clock proteins *Proc. Natl. Acad. Sci. USA* 96:151–156 (1999).

Amato, Race quickens for non–stick blood monitoring technology, *Science* 258:892–893 (1992).

Apt et al., Evolution of phycobiliproteins, *J. Mol. Biol.* 248: 79–96 (1995).

Baird et al., "Biochemistry, mutagenesis, and oligomerization of DsRed, a red fluorescent protein form coral", *PNAS*, 97(22):11984–11989; (2000).

Bondar et al., Cadmium–induced luminescence of recombinant photoprotein obelin, *Biochim. Biophys. Acta* 1231: 29–32 (1995).

Campbell et al., Formation of the $Ca^{2+}$–activated photoprotein obelin from apo–obelin and mRNA inside human neutrophils, *Biochem. J.* 252(1):143–9 (1988).

Cardullo et al. Detection of nucleic acid hybridization by nonradiative fluorescence resonance energy transfer *Pro.Natl. Acad. Sci. USA* 85:8790–9794 (1988).

Crescitelli, Adaptations of visual pigments to the photic environment of th edeep sea, *J. Exptl. Zool. Supp.* 5:66–75 (1991).

Database Derwent #008987167 (citing WO 9204577, Chemiluminescence prodn. in liq.–contg. vesssel—by placing reagent envelope in liq. or vessel base).

Fairchild et al., Oligomeric Structure, Enzyme Kinetics, and Substrate Specificity of the Phycocyanin_Subunit Phycocyanobilin Lyase, *The Journal of Biological Chemistry* 269(12): 8686–8694 (1994).

Frackman et al., "Cloning, Organization, and Expression of the Bioluminescence Genes of *Xenorhabdus luminescens,*" *J. Bacteriol.*, 172(10):5767–5773; (1990).

Goldmacher et al., "Photoactivation of Toxin Conjugates", *Bioconj. Chem.*, 3:104–107; (1992).

Gautier et al., Alternate determination of ATP and NADH with a single bioluminescence–based fiber–optic sensor, Fifth International Conference on Solid State Sensors and Actuators and Eurosensors III, Montreux, Switzerland, Jun. 25–30, 1989.

Gilbert et al., Expression of genes involved in phycocyanin biosynthesis following recoivery of *Synechococcus* PCC 6301 from nitrogen starvation, and the effect of gabaculine of *cpc*Ba transcript levels, *FEMS Microbiol. Lett.* 140: 93–98 (1996).

Glazer, Phycobilisomes: structure and dynamics, *Ann. Rev. Microbiol.* 36: 173–98 (1982).

Goldstein et al., Characterization of the Cellulose–Binding Domain of the *Clostridium cellulovorans* Cellulose–Binding Protein A, *Journal of Bacteriology* 175(18): 5762–5768 (1993).

Hart et al., *Renilla reniformis* Bioluminescence: Luciferase–Catalyzed Production of Nonradiating Excited States from Luciferin Analogues and Elucidation of the Excited State Species Involved in Energy Transfer to *Renilla* Green Fluorescent Protein, *Biochemistry* 18(11):2204–2210 (1979).

Houmard et al., Genes encoding core components of the phycobilisome in cyanobacterium *Calothrix* sp. srain PCC 7601: occurrence of a multigene family, *J. Bacteriol.* 170(12): 5512–5521 (1988).

Illarionov et al., "Sequence of the cDNA encoding the $Ca^{2+}$–activated photoprotein obelin from the hydroid polyp *Obelia longissima*", *Gene*, 153:273–274; (1995).

Johnson, F.H., Luminescence, Narcosis, and Life in the Deep Sea, *Vantage Press, NY* pp. 50–56 (1988).

Kronic, The use of phycobiliproteins as flkuorescent labels in immunoassay, *J. Immunolog. Meth.* 92: 1–13 (1986).

Liu et al., A cyanidium caldarium Allophycocyanin_subunit gene, *Plant Physiol.* 103:293–294. (1993).

Lucas et al., Coelenterazine is a superoxide anion–sensitive chemiluminescent probe: its usefulness in the assay of respiratory burst in neutrophils, *Analyt. Biochem.* 206(2):273–277 (1992).

Morin et al., "Energy Transfer in_Bioluminescent System", *J. Cell Physiol.*, 77:313–318; (1971).

Müller and Campbell, "The chromophore of pholasin: A highly luminescent protein", *J. Biolumin. Chemilum.* 5:25–30 (1990).

Nicoli et al., Bacterial luciferase: The hydrophobic environment of the reactive sulfhydryl, *J. Biol. Chem.* 249: 2393–2396 (1974).

O'Day et al., *Aristostomias scintillans* (*Malacostiedae*): a deep sea fish with visual pigments apparently adapted to its own bioluminescence, *Vision Res.* 14:545–550 (1974).

Peerce et al. Distance between substrate sites on the Na–glucose cotransporter by fluoresence energy transfer *Proc. Natl. Acad. Sci. USA* 83:8092–8096 (1986).

Pilot et al., Cloning and sequencing of the genes encoding the_and_subunits of C–phycocyanin from the cyanobacterium *Agmenellum quadruplicatum*, *Proc. Natl. Acad. Sci. USA* 81:6983–6987 (1984).

Senter et al., "Novel Photocleavable Protein Crosslinking Reagents and their Use in the Preparation of Antibody–toxin Conjugates", *Photochem. & Photobiol.*, 42(3):231–237; (1985).

Shimomura et al., Resistivity to denaturation of the apoprotein of aequorin and reconstitution of the luminescent photoprotein from the partially denatured apoprotein, *Biochem J.* 199:825–828 (1981).

Shimomura et al., Regeneration of the photoprotein aequorin, *Nature* 256: 236–238 (1975).

Shimomura et al., The relative rate of aequorin regeneration from apoaequorin and coelenterazine analogues, *Biochem. J.* 296(Pt. 3): 549–551 (1993).

Shimomura, Bioluminescence in the sea: photoprotein systems [Review], Symposia of the *Society for Experimental Biology* 39: 351–372 (1985).

Shimomura, "Cause of spectral variation in the luminescence of semisynthetic aequorins", *Biochem J. 306*:537–543 (1995).

Shimomura et al., Peroxidized coelenterazine, the active group in the photoprotein aequorin, *Proc. Natl. Acad. Sci. USA 75(6)*: 2611–5 (1978).

Smalley et al., "Localization of fluorescent compounds in the firefly light organ", *J. Histochem. Cytochem. 28(4)*:323–329 (1980).

Smith et al., Bioluminescent immunoassays using streptavidin and biotin conjugates of recombinant aequorin, reprinted from *American Biotechnology Laboratory*, Apr. 1995.

Stability of AquaLite®: lyophilized and in solution, *SeaLite Sciences Technical Report No. 8* (1994).

Stephenson et al. Studies on the Luminescent Response of the $Ca^{2+}$–Activated Photoprotein, Obelin *Biochimica et Biophysica Acta 678*:65–75 (1981).

Tsuji et al., Mechanism of the enzyme–catalyzed oxidation of *Cypridina* and firefly luciferins studied by means of $^{17}O_2$ and $H_2^{18}O^{1,}$ *Biochem. Biophys.Res. Commun. 74(2)*:606–613 (1977).

Vysotski et al., $Mn^{2+}$–activated luminescence of the photoprotein obelin, *Arch. Bioch. Biophys. 316*:92–99 (1995).

Vysotski et al., Luminescence of $Ca^{2+}$–activated photoprotein obelin initiated by NaOCI and $MnCl_2$, *J. Biolumin. Chemilumin. 8*:301–305 (1993).

Wall et al., "The structural basis for red fluorescence in the tetrameric GFP homolog DsRed", *Nature Structural Biol., 7(12)*:1133–1138; (2000).

Ward et al. Reversible Denaturation of the Aequorea Green–Fluorescent Protein: Physicial Separation and Characterization of the Renatured Protein *Biochemistry 21*:4535–4540 (1982).

Ward, Properties of the Coelenterate Green–Fluorescent Proteins *Bioluminescence and Chemiluminescence* 235–242 (1981).

Ward, General Aspects of Bioluminescence, in *Chemi– and Bioluminescence*, Ch. 7, Burr, ed., Marcel Dekker, Inc., New York.

Ward et al. Energy Transfer Via Protein–Protein Interation in Renilla Bioluminescence *Photochemistry and Photobiology 27*:389–396 (1978).

Ward, Energy Transfer Processes in Bioluminescence *Photochem. Photobiol. Rev. 4*:1–57.

Ward et al., An energy transfer protein in coelenterate bioluminescence, *J. Biol. Chem. 254*: 781–788 (1979).

Ward et al. In Vitro Energy Transfer in Renilla Bioluminescence *The Journal of Physical Chemistry 8*:2289–2291 (1976).

Watanabe et al., Bunding of murine monoclonal antibodies to the active and inactive configurations of aequorin, *FEBS Lett. 246(1–2)*: 73–77 (1989).

Watkins et al., Requirement of the C–terminal proline residue for stability of the $Ca^{(2+)}$–activated photoprotein aequorin, *Biochem. J. 293(Pt.1)*: 181–185 (1993).

Welches et al., Active center studies on bacterial luciferase: Modification of the enzyme with 2,4–dinitrofluorobenzene, *Biochemistry 20*: 512–517 (1981).

Widder et al., "Far red bioluminescence from two deep–sea fishes", *Science 225*:512–514 (1984).

Wienhausen et al., Luciferases from different species of fireflies are antigenically similar, *Photochem. Photobiol. 42*: 609–611 (1985).

Yarbrough et al., "Refined crystal structure of DsRed, a red fluorescent protein from coral, at 2.0–Å resolution", *PNAS, 98(2)*:462–467; (2001).

Yen et al., "Synthesis of water–soluble copolymers containing photocleavable bonds", *Makromol. Chem., 190*:69–82; (1989).

Ziegler et al., Active center studies on bacterial luciferase: Locations of the protease labile regions and the reactive cysteinyl residue in the primary structure of the subunit, *Bioluminescence and Chemiluminescence. Basic Chemistry and Analytical Applications*, DeLuca et al., eds., pp. 376–377, Academic Press (1981).

Altschul et al., "Basic Local Alignment Search Tool", *J. Mol. Biol., 215*:403–410; (1990).

Anderson, *Radiolaria*, Springer–Verlag, New York (1983).

Aviv et al., Purification of Biologically Active Globin Messenger RNA by Chromatography on Oligothymidylic acid–Cellulose, *Proc. Natl. Acad. Sci. USA 69(6)*:1408–1412 (1972).

Batra et al., "Insertion of Constant Region Domains of Human IgG, into CD4–PE40 Increases Its Plasma Half–life", *Molecular Immunol., 30(4)*:379–386; (1993).

Bayer and Wichek (1980) *The Use of Avidin/Biotin Complex as a Tool in Molecular Biology. Meth. Biochem. Anal. 26*, 1–45.

Berg et al., Long–chain polystyrene–grafted polyethylene film matrix: a new support for solid–phase peptide synthesis, *J. Am. Chem. Soc. 111*:8026–8027 (1989).

Berg et al., Peptide synthesis on polystyrene–grafted polyethylene sheets, *Pept., Proc. Eur. Pept. Symp., 20th*, Jung et al. (Eds.), pp. 196–198 (1989).

Berg et al., Polystyrene–grafted polyethylene: Design of film and felt matrices for solid–phase peptide synthesis, *Innovation Perspect. Solid Phase Synth. Collect. Pap., Int. Symp., 1st*, Epton (ed.), pp. 453–459 (1990).

Biocomputing: *Informatics and Genome Projects*, Book: Smith, D.W., Ed., Academic Press, New York; (1993).

Bodanszky and Bodanszky, *The Practice of Peptide Synthesis*, Springer–Verlag, New York, (1984).

Bunnin et al. The combinatorial synthesis and chemical and biological evaluation of a 1,4–benzodiazepine library, *Proc. Natl. Acad. Sci. USA, 91*:4708–4712 (1994).

Carlsson et al. Protein Thiolation and Reversible Protein–Protein Conjugation *Biochem. J. 173*: 723–737 (1978).

Carrillo et al., "The Multiple Sequence Alignment Problem in Biology", *SIAM J. Applied Math, 48(5)*:1073–1082; (1988).

Childress, "Oxygen minimum layer: Vertical distribution and respiration of the mysid gnathophausia ingens", *Science* 160:1242–1243 (1968).

Chirgwin et al., Isolation of Biologically Active Ribonucleic Acid from Sources Enriched in Ribonuclease, *Biochemistry* 18(24):5294–5299 (1979).

*Computational Molecular Biology*, Book: Lesk, A.M., ed., Oxford University Press, New York; (1988).

*Computer Analysis of Sequence Data*, Book: Part I, Griffin, A.M., and Griffin, H.G., eds., Humana Press, New Jersey; (1994).

Cumber et al., "Structural Features of the Antibody–A Chain Linkage that Influence the Activity and Stability of Ricin A Chain Immunotoxins", *3(5)*:397–401; (1992).

Devereux et al., "A comprehensive set of sequence analysis programs for the VAX", *Nucl. Acids Res., 12(1)*:387–395; (1984).

DeWitt et al., Diversomers: an approach to nonpeptide, nonoligomeric chemical diversity, *Proc. Natl. Acad. Sci. USA 90*: 6909–6913 (1993).

DeWitt et al., DIVERSOMER™ Technology: solid phase synthesis, automation, and integration for the generation of chemical diversity, *Drug Dev Res* 33:116–124 (1994).

DIALOG Abstract 002042687, citing: JP 7241192.

Düzgunes et al., Fusion of phospholipid vesicles induced by divalent cations and protons; modulation by phase trasitions, free fatty acids, monovalent cations, and polyamines, *Cell Fusion, Ch. 11 Divalent Cations and Protons*, Sowers, A.E. (ed.) pp. 241–267 (1984).

Fattom et al., "Comprehensive Immunogenicity of Conjugates Composed of the *Staphylococcus aureus* Type 8 Capsular Polysaccharide Bound to Carrier Proteins by Adipic Acid Dihydrazide or N–Succinimidyl–3–(2–Pyridyldithio)propionate", *Infection & Immun.*, 60(2):584–589; (1992).

Goodchild, "Conjugates of oligonucleotides and modified oligonucleotides: A review of their synthesis and properties", *Perspectives in Bioconjugate Chemistry*, Mears, ed., American Chemical Society, Washington, D.C., Ch 6, pp. 77–99 (1993).

Gordon et al. Topographical localization of the C–terminal region of the voltage–dependent sodium channel from *Electrophorus electricus* using antibodies raised against a synthetic peptide *Proc. Natl. Acad Sci.* 84:308–312 (1987).

Gribskov et al., "Sigma factors from *E. coli*, *B. subtilis*, phage SP01, and phage T4 are homologous proteins", *Nucl. Acids Res.*, 14(16):6745–6762; (1986).

*Guide to Human Genome Computing*, Book: Martin J. Bishop, ed., Academic Press, San Diego; (1994).

Guyomard et al., Integration and germ line transmission of foreign genes microinjected into fertilized trout eggs, *Biochimie* 71:857–863 (1989).

Hazum et al., A photocleavable protecting group for the thiol function of cysteine, *Pept., Proc. Eur. Pept. Symp., 16th*, Brunfeldt, K (Ed) pp. 105–110 (1981).

Hermanson et al., *Immobilized Affinity Ligand Techniques*, Chaps. 1 and 2, Academic Press, Inc. (1992).

*Immobilized Biochemicals and Affinity Chromatography*, Advances in Experimental Medicine and Biology, vol. 42, ed. R. Dunlap, Plenum Press, N.Y. (1974) Table of Contents.

*Immobilized Enzyme, Antigens, Antibodies and Peptides, Preparation and Characterization*, Marcel Dekker, Inc., N.Y., Howard H. Weetall (ed.) (1975).

Jellinek et al., "Potent 2'–Amino–2'–deoxypyrimidine RNA Inhibitors of Basic Fibroblast Growth Factor", *Biochem.*, 34:11363–11372; (1995).

Kennedy and Cabral, Immobilized Enzymes, in *Solid Phase Biochemistry, Analytical and Synthetic Aspects*, Scouten, Ed., 7:253–391 (1983).

Kent et al., Preparation and properties of tert–butyloxcarbonylaminocayl–4–(oxymethyl) phenylacetamidomethyl–(Kel F–g–styrene) resin, an insoluble, noncrosslinked support for solid phase peptide synthesis, *Israel J. Chem.* 17:243–247 (1978).

Kozak, Structural Features in Eukaryotic mRNAs that Modulate the Initiation of Translation *The Journal of Biological Chemistry* 266:19867–19870 (1991).

Kröger et al., "A new calcium binding glycoprotein family constitutes a major diatom cell wall component", *EMBO* 13:4676–4683 (1996).

Kröger et al., "Frustulins: domain consevation in a protein family associated with diatom cell wall", *Eur. J. Biochem.* 239:259–264 (1996).

Lin et al., "Modified RNA sequence pools for in vitro selection", *Nucl. Acids Res.*, 22(24):5229–5234; (1994).

*Liposome Technology, Targeted Drug Delivery and Biological Interaction*, vol. III, G. Gregoriadis (ed.), CRC Press, Inc. (1984) Table of Contents.

Mahan et al., "Phase Change Enzyme Immunoassay", *Anal. Biochem.*, 162:163–170; (1987).

Mengeling et al., A microplate assay for analysis of solution–phase glycosyltransferase reactions: Determination of kinetic constants, *Anal. Biochem.* 199:286–292 (1991).

Millon et al., "Synthesis of a new reagent, ethyl 4–azidobenzoylaminoacetimidate, and its use for RNA–protein cross–linking within *Escherichia coli* ribosomal 30–S subunits", *Eur. J. Biochem.* 110:485–492 (1980).

*Molecular Biology of the Gene*, 4th Edition, 1987, ed. Watson et al. The Benjamin/Cummings Pub. co. p. 224.

Mosbach, AMP and NAD as 'general ligands', *Affinity Techniques, Enzyme Purification: Part B. Methods in Enzymology*, vol. 34, W. B. Jakoby, et al. (eds.), Acad. Press, N.Y. (1974).

Mosbach et al. Immobilization of enzymes to various acrylic copolymers. *Methods in Enzymology* 44:53–65 (1976).

Mosbach et al. Immobilized coenzymes. *Methods in Enzymology* 44:859–887 (1976).

Mosbach, K and Mattiasson, B. Multistep enzyme systems. *Methods in Enzymology* 44:453–478 (1976).

Mosbach, K. Immobilized Enzymes. *Methods in Enzymology* 44:3–7 (1976).

Nakamura et al., DNA Sequence of the Gene for the Outer Membrane Lipoprotein of *E. coli*: an Extremely AT–Rich Promoter, *Cell* 18:1109–1117 (1979).

Needleman et al., "A General Method Applicable to the Search for Similarities in the Amino Acid Sequence of Two Proteins", *J. MOl. Biol.*, 48:443–453; (1970).

Nogrady, Medicinal Chemistry, A Biochemical Approach, *Oxford University Press, New York* pp. 388–392.

Ozato et al., Production of transgeniuc fish: introduction and expression of chicken—crystalline gene in medaka embryos, *Cell Differ. Devel.* 19:237–244 (1986).

Pagratis et al., "Potent 2'–amino–, and 2'–fluoro–2'–deoxyribonucleotide RNA inhibitors of keratinocyte growth factor", *Nature Biotechnol.*, 15:68–73; (1997).

Pearson et al., "Improved tools for biological sequence comparison", *Proc. Natl. Acad. Sci. U.S.A., 85*:2444–2448; (1988).

Peffer et al., "Strand–invasion of duplex DNA by peptide nucleic acid oligomers", *Proc. Natl. Acad. Sci. U.S.A.* 90:10648–10652 (1993).

Pierce Catalog, pp. T123–T154, (1994).

*Pierce Catalog & Handbook*, pp. O90–O110, T155–T200 (1994).

Pierce Catalog, ImmunoTechnology Catalog & Handbook (1992–1993).

Sambrook et al., Molecular Cloning, 2nd ed., Cold Springs Harbor Laboratory press, New York (1989).

Sanger et al., DNA sequencing with chain–terminating inhibitors, *Proc. Natl. Acad. Sci. USA* 74(12):5463–5467 (1977).

Schwartz and Dayhoff, eds., Book: #23 "Matrices for Detecting Distant Relationships", *Atlas of Protein Sequence and Structure*, National Biomedical Research Foundation, pp. 353–358; (1979).

*Sequence Analysis in Molecular Biology*, Book: von Heijne, Academic Press, Inc., (1987).

*Sequence Analysis Primer*, Book: Gribskov M. and Devereux J., eds., Stockton Press, New York; (1991).

Smith et al., "Comparison of Biosequences", *Adv. Appl. Math.*, *2*:482–489; (1981).

Stewart and Young, Laboratory techniques in solid phase peptide synthesis, *Solid Phase Peptide Synthesis*, 2d Ed., Pierce Chemical Co., pp. 53–73 (1984).

Studier et al. Use of T7 RNA Polymerase to Direct Expression of Cloned Genes *Methods in Enzymology 185*: 60–89 (1990).

Thorpe et al., "New Coupling Agents for the Synthesis of Immunotoxins Containing a Hindered Disulfide Bond with Improved Stability in Vivo", *Cancer Res., 47*:5924–5931; (1987).

Tomme et al., Cellulose–Binding Domains: Classification and Properties, *American Chemical Society* pp. 142–163 (1995).

Travis, J., X–rays speed healing of rat spinal cords, *Science News 150*:214, (1996).

Urlaub et al., Effect of Gamma Rays at the Dihydrofolate Reductase Locus: Deletions and Inversions, *Somatic Cell and Molecular Genetics* 12(6):555–566 (1986).

Walden et al., "Major Histocompatibility Complex–Restricted and Unrestricted Activation of Helper T Cell Lines by Liposome–Bound Antigens", *J. Mol. Cell. Immunol.,* *2*:191–197; (1986).

Wang et al. Implications for bcd mRNA localization from spatial distribution of exu protein in Drosophila oogenesis *Nature 369*:400–403 (1994).

Wawrzynczak et al., "Molecular and biological properties of an abrin A chain immunotoxin designed for therapy of human small cell lung cancer", *Br. J. Cancer, 66*:361–366; (1992).

Wellhöner et al., "Uptake and Concentration of Bioactive Macromolecules by K562 Cells via the Transferrin Cycle Utilizing an Acid–labile Transferrin Conjugate", *J. Biol. Chem., 266(7)*:4309–4314; (1991).

Wu et al. Resonance Energy Transfer: Methods and Application *Analytical Biochemistry 218*:1–13 (1994).

\* cited by examiner

Utilization of advantageous GFP surfaces with
substituted fluorophores

```
              60           *         80
RM-GFP    :  GAPLPFAFDIVSPAFQYGNRTFTKYPNDIS--  :  83
Pt-GFP    :  GGPLPFAFDIVSIAFQYGNRTFTKYPDDIA--  :  83
RR-GFP    :  GAPLPFAFDIVSVAFSYGNRAYTGYPEEIS--  :  80
cFP484    :  GAPLPFSYDILSNAFQYGNRALTKYPDDIA--  :  83
drFP583   :  GGPLPFAWDILSPQFQYGSKVYVKHPADIP--  :  80
asFP595   :  GGPLPFAFHILSTSCMYGSKTFIKYVSGIP--  :  77
dsFP483   :  GGPLPFGWHILCPQFQYGNKAFVHHPDNIH--  :  80
amFP486   :  GGPLAFSFDILSTVFKYGNRCFTAYPTSMP--  :  82
zFP506    :  GGPLPFAEDILSAAFNYGNRVFTEYPQDIV--  :  80
zFP538    :  GGPLPFSEDILSAGFKYGDRIFTEYPQDIV--  :  80
             ====================
```

RENILLA RENIFORMIS FLUORESCENT PROTEINS, NUCLEIC ACIDS ENCODING THE FLUORESCENT PROTEINS AND THE USE THEREOF IN DIAGNOSTICS, HIGH THROUGHPUT SCREENING AND NOVELTY ITEMS

RELATED APPLICATIONS

Benefit of priority under 35 U.S.C. §119(e) is claimed to U.S. provisional application Ser. No. 60/189,691, filed Mar. 15, 2000, to Bryan et al., entitled "*RENILLA RENIFORMIS* FLUORESCENT PROTEINS, NUCLEIC ACIDS ENCODING THE FLUORESCENT PROTEINS AND THE USE THEREOF IN DIAGNOSTICS, HIGH THROUGHPUT SCREENING AND NOVELTY ITEMS" is claimed.

This application is related to allowed U.S. application Ser. No. 09/277,716, filed Mar. 26, 1999, to Bruce Bryan and Christopher Szent-Gyorgyi, entitled "LUCIFERASES, FLUORESCENT PROTEINS, NUCLEIC ACIDS ENCODING THE LUCIFERASES AND FLUORESCENT PROTEINS AND THE USE THEREOF IN DIAGNOSTICS, HIGH THROUGHPUT SCREENING AND NOVELTY ITEMS." This application is related to International PCT application No. WO 99/49019 to Bruce Bryan and Prolume, LTD., entitled "LUCIFERASES, FLUORESCENT PROTEINS, NUCLEIC ACIDS ENCODING THE LUCIFERASES AND FLUORESCENT PROTEINS AND THE USE THEREOF IN DIAGNOSTICS, HIGH THROUGHPUT SCREENING AND NOVELTY ITEMS."

This application is also related to subject matter in U.S. application Ser. No. 08/757,046, filed Nov. 25, 1996, to Bruce Bryan entitled "BIOLUMINESCENT NOVELTY ITEMS", now U.S. Pat. No. 5,876,995, issued Mar. 2, 1999, and in U.S. application Ser. No. 08/597,274, filed Feb. 6, 1996, to Bruce Bryan, entitled "BIOLUMINESCENT NOVELTY ITEMS". This application is also related to U.S. application Ser. No. 08/908,909, filed Aug. 8, 1997, to Bruce Bryan entitled "DETECTION AND VISUALIZATION OF NEOPLASTIC TISSUE AND OTHER TISSUES". The application is also related to U.S. application Ser. No. 08/990,103, filed Dec. 12, 1997, to Bruce Bryan entitled "APPARATUS AND METHODS FOR DETECTING AND IDENTIFYING INFECTIOUS AGENTS".

Where permitted, the subject matter of each of the above noted applications and patents is herein incorporated by reference in its entirety.

FIELD OF INVENTION

Provided herein are isolated and purified nucleic acids and encoded fluorescent proteins from *Renilla reniformis* and uses thereof.

BACKGROUND OF THE INVENTION

Luminescence is a phenomenon in which energy is specifically channeled to a molecule to produce an excited state. Return to a lower energy state is accompanied by release of a photon (hγ). Luminescence includes fluorescence, phosphorescence, chemiluminescence and bioluminescence. Bioluminescence is the process by which living organisms emit light that is visible to other organisms. Luminescence may be represented as follows:

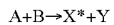

where X* is an electronically excited molecule and hγ represents light emission upon return of X* to a lower energy state. Where the luminescence is bioluminescence, and creation of the excited state is derived from an enzyme catalyzed reaction. The color of the emitted light in a bioluminescent (or chemiluminescent or other luminescent) reaction is characteristic of the excited molecule, and is independent from its source of excitation and temperature.

An essential condition for bioluminescence is the use of molecular oxygen, either bound or free in the presence of a luciferase. Luciferases, are oxygenases, that act on a substrate, luciferin, in the presence of molecular oxygen and transform the substrate to an excited state. Upon return to a lower energy level, energy is released in the form of light (for reviews see, e.g., McElroy et al. (1966) in *Molecular Architecture in Cell Physiology*, Hayashi et al., eds., Prentice-Hall, Inc., Englewood Cliffs, N.J., pp. 63–80; Ward et al., Chapter 7 in Chemi-and Bioluminescence, Burr, ed., Marcel Dekker, Inc. NY, pp. 321–358; Hastings, J. W. in (1995) *Cell Physiology Source Book*, N. Sperelakis (ed.), Academic Press, pp 665–681; *Luminescence, Narcosis and Life in the Deep Sea*, Johnson, Vantage Press, NY, see, esp. pp. 50–56).

Though rare overall, bioluminescence is more common in marine organisms than in terrestrial organisms. Bioluminescence has developed from as many as thirty evolutionarily distinct origins and, thus, is manifested in a variety of ways so that the biochemical and physiological mechanisms responsible for bioluminescence in different organisms are distinct. Bioluminescent species span many genera and include microscopic organisms, such as bacteria (primarily marine bacteria including *Vibrio* species), fungi, algae and dinoflagellates, to marine organisms, including arthropods, mollusks, echinoderms, and chordates, and terrestrial organisms including annelid worms and insects.

Assays Employing Bioluminescence

During the past twenty years, high-sensitivity biochemical assays used in research and in medicine have increasingly employed luminescence and fluorescence rather than radioisotopes. This change has been driven partly by the increasing expense of radioisotope disposal and partly by the need to find more rapid and convenient assay methods. More recently, the need to perform biochemical assays in situ in living cells and whole animals has driven researchers toward protein-based luminescence and fluorescence. The uses of firefly luciferase for ATP assays, aequorin and obelin as calcium reporters, *Vargula* luciferase as a neurophysiological indicator, and the *Aequorea* green fluorescent protein as a protein tracer and pH indicator show the potential of bioluminescence-based methods in research laboratories.

Bioluminescence is also beginning to directly impact medicine and biotechnology; for example, *Aequorea* green fluorescent protein (GFP) is employed to mark cells in murine model systems and as a reporter in high throughput drug screening. *Renilla* luciferase is under development for use in diagnostic platforms.

Bioluminescence Generating Systems

Bioluminescence, as well as other types of chemiluminescence, is used for quantitative determinations of specific substances in biology and medicine. For example, luciferase genes have been cloned and exploited as reporter genes in numerous assays, for many purposes. Since the different luciferase systems have different specific requirements, they may be used to detect and quantify a variety of substances. The majority of commercial bioluminescence applications are based on firefly (*Photinus pyralis*) luciferase. One of the first and still widely used assays involves the use of firefly luciferase to detect the presence of ATP. It is also used to detect and quantify other substrates or co-factors in the reaction. Any reaction that produces or utilizes NAD(H), NADP(H) or long chain aldehyde, either directly or indirectly, can be coupled to the light-emitting reaction of bacterial luciferase.

Another luciferase system that has been used commercially for analytical purposes is the Aequorin system. The purified jellyfish photoprotein, aequorin, is used to detect and quantify intracellular $Ca^{2+}$ and its changes under various experimental conditions. The Aequorin photoprotein is relatively small (~20 kDa), nontoxic, and can be injected into cells in quantities adequate to detect calcium over a large concentration range ($3 \times 10^{-7}$ to $10^{-4}$ M).

Because of their analytical utility, luciferases and substrates have been studied and well-characterized and are commercially available (e.g., firefly luciferase is available from Sigma, St. Louis, Mo., and Boehringer Mannheim Biochemicals, Indianapolis, Ind.; recombinantly produced firefly luciferase and other reagents based on this gene or for use with this protein are available from Promega Corporation, Madison, Wis.; the aequorin photoprotein luciferase from jellyfish and luciferase from *Renilla* are commercially available from Sealite Sciences, Bogart, Ga.; coelenterazine, the naturally-occurring substrate for these luciferases, is available from Molecular Probes, Eugene, Oreg.). These luciferases and related reagents are used as reagents for diagnostics, quality control, environmental testing and other such analyses.

Because of the utility of luciferases as reagents in analytical systems and the potential for use in high throughput screening systems, there is a need to identify and isolate a variety of luciferases that have improved or different spectral properties compared to those presently available. For all these reasons, it would be advantageous to have luciferases from a variety of species, such as *Gaussia* and various *Renilla* species available.

Fluorescent Proteins

Reporter genes, when co-transfected into recipient cells with a gene of interest, provide a means to detect transfection and other events. Among reporter genes are those that encode fluorescent proteins. The bioluminescence generating systems described herein are among those used as reporter genes. To increase the sensitivity bioluminescence generating systems have been combined with fluorescent compounds and proteins, such as naturally fluorescent phycobiliproteins. Also of interest are the fluorescent proteins that are present in a variety of marine invertebrates, such as the green and blue fluorescent proteins, particularly the green fluorescent protein (GFP) of *Aequorea victoria*.

The green fluorescent proteins (GFP) constitute a class of chromoproteins found only among certain bioluminescent coelenterates. These accessory proteins are fluorescent and function as the ultimate bioluminescence emitter in these organisms by accepting energy from enzyme-bound, excited-state oxyluciferin (e.g., see Ward et al. (1979) *J. Biol. Chem.* 254:781–788; Ward et al. (1978) *Photochem. Photobiol.* 27:389–396; Ward et al. (1982) *Biochemistry* 21:4535–4540).

The best characterized GFPs are those isolated from the jellyfish species *Aequorea*, particularly *Aequorea victoria* (*A. victoria*) and *Aequorea forskålea* (Ward et al. (1982) *Biochemistry* 21:4535–4540; Prendergast et al. (1978) *Biochemistry* 17:3448–3453). Purified *A. victoria* GFP is a monomeric protein of about 27 kDa that absorbs blue light with excitation wavelength maximum of 395 nm, with a minor peak at 470 nm, and emits green fluorescence with an emission wavelength of about 510 nm and a minor peak near 540 nm (Ward et al. (1979) *Photochem. Photobiol. Rev* 4:1–57). This GFP has certain limitations. The excitation maximum of the wildtype GFP is not within the range of wavelengths of standard fluorescein detection optics.

The detection of green fluorescence does not require any exogenous substrates or co-factors. Instead, the high level of fluorescence results from the intrinsic chromophore of the protein. The chromophore includes modified amino acid residues within the polypeptide chain. For example, the fluorescent chromophore of *A. victoria* GFP is encoded by the hexapeptide sequence, FSYGVQ, encompassing amino acid residues 64–69. The chromophore is formed by the intramolecular cyclization of the polypeptide backbone at residues Ser65 and Gly67 and the oxidation of the α-β bond of residue Tyr66 (e.g., see Cody et al. (1993) *Biochemistry* 32:1212–1218; Shimomura (1978) *FEBS Letters* 104:220–222; Ward et al. (1989) *Photochem. Photobiol.* 49:62S). The emission spectrum of the isolated chromophore and the denatured protein at neutral pH do not match the spectrum of the native protein, suggesting that chromophore formation occurs post-translationally (e.g., see Cody et al. (1993) *Biochemistry* 32:1212–1218).

In addition, the crystal structure of purified *A. victoria* GFP has been determined (e.g., see Ormö (1996) *Science* 273:1392–1395). The predominant structural features of the protein are an 11-stranded β barrel that forms a nearly perfect cylinder wrapping around a single central α-helix, which contains the modified p-hydroxybenzylideneimadaxolidinone chromophore. The chromophore is centrally located within the barrel structure and is completely shielded from exposure to bulk solvent.

DNA encoding an isotype of *A. victoria* GFP has been isolated and its nucleotide sequence has been determined (e.g., see Prasher (1992) *Gene* 111:229–233). The *A. victoria* cDNA contains a 714 nucleotide open reading frame that encodes a 238 amino acid polypeptide of a calculated $M_r$ of 26,888 Da. Recombinantly expressed *A. victoria* GFPs retain their ability to fluoresce in vivo in a wide variety organisms, including bacteria (e.g., see Chalfie et al. (1994) *Science* 263:802–805; Miller et al. (1997) *Gene* 191:149–153), yeast and fungi (Fey et al. (1995) *Gene* 165:127–130; Straight et al. (1996) *Curr. Biol.* 6:1599–1608; Cormack et al. (1997) *Microbiology* 143:303-311), *Drosophila* (e.g., see Wang et al. (1994) *Nature* 369:400–403; Plautz (1996) *Gene* 173:83–87), plants (Heinlein et al. (1995); Casper et al. (1996) *Gene* 173:69–73), fish (Amsterdam et al. (1995), and mammals (Ikawa et al. (1995). *Aequorea* GFP vectors and isolated *Aequorea* GFP proteins have been used as markers for measuring gene expression, cell migration and localization, microtubule formation and assembly of functional ion channels (e.g., see Terry et al. (1995) *Biochem. Biophys. Res. Commun.* 217:21–27; Kain et al. (1995) *Biotechniques* 19:650–655). The *A. victoria* GFP, however, is not ideal for use in analytical and diagnostic processes. Consequently GFP mutants have been selected with the hope of identifying mutants that have single excitation spectral peaks shifted to the red.

In fact a stated purpose in constructing such mutants has been to attempt to make the *A. victoria* GFP more like the GFP from *Renilla*, but which has properties that make it far more ideal for use as an analytical tool. For many practical applications, the spectrum of *Renilla* GFP is preferable to that of the *Aequorea* GFP, because wavelength discrimination between different fluorophores and detection of resonance energy transfer are easier if the component spectra are tall and narrow rather than low and broad (see, U.S. Pat. No. 5,625,048). Furthermore, the longer wavelength excitation peak (475 nm) of *Renilla* GFP is almost ideal for fluorescein filter sets and is resistant to photobleaching, but has lower amplitude than the shorter wavelength peak at 395 nm, which is more susceptible to photobleaching (Chalfie et al. (1994) *Science* 263:802–805).

There exists a phylogenetically diverse and largely unexplored repertoire of bioluminescent proteins that are a reservoir for future development. For these reasons, it would be desirable to have a variety of new luciferases and fluorescent proteins, particularly, *Renilla reniformis* GFP available rather than use muteins of *A. victoria* GFP. Published International PCT application No. WO 99/49019 (see, also, allowed U.S. application Ser. No. 09/277,716) provides a variety of GFPs including those from *Renilla* species. It remains desirable to have a variety of GFPs and luciferases available in order to optimize systems for particular applications and to improve upon existing methods. Therefore, it is an object herein to provide isolated nucleic acid molecules encoding *Renilla reniformis* GFP and the protein encoded thereby. It is also an object herein to provide bioluminescence generating systems that include the luciferases, luciferins, and also include *Renilla reniformis* GFP.

SUMMARY OF THE INVENTION

"Isolated nucleic acid molecules that encode *Renilla reniformis* fluorescent proteins are provided. Nucleic acid probes and primers derived therefrom are also provided. Functionally equivalent nucleic acids, such as those that hybridize under conditions of high stringency to the disclosed molecules and those that have high sequence identity, are also contemplated. Nucleic acid molecules and the encoded proteins are set forth in SEQ ID. NOs. 23–27, an exemplary mutein is set forth in SEQ ID. NO. 33. Also contemplated are nucleic acid molecules that encode the protein set forth in SEQ ID. NO. 27."

Host cells, including bacterial, yeast and mammalian host cells, and plasmids for expression of the nucleic acids encoding the *Renilla reniformis* green fluorescent protein (GFP), are also provided. Combinations of luciferases and the *Renilla reniformis* GFP are also provided.

The genes can be modified by substitution of codons optimized for expression in selected host cells or hosts, such as humans and other mammals, or can be mutagenized to alter the emission properties. Mutations that alter spectral properties are also contemplated.

Such mutations may be identified by substituting each codon with one encoding another amino acid, such as alanine, and determining the effect on the spectral properties of the resulting protein. Particular regions of interest are those in which corresponding the sites mutated in other GFPs, such Aequora to produce proteins with altered spectral properties are altered.

The *Renilla reniformis* GFP may be used in combination with nucleic acids encoding luciferases, such as those known to those of skill in the art and those that are described in copending allowed U.S. application Ser. No. 09/277,716 (see, also, Published International PCT application No. WO 99/49019).

Compositions containing the *Renilla reniformis* GFP or the *Renilla reniformis* GFP and luciferase combination are provided. The compositions can take any of a number of forms, depending on the intended method of use therefor. In certain embodiments, for example, the compositions contain a *Gaussia* luciferase, *Gaussia* luciferase peptide or *Gaussia* luciferase fusion protein, formulated for use in luminescent novelty items, immunoassays, donors in FET (fluorescent energy transfer) assays, FRET (fluorescent resonance energy transfer) assays, HTRF (homogeneous time-resolved fluorescence) assays or used in conjunction with multi-well assay devices containing integrated photodetectors, such as those described herein.

The bioluminescence-generating system includes, in addition to the luciferase, a *Renilla reniformis* GFP or mutated form thereof. These compositions can be used in a variety of methods and systems, such as those included in conjunction with diagnostic systems for the in vivo detection of neoplastic tissues and other tissues, such as those methods described herein.

Combinations of the *Renilla reniformis* GFP with articles of manufacture to produce novelty items are provided. These novelty items are designed for entertainment, recreation and amusement, and include, but are not limited to: toys, particularly squirt guns, toy cigarettes, toy "Halloween" eggs, footbags and board/card games; finger paints and other paints, slimy play material; textiles, particularly clothing, such as shirts, hats and sports gear suits, threads and yarns; bubbles in bubble making toys and other toys that produce bubbles; balloons; figurines; personal items, such as cosmetics, bath powders, body lotions, gels, powders and creams, nail polishes, make-up, toothpastes and other dentifrices, soaps, body paints, and bubble bath; items such as inks, paper; foods, such as gelatins, icings and frostings; fish food containing luciferins and transgenic fish, particularly transgenic fish that express a luciferase; plant food containing a luciferin or luciferase, preferably a luciferin for use with transgenic plants that express luciferase; and beverages, such as beer, wine, champagne, soft drinks, and ice cubes and ice in other configurations; fountains, including liquid "fireworks" and other such jets or sprays or aerosols of compositions that are solutions, mixtures, suspensions, powders, pastes, particles or other suitable form. The combinations optionally include a bioluminescence generating system. The bioluminescence generating systems can be provided as two compositions: a first composition containing a luciferase and a second composition containing one or more additional components of a bioluminescence generating system.

Any article of manufacture that can be combined with a bioluminescence-generating system as provided herein and thereby provide entertainment, recreation and/or amusement, including use of the items for recreation or to attract attention, such as for advertising goods and/or services that are associated with a logo or trademark is contemplated herein. Such uses may be in addition to or in conjunction with or in place of the ordinary or normal use of such items. As a result of the combination, the items glow or produce, such as in the case of squirt guns and fountains, a glowing fluid or spray of liquid or particles. The novelty in the novelty item derives from its bioluminescence.

GFPS

"Isolated nucleic acids that encode GFP from *Renilla reniformis* are provided herein. Also provided are isolated and purified nucleic acids that encode a component of the bioluminescence generating system and the green fluorescent protein (GFP) (see SEQ ID NOs. 23–27). In particular, nucleic acid molecules that encode *Renilla reniformis* green fluorescent protein (GFPs) and nucleic acid probes and primers derived therefrom are provided (see SEQ ID NOs. 23–26).

Nucleic acid probes and primers containing 14, 16, 30, 100 or more contiguous nucleotides from any of SEQ ID NOs. 23–26 are provided. Nucleic acid probes can be labeled, if needed, for detection, containing at least about 14, preferably at least about 16, or, if desired, 20 or 30 or more, contiguous nucleotides of the sequence of nucleotides encoding the *Renilla reniformis* GFP."

Methods using the probes for the isolation and cloning of GFP-encoding DNA in *Renilla reniformis* are also provided. Vectors containing DNA encoding the *Renilla reniformis* GFP are provided. In particular, expression vectors that contain DNA encoding a *Renilla reniformis* or in operational association with a promoter element that allows for the constitutive or inducible expression of *Renilla reniformis* are provided.

The vectors are capable of expressing the *Renilla reniformis* GFP in a wide variety of host cells. Vectors for producing chimeric *Renilla reniformis* GFP/luciferase fusion proteins and/or polycistronic mRNA containing a promoter element and a multiple cloning site located upstream or downstream of DNA encoding *Renilla reniformis* GFP are also provided.

Recombinant cells containing heterologous nucleic acid encoding a *Renilla reniformis* GFP are also provided. Purified *Renilla reniformis* GFP peptides and compositions containing the *Renilla* GFPs and GFP peptides alone or in combination with at least one component of a bioluminescence-generating system, such as a *Renilla* luciferase, are provided. The *Renilla* GFP and GFP peptide compositions can be used, for example, to provide fluorescent illumination of novelty items or used in methods of detecting and visualizing neoplastic tissue and other tissues, detecting infectious agents using immunoassays, such homogenous immunoassays and in vitro fluorescent-based screening assays using multi-well assay devices, or provided in kits for carrying out any of the above-described methods. In particular, these proteins may be used in FP (fluorescence polarization) assays, FET (fluorescent energy transfer) assays, FRET (fluorescent resonance energy transfer) assays and HTRF (homogeneous time-resolved fluorescence) assays and also in the BRET assays and sensors provided herein.

Non-radioactive energy transfer reactions, such as FET or FRET, FP and HTRF assays, are homogeneous luminescence assays based on energy transfer and are carried out between a donor luminescent label and an acceptor label (see, e.g., Cardullo et al. (1988) *Proc. Natl. Acad. Sd. U.S.A.* 85:8790–8794; Peerce et al. (1986) *Proc. Natl. Acad. Sci. U.S.A.* 83:8092–8096; U.S. Pat. No. 4,777,128; U.S. Pat. No. 5,162,508; U.S. Pat. No. 4,927,923; U.S. Pat. No. 5,279,943; and International PCT Application No. WO 92/01 225). Non-radioactive energy transfer reactions using GFPs have been developed (see, International PCT application Nos. WO 98/02571 and WO 97/28261). Non-radioactive energy transfer reactions using GFPs and luciferases, such as a luciferase and its cognate GFP (or multimers thereof), such as in a fusion protein, are contemplated herein.

Nucleic acids that exhibit substantial sequence identity with the nucleic acids provided herein are also contemplated. These are nucleic acids that can be produced by substituting codons that encode conservative amino acids and also nucleic acids that exhibit at least about 80%, preferably 90 or 95% sequence identity. Sequence identity refers to identity as determined using standard programs with default gap penalties and other defaults as provided by the manufacturer thereof.

The nucleic acids provide an opportunity to produce luciferases and GFPs, which have advantageous application in all areas in which luciferase/luciferins and GFPs have application. The nucleic acids can be used to obtain and produce GFPs and GFPs from other, particularly *Renilla*, species using the probes described herein that correspond to conserved regions. These GFPs provide a means to amplify the output signal of bioluminescence generating systems. *Renilla* GFP has a single excitation absorbance peak in blue light (and around 498 nm) and a predominantly single emission peak around 510 nm (with a small shoulder near 540 nm). This spectrum provides a means for it to absorb blue light and efficiently convert it to green light. This results in an amplification of the output. When used in conjunction with a bioluminescence generating system that yields blue light, such as *Aequorea* or *Renilla* or *Vargula* (*Cypridina*), the output signal for any application, including diagnostic applications, is amplified. In addition, this green light can serve as an energy donor in fluorescence-based assays, such as fluorescence polarized assays, FET (fluorescent energy transfer) assays, FRET (fluorescent resonance energy transfer) assays and HTRF (homogeneous time-resolved fluorescence) assays. Particular assays, herein referred to as BRET (bioluminescence resonance energy transfer assays in which energy is transferred from a bioluminescence reaction of a luciferase to a fluorescent protein), arc provided.

Non-radioactive energy transfer reactions, such as FET or FRET, FP and HTRF assays, are homogeneous luminescence assays based on energy transfer that are carried out between a donor luminescent label and an acceptor label (see, e.g., Cardullo et al. (1988) *Proc. Natl. Acad. Sci. U.S.A.* 85:8790–8794; Peerce et al. (1986) *Proc. Natl. Acad. Sc. U.S.A.* 83:8092–8096; U.S. Pat. No. 4,777,128; U.S. Pat. No. 5,162,508; U.S. Pat. No. 4,927,923; U.S. Pat. No. 5,279,943; and International PCT Application No. WO 92/01225). Non-radioactive energy transfer reactions using GFPs have been developed (see, International PCT application Nos. WO 98/02571 and WO 97/28261).

Mutagenesis of the GFPs is contemplated herein, particularly mutagenesis that results in modified GFPs that have red-shifted excitation and emission spectra. The resulting systems have higher output compared to the unmutagenized forms. These GFPs may be selected by random mutagenesis and selection for GFPs with altered spectra or by selected mutagenesis of the chromophore region of the GFP.

"The DNA may be introduced as a linear DNA molecule (fragment) or may be included in an expression vector for stable or transient expression of the encoding DNA. In certain embodiments, the cells that contain DNA or RNA encoding a *Renilla* GFP also express the recombinant *Renilla* GFP or polypeptide. It is preferred that the cells selected to express functional GFPs that retain the ability to fluorescence and that are not toxic to the host cell. In some embodiments, cells may also include heterologous nucleic acid encoding a component of a bioluminescence-generating system, preferably a photoprotein or luciferase. In preferred embodiments, the nucleic acid encoding the bioluminescence-generating system component is isolated from the species *Aequorea, Vargula, Pleuromamma, Ptilosarcus* or *Renilla*. In more preferred embodiments, the bioluminescence-generating system component is a *Renilla reniformis* luciferase or mullen including the amino acid sequence set forth in SEQ ID NO. 19 or the *Pleuromamma* luciferase set forth in SEQ ID NO. 28, or the *Gaussia* luciferase set forth in SEQ ID NO. 19."

The GFPs provided herein may be used in combination with any suitable bioluminescence generating system, but is preferably used in combination with a *Renilla* or *Aequorea, Pleuromamma* or *Gaussia* luciferase.

Purified *Renilla* GFPs, particularly purified *Renilla reniformis* GFP peptides are provided. Presently preferred *Renilla* GFP for use in the compositions herein is *Renilla reniformis* GFP including the sequence of amino acids set forth above and in the Sequence Listing.

Fusions of the nucleic acid, particularly DNA, encoding *Renilla* GFP with DNA encoding a luciferase are also provided herein.

The cells that express functional luciferase and/or GFP, which may be used alone or in conjunction with a bioluminescence-generating system, in cell-based assays and screening methods, such as those described herein.

Presently preferred host cells for expressing GFP and luciferase are bacteria, yeasts, fungi, plant cells, insect cells and animal cells.

The luciferases and GFPs or cells that express them also may be used in methods of screening for bacterial contamination and methods of screening for metal contaminants. To screen for bacterial contamination, bacterial cells that express the luciferase and/or GFP are put in autoclaves or in other areas in which testing is contemplated. After treatment or use of the area, the area is tested for the presence of glowing bacteria. Presence of such bacteria is indicative of a failure to eradicate other bacteria. Screening for heavy metals and other environmental contaminants can also be performed with cells that contain the nucleic dependent upon the particular heavy metal or contaminant.

The systems and cells provided herein can be used for high throughout screening protocols, intracellular assays, medical diagnostic assays, environmental testing, such as tracing bacteria in water supplies, in conjunction with enzymes for detecting heavy metals, in spores for testing autoclaves in hospital, foods and industrial autoclaves. Non-pathogenic bacteria containing the systems can be included in feed to animals to detect bacterial contamination in animal products and in meats.

Compositions containing a *Renilla* GFP are provided. The compositions can take any of a number of forms, depending on the intended method of use therefor. In certain embodiments, for example, the compositions contain a *Renilla* GFP or GFP peptide, preferably *Renilla mulleri* GFP or *Renilla reniformis* GFP peptide, formulated for use in luminescent novelty items, immunoassays, FET (fluorescent energy transfer) assays, FRET (fluorescent resonance energy transfer) assays, HTRF (homogeneous time-resolved fluorescence) assays or used in conjunction with multi-well assay devices containing integrated photodetectors, such as those described herein. In other instances, the GFPs are used in beverages, foods or cosmetics.

Compositions that contain a *Renilla reniformis* GFP or GFP peptide and at least one component of a bioluminescence-generating system, preferably a luciferase, luciferin or a luciferase and a luciferin, are provided. In preferred embodiments, the luciferase/luciferin bioluminescence-generating system is selected from those isolated from: an insect system, a coelenterate system, a ctenophore system, a bacterial system, a mollusk system, a crustacea system, a fish system, an annelid system, and an earthworm system. Bioluminescence-generating systems include those isolated from *Renilla, Aequorea,* and *Vargula, Gaussia* and *Pleuromamma.*

Combinations containing a first composition containing a *Renilla reniformis* GEP or *Ptilosarcus* GFP or mixtures thereof and a second composition containing a bioluminescence-generating system for use with inanimate articles of manufacture to produce novelty items are provided. These novelty items, which are articles of manufacture, are designed for entertainment, recreation and amusement, and include, but are not limited to: toys, particularly squirt guns, toy cigarettes, toy "Halloween" eggs, footbags and board/card games; finger paints and other paints, slimy play material; textiles, particularly clothing, such as shirts, hats and sports gear suits, threads and yarns; bubbles in bubble making toys and other toys that produce bubbles; balloons; figurines; personal items, such as bath powders, body lotions, gels, powders and creams, nail polishes, cosmetics including make-up, toothpastes and other dentifrices, soaps, cosmetics, body paints, and bubble bath, bubbles made from non-detergent sources, particularly proteins such as albumin and other non-toxic proteins; in fishing lures and glowing transgenic worms, particularly crosslinked polyacrylamide containing a fluorescent protein and/or components of a bioluminescence generating system, which glow upon contact with water; items such as inks, paper; foods, such as gelatins, icings and frostings; fish food containing luciferins and transgenic animals, such as transgenic fish, worms, monkeys, rodents, ungulates, ovine, ruminants and others, that express a luciferase and/or *Renilla reniformis* GFP; transgenic worms that express *Renilla reniformis* GFP and are used as lures; plant food containing a luciferin or luciferase, preferably a luciferin for use with transgenic plants that express luciferase and *Renilla reniformis* GFP, transgenic plants that express *Renilla reniformis* GFP, particularly ornamental plants, such as orchids, roses, and other plants with decorative flowers; transgenic plants and animals in which the *Renilla reniformis* GFP is a marker for tracking introduction of other genes; and beverages, such as beer, wine, champagne, soft drinks, milk and ice cubes and ice in other configurations containing *Renilla reniformis* GFP; fountains, including liquid "fireworks" and other such jets or sprays or aerosols of compositions that are solutions, mixtures, suspensions, powders, pastes, particles or other suitable forms.

Any article of manufacture that can be combined with a bioluminescence-generating system and *Renilla reniformis* GFP or with just a *Renilla reniformis* GFP, as provided herein, that thereby provides entertainment, recreation and/or amusement, including use of the items for recreation or to attract attention, such as for advertising goods and/or services that are associated with a logo or trademark is contemplated herein. Such uses may be in addition to or in conjunction with or in place of the ordinary or normal use of such items. As a result of the combination, the items glow or produce, such as in the case of squirt guns and fountains, a glowing fluid or spray of liquid or particles.

Methods for diagnosis and visualization of tissues in vivo or in situ using compositions containing a *Renilla reniformis* GFP and/or a *Renilla reniformis* or *mulleri* luciferase or others of the luciferases and/or GFPs provided herein are provided. For example, the *Renilla reniformis* GFP protein can be used in conjunction with diagnostic systems that rely on bioluminescence for visualizing tissues in situ. The systems are particularly useful for visualizing and detecting neoplastic tissue and specialty tissue, such as during non-invasive and invasive procedures. The systems include compositions containing conjugates that include a tissue specific, particularly a tumor-specific, targeting agent linked to a targeted agent, a *Renilla reniformis* GFP, a luciferase or luciferin. The systems also include a second composition that contains the remaining components of a bioluminescence generating reaction and/or the *Renilla reniformis* GFP. In some embodiments, all components, except for activators, which are provided in situ or are present in the body or tissue, are included in a single composition.

Methods for diagnosis and visualization of tissues in vivo or in situ using compositions containing a *Gaussia* luciferase are provided. For example, the *Gaussia* luciferase or *Gaussia* luciferase peptide can be used in conjunction with diagnostic systems that rely on bioluminescence for visualizing tissues in situ. The systems are particularly useful for visualizing and detecting neoplastic tissue and specialty tissue, such as during non-invasive and invasive procedures. The systems include compositions containing conjugates that include a tissue specific, particularly a tumor-specific, targeting agent linked to a targeted agent, a *Gaussia* luciferase, a GFP or luciferin. The systems also include a second composition that contains the remaining components of a bioluminescence generating reaction and/or the *Gaussia* luciferase. In some embodiments, all components, except for activators, which are provided in situ or are present in the body or tissue, are included in a single composition.

In particular, the diagnostic systems include two compositions. A first composition that contains conjugates that, in preferred embodiments, include antibodies directed against tumor antigens conjugated to a component of the bioluminescence generating reaction, a luciferase or luciferin, preferably a luciferase are provided. In certain embodiments, conjugates containing tumor-specific targeting agents are linked to luciferases or luciferins. In other embodiments, tumor-specific targeting agents are linked to microcarriers that are coupled with, preferably more than one of the bioluminescence generating components, preferably more than one luciferase molecule.

The second composition contains the remaining components of a bioluminescence generating system, typically the luciferin or luciferase substrate. In some embodiments, these components, particularly the luciferin are linked to a protein, such as a serum albumin, or other protein carrier. The carrier and time release formulations permit systemically administered components to travel to the targeted tissue without interaction with blood cell components, such as hemoglobin that deactivates the luciferin or luciferase.

Methods for diagnosing diseases, particularly infectious diseases, using chip methodology (see, e.g., copending U.S. application Ser. No. 08/990,103) a luciferase/luciferin bioluminescence-generating system and a *Renilla reniformis* GFP are provided. In particular, the chip includes an integrated photodetector that detects the photons emitted by the bioluminescence-generating system, particularly using luciferase encoded by the nucleic acids provided herein and/or *Renilla reniformis* GFP.

In one embodiment, the chip is made using an integrated circuit with an array, such as an X-Y array, of photodetectors. The surface of circuit is treated to render it inert to conditions of the diagnostic assays for which the chip is intended, and is adapted, such as by derivatization for linking molecules, such as antibodies. A selected antibody or panel of antibodies, such as an antibody specific for a bacterial antigen, is affixed to the surface of the chip above each photodetector. After contacting the chip with a test sample, the chip is contacted with a second antibody linked to a *Renilla* GFP, a chimeric antibody-*Renilla* GFP fusion protein or an antibody linked to a component of a bioluminescence generating system, such as a luciferase or luciferin, that are specific for the antigen. The remaining components of the bioluminescence generating reaction are added, and, if any of the antibodies linked to a component of a bioluminescence generating system are present on the chip, light will be generated and detected by the adjacent photodetector. The photodetector is operatively linked to a computer, which is programmed with information identifying the linked antibodies, records the event, and thereby identifies antigens present in the test sample.

Methods for generating chimeric GFP fusion proteins are provided. The methods include linking DNA encoding a gene of interest, or portion thereof, to DNA encoding a GFP coding region in the same translational reading frame. The encoded-protein of interest may be linked in-frame to the amino- or carboxyl-terminus of the GFP. The DNA encoding the chimeric protein is then linked in operable association with a promoter element of a suitable expression vector. Alternatively, the promoter element can be obtained directly from the targeted gene of interest and the promoter-containing fragment linked upstream of the GFP coding sequence to produce chimeric GFP proteins or to produce polycistronic mRNAs that encode the *Renilla reniformis* GFP and a luciferase, preferably a *Renilla* luciferase, more preferably *Renilla reniformis* luciferase.

Methods for identifying compounds using recombinant cells that express heterologous DNA encoding a *Renilla reniformis* GFP under the control of a promoter element of a gene of interest are provided. The recombinant cells can be used to identify compounds or ligands that modulate the level of transcription from the promoter of interest by measuring *Renilla reniformis* GFP-mediated fluorescence. Recombinant cells expressing the chimeric *Renilla reniformis* GFP or polycistronic mRNA encoding *Renilla reniformis* and a luciferase, may also be used for monitoring gene expression or protein trafficking, or determining the cellular localization of the target protein by identifying localized regions of GFP-mediated fluorescence within the recombinant cell.

Other assays using the GFPs and/or luciferases are contemplated herein. Any assay or diagnostic method known used by those of skill in the art that employ *Aequora* GFPs and/or other luciferases are contemplated herein.

Kits containing the GFPs for use in the methods, including those described herein, are provided. In one embodiment, the kits containing an article of manufacture and appropriate reagents for generating bioluminescence are provided. The kits containing such soap compositions, with preferably a moderate pH (between 5 and 8) and bioluminescence generating reagents, including luciferase and luciferin and the GFP are provided herein. These kits, for example, can be used with a bubble-blowing or producing toy. These kits can also include a reloading or charging cartridge or can be used in connection with a food.

In another embodiment, the kits are used for detecting and visualizing neoplastic tissue and other tissues and include a first composition that contains the GFP and at least one component of a bioluminescence generating system, and a second that contains the activating composition, which contains the remaining components of the bioluminescence generating system and any necessary activating agents.

Thus, these kits will typically include two compositions, a first composition containing the GFP formulated for systemic administration (or in some embodiments local or topical application), and a second composition containing the components or remaining components of a bioluminescence generating system, formulated for systemic, topical or local administration depending upon the application. Instructions for administration will be included.

In other embodiments, the kits are used for detecting and identifying diseases, particularly infectious diseases, using multi-well assay devices and include a multi-well assay device containing a plurality of wells, each having an integrated photodetector, to which an antibody or panel of antibodies specific for one or more infectious agents are attached, and composition containing a secondary antibody, such as an antibody specific for the infectious agent that is linked to a *Renilla reniformis* GFP protein, a chimeric antibody-*Renilla reniformis* GFP fusion protein or F(Ab)$_2$ antibody fragment-*Renilla reniformis* GFP fusion protein. A second composition contains a bioluminescence generating system that emits a wavelength of light within the excitation range of the *Renilla mulleri* GFP, such as species of *Renilla* or *Aequorea*, for exciting the *Renilla reniformis*, which produces light that is detected by the photodetector of the device to indicate the presence of the agent.

As noted above, fusions of nucleic acid encoding the luciferases and or GFPs provided herein with other luciferases and GFPs are provided. Of particular interest are fusions that encode pairs of luciferases and GFPs, such as a *Renilla* luciferase and a *Renilla* GFP (or a homodimer or other multiple of a *Renilla* GFP). The luciferase and GFP bind and in the presence of a luciferin will produced fluorescence that is red shifted compared to the luciferase in the absence of the GFP. This fusion or fusions in which the GFP and luciferase are linked via a target, such as a peptide, can be used as a tool to assess anything that interacts with the linker.

Muteins of the GFPs and luciferases are provided. Of particular interest are muteins, such as temperature sensitive muteins, of the GFP and luciferases that alter their interaction, such as mutations in the *Renilla* luciferase and *Renilla* GFP that alters their interaction at a critical temperature.

Antibodies, polyclonal and monoclonal antibodies that specifically bind to any of the proteins encoded by the nucleic acids provided herein are also provided. These antibodies, monoclonal or polyclonal, can be prepared employing standard techniques, known to those of skill in the art. In particular, immunoglobulins or antibodies obtained from the serum of an animal immunized with a substantially pure preparation of a luciferase or GFP provided herein or an or epitope-containing fragment thereof are provided. Monoclonal antibodies are also provided. The immunoglobulins that are produced have, among other properties, the ability to specifically and preferentially bind to and/or cause the immunoprecipitation of a GFP or luciferase, particularly a *Renilla* or *Ptilosarcus* GFP or a *Pleuromamma, Gaussia* or *Renilla mulleri* luciferase, that may be present in a biological sample or a solution derived from such a biological sample.

DESCRIPTION OF THE FIGURES

"FIG. 4 depicts the substitution of altered fluorophores into the background of *Ptilosarcus, Renilla mulleri* and *Renilla reniformis* GFPs (the underlined regions correspond to amino acids 56–75 of SEQ ID NO. 27 *Renilla reniformis* GFP; amino acids 59–78 of SEQ ID NO. 16 *Renilla mulleri* GFP; and amino acids 59–78 of SEQ ID NO. 32 for *Ptilosarcus* GFP)."

FIG. 5 depicts the three anthozoan fluorescent proteins for which a crystal structure exists; another is available commercially from Clontech as dsRed (from *Discosoma striata*; also known as drFP583, as in this alignment); a dark gray background depicts amino acid conservation, and a light gray background depicts shared physicochemical properties.

FIG. 6 compares the sequences of a variety of GFPs, identifying sites for mutation to reduce multimerization; abbreviations are as follows: *Amemonia majona* is amFP486; *Zoanthus* sp. zFP506 and zFP538; *Discosoma* sp. "red" is drFP583; *Clavularia* sp. is cFP484; and the GFP from the anthozoal *A. sulcata* is designated FP595.

DETAILED DESCRIPTION OF THE INVENTION

Figure 1:
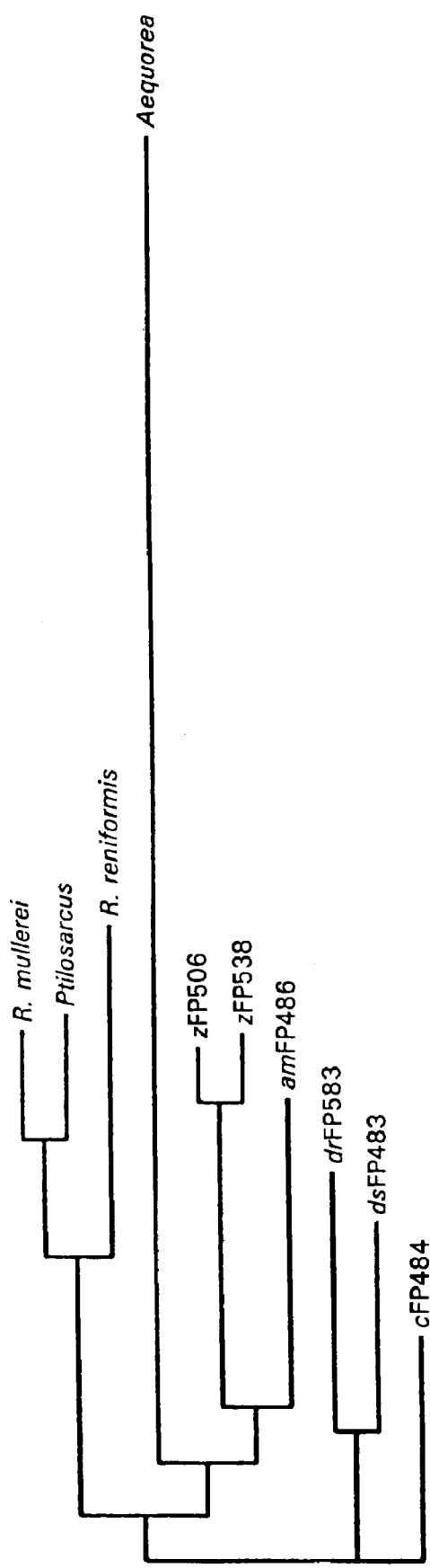
FIG. 1 depicts phylogenetic relationships among the anthozoan GFPs.
Figure 2A:
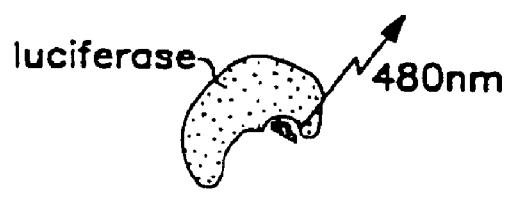
FIGS. 2A–D illustrate the underlying principle of Bioluminescent Resonance Energy Transfer (BRET) and its use as sensor: A) in isolation, a luciferase, preferably an anthozoan luciferase, emits blue light from the coelenterazine-derived chromophore; B) in isolation, a GFP, preferably an anthozoan GFP that binds to the luciferase, that is excited with blue-green light emits green light from its integral peptide based fluorophore; C) when the luciferase and GFP associate as a complex in vivo or in vitro, the luciferase non-radiatively transfers its reaction energy to the GFP flurophore, which then emits the green light; D) any molecular interaction that disrupts the luciferase-GEP complex can be quantitatively monitored by observing the spectral shift from green to blue light.
Figure 2C:
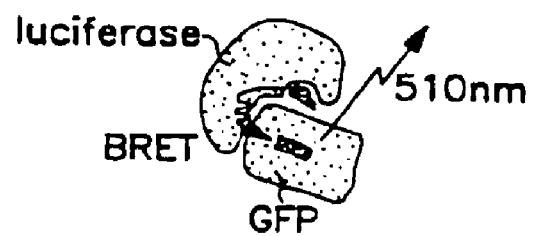
Figure 2B:
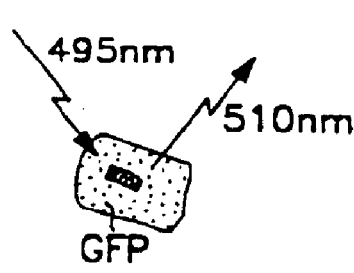
Figure 2D:
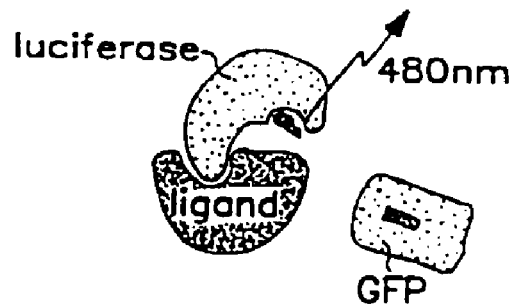

A. Definitions
B. Fluorescent Proteins
1. Green and blue fluorescent proteins
2. *Renilla reniformis* GFP
C. Bioluminescence Generating Systems and Components
 1. General description
  a. Luciferases
  b. Luciferins
  c. Activators
  d. Reactions
 2. The *Renilla* system
 3. Ctenophore systems
 4. The aequorin system
  a. Aequorin and related photoproteins
  b. Luciferin
 5. Crustacean, particularly *Cyrpidina* systems
  a. *Vargula* luciferase
   (1) Purification from *Cypridina*
   (2) Preparation by Recombinant Methods
  b. *Vargula* luciferin
  c. Reaction
 6. Insect bioluminescent systems including fireflies, click beetles, and other insect system
  a. Luciferase
  b. Luciferin
  c. Reaction
 7. Other systems
  a. Bacterial systems
   (1) Luciferases
   (2) Luciferins
   (3) Reactions
  b. Dinoflagellate bioluminescence generating systems
D. Isolation and Identification of Nucleic Acids Encoding Luciferases and GFPs
 1. Isolation of specimens of the genus *Renilla*
 2. Preparation of *Renilla* cDNA expression libraries
  a. RNA isolation and cDNA synthesis
  b. Construction of cDNA expression libraries
 3. Cloning of *Renilla reniformis* Green Fluorescent Protein
 4. Isolation and identification of DNA encoding *Renilla mulleri* GFP 5. Isolation and identification of DNA encoding *Renilla mulleri* luciferase
E. Recombinant Expression of Proteins
1. DNA encoding *Renilla* proteins
2. DNA constructs for recombinant production of *Renilla reniformis* and other proteins
3. Host organisms for recombinant production of *Renilla* proteins
4. Methods for recombinant production of *Renilla* proteins
5. Recombinant cells expressing heterologous nucleic acid encoding luciferases and GFPs
F. Compositions and Conjugates
1. *Renilla* GFP compositions
2. *Renilla* luciferase compositions
3. Conjugates
   a. Linkers
   b. Targeting Agents
   c. Anti-tumor Antigen Antibodies
   d. Preparation of the conjugates
4. Formulation of the compositions for use in the diagnostic systems
   a. The first composition: formulation of the conjugates
   b. The second composition
   c. Practice of the reactions in combination with targeting agents
G. Combinations
H. Exemplary uses of *Renilla reniformis* GFPs and encoding nucleic acid molecules
1. Methods for diagnosis of neoplasms and other tissues
2. Methods of diagnosing diseases
3. Methods for generating *Renilla mulleri* luciferase, *Pleuromamma* luciferase and *Gaussia* luciferase fusion proteins with *Renilla reniformis* GFP
4. Cell-based assays for identifying compounds
I. Kits
J. Muteins
1. Mutation of GFP surfaces to disrupt multimerization
2. Use of advantageous GFP surfaces with substituted fluorophores
K. Transgenic Plants and Animals
L. Bioluminescence Resonance Energy Transfer (BRET) System
1. Design of sensors based on BRET
2. BRET Sensor Architectures
3. Advantages of BRET sensors
A. Definitions Unless defined otherwise, all technical and scientific terms used herein have the same meaning as is commonly understood by one of skill in the art to which this invention belongs. All patents, applications and publications of referred to throughout the disclosure are incorporated by reference in their entirety.

As used herein, chemiluminescence refers to a chemical reaction in which energy is specifically channeled to a molecule causing it to become electronically excited and subsequently to release a photon thereby emitting visible light. Temperature does not contribute to this channeled energy. Thus, chemiluminescence involves the direct conversion of chemical energy to light energy.

"As used herein, luminescence refers to the detectable electromagnetic (EM) radiation, generally, ultraviolet (UV), infrared (IR) or visible EM radiation that is produced when the excited product of an exergic chemical process reverts to its ground state with the emission of light. Chemiluminescence is luminescence that results from a chemical reaction. Bioluminescence is chemiluminescence that results from a chemical reaction using biological molecules (or synthetic versions or analogs thereof) as substrates and/or enzymes.

As used herein, bioluminescence, which is a type of chemiluminescence, refers to the emission of light by biological molecules, particularly proteins. The essential condition for bioluminescence is molecular oxygen, either bound or free in the presence of an oxygenase, a luciferase, which acts on a substrate, a luciferin. Bioluminescence is generated by an enzyme or other protein (luciferase) that is an oxygenase that acts on a substrate luciferin (a bioluminescence substrate) in the presence of molecular oxygen and transforms the substrate to an excited state, which upon return to a lower energy level releases the energy in the form of light.

As used herein, the substrates and enzymes for producing bioluminescence are generically referred to as luciferin and luciferase, respectively. When reference is made to a particular species thereof, for clarity, each generic term is used with the name of the organism from which it derives, for example, bacterial luciferin or firefly luciferase.

As used herein, luciferase refers to oxygenases that catalyze a light emitting reaction. For instance, bacterial luciferases catalyze the oxidation of flavin mononucleotide (FMN) and aliphatic aldehydes, which reaction produces light. Another class of luciferases, found among marine arthropods, catalyzes the oxidation of *Cypridina* (*Vargula*) luciferin, and another class of luciferases catalyzes the oxidation of *Coleoptera* luciferin.

Thus, luciferase refers to an enzyme or photoprotein that catalyzes a bioluminescent reaction (a reaction that produces bioluminescence). The luciferases, such as firefly and *Gaussia* and *Renilla* luciferases, that are enzymes which act catalytically and are unchanged during the bioluminescence generating reaction. The luciferase photoproteins, such as the aequorin photoprotein to which luciferin is non-covalently bound, are changed, such as by release of the luciferin, during bioluminescence generating reaction. The luciferase is a protein that occurs naturally in an organism or a variant or mutant thereof, such as a variant produced by mutagenesis that has one or more properties, such as thermal stability, that differ from the naturally-occurring protein. Luciferases and modified mutant or variant forms thereof are well known. For purposes herein, reference to luciferase refers to either the photoproteins or luciferases.

Thus, reference, for example, to "*Gaussia* luciferase" means an enzyme isolated from member of the genus *Gaussia* or an equivalent molecule obtained from any other source, such as from another related copepod, or that has been prepared synthetically. It is intended to encompass *Gaussia* luciferases with conservative amino acid substitutions that do not substantially alter activity. Suitable conservative substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., Watson et al. *Molecular Biology of the Gene,* 4th Edition, 1987, The Bejacmin/Cummings Pub. co., p. 224).

"*Renilla* GFP" refers to GFPs from the genus *Renilla* and to mutants or variants thereof. It is intended to encompass *Renilla* GFPs with conservative amino acid substitutions that do not substantially alter activity and physical properties, such as the emission spectra and ability to shift the spectral output of bioluminescence generating systems.

Such substitutions are preferably made in accordance with those set forth in TABLE 1 as follows:

TABLE 1

| Original residue | Conservative substitution |
|---|---|
| Ala (A) | Gly; Ser |
| Arg (R) | Lys |
| Asn (N) | Gln; His |
| Cys (C) | Ser |
| Gln (Q) | Asn |
| Glu (E) | Asp |
| Gly (G) | Ala; Pro |
| His (H) | Asn; Gln |
| Ile (I) | Leu; Val |
| Leu (L) | Ile; Val |
| Lys (K) | Arg; Gln; Glu |
| Met (M) | Leu; Tyr; Ile |
| Phe (F) | Met; Leu; Tyr |
| Ser (S) | Thr |
| Thr (T) | Ser |
| Trp (W) | Tyr |
| Tyr (Y) | Trp; Phe |
| Val (V) | Ile; Leu |

Other substitutions are also permissible and may be determined empirically or in accord with known conservative substitutions.

The luciferases and luciferin and activators thereof are referred to as bioluminescence generating reagents or components. Typically, a subset of these reagents will be provided or combined with an article of manufacture. Bioluminescence will be produced upon contacting the combination with the remaining reagents. Thus, as used herein, the component luciferases, luciferins, and other factors, such as $O_2$, $Mg^{2+}$, $Ca^{2+}$ are also referred to as bioluminescence generating reagents (or agents or components).

"As used herein, a *Renilla reniformis* green fluorescent protein (GEP) refers to a fluorescent protein that is encoded by a sequence of nucleotides that encodes the protein of SEQ ID NO. 27 or to a green fluorescent protein from *Renilla reniformis* having at least 80%, 90% or 95% or greater sequence identity thereto; or that is encoded by a sequence of nucleotides that hybridizes under high stringency along its full length to the coding portion of the sequence of nucleotides set forth in any of SEQ ID NOs. 23–25. A *Renilla reniformis* GEP is protein that is fluorescent and is produced in a *Renilla reniformis*."

As used herein, bioluminescence substrate refers to the compound that is oxidized in the presence of a luciferase, and any necessary activators, and generates light. These substrates are referred to as luciferins herein, are substrates that undergo oxidation in a bioluminescence reaction. These bioluminescence substrates include any luciferin or analog thereof or any synthetic compound with which a luciferase interacts to generate light. Preferred substrates are those that are oxidized in the presence of a luciferase or protein in a light-generating reaction. Bioluminescence substrates, thus, include those compounds that those of skill in the art recognize as luciferins. Luciferins, for example, include firefly luciferin, *Cypridina* (also known as *Vargula*) luciferin (coelenterazine), bacterial luciferin, as well as synthetic analogs of these substrates or other compounds that are oxidized in the presence of a luciferase in a reaction the produces bioluminescence.

As used herein, capable of conversion into a bioluminescence substrate means susceptible to chemical reaction, such as oxidation or reduction, that yields a bioluminescence substrate. For example, the luminescence producing reaction of bioluminescent bacteria involves the reduction of a flavin mononucleotide group (FMN) to reduced flavin mononucleotide ($FMNH_2$) by a flavin reductase enzyme. The reduced flavin mononucleotide (substrate) then reacts with oxygen (an activator) and bacterial luciferase to form an intermediate peroxy flavin that undergoes further reaction, in the presence of a long-chain aldehyde, to generate light. With respect to this reaction, the reduced flavin and the long chain aldehyde are substrates.

As used herein, a bioluminescence generating system refers to the set of reagents required to conduct a bioluminescent reaction. Thus, the specific luciferase, luciferin and other substrates, solvents and other reagents that may be required to complete a bioluminescent reaction form a bioluminescence system. Thus a bioluminescence generating system refers to any set of reagents that, under appropriate reaction conditions, yield bioluminescence. Appropriate reaction conditions refers to the conditions necessary for a bioluminescence reaction to occur, such as pH, salt concentrations and temperature. In general, bioluminescence systems include a bioluminescence substrate, luciferin, a luciferase, which includes enzymes luciferases and photoproteins, and one or more activators. A specific bioluminescence system may be identified by reference to the specific organism from which the luciferase derives; for example, the *Vargula* (also called *Cypridina*) bioluminescence system (or *Vargula* system) includes a *Vargula* luciferase, such as a luciferase isolated from the ostracod, *Vargula* or produced using recombinant means or modifications of these luciferases. This system would also include the particular activators necessary to complete the bioluminescence reaction, such as oxygen and a substrate with which the luciferase reacts in the presence of the oxygen to produce light.

The luciferases provided herein may be incorporated into bioluminescence generating systems and used, as appropriate, with the GFPs provided herein or with other GFPs. Similarly, the GFPs provided herein may be used with known bioluminescence generating systems.

As used herein, the amino acids, which occur in the various amino acid sequences appearing herein, are identified according to their well-known, three-letter or one-letter abbreviations. The nucleotides, which occur in the various DNA molecules, are designated with the standard single-letter designations used routinely in the art.

As used herein, a fluorescent protein refers to a protein that possesses the ability to fluoresce (i.e., to absorb energy at one wavelength and emit it at another wavelength). These proteins can be used as a fluorescent label or marker and in any applications in which such labels would be used, such as immunoassays, CRET, FRET, and FET assays, and in the assays designated herein as BRET assays. For example, a green fluorescent protein refers to a polypeptide that has a peak in the emission spectrum at about 510 nm.

As used herein, the term BRET (Bioluminescence Resonance Energy Transfer) refers to non-radiative luciferase-to-FP energy transfer. It differs from (Fluorescence Resonance Energy Transfer), which refers to energy transfer between chemical fluors.

As used herein, a BRET system refers the combination of a FP, in this case *Renilla reniformis* GFP and a luciferase for resonance energy transfer. BRET refers to any method in which the luciferase is used to generate the light upon reaction with a luciferin which is then non-radiatively transferred to a FP. The energy is transferred to a FP, particularly a GFP, which focuses and shifts the energy and emits it at a different wavelength. In preferred embodiments, the BRET system includes a bioluminescence generating system and a *Renilla reniformis* GFP. The bioluminescence generating system is preferably a *Renilla* system. Hence, the preferred pair is a *Renilla* luciferase and a *Renilla* GFP, which specifically interact. Alterations in the binding will be reflected in changes in the emission spectra of light produced by the luciferase. As a result the pair can function as a sensor of external events.

As used herein, a biosensor (or sensor) refers to a BRET system for use to detect alterations in the environment in vitro or in vivo in which the BRET system is used.

As used herein, modulator with reference to a BRET system refers to a molecule or molecules that undergo a conformation change in response to interaction with another molecule thereby affecting the proximity and/or orientation of the GFP and luciferase in the BRET system. Modulators include, but are not limited to, a protease site, a second messenger binding site, an ion binding molecule, a receptor, an oligomer, an enzyme substrate, a ligand, or other such binding molecule. If the GFP and luciferase are each linked to the modulator, changes in conformation alter the spacial relationship between the GFP and luciferase. The modulator can be a single entity covalently attached to one or both of the luciferase and GFP; it can be two separate entities each linked to either the luciferase or GFP. The modulator(s), GFP and luciferase can be a single fusion protein, or a fusion protein of at least two of the entities. The components can be chemically linked, such as through thiol or disulfide linkages, using linkers as provided herein. The GFP and luciferase can be linked directly or via linker, which can be a chemical linkage.

As used herein, "not strictly catalytically" means that the photoprotein acts as a catalyst to promote the oxidation of the substrate, but it is changed in the reaction, since the bound substrate is oxidized and bound molecular oxygen is used in the reaction. Such photoproteins are regenerated by addition of the substrate and molecular oxygen under appropriate conditions known to those of skill in this art.

As used herein, "nucleic acid" refers to a polynucleotide containing at least two covalently linked nucleotide or nucleotide analog subunits. A nucleic acid can be a deoxyribonucleic acid (DNA), a ribonucleic acid (RNA), or an analog of DNA or RNA. Nucleotide analogs are commercially available and methods of preparing polynucleotides containing such nucleotide analogs are known (Lin et al. (1994) *Nucl. Acids Res.* 22:5220–5234; Jellinek et al. (1995) *Biochemistry* 34:11363–11372; Pagratis et al. (1997) *Nature Biotechnol.* 15:68–73). The nucleic acid can be single-stranded, double-stranded, or a mixture thereof. For purposes herein, unless specified otherwise, the nucleic acid is double-stranded, or it is apparent from the context.

As used herein, a second messenger includes, but are not limited to, cAMP, cGMP, inositol phosphates, such as IP2 and IP3, NO (nitric oxide), $Ca^{2+}$, ceramide; DAG and arachidonic acid.

Hence, the term "nucleic acid" refers to single-stranded and/or double-stranded polynucleotides, such as deoxyribonucleic acid (DNA) and ribonucleic acid (RNA), as well as analogs or derivatives of either RNA or DNA. Also included in the term "nucleic acid" are analogs of nucleic acids such as peptide nucleic acid (PNA), phosphorothioate DNA, and other such analogs and derivatives.

As used herein, the term "nucleic acid molecule" and "nucleic acid fragment" are used interchangeably.

As used herein, DNA is meant to include all types and sizes of DNA molecules including cDNA, plasmids and DNA including modified nucleotides and nucleotide analogs.

As used herein, nucleotides include nucleoside mono-, di-, and triphosphates. Nucleotides also include modified nucleotides, such as, but are not limited to, phosphorothioate nucleotides and deazapurine nucleotides and other nucleotide analogs.

"As used herein, a nucleic acid probe is single-stranded DNA or RNA that has a sequence of nucleotides that includes at least 14 contiguous bases, preferably at least 16 contiguous bases, typically about 30, that are the same as (or the complement of) any 14 or more contiguous bases set forth in any of SEQ ID NOs. 23–25 and herein. Among the preferred regions from which to construct probes include 5' and/or 3' coding sequences, sequences predicted to encode regions that are conserved among *Renilla* species GFPs are for isolating GFP-encoding nucleic acid from *Renilla* libraries."

In preferred embodiments, the nucleic acid probes are degenerate probes of at least 14 nucleotides, preferably 16 to 30 nucleotides, that are based on amino acids of *Renilla reniformis* set forth in above.

As used herein, vector (or plasmid) refers to discrete elements that are used to introduce heterologous DNA into cells for either expression or replication thereof. Selection and use of such vehicles are well within the skill of the artisan. An expression vector includes vectors capable of expressing DNA operatively linked with regulatory sequences, such as promoter regions, that are capable of effecting expression of such DNA molecules. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those which integrate into the host cell genome. Presently preferred plasmids for expression of *Gaussia* luciferase, *Renilla* GFP and luciferase are those that are expressed in bacteria and yeast, such as those described herein.

As used herein, a promoter region or promoter element refers to a segment of DNA or RNA that controls transcription of the DNA or RNA to which it is operatively linked. The promoter region includes specific sequences that are sufficient for RNA polymerase recognition, binding and transcription initiation. This portion of the promoter region is referred to as the promoter. In addition, the promoter region includes sequences that modulate this recognition, binding and transcription initiation activity of RNA polymerase. These sequences may be cis acting or may be responsive to trans acting factors. Promoters, depending upon the nature of the regulation, may be constitutive or regulated. Exemplary promoters contemplated for use in prokaryotes include the bacteriophage T7 and T3 promoters, and the like.

As used herein, operatively linked or operationally associated refers to the functional relationship of DNA with regulatory and effector sequences of nucleotides, such as promoters, enhancers, transcriptional and translational stop sites, and other signal sequences. For example, operative linkage of DNA to a promoter refers to the physical and functional relationship between the DNA and the promoter such that the transcription of such DNA is initiated from the promoter by an RNA polymerase that specifically recognizes, binds to and transcribes the DNA. In order to optimize expression and/or in vitro transcription, it may be necessary to remove, add or alter 5' untranslated portions of the clones to eliminate extra, potentially inappropriate alternative translation initiation (i.e., start) codons or other sequences that may interfere Owith or reduce expression, either at the level of transcription or translation. Alternatively, consensus ribosome binding sites (see, e.g., Kozak (1991) *J. Biol. Chem.* 266:19867–19870) can be inserted immediately 5' of the start codon and may enhance expression. The desirability of (or need for) such modification may be empirically determined.

As used herein, to target a targeted agent, such as a luciferase, means to direct it to a cell that expresses a selected receptor or other cell surface protein by linking the agent to a such agent. Upon binding to or interaction with the receptor or cell surface protein, the targeted agent can be reacted with an appropriate substrate and activating agents, whereby bioluminescent light is produced and the tumorous tissue or cells distinguished from non-tumorous tissue.

As used herein, an effective amount of a compound for treating a particular disease is an amount that is sufficient to ameliorate, or in some manner reduce the symptoms associated with the disease. Such amount may be administered as a single dosage or may be administered according to a regimen, whereby it is effective. The amount may cure the disease but, typically, is administered in order to ameliorate the symptoms of the disease. Repeated administration may be required to achieve the desired amelioration of symptoms.

As used herein, an effective amount of a conjugate for diagnosing a disease is an amount that will result in a detectable tissue. The tissues are detected by visualization either without aid from a detector more sensitive than the human eye, or with the use of a light source to excite any fluorescent products.

As used herein, visualizable means detectable by eye, particularly during surgery under normal surgical conditions, or, if necessary, slightly dimmed light.

As used herein, pharmaceutically acceptable salts, esters or other derivatives of the conjugates include any salts, esters or derivatives that may be readily prepared by those of skill in this art using known methods for such derivatization and that produce compounds that may be administered to animals or humans without substantial toxic effects and that either are pharmaceutically active or are prodrugs.

As used herein, treatment means any manner in which the symptoms of a conditions, disorder or disease are ameliorated or otherwise beneficially altered. Treatment also encompasses any pharmaceutical use of the compositions herein.

As used herein, amelioration of the symptoms of a particular disorder by administration of a particular pharmaceutical composition refers to any lessening, whether permanent or temporary, lasting or transient that can be attributed to or associated with administration of the composition.

As used herein, substantially pure means sufficiently homogeneous to appear free of readily detectable impurities as determined by standard methods of analysis, such as thin layer chromatography (TLC), gel electrophoresis and high performance liquid chromatography (HPLC), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers or isomers. In such instances, further purification might increase the specific activity of the compound.

As used herein, a prodrug is a compound that, upon in vivo administration, is metabolized or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) *Medicinal Chemistry A Biochemical Approach*, Oxford University Press, New York, pages 388–392).

As used herein, biological activity refers to the in vivo activities of a compound or physiological responses that result upon in vivo administration of a compound, composition or other mixture. Biological activity, thus, encompasses therapeutic effects and pharmaceutical activity of such compounds, compositions and mixtures. Biological activities may be observed in in vitro systems designed to test or use such activities. Thus, for purposes herein the biological activity of a luciferase is its oxygenase activity whereby, upon oxidation of a substrate, light is produced.

As used herein, targeting agent (TA) refers to an agent that specifically or preferentially targets a linked targeted agent, a luciferin or luciferase, to a neoplastic cell or tissue.

As used herein, tumor antigen refers to a cell surface protein expressed or located on the surface of tumor cells.

As used herein, neoplastic cells include any type of transformed or altered cell that exhibits characteristics typical of transformed cells, such as a lack of contact inhibition and the acquisition of tumor-specific antigens. Such cells include, but are not limited to leukemic cells and cells derived from a tumor.

As used herein, neoplastic disease is any disease in which neoplastic cells are present in the individual afflicted with the disease. Such diseases include, any disease characterized as cancer.

As used herein, metastatic tumors refers to tumors that are not localized in one site.

As used herein, specialty tissue refers to non-tumorous tissue for which information regarding location is desired. Such tissues include, for example, endometriotic tissue, ectopic pregnancies, tissues associated with certain disorders and myopathies or pathologies.

As used herein, a receptor refers to a molecule that has an affinity for a given ligand. Receptors may be naturally-occurring or synthetic molecules. Receptors may also be referred to in the art as anti-ligands. As used herein, the receptor and anti-ligand are interchangeable. Receptors can be used in their unaltered state or as aggregates with other species. Receptors may be attached, covalently or noncovalently, or in physical contact with, to a binding member, either directly or indirectly via a specific binding substance or linker. Examples of receptors, include, but are not limited to: antibodies, cell membrane receptors surface receptors and internalizing receptors, monoclonal antibodies and antisera reactive with specific antigenic determinants (such as on viruses, cells, or other materials), drugs, polynucleotides, nucleic acids, peptides, cofactors, lectins, sugars, polysaccharides, cells, cellular membranes, and organelles.

Examples of receptors and applications using such receptors, include but are not restricted to:

a) enzymes: specific transport proteins or enzymes essential to survival of microorganisms, which could serve as targets for antibiotic (ligand) selection;

b) antibodies: identification of a ligand-binding site on the antibody molecule that combines with the epitope of an antigen of interest may be investigated; determination of a sequence that mimics an antigenic epitope may lead to the development of vaccines of which the immunogen is based on one or more of such sequences or lead to the development of related diagnostic agents or compounds useful in therapeutic treatments such as for auto-immune diseases c) nucleic acids: identification of ligand, such as protein or RNA, binding sites;

d) catalytic polypeptides: polymers, preferably polypeptides, that are capable of promoting a chemical reaction involving the conversion of one or more reactants to one or more products; such polypeptides generally include a binding site specific for at least one reactant or reaction intermediate and an active functionality proximate to the binding site, in which the functionality is capable of chemically modifying the bound reactant (see, e.g., U.S. Pat. No. 5,215,899);

e) hormone receptors: determination of the ligands that bind with high affinity to a receptor is useful in the development of hormone replacement therapies; for example, identification of ligands that bind to such receptors may lead to the development of drugs to control blood pressure; and f) opiate receptors: determination of ligands that bind to the opiate receptors in the brain is useful in the development of less-addictive replacements for morphine and related drugs.

As used herein, antibody includes antibody fragments, such as Fab fragments, which are composed of a light chain and the variable region of a heavy chain.

As used herein, an antibody conjugate refers to a conjugate in which the targeting agent is an antibody.

As used herein, antibody activation refers to the process whereby activated antibodies are produced. Antibodies are activated upon reaction with a linker, such as heterobifunctional reagent.

As used herein, a surgical viewing refers to any procedure in which an opening is made in the body of an animal. Such procedures include traditional surgeries and diagnostic procedures, such as laparoscopies and arthroscopic procedures.

As used herein, humanized antibodies refer to antibodies that are modified to include "human" sequences of amino acids so that administration to a human will not provoke an immune response. Methods for preparation of such antibodies are known. For example, the hybridoma that expresses the monoclonal antibody is altered by recombinant DNA techniques to express an antibody in which the amino acid composition of the non-variable regions is based on human antibodies. Computer programs have been designed to identify such regions.

As used herein, ATP, AMP, NAD+ and NADH refer to adenosine triphosphate, adenosine monophosphate, nicotinamide adenine dinucleotide (oxidized form) and nicotinamide adenine dinucleotide (reduced form), respectively.

As used herein, production by recombinant means by using recombinant DNA methods means the use of the well known methods of molecular biology for expressing proteins encoded by cloned DNA.

As used herein, substantially identical to a product means sufficiently similar so that the property of interest is sufficiently unchanged so that the substantially identical product can be used in place of the product.

As used herein equivalent, when referring to two sequences of nucleic acids means that the two sequences in question encode the same sequence of amino acids or equivalent proteins. When "equivalent" is used in referring to two proteins or peptides, it means that the two proteins or peptides have substantially the same amino acid sequence with only conservative amino acid substitutions (see, e.g., Table 1, above) that do not substantially alter the activity or function of the protein or peptide. When "equivalent" refers to a property, the property does not need to be present to the same extent (e.g., two peptides can exhibit different rates of the same type of enzymatic activity), but the activities are preferably substantially the same. "Complementary," when referring to two nucleotide sequences, means that the two sequences of nucleotides are capable of hybridizing, preferably with less than 25%, more preferably with less than 15%, even more preferably with less than 5%, most preferably with no mismatches between opposed nucleotides. Preferably the two molecules will hybridize under conditions of high stringency.

As used herein: stringency of hybridization in determining percentage mismatch is as follows:
1) high stringency: 0.1×SSPE, 0.1% SDS, 65° C.
2) medium stringency: 0.2×SSPE, 0.1% SDS, 50° C.
3) low stringency: 1.0×SSPE, 0.1% SDS, 50° C.

It is understood that equivalent stringencies may be achieved using alternative buffers, salts and temperatures.

The term "substantially" identical or homologous or similar varies with the context as understood by those skilled in the relevant art and generally means at least 70%, preferably means at least 80%, more preferably at least 90%, and most preferably at least 95% identity. The terms "homology" and "identity" are often used interchangeably. In general, sequences are aligned so that the highest order match is obtained (see, e.g.: *Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part I*, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991; Carillo et al. (1988) *SIAM J Applied Math* 48:1073).

By sequence identity, the number of conserved amino acids are determined by standard alignment algorithms programs, and are used with default gap penalties established by each supplier. Substantially homologous nucleic acid molecules would hybridize typically at moderate stringency or at high stringency all along the length of the nucleic acid of interest. Also contemplated are nucleic acid molecules that contain degenerate codons in place of codons in the hybridizing nucleic acid molecule.

Whether any two nucleic acid molecules have nucleotide sequences that are at least 80%, 85%, 90%, 95%, 96%, 97%, 98% or 99% "identical" can be determined using known computer algorithms such as the "FAST A" program, using for example, the default parameters as in Pearson et al. (1988) *Proc. Natl. Acad. Sci. USA* 85:2444 (other programs include the GCG program package (Devereux, J., et al., *Nucleic Acids Research* 12(I):387 (1984)), BLASTP, BLASTN, FASTA (Atschul, S. F., et al., *J Molec Biol* 215:403 (1990); Guide to Huge Computers, Martin J. Bishop, ed., Academic Press, San Diego, 1994, and Carillo et al. (1988) *SIAM J Applied Math* 48:1073). For example, the BLAST function of the National Center for Biotechnology Information database may be used to determine identity.

Other commercially or publicly available programs include, DNAStar "MegAlign" program (Madison, Wis.) and the University of Wisconsin Genetics Computer Group (UWG) "Gap" program (Madison Wis.)). Percent homology or identity of proteins and/or nucleic acid moleucles may be determined, for example, by comparing sequence information using a GAP computer program (e.g., Needleman et al. (1970) *J. Mol. Biol.* 48:443, as revised by Smith and Waterman ((1981) *Adv. Appl. Math.* 2:482). Briefly, the GAP program defines similarity as the number of aligned symbols (i.e., nucleotides or amino acids) which are similar, divided by the total number of symbols in the shorter of the two sequences. Default parameters for the GAP program may include: (1) a unary comparison matrix (containing a value of 1 for identities and 0 for non-identities) and the weighted comparison matrix of Gribskov et al (1986) *Nucl. Acids Res.* 14:6745, as described by Schwartz and Dayhoff, eds., ATLAS OF PROTEIN SEQUENCE AND STRUCTURE, National Biomedical Research Foundation, pp. 353–358 (1979); (2) a penalty of 3.0 for each gap and an additional 0.10 penalty for each symbol in each gap; and (3) no penalty for end gaps.

Therefore, as used herein, the term "identity" represents a comparison between a test and a reference polypeptide or polynucleotide. For example, a test polypeptide may be defined as any polypeptide that is 90% or more identical to a reference polypeptide. As used herein, the term at least "90% identical to" refers to percent identities from 90 to 99.99 relative to the reference polypeptides. Identity at a level of 90% or more is indicative of the fact that, assuming for exemplification purposes a test and reference polynucleotide length of 100 amino acids are compared. No more than 10% (i.e., 10 out of 100) amino acids in the test polypeptide differs from that of the reference polypeptides. Similar comparisons may be made between a test and reference polynucleotides. Such differences may be represented as point mutations randomly distributed over the entire length of an amino acid sequence or they may be clustered in one or more locations of varying length up to the maximum allowable, e.g. $^{10}/_{100}$ amino acid difference (approximately 90% identity). Differences are defined as nucleic acid or amino acid substitutions, or deletions. At level of homologies or identities above about 85–90%, the result should be independent of the program and gap parameters set; such high levels of identity readily can be assess, often without relying on software.

As used herein, primer refers to an oligonucleotide containing two or more deoxyribonucleotides or ribonucleotides, preferably more than three, from which synthesis of a primer extension product can be initiated. Experimental conditions conducive to synthesis include the presence of nucleoside triphosphates and an agent for polymerization and extension, such as DNA polymerase, and a suitable buffer, temperature and pH.

As used herein, a composition refers to any mixture. It may be a solution, a suspension, liquid, powder, a paste, aqueous, non-aqueous or any combination thereof.

As used herein, a combination refers to any association between two or among more items.

As used herein, fluid refers to any composition that can flow. Fluids thus encompass compositions that are in the form of semi-solids, pastes, solutions, aqueous mixtures, gels, lotions, creams and other such compositions.

As used herein, complementary refers to the topological compatibility or matching together of interacting surfaces of a ligand molecule and its receptor. Thus, the receptor and its ligand can be described as complementary, and furthermore, the contact surface characteristics are complementary to each other.

As used herein, a ligand-receptor pair or complex formed when two macromolecules have combined through molecular recognition to form a complex.

As used herein, a substrate refers to any matrix that is used either directly or following suitable derivatization, as a solid support for chemical synthesis, assays and other such processes. Preferred substrates herein, are silicon substrates or siliconized substrates that are derivitized on the surface intended for linkage of anti-ligands and ligands and other macromolecules, including the fluorescent proteins, phycobiliproteins and other emission shifters.

As used herein, a matrix refers to any solid or semisolid or insoluble support on which the molecule of interest, typically a biological molecule, macromolecule, organic molecule or biospecific ligand is linked or contacted. Typically a matrix is a substrate material having a rigid or semi-rigid surface. In many embodiments, at least one surface of the substrate will be substantially flat, although in some embodiments it may be desirable to physically separate synthesis regions for different polymers with, for example, wells, raised regions, etched trenches, or other such topology. Matrix materials include any materials that are used as affinity matrices or supports for chemical and biological molecule syntheses and analyses, such as, but are not limited to: polystyrene, polycarbonate, polypropylene, nylon, glass, dextran, chitin, sand, pumice, polytetrafluoroethylene, agarose, polysaccharides, dendrimers, buckyballs, polyacrylamide, Kieselguhr-polyacrylamide non-covalent composite, polystyrene-polyacrylamide covalent composite, polystyrene-PEG (polyethyleneglycol) composite, silicon, rubber, and other materials used as supports for solid phase syntheses, affinity separations and purifications, hybridization reactions, immunoassays and other such applications.

As used herein, the attachment layer refers the surface of the chip device to which molecules are linked. Typically, the chip is a semiconductor device, which is coated on a least a portion of the surface to render it suitable for linking molecules and inert to any reactions to which the device is exposed. Molecules are linked either directly or indirectly to the surface, linkage may be effected by absorption or adsorption, through covalent bonds, ionic interactions or any other interaction. Where necessary the attachment layer is adapted, such as by derivatization for linking the molecules.

B. Fluorescent Proteins

The GFP from *Aequorea* and that of the sea pansy *Renilla reniformis* share the same chromophore, yet *Aequorea* GFP has two absorbance peaks at 395 and 475 nm whereas *Renilla* GFP has only a single absorbance peak at 498 nm, with about 5.5 fold greater monomer extinction coefficient than the major 395 nm peak of the *Aequorea* protein (Ward, W. W. in Bioluminescence and Chemiluminescence (eds. DeLuca, M. A. & McElroy, W. D.) 235–242 (Academic Press, New York, 1981)). The spectra of the isolated chromophore and denatured protein at neutral pH do not match the spectra of either native protein (Cody, C. W. et al. (1993) *Biochemistry* 32:1212–1218).

1. Green and Blue Fluorescent Proteins

As described herein, blue light is produced using the *Renilla* luciferase or the *Aequorea* photoprotein in the presence of $Ca^{2+}$ and the coelenterazine luciferin or analog thereof. This light can be converted into a green light if a green fluorescent protein (GFP) is added to the reaction. Green fluorescent proteins, which have been purified (see, e.g., Prasher et al. (1992) *Gene* 111:229–233) and also cloned (see, e.g., International PCT Application No. WO 95/07463, which is based on U.S. application Ser. No.

08/119,678 and U.S. application Ser. No. 08/192,274, which are herein incorporated by reference), are used by cnidarians as energy-transfer acceptors. GFPs fluoresce in vivo upon receiving energy from a luciferase-oxyluciferein excited-state complex or a Ca²⁺-activated photoprotein. The chromophore is modified amino acid residues within the polypeptide. The best characterized GFPs are those of *Aequorea* and *Renilla* (see, e.g., Prasher et al. (1992) *Gene* 111:229–233; Hart, et al. (1979) *Biochemistry* 18:2204–2210). For example, a green fluorescent protein (GFP) from *Aequorea victoria* contains 238 amino acids, absorbs blue light and emits green light. Thus, inclusion of this protein in a composition containing the aequorin photoprotein charged with coelenterazine and oxygen, can, in the presence of calcium, result in the production of green light. Thus, it is contemplated that GFPs may be included in the bioluminescence generating reactions that employ the aequorin or *Renilla* luciferases or other suitable luciferase in order to enhance or alter color of the resulting bioluminescence.

2. *Renilla reniformis* GFP

"Purified *Renilla reniformis* GFP and muteins thereof are provided. Presently preferred *Renilla* GFP for use in the compositions herein is *Renilla reniformis* GFP having the sequence of amino acids set forth in SEQ ID NO. 27. The *Renilla* GFP and GFP peptides can be isolated from natural sources or isolated from a prokaryotic or eukaryotic cell transfected with nucleic acid that encodes the *Renilla* GFP and/or GFP peptides, such as those encoded by the sequences of nucleotides set forth in SEQ ID NOS. 23–25.

The encoding nucleic acid molecules are provided. Preferred are those that encode the protein having the sequence of amino acids (SEQ ID NO. 27):

mdlaklglkevmptkinleglvgdhafs-megvgegnilegtqevkisvtkgaplpfafdivsv afsygnrayt-gypeeisdyflqsfpegfty-erniryqdggtaivksdisledgkfivnvdfkakdl rrmgpvmqqdivgmqpsyesmytnvts-vigeciiafklqtgkhftyhmrtvykskkpvet mplyhfiqhrlvktnvdtasgyvvqhetaiaahstikkiegslp, and is preferably the sequence set forth in SEQ ID NO. 26.

In particular, nucleic acid molecules encoding a *Renilla reniformis* GFP having any of the following sequences are provided (see SEQ ID NOs. 23–25):"

```
Renilla renformis GFP Clone-1
GGCACGAGGGTTTCCTGACACAATAAAAACCTTTCAAATTGTTTCTC

TGTAGCAGTAAGTATGGATCTCGCAAAACTTGGTTTGAAGGAAGTG

ATGCCTACTAAAATCAACTTAGAAGGACTGGTTGGCGACCACGCTT

TCTCAATGGAAGGAGTTGGCGAAGGCAACATATTGGAAGGAACTCA

AGAGGTGAAGATATCGGTAACAAAAGGCGCACCACTCCCATTCGC

ATTTGATATCGTATCTGTGGCTTTTTCATATGGGAACAGAGCTTA

TACCGGTTACCCAGAAGAAATTCCGACTACTTCCTCCAGTCGTT

TCCAGAAGGCTTTACTTACGAGAGAAACATTCGTTATCA

AGATGGAGGAACTGCAATTGTTAAATCTGATATAAGCTTGGAA

GATGGTAAATTCATAGTGAATGTAGACTTCAAAGCGAAGGATCT

ACGTCGCATGGACCAGTCATGCAGCAAGACATCGTGGGTATGCA

GCCATCGTATGAGTCAATGTACACCAATGTCACTTCAGTTATAGGGGA
```

```
ATGTATAATAGCATTCAAACTTCAAACTGGCAAGCATTTCACTTACCA

CATGAGGACAGTTTACAAATCAAAGAAGCCAGTGGAAACTATGCCA

TTGTATCATTTCATCCAGCATCGCCTCGTTAAGACCAATGTGGACA

CAGCCAGTGGTTACGTTGTGCAACACGAGACAGCAATTGCAGCGCATTC

TACAATCAAAAAAATTGAAGGCTCTTTACCATAGATACCTGTACACAAT

TATTCTATGCACGTAGCATTTTTTTGGAAATATAAGTGGTATTGTTCAAT

AAAATATTAAATATAAAAAAAAAAAAAAAAAAAAAAAA;

Renilla renformis GFP Clone-2
GGCACGAGGCTGACACAATAAAAAACCTTTCAAATTGTTTCTCTGTAGC

AGGAAGTATGGATCTCGCAAAACTTGGTTTGAAGGAAGTGATGCCTACT

AAAATCAACTTAGAAGGACTGGTTGGCGACCACGCTTTCTCAATGGAAG

GAGTTGGCGAAGGCAACATATTGGAAGGAACTCAAGAGGTGAAGATAT

CGGTAACAAAAGGCGCACCACTCCCATTCGCATTTGATATCGTATCTGT

TGCTTTCTCATATGGGAACAGAGCTTATACTGGTTACCCAGAAGAAATT

TCCGACTACTTCCTCCAGTCGTTTCCAGAAGGCTTTACTTACGAGAGAA

ACATTCGTTATCAAGATGGAGGAACTGCAATTGTTAAATCTGATATAAG

CTTGGAAGATGGTAAATTCATAGTGAATGTAGACTTCAAAGCGAAGGAT

CTACGTCGCATGGGACCAGTCATGCAGCAAGACATCGTGGGTATGCAG

CCATCGTATGAGTCAATGTACACCAATGTCACTTCAGTTATAGGGGA

ATGTATAATAGCATTCAAACTTCAAACTGGCAAACATTTCACTTACCAC

ATGAGGACAGTTTACAAATCAAAGAAGCCAGTGGAAACTATGCCATTG

TATCATTTCATCCAGCATCGCCTCGTTAAGACCAATGTGGACACAGCCA

GTGGTTACGTTGTGCAACACGAGACAGCAATTGCAGCGCATTCTACAAT

CAAAAAAATTGAAGGCTCTTTACCATAGATATCTATACACAATTA

TTCTATGCACGTAGCATTTTTTTGGAAATATAAGTGGTATTGTTCAATAA

AATATTAAATATAAAAAAAAAAAAAAAAAAAAAAAA; and

Renilla renformis GEP Clone-3
GGCACGAGGGTTTCCTGACACAATAAAAACCTTTCAAATTGTTTCTCTG

TAGCAGTAAGTATGGATCTCGCAAAACTTGGTTTGAAGGAAGTGATGCC

TACTAAAATCAACTTAGAAGGACTGGTTGGCGACCACGCTTTCTCAATG

GAAGGAGTTGGCGAAGGCAACATATTGGAAGGAACTCAAGAGGTGAAG

ATATCGGTAACAAAAGGCGCACCACTCCCATTCGCATTTGATATCGTAT

CTGTGGCTTTTTCATATGGGAACAGAGCTTATACCGGTTACCCAGAAGA

AATTTCCGACTACTTCCTCCAGTCGTTTCCAGAAGGCTTTACTTACGAGA

GAAACATTCGTTATCAAGATGGAGGAACTGCAATTGTTAAATCTGATAT

AAGCTTGGAAGATGGTAAATTCATAGTGAATGTAGACTTCAAAGCGAA

GGATCTACGTCGCATGGGACCAGTCATGCAGCAAGACATCGTGGGTAT

GCAGCCATCGTATGAGTCAATGTACACCAATGTCACTTCAGTTATAGGG

GAATGTATAATAGCATTCAAACTTCAAACTGGCAAGCATTTCACTTACC

ACATGAGGACAGTTTACAAATCAAAGAAGCCAGTGGAAACTATGCCAT

TGTATCATTTCATCCAGCATCGCCTCGTTAAGACCAATGTGGACACAGC
```

-continued

```
CAGTGGTTACGTTGTGCAACACGAGACAGCAATTGCAGCGCATTCTACA

ATCAAAAAAATTGAAGGCTCTTTACCATAGATACCTGTACACAATTA

TTCTATGCACGTAGCATTTTTTTGGAAATATAAGTGGTATTGTTCAATAA

AATATTAAATATATGCTTTTGCAAAAAAAAAAAAAAAAAAAAAAA.
```

"An exemplary mutein is set forth in SEQ ID NO. 33, and humanized codon are set forth in SEQ ID NO. 26."

Also contemplated are the coding portion of the sequence of nucleotides that hybridize under moderate or high stringency to the sequence of nucleotides set forth above, particularly when using probes provided herein. Probes derived from this nucleic acid that can be used in methods provided herein to isolate GFPs from any *Renilla reniformis* species are provided. In an exemplary embodiment, nucleic acid encoding *Renilla reniformis* GFP is provided. This nucleic acid encodes the sequence of amino acids set forth above.

GFPs, including the *Renilla reniformis* protein provided herein, are activated by blue light to emit green light and thus may be used in the absence of luciferase and in conjunction with an external light source with novelty items (see U.S. Pat. Nos. 5,876,995, 6,152,358 and 6,113,886) and in conjunction with bioluminescence generating system for novelty items (see U.S. Pat. Nos. 5,876,995, 6,152,358 and 6,113,886), for tumor diagnosis (see, allowed co-pending U.S. application Ser. No. 08/908,909) and in biochips (see, U.S. application Ser. No. 08/990,103, which is published as International PCT application No. WO 98/26277).

*Renilla reniformis* GFP is intended for use in any of the novelty items and combinations, such as the foods, including beverages, greeting cards, and toys, including bubble making toys, particularly bubble-making compositions or mixtures. Also of particular interest are the use of these proteins in cosmetics, particularly face paints or make-up, hair colorants or hair conditioners, mousses or other such products and skin creams. Such systems are particularly of interest because no luciferase is needed to activate the photoprotein and because the proteins are non-toxic and safe to apply to the skin, hair, eyes and to ingest. These fluorescent proteins may also be used in addition to bioluminescence generating systems to enhance or create an array of different colors. Transgenic animals and plants that express the *Renilla reniformis* GFP-encoding nucleic acid are also provided. Such animals and plants, include transgenic fish, transgenic worms for use, for example, as lures for fishing; transgenic animals, such as monkeys and rodents for research in which a marker gene is used, and transgenic animals as novelty items and to produce glowing foods, such as ham, eggs, chicken, and other meats; transgenic plants in which the *Renilla reniformis* is a marker, and also transgenic plants that are novelty items, particularly ornamental plants, such as glowing orchids, roses and other flowering plants.

The *Renilla reniformis* GFP may be used alone or in combination with bioluminescence generating systems to produce an array of colors. They may be used in combinations such that the color of, for example, a beverage changes over time, or includes layers of different colors. The cloning and expression of *Renilla reniformis* GFP and uses thereof are described below.

C. Bioluminescence Generating Systems and Components

The following is a description of bioluminescence generating systems and the components thereof. The *Renilla reniformis* GFP provided herein can be used alone for a variety of applications, and with any compatible bioluminescence generating systems.

A bioluminescence-generating system refers to the components that are necessary and sufficient to generate bioluminescence. These include a luciferase, luciferin and any necessary co-factors or conditions. Virtually any bioluminescent system known to those of skill in the art will be amenable to use in the apparatus, systems, combinations and methods provided herein. Factors for consideration in selecting a bioluminescent-generating system, include, but are not limited to: the targeting agent used in combination with the bioluminescence; the medium in which the reaction is run; stability of the components, such as temperature or pH sensitivity; shelf life of the components; sustainability of the light emission, whether constant or intermittent; availability of components; desired light intensity; color of the light; and other such factors. Such bioluminescence generating systems are known (see those described in U.S. Pat. Nos. 5,876,995, 6,152,358 and 6,113,886).

1. General Description

In general, bioluminescence refers to an energy-yielding chemical reaction in which a specific chemical substrate, a luciferin, undergoes oxidation, catalyzed by an enzyme, a luciferase. Bioluminescent reactions are easily maintained, requiring only replenishment of exhausted luciferin or other substrate or cofactor or other protein, in order to continue or revive the reaction. Bioluminescence generating reactions are well-known to those of skill in this art and any such reaction may be adapted for use in combination with articles of manufacture as described herein.

There are numerous organisms and sources of bioluminescence generating systems, and some representative genera and species that exhibit bioluminescence are set forth in the following table (reproduced in part from Hastings in (1995) *Cell Physiology:Source Book*, N. Sperelakis (ed.), Academic Press, pp 665–681):

TABLE 2

Representative luminous organism

| Type of Organism | Representative genera |
|---|---|
| Bacteria | Photobacterium |
|  | Vibrio |
|  | Xenorhabdus |
| Mushrooms | Panus, Armillaria |
|  | Pleurotus |
| Dinoflagellates | Gonyaulax |
|  | Pyrocystis |
|  | Noctiluca |
| Cnidaria (coelenterates) |  |
| Jellyfish | Aequorea |
| Hydroid | Obelia |
| Sea Pansy | Renilla |
| Ctenophores | Mnemiopsis |
|  | Beroe |
| Annelids |  |
| Earthworms | Diplocardia |
| Marine polychaetes | Chaetopterus, Phyxotrix |
| Syllid fireworm | Odontosyllis |
| Molluscs |  |
| Limpet | Latia |
| Clam | Pholas |
| Squid | Heteroteuthis |
|  | Heterocarpus |
| Crustacea |  |
| Ostracod | Vargula (Cypridina) |
| Shrimp (euphausids) | Meganyctiphanes |
|  | Acanthophyra |
|  | Oplophorus |
|  | Gnathophausia |

TABLE 2-continued

Representative luminous organism

| Type of Organism | Representative genera |
|---|---|
| Decapod | Sergestes |
| Copepods | |
| Insects | |
| Coleopterids (beetles) | |
| Firefly | Photinus, Photuris |
| Click beetles | Pyrophorus |
| Railroad worm | Phengodes, Phrixothrix |
| Diptera (flies) | Arachnocampa |
| Echinoderms | |
| Brittle stars | Ophiopsila |
| Sea cucumbers | Laetmogone |
| Anthozoans | Renilla |
| Chordates | |
| Tunicates | Pyrosoma |
| Fish | |
| Cartilaginous | Squalus |
| Bony | |
| Ponyfish | Leiognathus |
| Flashlight fish | Photoblepharon |
| Angler fish | Cryptopsaras |
| Midshipman | Porichthys |
| Lantern fish | Benia |
| Shiny loosejaw | Aristostomias |
| Hatchet fish | Agyropelecus |
| and other fish | Pachystomias |
| | Malacosteus |
| Midwater fish | Cyclothone |
| | Neoscopelus |
| | Tarletonbeania |

Other bioluminescent organisms contemplated for use herein are *Gonadostomias, Gaussia* (copepods), *Watensia, Halisturia,* Vampire squid, *Glyphus, Mycotophids* (fish), *Vinciguerria, Howella, Florenciella, Chaudiodus, Melanocostus* and Sea Pens.

It is understood that a bioluminescence generating system may be isolated from natural sources, such as those in the above Table, or may be produced synthetically. In addition, for uses herein, the components need only be sufficiently pure so that mixture thereof, under appropriate reaction conditions, produces a glow so that cells and tissues can be visualized during a surgical procedure.

Thus, in some embodiments, a crude extract or merely grinding up the organism may be adequate. Generally, however, substantially pure components are used. Also, components may be synthetic components that are not isolated from natural sources. DNA encoding luciferases is available (see, e.g., SEQ ID NOs. 1–13) and synthetic and alternative substrates have been devised. The DNA listed herein is only representative of the DNA encoding luciferases that are available.

Any bioluminescence generating system, whether synthetic or isolated form natural sources, such as those set forth in Table 2, elsewhere herein or known to those of skill in the art, is intended for use in the combinations, systems and methods provided herein. Chemiluminescence systems per se, which do not rely on oxygenases (luciferases) are not encompassed herein.

(a) Luciferases

Luciferases refer to any compound that, in the presence of any necessary activators, catalyze the oxidation of a bioluminescence substrate (luciferin) in the presence of molecular oxygen, whether free or bound, from a lower energy state to a higher energy state such that the substrate, upon return to the lower energy state, emits light. For purposes herein, luciferase is broadly used to encompass enzymes that act catalytically to generate light by oxidation of a substrate and also photoproteins, such as aequorin, that act, though not strictly catalytically (since such proteins are exhausted in the reaction), in conjunction with a substrate in the presence of oxygen to generate light. These luciferases, including photoproteins, such as aequorin, are herein also included among the luciferases. These reagents include the naturally-occurring luciferases (including photoproteins), proteins produced by recombinant DNA, and mutated or modified variants thereof that retain the ability to generate light in the presence of an appropriate substrate, co-factors and activators or any other such protein that acts as a catalyst to oxidize a substrate, whereby light is produced.

Generically, the protein that catalyzes or initiates the bioluminescent reaction is referred to as a luciferase, and the oxidizable substrate is referred to as a luciferin. The oxidized reaction product is termed oxyluciferin, and certain luciferin precursors are termed etioluciferin. Thus, for purposes herein bioluminescence encompasses light produced by reactions that are catalyzed by (in the case of luciferases that act enzymatically) or initiated by (in the case of the photoproteins, such as aequorin, that are not regenerated in the reaction) a biological protein or analog, derivative or mutant thereof.

For clarity herein, these catalytic proteins are referred to as luciferases and include enzymes such as the luciferases that catalyze the oxidation of luciferin, emitting light and releasing oxyluciferin. Also included among luciferases are photoproteins, which catalyze the oxidation of luciferin to emit light but are changed in the reaction and must be reconstituted to be used again. The luciferases may be naturally occurring or may be modified, such as by genetic engineering to improve or alter certain properties. As long as the resulting molecule retains the ability to catalyze the bioluminescent reaction, it is encompassed herein.

Any protein that has luciferase activity (a protein that catalyzes oxidation of a substrate in the presence of molecular oxygen to produce light as defined herein) may be used herein. The preferred luciferases are those that are described herein or that have minor sequence variations. Such minor sequence variations include, but are not limited to, minor allelic or species variations and insertions or deletions of residues, particularly cysteine residues. Suitable conservative substitutions of amino acids are known to those of skill in this art and may be made generally without altering the biological activity of the resulting molecule. Such substitutions are preferably made in accordance with those set forth in TABLE 1 as described above.

The luciferases may be obtained commercially, isolated from natural sources, expressed in host cells using DNA encoding the luciferase, or obtained in any manner known to those of skill in the art. For purposes herein, crude extracts obtained by grinding up selected source organisms may suffice. Since large quantities of the luciferase may be desired, isolation of the luciferase from host cells is preferred. DNA for such purposes is widely available as are modified forms thereof.

"Examples of luciferases include, but are not limited to, those isolated from the ctenophores *Mnemiopsis* (mnemiopsin) and *Beroe ovata* (berovin), those isolated from the coelenterates *Aequorea* (aequorin), *Obelia* (obelin), *Pelagia*, the *Renilla* luciferase, the luciferases isolated from the mollusca *Pholas* (pholasin), the luciferases isolated from fish, such as *Aristostomias, Pachystomias* and *Porichthys* and from the ostracods, such as *Cyprindina* (also referred to as *Vargula*). Preferred luciferases for use herein are the Aequorin protein, *Renilla* luciferase and *Cypridina* (also called *Vargula*) luciferase (see, e.g., SEQ ID NOs. 1, 2, and 4–13). Also, preferred are luciferases which react to produce red and/or near infrared light. These include luciferases found in species of *Aristostomias*, such as *A. scintillans*, *Pachystomias, Malacosteus*, such as *M. niger*."

(b) Luciferins

The substrates for the reaction or for inclusion in the conjugates include any molecule(s) with which the luciferase reacts to produce light. Such molecules include the naturally-occurring substrates, modified forms thereof, and synthetic substrates (see, e.g., U.S. Pat. Nos. 5,374,534 and 5,098,828). Exemplary luciferins include those described herein, as well as derivatives thereof, analogs thereof, synthetic substrates, such as dioxetanes (see, e.g., U.S. Pat. Nos. 5,004,565 and 5,455,357), and other compounds that are oxidized by a luciferase in a light-producing reaction (see, e.g., U.S. Pat. Nos. 5,374,534, 5,098,828 and 4,950,588). Such substrates also may be identified empirically by selecting compounds that are oxidized in bioluminescent reactions.

(c) Activators

The bioluminescent generating systems also require additional components discussed herein and known to those of skill in the art. All bioluminescent reactions require molecular oxygen in the form of dissolved or bound oxygen. Thus, molecular oxygen, dissolved in water or in air or bound to a photoprotein, is the activator for bioluminescence reactions. Depending upon the form of the components, other activators include, but are not limited to, ATP (for firefly luciferase), flavin reductase (bacterial systems) for regenerating $FMNH_2$ from FMN, and $Ca^{2+}$ or other suitable metal ion (aequorin).

Most of the systems provided herein will generate light when the luciferase and luciferin are mixed and exposed to air or water. The systems that use photoproteins that have bound oxygen, such as aequorin, however, will require exposure to $Ca^{2+}$ (or other suitable metal ion), which can be provided in the form of an aqueous composition of a calcium salt. In these instances, addition of a $Ca^{2+}$ (or other suitable metal ion) to a mixture of luciferase (aequorin) and luciferin (such as coelenterazine) will result in generation of light. The *Renilla* system and other Anthozoa systems also require $Ca^{2+}$ (or other suitable metal ion).

If crude preparations are used, such as ground up *Cypridina* (shrimp) or ground fireflies, it may be necessary to add only water. In instances in which fireflies (or a firefly or beetle luciferase) are used the reaction may only require addition ATP. The precise components will be apparent, in light of the disclosure herein, to those of skill in this art or may be readily determined empirically.

It is also understood that these mixtures will also contain any additional salts or buffers or ions that are necessary for each reaction to proceed. Since these reactions are well-characterized, those of skill in the art will be able to determine precise proportions and requisite components. Selection of components will depend upon the apparatus, article of manufacture and luciferase. Various embodiments are described and exemplified herein; in view of such description, other embodiments will be apparent.

(d) Reactions

In all embodiments, all but one component, either the luciferase or luciferin, of a bioluminescence generating system will be mixed or packaged with or otherwise combined. Since the result to be achieved is the production of light visible to the naked eye for qualitative, not quantitative, diagnostic purposes, the precise proportions and amounts of components of the bioluminescence reaction need not be stringently determined or met. They must be sufficient to produce light. Generally, an amount of luciferin and luciferase sufficient to generate a visible glow is used; this amount can be readily determined empirically and is dependent upon the selected system and selected application. Where quantitative measurements are required, more precision may be required.

For purposes herein, such amount is preferably at least the concentrations and proportions used for analytical purposes by those of skill in the such arts. Higher concentrations may be used if the glow is not sufficiently bright. Alternatively, a microcarrier coupled to more than one luciferase molecule linked to a targeting agent may be utilized to increase signal output. Also because the conditions in which the reactions are used are not laboratory conditions and the components are subject to storage, higher concentration may be used to overcome any loss of activity. Typically, the amounts are 1 mg, preferably 10 mg and more preferably 100 mg, of a luciferase per liter of reaction mixture or 1 mg, preferably 10 mg, more preferably 100 mg. Compositions may contain at least about 0.01 mg/l, and typically 0.1 mg/l, 1 mg/l, 10 mg/l or more of each component on the item. The amount of luciferin is also between about 0.01 and 100 mg/l, preferably between 0.1 and 10 mg/l, additional luciferin can be added to many of the reactions to continue the reaction. In embodiments in which the luciferase acts catalytically and does not need to be regenerated, lower amounts of luciferase can be used. In those in which it is changed during the reaction, it also can be replenished; typically higher concentrations will be selected. Ranges of concentration per liter (or the amount of coating on substrate the results from contacting with such composition) of each component on the order of 0.1 to 20 mg, preferably 0.1 to 10 mg, more preferably between about 1 and 10 mg of each component will be sufficient. When preparing coated substrates, as described herein, greater amounts of coating compositions containing higher concentrations of the luciferase or luciferin may be used.

Thus, for example, in presence of calcium, 5 mg of luciferin, such as coelenterazine, in one liter of water will glow brightly for at least about 10 to 20 minutes, depending on the temperature of the water, when about 10 mg of luciferase, such as aequorin photoprotein luciferase or luciferase from *Renilla*, is added thereto. Increasing the concentration of luciferase, for example, to 100 mg/l, provides a particularly brilliant display of light.

It is understood, that concentrations and amounts to be used depend upon the selected bioluminescence generating system but these may be readily determined empirically. Proportions, particularly those used when commencing an empirical determination, are generally those used for analytical purposes, and amounts or concentrations are at least those used for analytical purposes, but the amounts can be increased, particularly if a sustained and brighter glow is desired.

For purposes herein, *Renilla reniformis* GFP is added to the reaction in order to shift the spectrum of the generated light.

2. The *Renilla* System

*Renilla*, also known as soft coral sea pansies, are members of the class of coelenterates Anthozoa, which includes other bioluminescent genera, such as *Cavarnularia, Ptilosarcus, Stylatula, Acanthoptilum,* and *Parazoanthus*. Bioluminescent members of the Anthozoa genera contain luciferases and luciferins that are similar in structure (see, e.g., Cormier et al. (1973) *J. Cell. Physiol.* 81:291–298; see, also Ward et al. (1975) *Proc. Natl. Acad. Sci. U.S.A.* 72:2530–2534). The luciferases and luciferins from each of these anthozoans crossreact with one another and produce a characteristic blue luminescence.

*Renilla* luciferase and the other coelenterate and ctenophore luciferases, such as the aequorin photoprotein, use imidazopyrazifle substrates, particularly the substrates generically called coelenterazine (see, formulae (I) and (II) of Section C.4.b, below). Other genera that have luciferases that use a coelenterazine include: squid, such as *Chiroteuthis, Eucleoteuthis, Onychoteuthis, Watasenia*, cuttlefish, *Sepiolina*; shrimp, such as *Oplophorus, Acanthophyra, Sergestes*, and *Gnathophausia*; deep-sea fish, such as *Argyropelecus, Yarella, Diaphus, Gonadostomias* and *Neoscopelus*.

*Renilla* luciferase does not, however, have bound oxygen, and thus requires dissolved oxygen in order to produce light in the presence of a suitable luciferin substrate. Since *Renilla* luciferase acts as a true enzyme (i.e., it does not have to be reconstituted for further use) the resulting luminescence can be long-lasting in the presence of saturating levels of luciferin. Also, *Renilla* luciferase is relatively stable to heat.

"*Renilla* luciferases, DNA encoding *Renilla reniformis* luciferase, and use of the *Renilla reniformis* DNA to produce recombinant luciferase, as well as DNA encoding luciferase from other coelenterates, are well known and available (see, e.g., SEQ ID NO. 1, U.S. Pat. Nos. 5,418,155 and 5,292,658; see, also, Prasher et at. (1985) *Biochem. Biophys. Res. Commun.* 126:1259–1268; Coriner (1981) "*Renilla* and *Aequorea* bioluminescence" in *Bioluminescence and Chemiluminescence*, pp. 225–233; Charbonneau et at. (1979) *J. Biol. Chem.* 254:769–780; Ward et al. (1979) *J. Biol. Chem.* 254:781–788; Lorenz et al. (1981) *Proc. Natl. Acad. Sci. U.S.A.* 88:4438–4442; Hori et al. (1977) *Proc. Natl. Acad. Sci. U.S.A.* 74:4285–4287; Hori et al. (1975) *Biochemistry* 14:2371–2376; Hori et al. (1977) *Proc. Nat. Acad. Sci. U.S.A.* 74:4285–4287; Inouye et al. (1975) *Jap. Soc. Chem. Lett.* 141–144; and Matthews et al. (1979) *Biochemistry* 16:85–91. The DNA encoding *Renilla reniformis* luciferase and host cells containing such DNA provide a convenient means for producing large quantities of *Renilla reniformis* enzyme, such as in those known to those of skill in the art (see, e.g., U.S. Pat. Nos. 5,418,155 and 5,292,658, which describe recombinant production of *Renilla reniformis* luciferase)."

When used herein, the *Renilla* luciferase can be packaged in lyophilized form, encapsulated in a vehicle, either by itself or in combination with the luciferin substrate. Prior to use the mixture is contacted with an aqueous composition, preferably a phosphate buffered saline pH 7–8; dissolved $O_2$ will activate the reaction. Final concentrations of luciferase in the glowing mixture will be on the order of 0.01 to 1 mg/l or more. Concentrations of luciferin will be at least about $10^{-8}$ M, but 1 to 100 or more orders of magnitude higher to produce a long lasting bioluminescence.

In certain embodiments herein, about 1 to 10 mg, or preferably 2–5 mg, more preferably about 3 mg of coelenterazine will be used with about 100 mg of *Renilla* luciferase. The precise amounts, of course can be determined empirically, and, also will depend to some extent on the ultimate concentration and application. In particular, addition of about 0.25 ml of a crude extract from the bacteria that express *Renilla* to 100 ml of a suitable assay buffer and about 0.005 µg was sufficient to produce a visible and lasting glow (see, U.S. Pat. Nos. 5,418,155 and 5,292,658, which describe recombinant production of *Renilla reniformis* luciferase).

Lyophilized mixtures, and compositions containing the *Renilla* luciferase are also provided. The luciferase or mixtures of the luciferase and luciferin may also be encapsulated into a suitable delivery vehicle, such as a liposome, glass particle, capillary tube, drug delivery vehicle, gelatin, time release coating or other such vehicle. The luciferase may also be linked to a substrate, such as biocompatible materials.

3. Ctenophore Systems

Ctenophores, such as *Mnemiopsis* (mnemiopsin) and *Beroe ovata* (berovin), and coelenterates, such as *Aequorea* (aequorin), *Obelia* (obelin) and *Pelagia*, produce bioluminescent light using similar chemistries (see, e.g., Stephenson et al. (1981) *Biochimica et Biophysica Acta* 678:65–75; Hart et al. (1979) *Biochemistry* 18:2204–2210; International PCT Application No. WO 94/18342, which is based on U.S. application Ser. No. 08/017,116, U.S. Pat. No. 5,486,455 and other references and patents cited herein). The Aequorin and *Renilla* systems are representative and are described in detail herein as exemplary and as among the presently preferred systems. The Aequorin and *Renilla* systems can use the same luciferin and produce light using the same chemistry, but each luciferase is different. The Aequorin luciferase aequorin, as well as, for example, the luciferases mnemiopsin and berovin, is a photoprotein that includes bound oxygen and bound luciferin, requires $Ca^{2+}$ (or other suitable metal ion) to trigger the reaction, and must be regenerated for repeated use; whereas, the *Renilla* luciferase acts as a true enzyme because it is unchanged during the reaction and it requires dissolved molecular oxygen.

4. The Aequorin System

"The aequorin system is well known (see, e.g., Tsuji et al. (1986) "Site-specific mutagenesis of the calcium-binding photoprotein aequorin," *Proc. Natl. Acad. Sci. USA* 83:8107–8111; Prasher et al. (1985) "Cloning and Expression of the cDNA Coding for Aequorin, a Bioluminescent Calcium-Binding Protein," *Biochemical and Biophysical Research Communications* 126:1259–1268; Prasher et al. (1986) *Methods in Enzymology* 133:288–297; Prasher, et al. (1987) "Sequence Comparisons of cDNAs Encoding for Aequorin Isotypes," *Biochemistry* 26:1326–1332; Charbonneau et al. (1985) "Amino Acid Sequence of the Calcium-Dependent Photoprotein Aequorin," *Biochemistry* 24:6762–6771; Shimomura et al. (1981) "Resistivity to denaturation of the apoprotein of aequorin and reconstitution of the luminescent photoprotein from the partially denatured apoprotein," *Biochem. J.* 199:825–828; Inouye et al. (1989) *J. Biochem.* 105:473–477; Inouye et al. (1986) "Expression of Apoaequorin Complementary DNA in *Eseherichia coli*," *Biochemistry* 25:8425–8429; Inouye et al. (1985) "Cloning and sequence analysis of cDNA for the luminescent protein aequorin," *Proc. Natl. Acad. Sci USA* 82:3154–3158; Prendergast et al. (1978) "Chemical and Physical Properties of Aequorin and the Green Fluorescent Protein Isolated from *Aequorea forskalea*" *J. Am. Chem. Soc.* 17:3448–3453; European Patent Application 0 540 064 A1; European Patent Application 0 226 979 A2; European Patent Application 0 245 093 A1 and European Patent Application 0 245 093 B1; U.S. Pat. No. 5,093,240; U.S. Pat. No. 5,360,728; U.S. Pat. No. 5,139,937; U.S. Pat. No. 5,422,266; U.S. Pat. No. 5,023,181; U.S. Pat. No. 5,162,227; and SEQ ID NOs. 5–13, which set forth DNA encoding the apoprotein; and a form, described in U.S. Pat. No. 5,162,227, European Patent Application 0 540 064 A1 and Sealite Sciences Technical Report No. 3 (1994), is commercially available from Sealite, Sciences, Bogart, Ga. as AQUALITE®."

This system is among the preferred systems for use herein. As will be evident, since the aequorin photoprotein includes noncovalently bound luciferin and molecular oxygen, it is suitable for storage in this form as a lyophilized powder or encapsulated into a selected delivery vehicle. The system can be encapsulated into pellets, such as liposomes or other delivery vehicles. When used, the vehicles are contacted with a composition, even tap water, that contains $Ca^{2+}$ (or other suitable metal ion), to produce a mixture that glows.

a. Aequorin and Related Photoproteins

The photoprotein, aequorin, isolated from the jellyfish, Aequorea, emits light upon the addition of $Ca^{2+}$ (or other suitable metal ion). The aequorin photoprotein, which includes bound luciferin and bound oxygen that is released by $Ca^{2+}$, does not require dissolved oxygen. Luminescence is triggered by calcium, which releases oxygen and the luciferin substrate producing apoaqueorin.

The bioluminescence photoprotein aequorin is isolated from a number of species of the jellyfish Aequorea. It is a 22 kilodalton (kD) molecular weight peptide complex (see, e.g., Shimomura et al. (1962) J. Cellular and Comp. Physiol. 59:233–238; Shimomura et al. (1969) Biochemistry 8:3991–3997; Kohama et al. (1971) Biochemistry 10:4149–4152; and Shimomura et al. (1972) Biochemistry 11:1602–1608). The native protein contains oxygen and a heterocyclic compound coelenterazine, a luciferin, (see, below) noncovalently bound thereto. The protein contains three calcium binding sites. Upon addition of trace amounts $Ca^{2+}$ (or other suitable metal ion, such as strontium) to the photoprotein, it undergoes a conformational change that catalyzes the oxidation of the bound coelenterazine using the protein-bound oxygen. Energy from this oxidation is released as a flash of blue light, centered at 469 nm. Concentrations of calcium ions as low as $10^{-6}$ M are sufficient to trigger the oxidation reaction.

"Naturally-occurring apoaequorin is not a single compound but rather is a mixture of microheterogeneous molecular species. Aequoria jellyfish extracts contain as many as twelve distinct variants of the protein (see, e.g., Prasher et al. (187) Biochemistry 26:1326–1332; Blinks et al. (1975) Fed. Proc. 34:474). DNA encoding numerous forms has been isolated (see, e.g., SEQ ID NOs. 5–9 and 13)."

The photoprotein can be reconstituted (see, e.g., U.S. Pat. No. 5,023,181) by combining the apoprotein, such as a protein recombinantly produced in E. coli, with a coelenterazine, such as a synthetic coelenterazine, in the presence of oxygen and a reducing agent (see, e.g., Shimomura et al. (1975) Nature 256:236–238; Shimomura et al. (1981) Biochemistry J. 199:825–828), such as 2-mercaptoethanol, and also EDTA or EGTA (concentrations between about 5 to about 100 mM or higher for applications herein) tie up any $Ca^{2+}$ to prevent triggering the oxidation reaction until desired. DNA encoding a modified form of the apoprotein that does not require 2-mercaptoethanol for reconstitution is also available (see, e.g., U.S. Pat. No. U.S. Pat. No. 5,093,240). The reconstituted photoprotein is also commercially available (sold, e.g., under the trademark AQUALITE®, which is described in U.S. Pat. No. 5,162,227).

The light reaction is triggered by adding $Ca^{2+}$ at a concentration sufficient to overcome the effects of the chelator and achieve the $10^{-6}$ M concentration. Because such low concentrations of $Ca^{2+}$ can trigger the reaction, for use in the methods herein, higher concentrations of chelator may be included in the compositions of photoprotein. Accordingly, higher concentrations of added $Ca^{2+}$ in the form of a calcium salt will be required. Precise amounts may be empirically determined. For use herein, it may be sufficient to merely add water to the photoprotein, which is provided in the form of a concentrated composition or in lyophilized or powdered form. Thus, for purposes herein, addition of small quantities of $Ca^{2+}$, such as those present in phosphate buffered saline (PBS) or other suitable buffers or the moisture on the tissue to which the compositions are contacted, should trigger the bioluminescence reaction.

Numerous isoforms of the aequorin apoprotein have been identified and isolated. DNA encoding these proteins has been cloned, and the proteins and modified forms thereof have been produced using suitable host cells (see, e.g., U.S. Pat. Nos. 5,162,227, 5,360,728, 6,093,240; see, also, Prasher et al. (1985) Biophys. Biochem. Res. Commun. 126:1259–1268; Inouye et al. (1986) Biochemistry 25:8425–8429). U.S. Pat. No. 5,093,240; U.S. Pat. No. 5,360,728; U.S. Pat. No. 5,139,937; U.S. Pat. No. 5,288,623; U.S. Pat. No. 5,422,266; U.S. Pat. No. 5,162,227 and SEQ ID NOs. 5–13, which set forth DNA encoding the apoprotein; and a form is commercially available from Sealite, Sciences, Bogart, Ga. as AQUALITE®). DNA encoding apoaequorin or variants thereof is useful for recombinant production of high quantities of the apoprotein. The photoprotein is reconstituted upon addition of the luciferin, coelenterazine, preferably a sulfated derivative thereof, or an analog thereof, and molecular oxygen (see, e.g., U.S. Pat. No. 5,023,181). The apoprotein and other constituents of the photoprotein and bioluminescence generating reaction can be mixed under appropriate conditions to regenerate the photoprotein and concomitantly have the photoprotein produce light. Reconstitution requires the presence of a reducing agent, such as mercaptoethanol, except for modified forms, discussed below, that are designed so that a reducing agent is not required (see, e.g., U.S. Pat. No. 5,093,240).

For use herein, it is preferred aequorin is produced using DNA, such as that set forth in SEQ ID NOs. 5–13 and known to those of skill in the art or modified forms thereof. The DNA encoding aequorin is expressed in a host cell, such as E. coli, isolated and reconstituted to produce the photoprotein (see, e.g., U.S. Pat. Nos. 5,418,155, 5,292,658, 5,360, 728, 5,422,266, 5,162,227).

Of interest herein, are forms of the apoprotein that have been modified so that the bioluminescent activity is greater than unmodified apoaequorin (see, e.g., U.S. Pat. No. 5,360, 728, SEQ ID NOs. 10–12). Modified forms that exhibit greater bioluminescent activity than unmodified apoaequorin include proteins including sequences set forth in SEQ ID NOs. 10–12, in which aspartate 124 is changed to serine, glutamate 135 is changed to serine, and glycine 129 is changed to alanine, respectively. Other modified forms with increased bioluminescence are also available.

For use in certain embodiments herein, the apoprotein and other components of the aequorin bioluminescence generating system are packaged or provided as a mixture, which, when desired is subjected to conditions under which the photoprotein reconstitutes from the apoprotein, luciferin and oxygen (see, e.g., U.S. Pat. No. 5,023,181; and U.S. Pat. No. 5,093,240). Particularly preferred are forms of the apoprotein that do not require a reducing agent, such as 2-mercapto-ethanol, for reconstitution. These forms, described, for example in U.S. Pat. No. 5,093,240 (see, also Tsuji et al. (1986) Proc. Natl. Acac. Sci. U.S.A. 83:8107–8111), are modified by replacement of one or more, preferably all three cysteine residues with, for example serine. Replacement may be effected by modification of the DNA encoding the aequorin apoprotein, such as that set forth in SEQ ID NO. 5, and replacing the cysteine codons with serine."

The photoproteins and luciferases from related species, such as *Obelia* are also contemplated for use herein. DNA encoding the $Ca^{2+}$-activated photoprotein obelin from the hydroid polyp *Obelia longissima* is known and available (see, e.g., Illarionov et al. (1995) *Gene* 153:273–274; and Bondar et al. (1995) *Biochim. Biophys. Acta* 1231:29–32). This photoprotein can also be activated by $Mn^{2+}$ (see, e.g., Vysotski et al. (1995) *Arch. Bioch. Biophys.* 316:92–93, Vysotski et al. (1993) *J. Biolumin. Chemilumin.* 8:301–305).

In general for use herein, the components of the bioluminescence are packaged or provided so that there is insufficient metal ions to trigger the reaction. When used, the trace amounts of triggering metal ion, particularly $Ca^{2+}$ is contacted with the other components. For a more sustained glow, aequorin can be continuously reconstituted or can be added or can be provided in high excess.

b. Luciferin

The aequorin luciferin is coelenterazine and analogs therein, which include molecules including the structure (formula (I)):

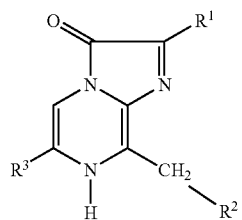

in which $R_1$ is $CH_2C_6H_5$ or $CH_3$; $R_2$ is $C_6H_5$, and $R_3$ is p-$C_6H_4OH$ or $CH_3$ or other such analogs that have activity. Preferred coelenterazine has the structure in which $R^1$ is p-$CH_2C_6H_4OH$, $R_2$ is $C_6H_5$, and $R_3$ is p-$C_6H_4OH$, which can be prepared by known methods (see, e.g., Inouye et al. (1975) *Jap. Chem. Soc., Chemistry Lttrs.* pp 141–144; and Hart et al. (1979) *Biochemistry* 18:2204–2210). Among the preferred analogs, are those that are modified, whereby the spectral frequency of the resulting light is shifted to another frequency.

The preferred coelenterazine has the structure (formula (II)):

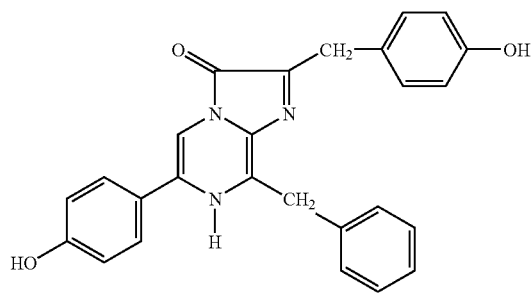

and sulfated derivatives thereof.

Another coelentratrazine has formula (V):

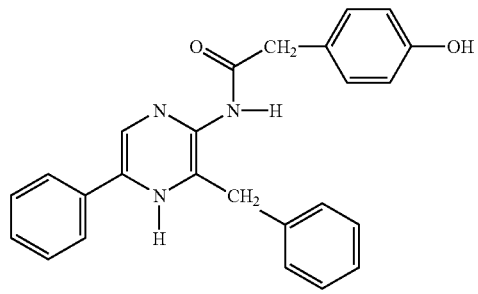

(see, Hart et al. (1979) *Biochemistry* 18:2204–2210). Using this derivative in the presence of luciferase all of the light is in the ultraviolet with a peak at 390 nm. Upon addition of GFP, all light emitted is now in the visible range with a peak at 509 nm accompanied by an about 200-fold increase in the amount of light emitted. Viewed with a cut-off filter of 470 nm, in the light yield in the absence of GFP would be about zero, and would be detectable in the presence of GFP. This provides the basis for an immunoassay described in the EXAMPLES.

The reaction of coelenterazine when bound to the aequorin photoprotein with bound oxygen and in the presence of $Ca^{2+}$ can represented as follows:

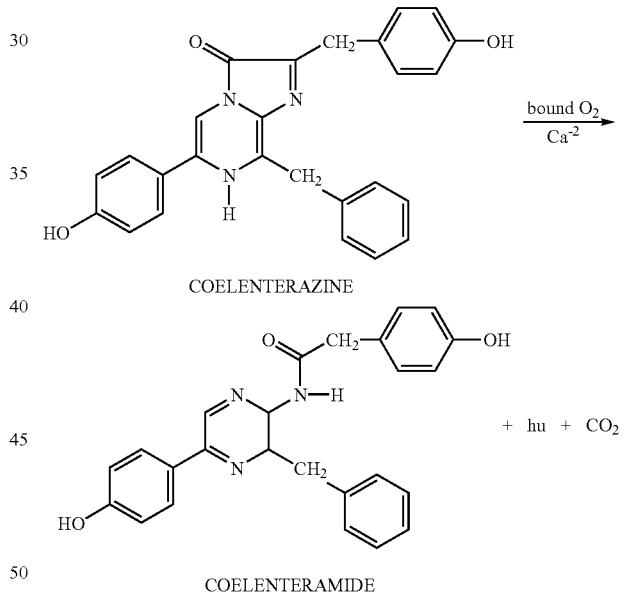

The photoprotein aequorin (which contains apoaequorin bound to a coelenterate luciferin molecule) and *Renilla* luciferase, discussed below, can use the same coelenterate luciferin. The aequorin photoprotein catalyses the oxidation of coelenterate luciferin (coelenterazine) to oxyluciferin (coelenteramide) with the concomitant production of blue light (lambda$_{max}$=469 nm).

Importantly, the sulfate derivative of the coelenterate luciferin (lauryl-luciferin) is particularly stable in water, and thus may be used in a coelenterate-like bioluminescent system. In this system, adenosine diphosphate (ADP) and a sulpha-kinase are used to convert the coelenterazine to the sulphated form. Sulfatase is then used to reconvert the lauryl-luciferin to the native coelenterazine. Thus, the more stable lauryl-luciferin is used in the item to be illuminated and the luciferase combined with the sulfatase are added to the luciferin mixture when illumination is desired.

Thus, the bioluminescent system of *Aequorea* is particularly suitable for use in the methods herein. The particular amounts and the manner in which the components are provided depends upon the type of neoplasia or specialty tissue to be visualized. This system can be provided in lyophilized form, that will glow upon addition of $Ca^{2+}$. It can be encapsulated, linked to microcarriers, such as microbeads, or in as a compositions, such as a solution or suspension, preferably in the presence of sufficient chelating agent to prevent triggering the reaction. The concentration of the aequorin photoprotein will vary and can be determined empirically. Typically concentrations of at least 0.1 mg/l, more preferably at least 1 mg/l and higher, will be selected. In certain embodiments, 1–10 mg luciferin/100 mg of luciferase will be used in selected volumes and at the desired concentrations will be used.

5. Crustacean, Particularly Cyrpidina Systems

The ostracods, such as *Vargula serratta, hilgendorfii* and *noctiluca* are small marine crustaceans, sometimes called sea fireflies. These sea fireflies are found in the waters off the coast of Japan and emit light by squirting luciferin and luciferase into the water, where the reaction, which produces a bright blue luminous cloud, occurs. The reaction involves only luciferin, luciferase and molecular oxygen, and, thus, is very suitable for application herein.

The systems, such as the *Vargula* bioluminescent systems, are particularly preferred herein because the components are stable at room temperature if dried and powdered and will continue to react even if contaminated. Further, the bioluminescent reaction requires only the luciferin/luciferase components in concentrations as low as 1:40 parts per billion to 1:100 parts per billion, water and molecular oxygen to proceed. An exhausted system can be renewed by addition of luciferin.

a. *Vargula* Luciferase

The *Vargula* luciferase is water soluble and is among those preferred for use in the methods herein. *Vargula* luciferase is a 555-amino acid polypeptide that has been produced by isolation from *Vargula* and also using recombinant technology by expressing the DNA in suitable bacterial and mammalian host cells (see, e.g., Thompson et al. (1989) *Proc. Natl. Acad. Sci. U.S.A.* 86:6567–6571; Inouye et al. (1992) *Proc. Natl. Acad. Sci. U.S.A.* 89:9584–9587; Johnson et al. (1978) *Methods in Enzymology LVII*:331–349; Tsuji et al. (1978) *Methods Enzymol.* 57:364–72; Tsuji (1974) *Biochemistry* 13:5204–5209; Japanese Patent Application No. JP 3–30678 Osaka; and European Patent Application No. EP 0 387 355 A1).

(1) Purification From *Cypridina*

Methods for purification of *Vargula* (*Cypridina*) luciferase are well known. For example, crude extracts containing the active can be readily prepared by grinding up or crushing the *Vargula* shrimp. In other embodiments, a preparation of *Cypridina hilgendorfi* luciferase can be prepared by immersing stored frozen *C. hilgendorfi* in distilled water containing, 0.5–5.0 M salt, preferably 0.5–2.0 M sodium or potassium chloride, ammonium sulfate, at 0–30° C., preferably 0–10° C., for 1–48 hr, preferably 10–24 hr, for extraction followed by hydrophobic chromatography and then ion exchange or affinity chromatography (TORAY IND INC, Japanese patent application JP 4258288, published Sep. 14, 1993; see, also, Tsuji et al. (1978) *Methods Enzymol.* 57:364–72 for other methods).

(2) Preparation by Recombinant Methods

The luciferase is preferably produced by expression of cloned DNA encoding the luciferase (European Patent Application No. 0 387 355 A1; International PCT Application No. WO 95/001542; see, also SEQ ID No. 5, which sets forth the sequence from Japanese Patent Application No. JP 3–30678 and Thompson et al. (1989) *Proc. Natl. Acad. Sci. U.S.A.* 86:6567–6571) DNA encoding the luciferase or variants thereof is introduced into *E. coli* using appropriate vectors and isolated using standard methods.

b. *Vargula* Luciferin

The natural luciferin is a substituted imidazopyrazine nucleus, such a compound of formula (III):

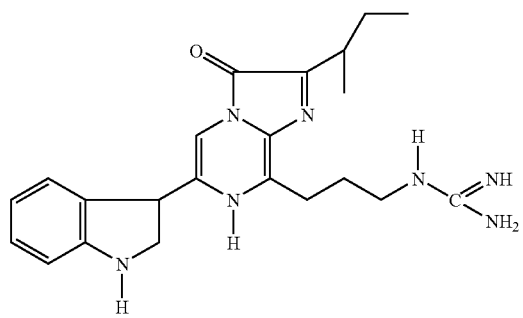

The luciferin can be isolated from ground dried *Vargula* by heating the extract, which destroys the luciferase but leaves the luciferin intact (see, e.g., U.S. Pat. No. 4,853,327).

Analogs thereof and other compounds that react with the luciferase in a light producing reaction also may be used.

Other bioluminescent organisms that have luciferases that can react with the *Vargula* luciferin include, the genera *Apogon, Parapriacanthus* and *Porichthys*.

c. Reaction

The luciferin upon reaction with oxygen forms a dioxetanone intermediate (which includes a cyclic peroxide similar to the firefly cyclic peroxide molecule intermediate). In the final step of the bioluminescent reaction, the peroxide breaks down to form $CO_2$ and an excited carbonyl. The excited molecule then emits a blue to blue-green light.

The optimum pH for the reaction is about 7. For purposes herein, any pH at which the reaction occurs may be used. The concentrations of reagents are those normally used for analytical reactions or higher (see, e.g., Thompson et al. (1990) *Gene* 96:257–262). Typically concentrations of the luciferase between 0.1 and 10 mg/l, preferably 0.5 to 2.5 mg/l will be used. Similar concentrations or higher concentrations of the luciferin may be used.

6. Insect Bioluminescent Systems Including Fireflies, Click Beetles, and other Insect System The biochemistry of firefly bioluminescence was the first bioluminescent system to be characterized (see, e.g., Wienhausen et al. (1985) *Photochemistry and Photobiology* 42:609–611; McElroy et al. (1966) in *Molecular Architecture in cell Physiology*, Hayashi et al., eds. Prentice Hall, Inc., Englewood Cliffs, N.J., pp. 63–80) and it is commercially available (e.g., from Promega Corporation, Madison, Wis., see, e.g., Leach et al. (1986) *Methods in Enzymology* 133:51–70, esp. Table 1). Luciferases from different species of fireflies are antigenically similar. These species include members of the genera *Photinus, Photurins* and *Luciola*. Further, the bioluminescent reaction produces more light at 30° C. than at 20° C., the luciferase is stabilized by small quantities of bovine albumin serum, and the reaction can be buffered by tricine.

a. Luciferase

"DNA clones encoding luciferases from various insects and the use to produce the encoded luciferase is well known.

For example, DNA clones that encode luciferase from *Photinus pyralis, luciola cruciata* (see, e.g., de West et al. (1985) *Proc. Natl. Acad. Sci. U.S.A.* 82:7870–7873; de West et al. (1986) *Methods in Enzymology* 133:3; U.S. Pat. No. 4,968,613, see, also SEQ ID NO. 3) are available. The DNA has also been expressed in *Saccharomyces* (see, e.g., Japanese Application No. JP *63317079*, published Dec. 26, 1988, KIKKOMAN CORP) and in tobacco."

In addition to the wild-type luciferase modified insect luciferases have been prepared. For example, heat stable luciferase mutants, DNA-encoding the mutants, vectors and transformed cells for producing the luciferases are available. A protein with 60% amino acid sequence homology with luciferases from *Photinus pyralis, Luciola mingrelica, L. cruciata* or *L. lateralis* and having luciferase activity is available (see, e.g., International PCT Application No. WO 95/25798). It is more stable above 30° C. than naturally-occurring insect luciferases and may also be produced at 37° C. or above, with higher yield.

"Modified luciferases can generate light at different wavelengths (compared with native luciferase), and thus, may be selected for their color-producing characteristics. For example, synthetic mutant beetle luciferase(s) and DNA encoding such luciferases that produce bioluminescence at a wavelength from wild-type luciferase are know (Promega Corp, International PCT Application No. WO 95/18853, which is based on U.S. application Ser. No. 08/177,081. The mutant beetle luciferase has an amino acid sequence differing from that of the corresponding wild-type Luciola cruciata (see, e.g., U.S. Pat. Nos. 5,182,202, 5,219,737, 5,352,598, see, also SEQ ID NO. 3) by a substitution(s) at one or two positions. The mutant luciferase produces a bioluminescence with a wavelength of peak intensity that differs by at least 1 nm from that produced by wild-type luciferases."

Other mutant luciferases can be produced. Mutant luciferases with the amino acid sequence of wild-type luciferase, but with at least one mutation in which valine is replaced by isoleucine at the amino acid number 233, valine by isoleucine at 239, serine by asparagine at 286, glycine by serine at 326, histidine by tyrosine at 433 or proline by serine at 452 are known (see, e.g., U.S. Pat. Nos. 5,219,737, and 5,330,906). The luciferases are produced by expressing DNA-encoding each mutant luciferase in *E. coli* and isolating the protein. These luciferases produce light with colors that differ from wild-type. The mutant luciferases catalyze luciferin to produce red ($\lambda$ 609 nm and 612 nm), orange ($\lambda$595 and 607 nm) or green ($\lambda$ 558 nm) light. The other physical and chemical properties of mutant luciferase are substantially identical to native wild type-luciferase. The mutant luciferase has the amino acid sequence of *Luciola cruciata* luciferase with an alteration selected from Ser 286 replaced by Asn, Gly 326 replaced by Ser, His 433 replaced by Tyr or Pro 452 replaced by Ser. Thermostable luciferases are also available (see, e.g., U.S. Pat. No. 5,229,285; see, also International PCT Application No. WO 95/25798, which provides *Photinus* luciferase in which the glutamate at position 354 is replaced with lysine and *Luciola* luciferase in which the glutamate at 356 is replaced with lysine).

These mutant luciferases as well as the wild type luciferases can be used in combination with the GFPs provided herein particularly in instances when a variety of colors are desired or when stability at higher temperatures is desired.

b. Luciferin

The firefly luciferin is a benzothiazole:

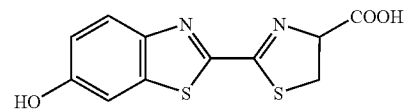

Analogs of this luciferin and synthetic firefly luciferins are also known to those of skill in art (see, e.g., U.S. Pat. No. 5,374,534 and 5,098,828). These include compounds of formula (IV) (see, U.S. Pat. No. 5,098,828):

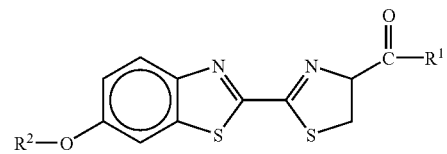

in which:

$R^1$ is hydroxy, amino, linear or branched $C_1$–$C_{20}$ alkoxy, $C_2$–$C_{20}$ alkyenyloxy, an L-amino acid radical bond via the $\alpha$-amino group, an oligopeptide radical with up to ten L-amino acid units linked via the $\alpha$-amino group of the terminal unit;

$R^2$ is hydrogen, $H_2PO_3$, $HSO_3$, unsubstituted or phenyl substituted linear or branched $C_1$–$C_{20}$ alkyl or $C_2$–$C_{20}$ alkenyl, aryl containing 6 to 18 carbon atoms, or $R^3$—C(O)—; and $R^3$ is an unsubstituted or phenyl substituted linear or branched $C_1$–$C_{20}$ alkyl or $C_2$–$C_{20}$ alkenyl, aryl containing 6 to 18 carbon atoms, a nucleotide radical with 1 to 3 phosphate groups, or a glycosidically attached mono- or disaccharide, except when formula (IV) is a D-luciferin or D-luciferin methyl ester.

Modified luciferins that have been modified to produce light of shifted frequencies are known to those of skill in the art.

c. Reaction

The reaction catalyzed by firefly luciferases and related insect luciferases requires ATP, $Mg^{2+}$ as well as molecular oxygen. Luciferin must be added exogenously. Firefly luciferase catalyzes the firefly luciferin activation and the subsequent steps leading to the excited product. The luciferin reacts with ATP to form a luciferyl adenylate intermediate. This intermediate then reacts with oxygen to form a cyclic luciferyl peroxy species, similar to that of the coelenterate intermediate cyclic peroxide, which breaks down to yield $CO_2$ and an excited state of the carbonyl product. The excited molecule then emits a yellow light; the color, however, is a function of pH. As the pH is lowered the color of the bioluminescence changes from yellow-green to red.

Different species of fireflies emit different colors of bioluminescence so that the color of the reaction will be dependent upon the species from which the luciferase is obtained. Additionally, the reaction is optimized at pH 7.8.

Addition of ATP and luciferin to a reaction that is exhausted produces additional light emission. Thus, the system, once established, is relatively easily maintained. Therefore, it is highly suitable for use herein in embodiments in which a sustained glow is desired.

7. Other Systems

Numerous other systems are known and have been described in detail for example in U.S. Pat. Nos. 5,876,995, 6,152,358 and 6,113,886).

a. Bacterial Systems

Luminous bacteria typically emit a continuous light, usually blue-green. When strongly expressed, a single bacterium may emit $10^4$ to $10^5$ photons per second. Bacterial bioluminescence systems include, among others, those systems found in the bioluminescent species of the genera *Photobacterium*, *Vibrio* and *Xenorhabdus*. These systems are well known and well characterized (see, e.g., Baldwin et al. (1984) *Biochemistry* 23:3663–3667; Nicoli et al. (1974) *J. Biol. Chem.* 249:2393–2396; Welches et al. (1981) *Biochemistry* 20:512–517; Engebrecht et al. (1986) *Methods in Enzymology* 133:83–99; Frackman et al. (1990) *J. of Bacteriology* 172:5767–5773; Miyamoto et al. (1986) *Methods in Enzymology* 133:70; U.S. Pat. No. 4,581,335).

(1) Luciferases

Bacterial luciferase, as exemplified by luciferase derived from *Vibrio harveyi* (EC 1.14.14.3, alkanol reduced-FMN-oxygen oxidoreductase 1-hydroxylating, luminescing), is a mixed function oxidase, formed by the association of two different protein subunits α and β. The α-subunit has an apparent molecular weight of approximately 42,000 kDa and the β-subunit has an apparent molecular weight of approximately 37,000 kDa (see, e.g., Cohn et al. (1989) *Proc. Natl. Acad. Sci. U.S.A.* 90:102–123). These subunits associate to form a 2-chain complex luciferase enzyme, which catalyzes the light emitting reaction of bioluminescent bacteria, such as *Vibrio harveyi* (U.S. Pat. No. 4,581,335; Belas et al. (1982) *Science* 218:791–793), *Vibrio fischeri* (Engebrecht et al. (1983) *Cell* 32:773–781; Engebrecht et al. (1984) *Proc. Natl. Acad. Sci. U.S.A.* 81:4154–4158) and other marine bacteria.

Bacterial luciferase genes have been cloned (see, e.g., U.S. Pat. No. 5,221,623; U.S. Pat. No. 4,581,335; European Patent Application No. EP 386 691 A). Plasmids for expression of bacterial luciferase, such as *Vibrio harveyi*, include pFIT001 (NRRL B-18080), pPALE001 (NRRL B-18082) and pMR19 (NRRL B-18081)) are known. For example the sequence of the entire lux regulon from *Vibiro fisheri* has been determined (Baldwin et al. (1984), *Biochemistry* 23:3663–3667; Baldwin et al. (1981) *Biochem.* 20:512–517; Baldwin et al. (1984) *Biochem.* 23:3663–3667; see, also, e.g., U.S. Pat. Nos. 5,196,318, 5,221,623, and 4,581,335). This regulon includes luxI gene, which encodes a protein required for autoinducer synthesis (see, e.g., Engebrecht et al. (1984) *Proc. Natl. Acad. Sci. U.S.A.* 81:4154–4158), the luxC, luxD, and luxE genes, which encode enzymes that provide the luciferase with an aldehyde substrate, and the luxA and luxB genes, which encode the alpha and beta subunits of the luciferase.

Lux genes from other bacteria have also been cloned and are available (see, e.g., Cohn et al. (1985) *J. Biol. Chem.* 260:6139–6146; U.S. Pat. No. 5,196,524, which provides a fusion of the luxA and luxB genes from *Vibrio harveyi*). Thus, luciferase alpha and beta subunit-encoding DNA is provided and can be used to produce the luciferase. DNA encoding the α (1065 bp) and β (984 bp) subunits, DNA encoding a luciferase gene of 2124 bp, encoding the alpha and beta subunits, a recombinant vector containing DNA encoding both subunits and a transformed *E. coli* and other bacterial hosts for expression and production of the encoded luciferase are available. In addition, bacterial luciferases are commercially available.

(2) Luciferins

Bacterial Luciferins Include:

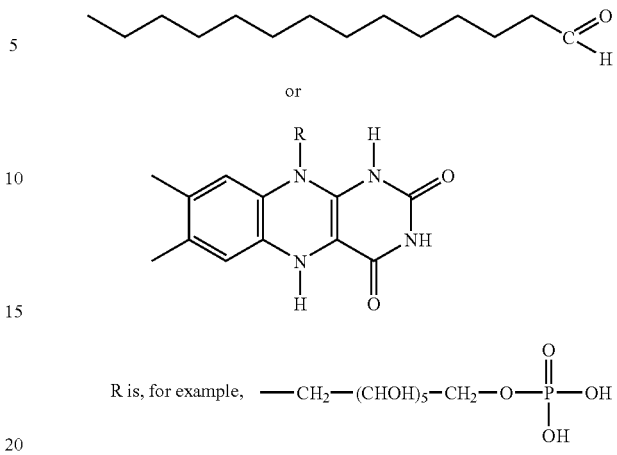

in which the tetradecanal with reduced flavin mononucleotide are considered luciferin since both are oxidized during the light emitting reaction.

(3) Reactions

The bacterial systems require, in addition to reduced flavin, five polypeptides to complete the bioluminescent reaction: two subunits, α and β, of bacterial luciferin and three units of a fatty acid reductase system complex, which supplies the tetradecanal aldehyde. Examples of bacterial bioluminescent systems useful in the apparatus and methods provided herein include those derived from *Vibrio fisheri* and *Vibrio harveyi*. One advantage to this system is its ability to operate at cold temperatures; certain surgical procedures are performed by cooling the body to lower temperatures.

Bacterial luciferase catalyzes the flavin-mediated hydroxylation of a long-chain aldehyde to yield carboxylic acid and an excited flavin; the flavin decays to ground state with the concomitant emission of blue green light ($\lambda_{max}$=490 nm; see, e.g., Legocki et al. (1986) *Proc. Natl. Acad. Sci. USA* 81:9080; see U.S. Pat. No. 5,196,524):

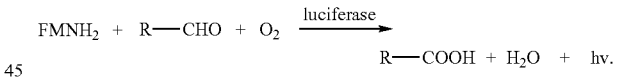

The reaction can be initiated by contacting reduced flavin mononucleotide (FMNH$_2$) with a mixture of the bacterial luciferase, oxygen, and a long-chain aldehyde, usually n-decyl aldehyde.

DNA encoding luciferase from the fluorescent bacterium *Alteromonas hanedai* is known (CHISSO CORP; see, also, Japanese application JP 7222590, published Aug. 22, 1995). The reduced flavin mononucleotide (FMNH$_2$; luciferin) reacts with oxygen in the presence of bacterial luciferase to produce an intermediate peroxy flavin. This intermediate reacts with a long-chain aldehyde (tetradecanal) to form the acid and the luciferase-bound hydroxy flavin in its excited state. The excited luciferase-bound hydroxy flavin then emits light and dissociates from the luciferase as the oxidized flavin mononucleotide (FMN) and water. In vivo FMN is reduced again and recycled, and the aldehyde is regenerated from the acid.

Flavin reductases have been cloned (see, e.g., U.S. Pat. No. 5,484,723; See SEQ ID NO. 14 for a representative sequence from this patent). These as well as NAD(P)H can be included in the reaction to regenerate FMNH$_2$ for reaction with the bacterial luciferase and long chain aldehyde. The flavin reductase catalyzes the reaction of FMN, which is the luciferase reaction, into $FMNH_2$; thus, if luciferase and the reductase are included in the reaction system, it is possible to maintain the bioluminescence reaction. Namely, since the bacterial luciferase turns over many times, bioluminescence continues as long as a long chain aldehyde is present in the reaction system.

The color of light produced by bioluminescent bacteria also results from the participation of a protein blue-florescent protein (BFP) in the bioluminescence reaction. This protein, which is well known (see, e.g., Lee et al. (1978) *Methods in Enzymology LVII*:226–234), may also be added to bacterial bioluminescence reactions in order to cause a shift in the color.

b. Dinoflagellate Bioluminescence Generating Systems

In dinoflagellates, bioluminescence occurs in organelles termed scintillons. These organelles are outpocketings of the cytoplasm into the cell vacuole. The scintillons contain only dinoflagellate luciferase and luciferin (with its binding protein), other cytoplasmic components being somehow excluded. The dinoflagellate luciferin is a tetrapyrrole related to chlorophyll:

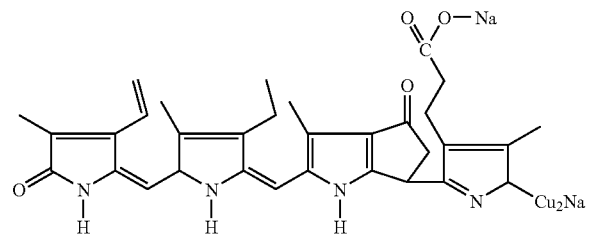

or an analog thereof.

The luciferase is a 135 kD single chain protein that is active at pH 6.5, but inactive at pH 8 (see, e.g., Hastings (1981) *Bioluminescence and Chemiluminescence*, DeLuca et al., eds. Academic Press, NY, pp. 343–360). Luminescent activity can be obtained in extracts made at pH 8 by simply shifting the pH from 8 to 6. This occurs in soluble and particulate fractions. Within the intact scintillon, the luminescent flash occurs for ~100 msec, which is the duration of the flash in vivo. In solution, the kinetics are dependent on dilution, as in any enzymatic reaction. At pH 8, the luciferin is bound to a protein (luciferin binding protein) that prevents reaction of the luciferin with the luciferase. At pH 6, however, the luciferin is released and free to react with the enzyme.

D. Isolation and Identification of Nucleic Acids Encoding Luciferases and GFPs

Nucleic acid encoding bioluminescent proteins are provided. Particularly, nucleic acid encoding *Renilla reniformis* GFP is provided.

1. Isolation of Specimens of the Genus *Renilla*

Specimens of *Renilla* are readily available from the oceans of the world, including the Gulf of Mexico, Pacific Ocean and Atlantic Ocean. *Renilla* typically live on the ocean bottom at about 30 to 100 feet deep and can be easily collected by dragging. For example, specimens of *R. kollikeri* can be obtained off the coast of California or Baja, Mexico. Alternatively, live specimens of *Renilla* may be purchased from a commercial supplier (e.g., Gulf Marine Incorporated, Panacea, Fla.). Upon capture or receipt, the specimens are washed thoroughly and may also be dissected to enrich for light-emitting tissues. The whole organisms or dissected tissues are then snap frozen and stored in liquid nitrogen.

As described in detail in the examples below, the frozen tissues were used as a source to isolate nucleic acids encoding *Renilla mulleri* GFP and luciferase (e.g., see SEQ ID NO. 15 and SEQ ID NO. 17, respectively).

2. Preparation of *Renilla* cDNA Expression Libraries

*Renilla* cDNA expression libraries may be prepared from intact RNA following the methods described herein or by other methods known to those of skill the art (e.g., see Sambrook et al. (1989) *Molecular Cloning: A Laboratory Manual*, Cold Spring Harbor Laboratory Press, Cold Spring Harbor, N.Y.; U.S. Pat. No. 5,292,658).

Typically, the preparation of cDNA libraries includes the isolation of polyadenylated RNA from the selected organism followed by single-strand DNA synthesis using reverse transcriptase, digestion of the RNA strand of the DNA/RNA hybrid and subsequent conversion of the single-stranded DNA to double stranded cDNA.

a. RNA Isolation and cDNA Synthesis

Whole *Renilla* or dissected *Renilla* tissues can be used a source of total cytoplasmic RNA for the preparation of *Renilla* cDNA. Total intact RNA can be isolated from crushed *Renilla* tissue, for example, by using a modification of methods generally known in the art (e.g., see Chirgwin et al. (1970) *Biochemistry* 18:5294–5299). After isolating total cellular RNA, polyadenylated RNA species are then easily separated from the nonpolyadenylated species using affinity chromatography on oligodeoxythymidylate cellulose columns, (e.g., as described by Aviv et al., (1972) *Proc. Natl. Acad. Sci. U.S.A.* 69:1408).

The purified *Renilla* polyA-mRNA is then subjected to a cDNA synthesis reaction to generate a cDNA library from total polyA-mRNA. Briefly, reverse transcriptase is used to extend an annealed polydT primer to generate an RNA/DNA duplex. The RNA strand is then digested using an RNase, e.g., RNase H, and following second-strand synthesis, the cDNA molecules are blunted-ended with S1 nuclease or other appropriate nuclease. The resulting double-stranded cDNA fragments can be ligated directly into a suitable expression vector or, alternatively, oligonucleotide linkers encoding restriction endonuclease sites can be ligated to the 5'-ends of the cDNA molecules to facilitate cloning of the cDNA fragments.

b. Construction of cDNA Expression Libraries

The best characterized vectors for the construction of cDNA expression libraries are lambda vectors. Lambda-based vectors tolerate cDNA inserts of about 12 kb and provide greater ease in library screening, amplification and storage compared to standard plasmid vectors. Presently preferred vectors for the preparation of *Renilla* cDNA expression libraries are the Lambda, Uni-Zap, Lambda-Zap II or Lambda-ZAP Express/EcoRI/XhoI vectors, which are known to those of skill in the art (e.g., see U.S. Pat. No. 5,128,256), and are also commercially available (Stratagene, La Jolla, Calif.).

Generally, the Lambda-Zap vectors combine the high efficiency of a bacteriophage lambda vector systems with the versatility of a plasmid system. Fragments cloned into these vectors can be automatically excised using a helper phage and recircularized to generate subclones in the pBK-derived phagemid. The pBK phagemid carries the neomycin-resistance gene for selection in bacteria and G418 selection in eukaryotic cells or may contain the β-lactamase resistance gene. Expression of the recombinant polypeptide is under the control of the lacZ promoter in bacteria and the CMV promoter in eukaryotes.

More specifically, these lambda-based vectors are composed of an initiator-terminator cassette containing the plasmid system, e.g., a pBK Bluescript derivative (Stratagene, San Diego), bracketed by the right and left arm of the bacteriophage lambda. The lambda arms allow for efficient packaging of replicated DNA whereas the excisable initiator-terminator cassette allows for easy cloning of the cDNA fragments and the generation of a plasmid library without the need for additional subcloning.

When used herein, cDNA fragments are inserted into the multiple cloning site contained within the initiator-terminator cassette of the Lambda-Zap vector to create a set of cDNA expression vectors. The set of cDNA expression vectors is allowed to infect suitable E. coli cells, followed by co-infection with a filamentous helper phage. Within the cell, trans-acting proteins encoded by the helper phage, e.g., the gene II protein of M13, recognize two separate domains positioned within the lambda arms of the vector and introduce single-stranded nicks flanking the intiator-terminator cassette. Upon a subsequent round of DNA synthesis, a new DNA strand is synthesized that displaces the existing nick strand liberating the initiator-terminator cassette. The displaced strand is then circularized, packaged as filamentous phage by the helper proteins and excreted from the cell. The BK plasmid containing the cDNA is recovered by infecting an F' strain of E. coli and plating the infected cells on solid medium supplemented with kanamycin for the selection of pBK-containing cells.

The Renilla cDNA expression library can be screened using a variety of methods known to those of skill in the art. For example, identification of Renilla GFP may be achieved using a functional screening method employing blue light and observing colonies visually for emission of green fluorescence or by observing light emission using one or more bandpass filter.

3. Cloning of Renilla reniformis Green Fluorescent Protein

Renilla reniformis GFP has 233 amino acids compared to GFPs from animals that contain luciferase-GFP bioluminescent systems Renilla mulleri, Ptilosarcus and Aequorea Victoria. Other such GFPs have 238 amino acids. At the amino acid level, Renilla reniformis is respectively 53, 51 and 19% identical to the GFPs from these animals. The extent of identity of Renilla reniformis GFP to the half dozen cloned anthozoan coral GFPs, which do not contain associated luciferases, ranges from 32 to 38%. The overall identity among these GFPs is surprisingly low for a protein evolved from a common ancestor. These relationships are depicted as a phylogenetic tree (FIG. 1).

Most surprising is the finding that the Renilla reniformis GFP is much more closely related to Ptilosarcus GFP (77% identity) than to Renilla reniformis GFP (53%). It is unclear why the sequence relatedness between these 3 GFPs does not follow traditional taxonomy. Given the sequence differences at the amino acid level, coding DNA sequences are surprisingly well conserved. Renilla reniformis GFP DNA is 56 and 59% identical to Renilla mulleri and Ptilosarcus GFP DNA.

Thus cloning Renilla reniformis GFP clone suggests why many groups may have failed in attempts to clone this gene by traditional methods. An attempt to sequence the entire protein by Edman degradation was difficult from the outset because the GFP was refractory to most attempts at specific proteolysis. Although over 80% of the protein was eventually accurately sequenced, a 30 amino acid region (1190–139 of SEQ ID NO. 27) had not been sequenced (as well as other regions, including amino acids 41–43, 65–71; SEQ ID NO. 27). This 30 amino acid region apparently is degraded by the proteolytic methods used into very small fragments that are difficult to isolate and sequence; proper ordering of sequenced fragments was also difficult.

The cloned DNA fragments can be replicated in bacterial cells, such as E. coli. A preferred DNA fragment also includes a bacterial origin of replication, to ensure the maintenance of the DNA fragment from generation to generation of the bacteria. In this way, large quantities of the DNA fragment can be produced by replication in bacteria. Preferred bacterial origins of replication include, but are not limited to, the f1-ori and col E1 origins of replication. Preferred hosts contain chromosomal copies of DNA encoding T7 RNA polymerase operably linked to an inducible promoter, such as the lacUV promoter (see, U.S. Pat. No. 4,952,496). Such hosts include, but are not limited to, lysogens E. coli strains HMS174(DE3)pLysS, BL21(DE3) pLysS, HMS174(DE3) and BL21 (DE3). Strain BL21 (DE3) is preferred. The pLys strains provide low levels of T7 lysozyme, a natural inhibitor of T7 RNA polymerase.

For expression and for preparation of muteins, such as temperature sensitive muteins, eukaryotic cells, among them, yeast cells, such as Saccharomyces are preferred.

Nucleic acid encoding fusion proteins of the luciferases and GFPs are also provided. The resulting fusion proteins are also provided. Nucleic acids that encode luciferase and GFPs as polycistronic mRNA or under the control of separate promoters are also provided. Methods of use thereof are also provided.

The GFP cloned from Renilla has spectral properties that make it extremely useful. These properties include very high quantum efficiency, high molar absorbency and efficient use with universally available fluorescein filters (e.g., Endo GFP filter set sold by Chroma). It is known that Renilla reniformis GFP is sixfold brighter than the wild-type Aequorea GFP on a molar basis, and three to fourfold brighter than the brightest mutant.

The Renilla mullerei GFP encoded by the nucleic acid clones provided herein exhibits similar functional characteristics, and the spectra appear identical with those from native reniformis GFP. Sequence comparison among the GFPs isolated from Aequorea victoria, Renilla mullerei, and Ptilosarcus reveal that the chromophore sequences of R. mullerei and Ptilosarcus are identical, and differ from A. victoria. These sequence differences point to protein sites that can be modified without affecting the essential fluorescence properties and also provide a means to identify residues that change these properties.

4. Isolation and Identification of DNA Encoding Renilla mulleri GFP

Methods for identification and cloning of GPFs from Renilla have been described (see, published International PCT application No. WO 99/49019, and copending allowed U.S. application Ser. No. 09/277,716). Nucleic acid encoding Renilla mulleri has been isolated. Briefly, a R. mulleri λ Uni-Zap cDNA expression plasmid library was prepared, transformed into competent E. coli cells and plated onto modified L-broth plates containing carbon black to absorb background fluorescence. Transformants were sprayed with a solution containing IPTG to induce expression of the recombinant Renilla GFP from the heterologous cDNA. To identify GFP expressing clones, transformants were placed in blue light, preferably 470 to 490 nm light, and colonies that emitted green fluorescence were isolated and grown in pure culture.

The nucleotide sequence of the cDNA insert of a green fluorescent transformant was determined (e.g., see SEQ ID NO. 15). The 1,079 cDNA insert encodes a 238 amino acid polypeptide that is only 23.5% identical to A. victoria GFP.

The recombinant protein exhibits excitation and emission spectra similar to those reported for live *Renilla* species.

5. Isolation and Identification of DNA Encoding *Renilla mulleri* Luciferase

The above-described *R. mulleri* cDNA expression library was also used to clone DNA encoding a *R. mulleri* luciferase. Single colony transformants were grown on modified L-broth plates containing carbon black and expression from the heterologous DNA was induced with IPTG, essentially as described above. After allowing time for expression, the transformants were sprayed with coelenterazine and screened for those colonies that emit blue light. Light-emitting colonies were isolated and grown in pure culture.

The nucleotide sequence of the cDNA insert contained in the light-emitting transformant was determined. The 1,217 cDNA insert encodes a 311 amino acid polypeptide. The recombinant protein exhibits excitation and emission spectra similar to those reported for live *Renilla* species.

E. Recombinant Expression of Proteins

1. DNA Encoding *Renilla* Proteins

As described above, DNA encoding a *Renilla* GFP or *Renilla* luciferase can be isolated from natural sources, synthesized based on *Renilla* sequences provided herein or isolated as described herein.

In preferred embodiments, the DNA fragment encoding a *Renilla* GFP has the sequence of amino acids set forth in SEQ ID NO. 27, encoded by nucleic acid, such as that set forth SEQ ID. NOs. 23–26 and 27.

A DNA molecule encoding a *Renilla* luciferase has the sequence of amino acids set forth in SEQ ID NO. 18. In more preferred embodiments, the DNA fragment encodes the sequence of amino acids encoded by nucleotides 31–963 of the sequence of nucleotides set forth in SEQ ID NO. 17.

2. DNA Constructs for Recombinant Production of *Renilla reniformis* GFP and other Proteins DNA is introduced into a plasmid for expression in a desired host. In preferred embodiments, the host is a bacterial host. The sequences of nucleotides in the plasmids that are regulatory regions, such as promoters and operators, are operationally associated with one another for transcription of the sequence of nucleotides that encode a *Renilla* GFP or luciferase. The sequence of nucleotides encoding the FGF mutein may also include DNA encoding a secretion signal, whereby the resulting peptide is a precursor of the *Renilla* GFP.

In preferred embodiments the DNA plasmids also include a transcription terminator sequence. The promoter regions and transcription terminators are each independently selected from the same or different genes.

A wide variety of multipurpose vectors suitable for the expression of heterologous proteins are known to those of skill in the art and are commercially available. Expression vectors containing inducible promoters or constitutive promoters that are linked to regulatory regions are preferred. Such promoters include, but are not limited to, the T7 phage promoter and other T7-like phage promoters, such as the T3, T5 and SP6 promoters, the trp, lpp, tet and lac promoters, such as the lacUV5, from *E. coli*; the SV40 promoter; the P10 or polyhedron gene promoter of baculovirus/insect cell expression systems, retroviral long-terminal repeats and inducible promoters from other eukaryotic expression systems.

Particularly preferred vectors for recombinant expression of *Renilla mulleri* in prokaryotic organisms are lac- and T7 promoter-based vectors, such as the well known Bluescript vectors, which are commercially available (Stratagene, La Jolla, Calif.).

3. Host Organisms for Recombinant Production of *Renilla* Proteins

Host organisms include those organisms in which recombinant production of heterologous proteins have been carried out, such as, but not limited to, bacteria (for example, *E. coli*), yeast (for example, *Saccharomyces cerevisiae* and *Pichia pastoris*), fungi, baculovirus/insect systems, amphibian cells, mammalian cells, plant cells and insect cells. Presently preferred host organisms are strains of bacteria or yeast. Most preferred host organisms are strains of *E. coli* or *Saccharomyces cerevisiae*.

4. Methods for Recombinant Production of *Renilla* Proteins

The DNA encoding a *Renilla* GFP or *Renilla mulleri* luciferase is introduced into a plasmid in operative linkage to an appropriate promoter for expression of polypeptides in a selected host organism. The DNA molecule encoding the *Renilla* GFP or luciferase may also include a protein secretion signal that functions in the selected host to direct the mature polypeptide into the periplasm or culture medium. The resulting *Renilla* GFP or luciferase can be purified by methods routinely used in the art, including methods described hereinafter in the Examples.

Methods of transforming suitable host cells, preferably bacterial cells, and more preferably *E. coli* cells, as well as methods applicable for culturing said cells containing a gene encoding a heterologous protein, are generally known in the art. See, for example, Sambrook et al. (1989) *Molecular Cloning: A Laboratory Manual*, Cold Spring Harbor Laboratory Press, Cold Spring Harbor, N.Y.

Once the *Renilla*-encoding DNA molecule has been introduced into the host cell, the desired *Renilla* GFP is produced by subjecting the host cell to conditions under which the promoter is induced, whereby the operatively linked DNA is transcribed. The cellular extracts of lysed cells containing the protein may be prepared and the resulting "clarified lysate" was employed as a source of recombinant *Renilla* GFP or *Renilla mulleri* luciferase. Alternatively, the lysate may be subjected to additional purification steps (e.g., ion exchange chromatography or immunoaffinity chromatography) to further enrich the lysate or provide a homogeneous source of the purified enzyme (see e.g., U.S. Pat. Nos. 5,292,658 and 5,418,155).

5. Recombinant Cells Expressing Heterologous Nucleic Acid Encoding *Renilla* GFP Cells, vectors and methods are described with respect to *Renilla*. The same cells, vectors and methods may be used for expressing luciferases and other GFPs from species including *Gaussia, Pleuromamma* and *Ptilosarcus*.

Recombinant cells containing heterologous nucleic acid encoding a *Renilla reniformis* GFP are provided. In preferred embodiments, the recombinant cells express the encoded *Renilla* GFP which is functional and non-toxic to the cell.

In certain embodiments, the recombinant cells may also include heterologous nucleic acid encoding a component of a bioluminescence-generating system, preferably a photoprotein of luciferase. In preferred embodiments, the nucleic acid encoding the bioluminescence-generating system component is isolated from the species *Aequorea, Vargula* or *Renilla*. In more preferred embodiments, the bioluminescence-generating system component is *Renilla mulleri* luciferase having the amino acid sequence set forth in SEQ ID NO. 18.

Recombinant host cells containing heterologous nucleic acid encoding a *Renilla mulleri* luciferase are also provided. In preferred embodiments, the heterologous nucleic acid encodes the sequence of amino acids as set forth in SEQ ID NO. 18. In more preferred embodiments, the heterologous nucleic acid encodes the sequence of nucleotides set forth in SEQ ID NO. 17.

Exemplary cells include bacteria (e.g., *E. coli*), plant cells, cells of mammalian origin (e.g., COS cells, mouse L cells, Chinese hamster ovary (CHO) cells, human embryonic kidney (HEK) cells, African green monkey cells and other such cells known to those of skill in the art), amphibian cells (e.g., *Xenopus laevis* oöcytes), yeast cells (e.g., *Saccharomyces cerevisiae, Pichia pastoris*), and the like. Exemplary cells for expressing injected RNA transcripts include *Xenopus laevis* oöcytes. Eukaryotic cells that are preferred for transfection of DNA are known to those of skill in the art or may be empirically identified, and include HEK293 (which are available from ATCC under accession #CRL 1573); Ltk⁻ cells (which are available from ATCC under accession #CCL1.3); COS-7 cells (which are available from ATCC under accession #CRL 1651); and DG44 cells (dhfr⁻ CHO cells; see, e.g., Urlaub et al. (1986) *Cell. Molec. Genet.* 12:555). Presently preferred cells include strains of bacteria and yeast.

The recombinant cells that contain the heterologous DNA encoding the *Renilla* GFP are produced by transfection with DNA encoding a *Renilla* GFP or luciferase or by introduction of RNA transcripts of DNA encoding a *Renilla* proteins using methods well known to those of skill in the art. The DNA may be introduced as a linear DNA fragment or may be included in an expression vector for stable or transient expression of the encoding DNA. The sequences set forth herein for *Renilla reniformis* GFP are presently preferred (see SEQ ID NOs. 23–25 and 27; see, also SEQ ID NO. 26, which sets forth human optimized codons).

Heterologous DNA may be maintained in the cell as an episomal element or may be integrated into chromosomal DNA of the cell. The resulting recombinant cells may then be cultured or subcultured (or passaged, in the case of mammalian cells) from such a culture or a subculture thereof. Also, DNA may be stably incorporated into cells or may be transiently expressed using methods known in the art.

The recombinant cells can be used in a wide variety of cell-based assay methods, such as those methods described for cells expressing wild type or modified *A. victoria* GFPs or GFP fusion proteins (e.g., see U.S. Pat. No. 5,625,048; International patent application Publication Nos. WO 95/21191; WO 96/23810; WO 96/27675; WO 97/26333; WO 97/28261; WO 97/41228; and WO 98/02571).

F. Compositions and Conjugates

Compositions and conjugates and methods of use are described with reference to *Renilla* proteins and nucleic acids. The same compositions and methods for preparation and use thereof are intended for use with other luciferases, such as *Pleuromamma* and *Ptilosarcus* proteins and nucleic acids.

1. *Renilla* GFP Compositions

Compositions containing a *Renilla* GFP or GFP peptide are provided. The compositions can take any of a number of forms, depending on the intended method of use therefor. In certain embodiments, for example, the compositions contain a *Renilla* GFP or GFP peptide, preferably *Renilla mulleri* GFP or *Renilla reniformis* GFP peptide, formulated for use in luminescent novelty items, immunoassays, FRET and FET assays. The compositions may also be used in conjunction with multi-well assay devices containing integrated photodetectors, such as those described herein.

Compositions that contain a *Renilla mulleri* GFP or GFP peptide and at least one component of a bioluminescence-generating system, preferably a luciferase, luciferin or a luciferase and a luciferin, are provided. In preferred embodiments, the luciferase/luciferin bioluminescence-generating system is selected from those isolated from: an insect system, a coelenterate system, a ctenophore system, a bacterial system, a mollusk system, a crustacea system, a fish system, an annelid system, and an earthworm system. Presently preferred bioluminescence-generating systems are those isolated from *Renilla, Aequorea*, and *Vargula*.

In more preferred embodiments, the bioluminescence-generating system component is a *Renilla mulleri* luciferase having the amino acid sequence set forth in SEQ ID NO. 18 or a *Renilla reniformis* luciferase. These compositions can be used in a variety of methods and systems, such as included in conjunction with diagnostic systems for the in vivo detection of neoplastic tissues and other tissues, such as those methods described in detail below.

These methods and products include any known to those of skill in the art in which luciferase is used, including, but not limited to U.S. application Ser. Nos. 08/757,046, 08/597, 274 and 08/990,103, U.S. Pat. No. 5,625,048; International patent application Publication Nos. WO 95/21191; WO 96/23810; WO 96/27675; WO 97/26333; WO 97/28261; WO 97/41228; and WO 98/02571).

2. *Renilla* Luciferase Compositions

DNA encoding the *Renilla mulleri* luciferase or *Renilla reniformis* luciferase is used to produce the encoded luciferase, which has diagnostic applications as well as use as a component of the bioluminescence generating systems as described herein, such as in beverages, and methods of diagnosis of neoplasia and in the diagnostic chips described herein. These methods and products include any known to those of skill in the art in which luciferase is used, including, but not limited to, U.S. application Ser. Nos. 08/757,046, 08/597,274 and 08/990,103, U.S. Pat. No. 5,625,048; International patent application Publication Nos. WO 95/21191; WO 96/23810; WO 96/27675; WO 97/26333; WO 97/28261; WO 97/41228; and WO 98/02571).

In other embodiments, the *Renilla* luciferase and the remaining components may be packaged as separate compositions, that, upon mixing, glow. For example, a composition containing *Renilla* luciferase may be provided separately from, and for use with, a separate composition containing a bioluminescence substrate and bioluminescence activator. In another instance, luciferase and luciferin compositions may be separately provided and the bioluminescence activator may be added after, or simultaneously with, mixing of the other two compositions.

3. Conjugates

Conjugates are provided herein for a variety of uses. Among them are for targeting to tumors for visualization of the tumors, particularly in situ during surgery. A general description of these conjugates and the uses thereof is described in allowed U.S. application Ser. No. 08/908,909. In practice, prior to a surgical procedure, the conjugate is administered via any suitable route, whereby the targeting agent binds to the targeted tissue by virtue of its specific interaction with a tissue-specific cell surface protein. During surgery the tissue is contacted, with the remaining component(s), typically by spraying the area or local injection, and any tissue to which conjugate is bound will glow. The glow should be sufficient to see under dim light or, if necessary, in the dark.

The conjugates that are provided herein contain a targeting agent, such as a tissue specific or tumor specific monoclonal antibody or fragment thereof linked either directly or via a linker to a targeted agent, a *Renilla* GFP, *Renilla* or Gaussia luciferase and other luciferases (including photoproteins or luciferase enzymes) or a luciferin. The targeted agent may be coupled to a microcarrier. The linking is effected either chemically, by recombinant expression of a fusion protein in instances when the targeted agent is a protein, and by combinations of chemical and recombinant expression. The targeting agent is one that will preferentially bind to a selected tissue or cell type, such as a tumor cell surface antigen or other tissue specific antigen.

Methods for preparing conjugates are known to those of skill in the art. For example, aequorin that is designed for conjugation and conjugates containing such aequorin have been produced (see, e.g., International PCT application No. WO 94/18342; see, also Smith et al. (1995) in *American Biotechnology Laboratory*). Aequorin has been conjugated to an antibody molecule by means of a sulfhydryl-reacting binding agent (Stultz et al. (1992) Use of Recombinant Biotinylated Apoaequorin from *Escherichia coli*. Biochemistry 31, 1433–1442). Such methods may be adapted for use herein to produce the luciferase coupled to protein or other such molecules, which are useful as targeting agents. *Vargula* luciferase has also been linked to other molecules (see, e.g., Japanese application No. JP 5064583, Mar. 19, 1993). Such methods may be adapted for use herein to produce luciferase coupled to molecules that are useful as targeting agents.

The conjugates can be employed to detect the presence of or quantitate a particular antigen in a biological sample by direct correlation to the light emitted from the bioluminescent reaction.

As an alternative, a component of the bioluminescence generating system may be modified for linkage, such as by addition of amino acid residues that are particularly suitable for linkage to the selected substrate. This can be readily effected by modifying the DNA and expressing such modified DNA to produce luciferase with additional residues at the N- or C-terminus.

Methods for preparing conjugates are known to those of skill in the art. For example, aequorin that is designed for conjugation and conjugates containing such aequorin have been produced (see, e.g., International PCT application No. WO 94/18342; see, also Smith et al. (1995) in *American Biotechnology Laboratory*). Aequorin has been conjugated to an antibody molecule by means of a sulfhydryl-reacting binding agent (Stultz et al. (1992) Use of Recombinant Biotinylated Apoaequorin from *Escherichia coli*. Biochemistry 31, 1433–1442). Such methods may be adapted for use herein to produce aequorin coupled to protein or other such molecules, which are useful as targeting agents. *Vargula* luciferase has also been linked to other molecules (see, e.g., Japanese application No. JP 5064583, Mar. 19, 1993). Such methods may be adapted for use herein to produce aequorin coupled to protein or other such molecules, which are useful as targeting agents. The bioluminescence generating reactions are used with the *Renilla reniformis* GFP provided herein.

a. Linkers

Any linker known to those of skill in the art may be used herein. Other linkers are suitable for incorporation into chemically produced conjugates. Linkers that are suitable for chemically linked conjugates include disulfide bonds, thioether bonds, hindered disulfide bonds, and covalent bonds between free reactive groups, such as amine and thiol groups. These bonds are produced using heterobifunctional reagents to produce reactive thiol groups on one or both of the polypeptides and then reacting the thiol groups on one polypeptide with reactive thiol groups or amine groups to which reactive maleimido groups or thiol groups can be attached on the other. Other linkers include, acid cleavable linkers, such as bismaleimideothoxy propane, acid labile-transferrin conjugates and adipic acid diihydrazide, that would be cleaved in more acidic intracellular compartments; cross linkers that are cleaved upon exposure to UV or visible light and linkers, such as the various domains, such as $C_H1$, $C_H2$, and $C_H3$, from the constant region of human $IgG_1$ (see, Batra et al. (1993) *Molecular Immunol.* 30:379–386). In some embodiments, several linkers may be included in order to take advantage of desired properties of each linker.

Chemical linkers and peptide linkers may be inserted by covalently coupling the linker to the TA and the targeted agent. The heterobifunctional agents, described below, may be used to effect such covalent coupling. Peptide linkers may also be linked by expressing DNA encoding the linker and TA, linker and targeted agent, or linker, targeted agent and TA as a fusion protein.

Flexible linkers and linkers that increase solubility of the conjugates are contemplated for use, either alone or with other linkers are contemplated herein.

Numerous heterobifunctional cross-linking reagents that are used to form covalent bonds between amino groups and thiol groups and to introduce thiol groups into proteins, are known to those of skill in this art (see, e.g., the PIERCE CATALOG, ImmunoTechnology Catalog & Handbook, 1992–1993, which describes the preparation of and use of such reagents and provides a commercial source for such reagents; see, also, e.g., Cumber et al. (1992) *Bioconjugate Chem.* 3:397–401; Thorpe et al. (1987) *Cancer Res.* 47:5924–5931; Gordon et al. (1987) *Proc. Natl. Acad. Sci.* 84:308–312; Walden et al. (1986) *J. Mol. Cell Immunol.* 2:191–197; Carlsson et al. (1978) *Biochem. J.* 173: 723–737; Mahan et al. (1987) *Anal. Biochem.* 162:163–170; Wawryznaczak et al. (1992) *Br. J. Cancer* 66:361–366; Fattom et al. (1992) *Infection & Immun.* 60:584–589). These reagents may be used to form covalent bonds between the TA and targeted agent. These reagents include, but are not limited to: N-succinimidyl-3-(2-pyridyldithio)propionate (SPDP; disulfide linker); sulfosuccinimidyl 6-(3-(2-pyridyidithio)propionamido)hexanoate (sulfo-LC-SPDP); succinimidyloxycarbonyl-α-methyl benzyl thiosulfate (SMBT, hindered disulfate linker); succinimidyl 6-(3-(2-pyridyidithio) propionamido)hexanoate (LC-SPDP); sulfo-succinimidyl 4-(N-maleimidomethyl)cyclohexane-1-carboxylate (sulfo-SMCC); succinimidyl 3-(2-pyridyidithio)-butyrate (SPDB; hindered disulfide bond linker); sulfosuccinimidyl 2-(7-azido-4-methylcoumarin-3-acetamide) ethyl-1,3'-dithiopropionate (SAED); sulfo-succinimidyl 7-azido-4-methylcoumarin-3-acetate (SAMCA); sulfosuccinimidyl 6-(alpha-methyl-alpha-(2-pyridyldithio)toluamido)-hexanoate (sulfo-LC-SMPT); 1,4-di-(3'-(2'-pyridyidithio)propion-amido)butane (DPDPB); 4-succinimidyloxycarbonyl-α-methyl-α-(2-pyridylthio) toluene (SMPT, hindered disulfate linker); sulfosuccinimidyl6(α-methyl-α-(2-pyridyldithio) toluamido)hexanoate (sulfo-LC-SMPT); m-maleimidobenzoyl-N-hydroxysuccinimide ester (MBS); m-maleimidobenzoyl-N-hydroxysulfosuccinimide ester (sulfo-MBS); N-succinimidyl(4-iodoacetyl)aminobenzoate (SIAB; thioether linker); sulfosuccinimidyl(4-iodoacetyl) amino benzoate (sulfo-SIAB); succinimidyl4(p-maleimidophenyl)butyrate (SMPB); sulfosuccinimidyl4-(p-maleimidophenyl)butyrate (sulfo-SMPB); azidobenzoyl hydrazide (ABH).

Acid cleavable linkers, photocleavable and heat sensitive linkers may also be used, particularly where it may be necessary to cleave the targeted agent to permit it to be more readily accessible to reaction. Acid cleavable linkers include, but are not limited to, bismaleimideothoxy propane; and adipic acid dihydrazide linkers (see, e.g., Fattom et al. (1992) *Infection & Immun.* 60:584–589) and acid labile transferrin conjugates that contain a sufficient portion of transferrin to permit entry into the intracellular transferrin cycling pathway (see, e.g., Welhöner et al. (1991) *J. Biol. Chem.* 266:4309–4314).

Photocleavable linkers are linkers that are cleaved upon exposure to light (see, e.g., Goldmacher et al. (1992) *Bioconj. Chem.* 3:104–107, which linkers are herein incorporated by reference), thereby releasing the targeted agent upon exposure to light. Photocleavable linkers that are cleaved upon exposure to light are known (see, e.g., Hazum et al. (1981) in *Pept., Proc. Eur. Pept. Symp.*, 16th, Brunfeldt, K (Ed), pp. 105–110, which describes the use of a nitrobenzyl group as a photocleavable protective group for cysteine; Yen et al. (1989) *Makromol. Chem* 190:69–82, which describes water soluble photocleavable copolymers, including hydroxypropylmethacrylamide copolymer, glycine copolymer, fluorescein copolymer and methylrhodamine copolymer; Goldmacher et al. (1992) *Bioconj. Chem.* 3:104–107, which describes a cross-linker and reagent that undergoes photolytic degradation upon exposure to near UV light (350 nm); and Senter et al. (1985) *Photochem. Photobiol* 42:231–237, which describes nitrobenzyloxycarbonyl chloride cross linking reagents that produce photocleavable linkages), thereby releasing the targeted agent upon exposure to light. Such linkers would have particular use in treating dermatological or ophthalmic conditions that can be exposed to light using fiber optics. After administration of the conjugate, the eye or skin or other body part can be exposed to light, resulting in release of the targeted moiety from the conjugate. Such photocleavable linkers are useful in connection with diagnostic protocols in which it is desirable to remove the targeting agent to permit rapid clearance from the body of the animal.

b. Targeting Agents

Targeting agents include any agent that will interact with and localize the targeted agent cells in a tumor or specialized tissue (targeted tissue). Such agents include any agent that specifically interacts with a cell surface protein or receptor that is present at sufficiently higher concentrations or amounts on the targeted tissue, whereby, when contacted with an appropriate bioluminescence generating reagent and activators produces light. These agents include, but are not limited to, growth factors, preferentially modified to not internalize, methotrexate, and antibodies, particularly, antibodies raised against tumor specific antigens. A plethora of tumor-specific antigens have been identified from a number of human neoplasms.

c. Anti-Tumor Antigen Antibodies

Polyclonal and monoclonal antibodies may be produced against selected antigens. Alternatively, many such antibodies are presently available. An exemplary list of antibodies and the tumor antigen for which each has been directed against is provided in U.S. application Ser. No. 08/908,909, which is incorporated by reference in its entirety. It is contemplated that any of the antibodies listed may be conjugated with a bioluminescence generating component following the methods provided herein.

Among the preferred antibodies for use in the methods herein are those of human origin or, more preferably, are humanized monoclonal antibodies. These are preferred for diagnosis of humans.

d. Preparation of the Conjugates

The methods for preparation of the conjugates for use in the tumor diagnostic methods can be used for preparation of the fusion proteins and conjugated proteins for use in the BRET system desribed below. Any method for linking proteins may be used. For example, methods for linking a luciferase to an antibody is described in U.S. Pat. No. 5,486,455. As noted above, the targeting agent and luciferin or luciferase may be linked directly, such as through covalent bonds, i.e., sulfhyryl bonds or other suitable bonds, or they may be linked through a linker. There may be more than one luciferase or luciferin per targeting agent, or more than one targeting agent per luciferase or luciferin.

Alternatively, an antibody, or F(Ab)$_2$ antigen-binding fragment thereof of other protein targeting agent may be fused (directly or via a linking peptide) to the luciferase using recombinant DNA technology. For example, the DNA encoding any of the anti-tumor antibodies of Table 3 may be ligated in the same translational reading frame to DNA encoding any of the above-described luciferases, e.g., SEQ ID NOs. 1–14 and inserted into an expression vector. The DNA encoding the recombinant antibody-luciferase fusion may be introduced into an appropriate host, such as bacteria or yeast, for expression.

4. Formulation of the Compositions for Use in the Diagnostic Systems

In most embodiments, the *Renilla* GFPS and components of the diagnostic systems provided herein, such as *Renilla* luciferase, are formulated into two compositions: a first composition containing the conjugate; and a second composition containing the remaining components of the bioluminescence generating system. The compositions are formulated in any manner suitable for administration to an animal, particularly a mammal, and more particularly a human. Such formulations include those suitable for topical, local, enteric, parenteral, intracystal, intracutaneous, intravitreal, subcutaneous, intramuscular, or intravenous administration.

For example, the conjugates, which in preferred embodiments, are a targeting agent linked to a luciferase (or photoprotein) are formulated for systemic or local administration. The remaining components are formulated in a separate second composition for topical or local application. The second composition will typically contain any other agents, such as spectral shifters that will be included in the reaction. It is preferred that the components of the second composition are formulated in a time release manner or in some other manner that prevents degradation and/or interaction with blood components.

a. The First Composition: Formulation of the Conjugates

As noted above, the conjugates either contain a luciferase or luciferin and a targeting agents. The preferred conjugates are formed between a targeting agent and a luciferase, particularly the *Gaussia*, *Renilla mulleri* or *Pleuromamma* luciferase. The conjugates may be formulated into pharmaceutical compositions suitable for topical, local, intravenous and systemic application. Effective concentrations of one or more of the conjugates are mixed with a suitable pharmaceutical carrier or vehicle. The concentrations or amounts of the conjugates that are effective requires delivery of an amount, upon administration, that results in a sufficient amount of targeted moiety linked to the targeted cells or tissue whereby the cells or tissue can be visualized during the surgical procedure. Typically, the compositions are formulated for single dosage administration. Effective concentrations and amounts may be determined empirically by testing the conjugates in known in vitro and in vivo systems, such as those described here; dosages for humans or other animals may then be extrapolated therefrom.

Upon mixing or addition of the conjugate(s) with the vehicle, the resulting mixture may be a solution, suspension, emulsion or the like. The form of the resulting mixture depends upon a number of factors, including the intended mode of administration and the solubility of the conjugate in the selected carrier or vehicle. The effective concentration is sufficient for targeting a sufficient amount of targeted agent to the site of interest, whereby when combined with the remaining reagents during a surgical procedure the site will glow. Such concentration or amount may be determined based upon in vitro and/or in vivo data, such as the data from the mouse xenograft model for tumors or rabbit ophthalmic model. If necessary, pharmaceutically acceptable salts or other derivatives of the conjugates may be prepared.

Pharmaceutical carriers or vehicles suitable for administration of the conjugates provided herein include any such carriers known to those skilled in the art to be suitable for the particular mode of administration. In addition, the conjugates may be formulated as the sole pharmaceutically ingredient in the composition or may be combined with other active ingredients.

The conjugates can be administered by any appropriate route, for example, orally, parenterally, intravenously, intradermally, subcutaneously, or topically, in liquid, semi-liquid or solid form and are formulated in a manner suitable for each route of administration. Intravenous or local administration is presently preferred. Tumors and vascular proliferative disorders, will typically be visualized by systemic, intradermal or intramuscular, modes of administration.

The conjugate is included in the pharmaceutically acceptable carrier in an amount sufficient to produce detectable tissue and to not result in undesirable side effects on the patient or animal. It is understood that number and degree of side effects depends upon the condition for which the conjugates are administered. For example, certain toxic and undesirable side effects are tolerated when trying to diagnose life-threatening illnesses, such as tumors, that would not be tolerated when diagnosing disorders of lesser consequence.

The concentration of conjugate in the composition will depend on absorption, inactivation and excretion rates thereof, the dosage schedule, and amount administered as well as other factors known to those of skill in the art. Typically an effective dosage should produce a serum concentration of active ingredient of from about 0.1 ng/ml to about 50–1000 μg/ml, preferably 50–100 μg/ml. The pharmaceutical compositions typically should provide a dosage of from about 0.01 mg to about 100–2000 mg of conjugate, depending upon the conjugate selected, per kilogram of body weight per day. Typically, for intravenous administration a dosage of about between 0.05 and 1 mg/kg should be sufficient. Local application for, such as visualization of ophthalmic tissues or local injection into joints, should provide about 1 ng up to 1000 μg, preferably about 1 μg to about 100 μg, per single dosage administration. It is understood that the amount to administer will be a function of the conjugate selected, the indication, and possibly the side effects that will be tolerated. Dosages can be empirically determined using recognized models.

The active ingredient may be administered at once, or may be divided into a number of smaller doses to be administered at intervals of time. It is understood that the precise dosage and duration of administration is a function of the disease condition being diagnosed and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Solutions or suspensions used for parenteral, intradermal, subcutaneous, or topical application can include any of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parental preparations can be enclosed in ampules, disposable syringes or multiple dose vials made of glass, plastic or other suitable material.

If administered intravenously, suitable carriers include physiological saline or phosphate buffered saline (PBS), and solutions containing thickening and solubilizing agents, such as glucose, polyethylene glycol, and polypropylene glycol and mixtures thereof. Liposomal suspensions may also be suitable as pharmaceutically acceptable carriers. These may be prepared according to methods known to those skilled in the art.

The conjugates may be prepared with carriers that protect them against rapid elimination from the body, such as time release formulations or coatings. Such carriers include controlled release formulations, such as, but not limited to, implants and microencapsulated delivery systems, and biodegradable, biocompatible polymers, such as ethylene vinyl acetate, polyanhydrides, polyglycolic acid, polyorthoesters, polylacetic acid and others.

The conjugates may be formulated for local or topical application, such as for topical application to the skin and mucous membranes, such as in the eye, in the form of gels, creams, and lotions and for application to the eye or for intracisternal or intraspinal application. Such solutions, particularly those intended for ophthalmic use, may be formulated as 0.01%–10% isotonic solutions, pH about 5–7, with appropriate salts. The ophthalmic compositions may also include additional components, such as hyaluronic acid. The conjugates may be formulated as aerosols for topical application (see, e.g., U.S. Pat. Nos. 4,044,126, 4,414,209, and 4,364,923).

Also, the compositions for activation of the conjugate in vivo during surgical procedures may be formulated as an aerosol. These compositions contain the activators and also the remaining bioluminescence generating agent, such as luciferin, where the conjugate targets a luciferase, or a luciferase, where the conjugate targets a luciferin, such as coelenterazine.

If oral administration is desired, the conjugate should be provided in a composition that protects it from the acidic environment of the stomach. For example, the composition can be formulated in an enteric coating that maintains its integrity in the stomach and releases the active compound in the intestine. Oral compositions will generally include an inert diluent or an edible carrier and may be compressed into tablets or enclosed in gelatin capsules. For the purpose of oral administration, the active compound or compounds can be incorporated with excipients and used in the form of tablets, capsules or troches. Pharmaceutically compatible binding agents and adjuvant materials can be included as part of the composition.

Tablets, pills, capsules, troches and the like can contain any of the following ingredients, or compounds of a similar nature: a binder, such as microcrystalline cellulose, gum tragacanth and gelatin; an excipient such as starch and lactose, a disintegrating agent such as, but not limited to, alginic acid and corn starch; a lubricant such as, but not limited to, magnesium stearate; a glidant, such as, but not limited to, colloidal silicon dioxide; a sweetening agent such as sucrose or saccharin; and a flavoring agent such as peppermint, methyl salicylate, and fruit flavoring.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The conjugates can also be administered as a component of an elixir, suspension, syrup, wafer, chewing gum or the like. A syrup may contain, in addition to the active compounds, sucrose as a sweetening agent and certain preservatives, dyes and colorings and flavors.

The active materials can also be mixed with other active materials that do not impair the desired action, or with materials that supplement the desired action, such as cisplatin for treatment of tumors.

Finally, the compounds may be packaged as articles of manufacture containing packaging material, one or more conjugates or compositions as provided herein within the packaging material, and a label that indicates the indication for which the conjugate is provided.

b. The Second Composition

The second composition will include the remaining components of the bioluminescence generating reaction. In preferred embodiments in which these components are administered systemically, the remaining components include the luciferin or substrate, and optionally additional agents, such as spectral shifters, particularly the GFPs provided herein. These components, such as the luciferin, can be formulated as described above for the conjugates. In some embodiments, the luciferin or luciferase in this composition will be linked to a protein carrier or other carrier to prevent degradation or dissolution into blood cells or other cellular components.

For embodiments, in which the second composition is applied locally or topically, they can be formulated in a spray or aerosol or other suitable means for local or topical application.

In certain embodiments described herein, all components, except an activator are formulated together, such as by encapsulation in a time release formulation that is targeted to the tissue. Upon release the composition will have been localized to the desired site, and will begin to glow.

In practice, the two compositions can be administered simultaneously or sequentially. Typically, the first composition, which contains the conjugate is administered first, generally an hour or two before the surgery, and the second composition is then administered, either preoperatively or during surgery.

The conjugates that are provided herein contain a targeting agent, such as a tissue specific or tumor specific monoclonal antibody or fragment thereof linked either directly or via a linker to a targeted agent, a luciferase (including photoproteins or luciferase enzymes) or a luciferin. The targeted agent may be coupled to a microcarrier. The linking is effected either chemically, by recombinant expression of a fusion protein in instances when the targeted agent is a protein, and by combinations of chemical and recombinant expression. The targeting agent is one that will preferentially bind to a selected tissue or cell type, such as a tumor cell surface antigen or other tissue specific antigen.

Methods for preparing conjugates are known to those of skill in the art. For example, aequorin that is designed for conjugation and conjugates containing such aequorin have been produced (see, e.g., International PCT application No. WO 94/18342; see, also Smith et al. (1995) in *American Biotechnology Laboratory*). Aequorin has been conjugated to an antibody molecule by means of a sulfhydryl-reacting binding agent (Stultz et al. (1992) Use of Recombinant Biotinylated Apoaequorin from *Escherichia coli* (*Biochemistry* 31:1433–1442). Such methods may be adapted for use herein to produce aequorin coupled to protein or other such molecules, which are useful as targeting agents. Vargula luciferase has also been linked to other molecules (see, e.g., Japanese application No. JP 5064583, Mar. 19, 1993). Such methods may be adapted for use herein to produce aequorin coupled to protein or other such molecules, which are useful as targeting agents.

Aequorin-antibody conjugates have been employed to detect the presence of or quantitate a particular antigen in a biological sample by direct correlation to the light emitted from the bioluminescent reaction.

As an alternative, the *Renilla* GFP or *Renilla mulleri* or *Gaussia* luciferase or a component of the bioluminescence generating system may be modified for linkage, such as by addition of amino acid residues that are particularly suitable for linkage to the selected substrate. This can be readily effected by modifying the DNA and expressing such modified DNA to produce luciferase with additional residues at the N- or C-terminus.

Selection of the system depends upon factors such as the desired color and duration of the bioluminescence desired as well as the particular item. Selection of the targeting agent primarily depends upon the type and characteristics of neoplasia or tissue to be visualized and the setting in which visualization will be performed.

The *Renilla reniformis* GFP is added to one or both compositions to act as a spectral shifter.

c. Practice of the Reactions in Combination with Targeting Agents

The particular manner in which each bioluminescence system will be combined with a selected targeting agent will be a function of the agent and the neoplasia or tissue to be visualized. In general, however, a luciferin, *Renilla* GFP, *Renilla mulleri, Pleuromamma* or *Gaussia* luciferase or other luciferase, of the reaction will be conjugated to the targeting agent, administered to an animal prior to surgery. During the surgery, the tissues of interest are contacted with the remaining component(s) of a bioluminescence generating system. Any tissue to which or with which the targeting agent reacts will glow.

Any color of visible light produced by a bioluminescence generating system is contemplated for use in the methods herein. Preferably the visible light is a combination of blue, green and/or red light of varying intensities and wavelengths. For visualizing neoplasia or specialty tissues through mammalian tissues or tumors deeply embedded in tissue, longer wavelengths of visible light, i.e., red and near infrared light, is preferred because wavelengths of near infrared light of about 700–1300 nm are known to penetrate soft tissue and bone (e.g., see U.S. Pat. No. 4,281,645).

In other embodiments, the conjugate can be applied to the tissues during surgery, such as by spraying a sterile solution over the tissues, followed by application of the remaining components. Tissues that express the targeted antigen will glow.

The reagents may be provided in compositions, such as suspensions, as powders, as pastes or any in other suitable sterile form. They may be provided as sprays, aerosols, or in any suitable form. The reagents may be linked to a matrix, particularly microbeads suitable for in vivo use and of size that they pass through capillaries. Typically all but one or more, though preferably all but one, of the components necessary for the reaction will be mixed and provided together; reaction will be triggered contacting the mixed component(s) with the remaining component(s), such as by adding $Ca^{2+}$, FMN with reductase, $FMNH_2$, ATP, air or oxygen.

In preferred embodiments the luciferase or luciferase/luciferin will be provided in combination with the targeting agent before administration to the patient. The targeting agent conjugate will then be contacted in vivo with the remaining components. As will become apparent herein, there are a multitude of ways in which each system may be combined with a selected targeting agent.

G. Combinations

*Renilla reniformis* GFP can be used in combination with articles of manufacture to produce novelty items. The *Renilla reniformis* GFP can be used with a bioluminescence generating system. Such items and methods for preparation are described in detail in U.S. Pat. Nos. 5,876,995, 6,152,358 and 6,113,886) These novelty items, which are articles of manufacture, are designed for entertainment, recreation and amusement, and include, but are not limited to: toys, particularly squirt guns, toy cigarettes, toy "Halloween" eggs, footbags and board/card games; finger paints and other paints, slimy play material; textiles, particularly clothing, such as shirts, hats and sports gear suits, threads and yarns; bubbles in bubble making toys and other toys that produce bubbles; balloons; figurines; personal items, such as bath powders, body lotions, gels, powders and creams, nail polishes, cosmetics including make-up, toothpastes and other dentifrices, soaps, body paints, and bubble bath; items such as fishing lures, inks, paper; foods, such as gelatins, icings and frostings; fish food containing luciferins and transgenic fish, particularly transgenic fish that express a luciferase; plant food containing a luciferin or luciferase, preferably a luciferin for use with transgenic plants that express luciferase; and beverages, such as beer, wine, champagne, soft drinks, and ice cubes and ice in other configurations; fountains, including liquid "fireworks" and other such jets or sprays or aerosols of compositions that are solutions, mixtures, suspensions, powders, pastes, particles or other suitable form.

Any article of manufacture that can be combined with a bioluminescence-generating system as provided herein and thereby provide entertainment, recreation and/or amusement, including use of the items for recreation or to attract attention, such as for advertising goods and/or services that are associated with a logo or trademark is contemplated herein. Such uses may be in addition to or in conjunction with or in place of the ordinary or normal use of such items. As a result of the combination, the items glow or produce, such as in the case of squirt guns and fountains, a glowing fluid or spray of liquid or particles.

H. Exemplary Uses of *Renilla reniformis* GFPs and Encoding Nucleic Acid Molecules 1. Methods for Diagnosis of Neoplasms and Other Tissues Methods for diagnosis and visualization of tissues in vivo or in situ, preferably neoplastic tissue, using compositions containing a *Renilla mulleri* or *Ptilosarcus* GFP and/or a *Renilla mulleri*, *Pleuromamma* or *Gaussia* luciferase are provided. For example, the *Renilla mulleri* GFP protein can be used in conjunction with diagnostic systems that rely on bioluminescence for visualizing tissues in situ, such as those described in co-pending application Ser. No. 08/908,909. The systems are particularly useful for visualizing and detecting neoplastic tissue and specialty tissue, such as during non-invasive and invasive procedures. The systems include compositions containing conjugates that include a tissue specific, particularly a tumor-specific, targeting agent linked to a targeted agent, such as a *Renilla reniformis* GFP, a luciferase or luciferin. The systems also include a second composition that contains the remaining components of a bioluminescence generating reaction and/or the GFP. In some embodiments, all components, except for activators, which are provided in situ or are present in the body or tissue, are included in a single composition.

In particular, the diagnostic systems include two compositions. A first composition that contains conjugates that, in preferred embodiments, include antibodies directed against tumor antigens conjugated to a component of the bioluminescence generating reaction, a luciferase or luciferin, preferably a luciferase are provided. In certain embodiments, conjugates containing tumor-specific targeting agents are linked to luciferases or luciferins. In other embodiments, tumor-specific targeting agents are linked to microcarriers that are coupled with, preferably more than one of the bioluminescence generating components, preferably more than one luciferase molecule.

The second composition contains the remaining components of a bioluminescence generating system, typically the luciferin or luciferase substrate. In some embodiments, these components, particularly the luciferin are linked to a protein, such as a serum albumin, or other protein carrier. The carrier and time release formulations, permit systemically administered components to travel to the targeted tissue without interaction with blood cell components, such as hemoglobin that deactivates the luciferin or luciferase.

2. Methods of Diagnosing Diseases

Methods for diagnosing diseases, particularly infectious diseases, using chip methodology, a luciferase/luciferin bioluminescence-generating system, including a *Gaussia*, *Pleuromamma* or *Renilla mulleri* luciferase plus a *Renilla reniformis* GFP, are provided. In particular, the chip includes an integrated photodetector that detects the photons emitted by the bioluminescence-generating system as shifted by the GFP. This chip device, which is described in copending U.S. application Ser. No. 08/990,103, which is published as International PCT application No. WO 98/26277, includes an integrated photodetector that detects the photons emitted by the bioluminescence generating system. The method may be practiced with any suitable chip device, including self-addressable and non-self addressable formats, that is modified as described herein for detection of generated photons by the bioluminescence generating systems. The chip device provided herein is adaptable for use in an array format for the detection and identification of infectious agents in biological specimens.

To prepare the chip, a suitable matrix for chip production is selected, the chip is fabricated by suitably derivatizing the matrix for linkage of macromolecules, and including linkage of photodiodes, photomultipliers CCD (charge coupled device) or other suitable detector, for measuring light production; attaching an appropriate macromolecule, such as a biological molecule or anti-ligand, e.g., a receptor, such as an antibody, to the chip, preferably to an assigned location thereon. Photodiodes are presently among the preferred detectors, and specified herein. It is understood, however, that other suitable detectors may be substituted therefor.

In one embodiment, the chip is made using an integrated circuit with an array, such as an X-Y array, of photodetectors, such as that described in co-pending U.S. application Ser. No. 08/990,103. The surface of circuit is treated to render it inert to conditions of the diagnostic assays for which the chip is intended, and is adapted, such as by derivatization for linking molecules, such as antibodies. A selected antibody or panel of antibodies, such as an antibody specific for particularly bacterial antigen, is affixed to the surface of the chip above each photodetector. After contacting the chip with a test sample, the chip is contacted with a second antibody linked to the GFP, such as the *Renilla* GFP, to form a chimeric antibody-GFP fusion protein or an antibody linked to a component of a bioluminescence generating system, such as a *Pleuromamma, Gaussia* or *R. mulleri* luciferase. The antibody is specific for the antigen. The remaining components of the bioluminescence generating reaction are added, and, if any of the antibodies linked to a component of a bioluminescence generating system are present on the chip, light will be generated and detected by the adjacent photodetector. The photodetector is operatively linked to a computer, which is programmed with information identifying the linked antibodies, records the event, and thereby identifies antigens present in the test sample.

3. Methods for Generating *Renilla mulleri* Luciferase, *Pleuromamma* Luciferase and *Gaussia* Luciferase Fusion Proteins with *Renilla reniformis* GFP.

Methods for generating GFP and luciferase fusion proteins are provided. The methods include linking DNA encoding a gene of interest, or portion thereof, to DNA encoding a *Renilla reniformis* GFP and a luciferase in the same translational reading frame. The encoded-protein of interest may be linked in-frame to the amino- or carboxyl-terminus of the GFP or luciferase. The DNA encoding the chimeric protein is then linked in operable association with a promoter element of a suitable expression vector. Alternatively, the promoter element can be obtained directly from the targeted gene of interest and the promoter-containing fragment linked upstream from the GFP or luciferase coding sequence to produce chimeric GFP proteins.

For example, a chimeric fusion containing the luciferase, preferably a *Renilla* luciferase, more preferably a *Renilla reniformis* luciferase, and *Renilla reniformis* GFP encoding DNA linked to the N-terminal portion of a cellulose binding domain is provided.

4. Cell-Based Assays for Identifying Compounds

Methods for identifying compounds using recombinant cells that express heterologous DNA encoding a *Renilla reniformis* GFP under the control of a promoter element of a gene of interest are provided. The recombinant cells can be used to identify compounds or ligands that modulate the level of transcription from the promoter of interest by measuring GFP-mediated fluorescence. Recombinant cells expressing chimeric GFPs may also be used for monitoring gene expression or protein trafficking, or determining the cellular localization of the target protein by identifying localized regions of GFP-mediated fluorescence within the recombinant cell.

I. Kits

"Kits may be prepared containing the *Renilla reniformis* GFP or the encoding nucleic acid molecules (see, SEQ ID NOs. 23–26) with or without components of a bioluminescence generating system for use in diagnostic and immunoassay methods and with the novelty items, including those described herein."

In one embodiment, the kits contain appropriate reagents and an article of manufacture for generating bioluminescence in combination with the article. These kits, for example, can be used with a bubble-blowing or producing toy or with a squirt gun. These kits can also include a reloading or charging cartridge.

In another embodiment, the kits are used for detecting and visualizing neoplastic tissue and other tissues and include a first composition that contains the *Renilla reniformis* GFP and a selected luciferase, such as a *Renilla mulleri, Renilla reniformis* or *Gaussia* luciferase, and a second that contains the activating composition, which contains the remaining components of the bioluminescence generating system and any necessary activating agents.

In other embodiments, the kits are used for detecting and identifying diseases, particularly infectious diseases, using multi-well assay devices and include a multi-well assay device containing a plurality of wells, each having an integrated photodetector, to which an antibody or panel of antibodies specific for one or more infectious agents are attached, and composition containing a secondary antibody, such as an antibody specific for the infectious agent that is linked, for example, to a *Renilla reniformis* GFP protein, a chimeric antibody-*Renilla reniformis* GFP fusion protein, $F(Ab)_2$ antibody fragment-*Renilla reniformis* GFP fusion protein or to such conjugates containing the, for example, *Gaussia* or *Renilla mulleri* or *reniformis*, luciferase. A second composition containing the remaining components of a bioluminescence generating system, such as system that emits a wavelength of light within the excitation range of the GFP, such as species of *Renilla* or *Aequorea*, for exciting the *Renilla* luciferase, which produces green light that is detected by the photodetector of the device to indicate the presence of the agent.

In further embodiments, the kits contain the components of the diagnostic systems. The kits comprise compositions containing the conjugates, preferably *Renilla* GFP and a *Gaussia*, or *Pleuromamma* or *Renilla mulleri* luciferase and remaining bioluminescence generating system components. The first composition in the kit typically contains the targeting agent conjugated to a GFP or luciferase. The second composition, contains at least the luciferin (substrate) and/or luciferase. Both compositions are formulated for systemic, local or topical application to a mammal. In alternative embodiments, the first composition contains the luciferin linked to a targeting agent, and the second composition contains the luciferase or the luciferase and a GFP.

In general, the packaging is non-reactive with the compositions contained therein and where needed should exclude water and or air to the degree those substances are required for the luminescent reaction to proceed.

Diagnostic applications may require specific packaging. The bioluminescence generating reagents may be provided in pellets, encapsulated as micro or macro-capsules, linked to matrices, preferably biocompatible, more preferably biodegradable matrices, and included in or on articles of manufacture, or as mixtures in chambers within an article of manufacture or in some other configuration. For example, a composition containing luciferase conjugate will be provided separately from, and for use with, a separate composition containing a bioluminescence substrate and bioluminescence activator.

Similarly, the *Renilla reniformis* GFP and selected luciferase and/or luciferin, such as a *Pleuromamma, Renilla mulleri* or *Gaussia* luciferase or luciferin, may be provided in a composition that is a mixture, suspension, solution, powder, paste or other suitable composition separately from or in combination with the remaining components, but in the absence of an activating component. Upon contacting the conjugate, which has been targeted to a selected tissue, with this composition the reaction commences and the tissue glows. In preferred embodiments, the tissue glows green emitting light near 510 nm. The luciferase, GFP and bioluminescence substrate, for example, are packaged to exclude water and/or air, the bioluminescence activator. Upon administration and release at the targeted site, the reaction with salts or other components at the site, including air in the case of surgical procedures, will activate the components. In some embodiments, it is desirable to provide at least the GFPs or one component of the bioluminescence generating system linked to a matrix substrate, which can then be locally or systemically administered.

Suitable dispensing and packaging apparatus and matrix materials are known to those of skill in the art, and preferably include all such apparatus described in U.S. patent Nos. see U.S. Pat. Nos. 5,876,995, 6,152,358 and 6,113,886.

J. Muteins

Muteins of the *Renilla reniformis* GFP are provided herein. Muteins in which conservative amino acid changes that do not alter its ability to act as an acceptor of energy generated by a *Renilla* luciferase/substrate reaction are provided. Also provided are muteins with altered properties, including muteins with altered spectral properties, muteins with altered surface properties that reduce multimerization, including dimerization.

1. Mutation of GFP Surfaces to Disrupt Multimerization

Figure 5:
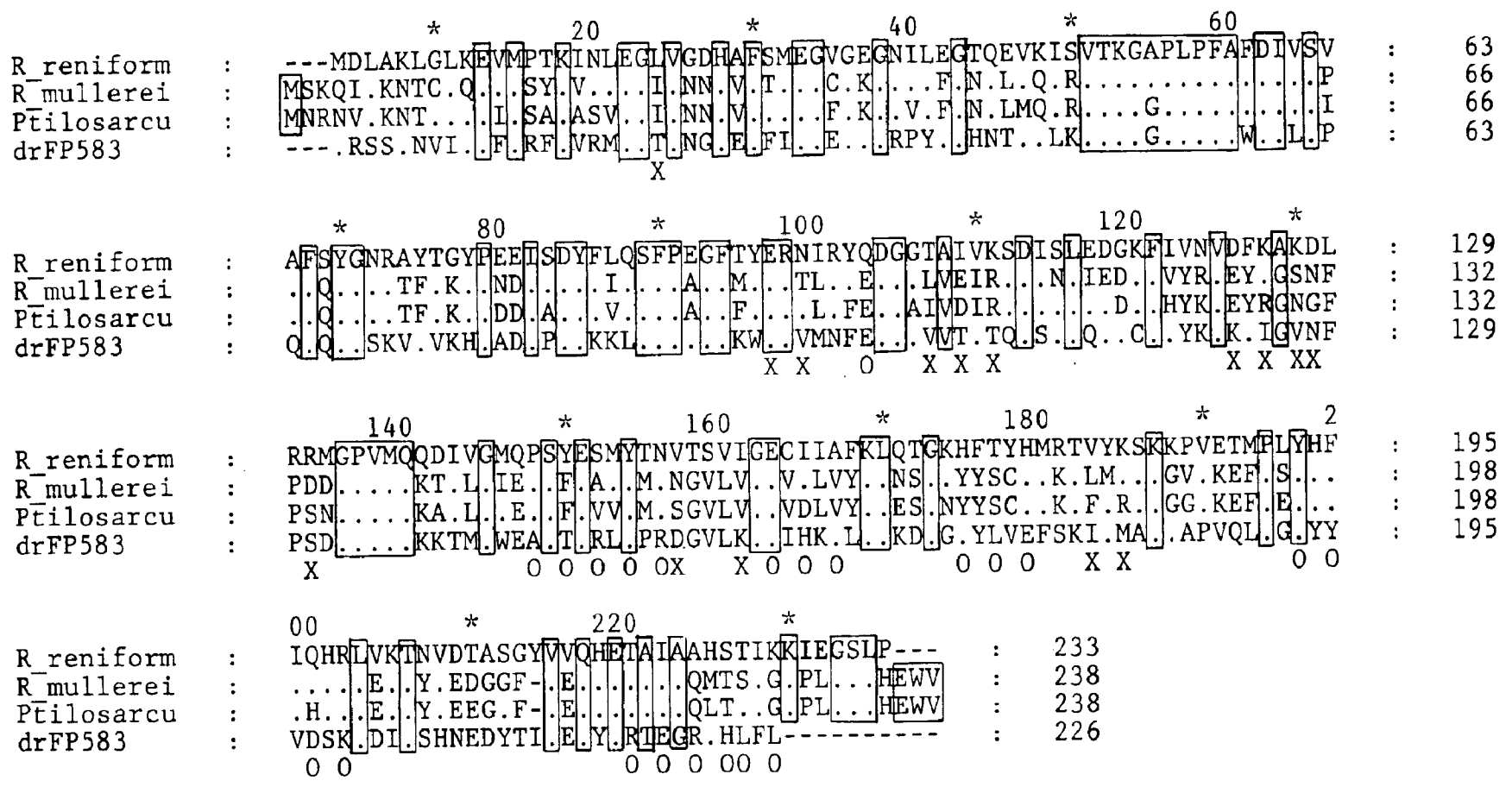
Figure 6:
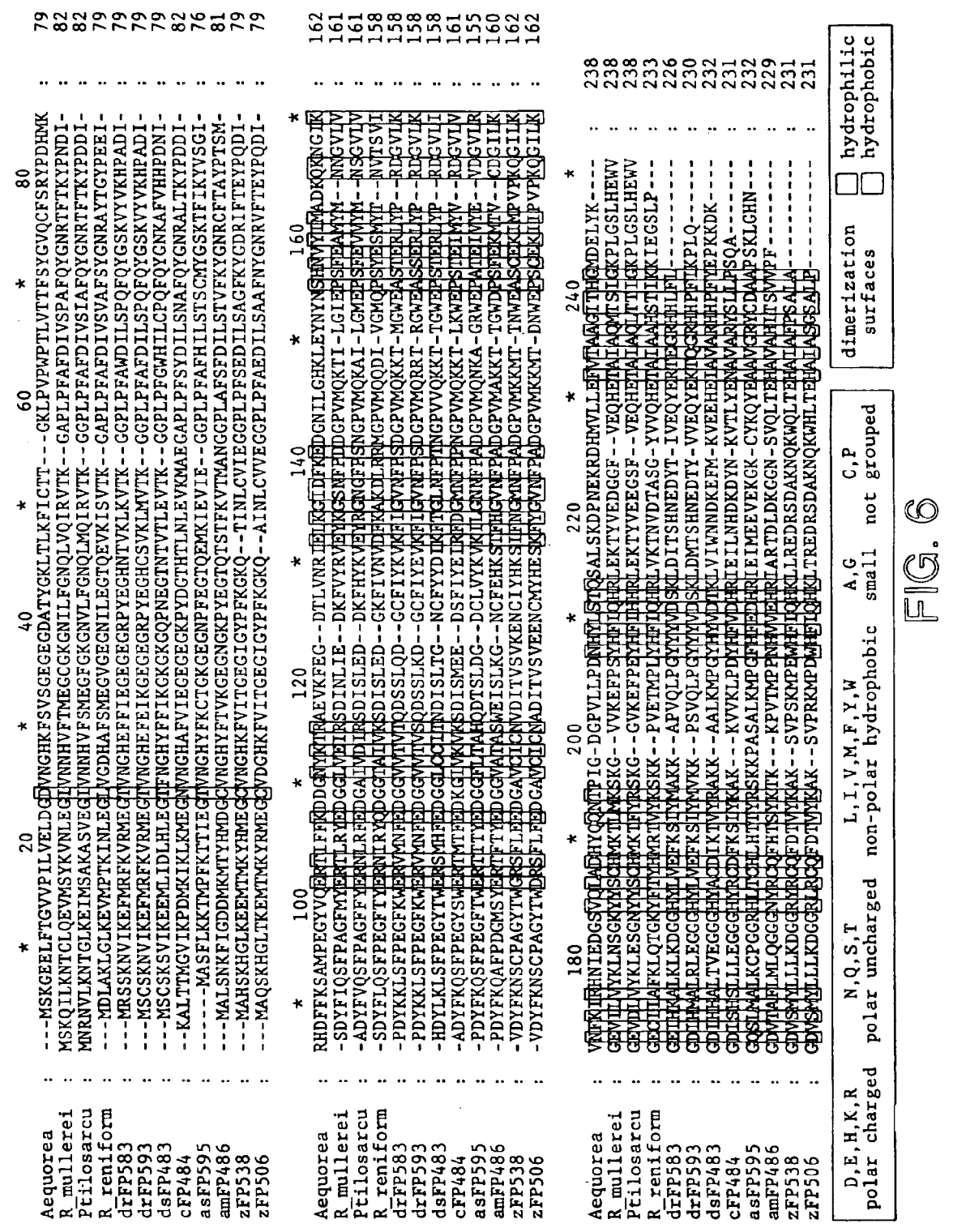

FIG. 5 depicts the three anthozoan fluorescent proteins for which a crystal structure exists; another is available commercially from Clontech as dsRed (also known as drFP583, as in this alignment) (Wall et al. (2000); *Nature Struct. Biol.* 7:1133–1138; Yarbrough et al. (2001) *Proc. Natl. Acad. Sci. U.S.A.* 98: 462–467). A dark gray background depicts amino acid conservation, and a light gray background depicts shared physiochemical properties. These crystal structures and biochemical characterization (Baird et al. (2000) *Proc. Natl. Acad. Sci. U.S.A.* 97: 11984–11989) show that dsRed exists as an obligate tetramer in vitro. Evidence also exists that dsRed multimerizes in living cells (Baird et al. (2000) *Proc. Natl. Acad. Sci. U.S.A.* 97: 11984–11989). Sedimentation and native gel electrophoresis studies indicate that *Ptilosarcus* and *Renilla mullerei* GFPs also form tetramers in vitro and multimerize in vivo. *Ptilosarcus* and *Renilla mullerei* GFPs diverge strongly in amino acid sequence from dsRed (39% and 38% identical, respectively). Computational polypeptide threading algorithms predict that these GFPs fold into essentially the same structure as dsRed, and also the much more sequence divergent *Aequorea victoria* GFP. *Renilla reniformis* GFP is similarly related in sequence to dsRed, *Ptilosarcus* and *Renilla mullerei* GFPs (37%, 51% and 53% identical, respectively), and thus is extremely likely to form similar multimers. Multimerization is undesirable for many applications that use GFP as the reporting moiety in chimeric protein fusion. Hence muteins in which the capacity to multimerize is reduced are provided. Thus provided are mutations of *Renilla reniformis* GFP that disrupt the formation of GFP multimers. Such mutations may also be effected in the *Ptilosarcus* and *Renilla mullerei* and other GFPs (see FIG. 6).

Two interaction surfaces within the dsRed tetramer, one primarily hydrophobic (residues marked by X) and one primarily hydrophilic (residues marked by O) have been described (see, Wall et al. (2000); *Nature Struct. Biol.* 7:1133–1138). In general, the corresponding residues vary considerably between the 4 GFPs in a complex way, although the physiochemical properties of the amino acids are often conserved. There are a few clusters of conserved residues, especially between *Ptilosarcus* and *Renilla mullerei* GFPs, in keeping with their 77% overall identity.

The scheme provided herein for disruption focuses on altering surface amino acid side chains so that the surfaces acquire or retain a hydrophilic character, and are also altered in their stereo-chemistry (the sizes of the side chains are altered). These GFP surface regions roughly map to the β-sheet secondary structures that comprise the GFP β-barrel tertiary structure. It is thus essential that the secondary structure in any surface mutants be retained, so that the choice of amino acid side chain substitutions is governed by this consideration.

It is also desirable to introduce mutations that alter change. For example, such mutations are those in which R, H and K residues have been replaced with D, such that the hydrophobic and hydrophilic surfaces now each contain 3 mutated residues (SEQ ID NO. 33; Lys to Asp at amino acids 108, 127 and 226, Arg to Asp at amino acids 131 and 199; His to Asp at amino acid 172.

Site directed mutagenesis techniques are used to introduce amino acid side chains that are amenable to aqueous solvation, and that significantly alter surface sterochemistry. Disruption of interacting surfaces involves loss-of-function mutagenesis. It is thus contemplated that altering only a few residues, perhaps even one, is sufficient.

2. Use of Advantageous GFP Surfaces with Substituted Fluorophores

Other surfaces of GFPs may be key determinants of GFP usefulness as reporters in living systems. A GFP surface may adventitiously interact with vital cellular components, thereby contributing to GFP-induced cytotoxicity. Anthozoan GFPs from bioluminescent luciferase-GFP systems serve fundamentally different biological functions than do anthozoan GFPs from coral and anemones. The *Renilla reniformis* GFP is present in low quantity and functions as a resonance energy acceptor in response to a dynamic neural network that enables a startled animal to emit light flashes. A coral GFP-like protein is present in large quantity and apparently is used primarily as a passive pigment; it may not have evolved to dynamically interact with sensitive cellular machinery. These two classes of anthozoan fluorescent proteins thus may have surfaces with markedly different biological properties.

FIG. 4 exemplifies the site for substitution for inserting fluorophores into the background of *Ptilosarcus, Renilla mulleri* and *Renilla reniformis* GFPs. In particular, the 20 amino acid region that lies between two highly conserved pralines with the corresponding 20 amino acid region from any other anthozoan GFP (the underlined regions corresponds to amino acids 56–75 of SEQ ID NO. 27 *Renilla reniformis* GFP; amino acids 59–78 of SEQ ID NO. 16 *Renilla mullerei* GFP; and amino acids 59–78 of SEQ ID NO. 32 for *Ptilosarcus* GFP) is replaced or modified. These 20 residues comprise the bulk of a polypeptide region that threads along the interior of the β-barrel structure that is characteristic of anthozoan GFPs (Wall et al. (2000) *Nature Struct. Biol.* 7:1133–1138; Yarbrough et al. (2001) *Proc. Natl. Acad. Sci. U.S.A.* 98:462467); replacement or modification alters spectral properties.

K. Transgenic Plants and Animals

As discussed above, transgenic animals and plants that contain the nucleic acid encoding the *Renilla reniformis* GFP are provided. Methods for producing transgenic plants and animals that express a GFP are known (see, e.g., U.S. Pat. No. 6,020,538).

Among the transgenic plants and animals provided are those that are novelty items, such as animals with eyes or fingernails or tusks or hair that glows fluorescently. Transgenic food animals, such as chickens and cows and pigs are contemplated from which glowing meat and eggs (green eggs and ham) can be obtained; glowing worms can serve as fishing lures. In addition, the *Renilla reniformis* can serve as a reporter to detect that a heterologous gene linked to the GFP gene is incorporated into the animal's genome or becomes part of the genome in some or all cells. The *Renilla reniformis* can similarly be used as a reporter for gene therapy. The GFP can be introduced into plants to make transgenic ornamental plants that glow, such as orchids and roses and other flowering plants. Also the GFP can be used as a marker in plants, such as by linking it to a promoter, such as Fos that responds to secondary messages to assess signal transduction. The GFP can be linked to adenylcyclase causing the plants to emit different spectral frequencies as the levels of adenylcyclase change.

L. Bioluminescence Resonance Energy Transfer (BRET) System

In nature, coelenterazine-using luciferases emit broadband blue-green light (max. ~480 nm). Bioluminescence Resonance Energy Transfer (BRET) is a natural phenomenon first inferred from studies of the hydrozoan *Obelia* (Morin & Hastings (1971) *J. Cell Physiol.* 77:313–18), whereby the green bioluminescent emission observed in vivo was shown to be the result of the luciferase non-radiatively transferring energy to an accessory green fluorescent protein (GFP). BRET was soon thereafter observed in the hydrozoan *Aequorea victoria* and the anthozoan *Renilla reniforms*. Although energy transfer in vitro between purified luciferase and GFP has been demonstrated in *Aequorea* (Morise et al. (1974) *Biochemistry* 13:2656–62) and *Renilla* (Ward & Cormier (1976) *J. Phys. Chem.* 80:2289–91) systems, a key difference is that in solution efficient radiationless energy transfer occurs only in *Renilla*, apparently due to the pre-association of one luciferase molecule with one GFP homodimer (Ward & Cormier (1978) Photochem. Photobiol. 27:389–96). The blue (486 nm) luminescent emission of *Renilla* luciferase can be completely converted to narrow band green emission (508 nm) upon addition of proper amounts of *Renilla* GFP (Ward & Cormier (1976) *J. Phys. Chem.* 80:2289–91). GFPs accept energy from excited states of luciferase-substrate complexes and re-emit the light as narrow-band green light (~510 nm). By virtue of the non-radiative energy transfer, the quantum yield of the luciferase is increased.

Luciferases and fluorescent proteins have many well-developed and valuable uses as protein tags and transcriptional reporters; BRET increases the sensitivity and scope of these applications. A GFP increases the sensitivity of the luciferase reporter by raising the quantum yield. A single luciferase fused (or chemically linked) to several spectrally distinct GFPs provides for the simultaneous use of multiple luciferase reporters, activated by addition of a single luciferin. By preparing two fusion proteins (or chemical conjugates), each containing a GFP having a different emission wavelength fused to identical luciferases, two or more reporters can be used with a single substrate addition. Thus multiple events may be monitored or multiple assays run using a single reagent addition. Such a reporter system is self-ratioing if the distribution of luciferin is uniform or reproducible.

The ability to conveniently monitor several simultaneous macromolecular events within a cell is a major improvement over current bioluminescent technology. BRET also enables completely new modes of reporting by exploiting changes in association or orientation of the luciferase and fluorescent protein. By making fusion proteins, the luciferase-GFP acceptor pair may be made to respond to changes in association or conformation of the fused moieties and hence serves as a sensor.

Energy transfer between two fluorescent proteins (FRET) as a physiological reporter has been reported (Miyawaki et al. (1997) *Nature* 388:882–7), in which two different GFPs were fused to the carboxyl and amino termini of calmodulin. Changes in calcium ion concentration caused a sufficient conformational change in calmodulin to alter the level of energy transfer between the GFP moieties. The observed change in donor emission was ~10% while the change in ratio was ~1.8.

FIG. 2, reproduced from allowed copending application U.S. application Ser. No. 09/277,716, illustrates the underlying principle of Bioluminescent Resonance Energy Transfer (BRET) using GFPs and luciferase, preferably cognate luciferase, and its use as sensor: A) in isolation, a luciferase, preferably an anthozoan luciferase, emits blue light from the coelenterazine-derived chromophore; B) in isolation, a GFP, preferably an anthozoan GFP that binds to the luciferase, that is excited with blue-green light emits green light from its integral peptide based fluorophore; C) when the luciferase and GFP associate as a complex in vivo or in vitro, the luciferase non-radiatively transfers its reaction energy to the GFP fluorophore, which then emits the green light; D) any molecular interaction that disrupts the luciferase-GFP complex can be quantitatively monitored by observing the spectral shift from green to blue light. Hence, the interaction or disruption thereof serves as a sensor.

The similar use of a luciferase-GFP pair in the presence of substrate luciferin has important advantages. First, there is no background and no excitation of the acceptor from the primary exciting light. Second, because the quantum yield of the luciferase is greatly enhanced by nonradiative transfer to GFP, background from donor emission is less, and the signal from the acceptor relatively greater. Third, the wavelength shift from the peak emission of luciferase (~480 nm) to that of the GFP (typically 508–510 nm) is large, minimizing signal overlap. All three factors combine to increase the signal-to-noise ratio. The concentration of the GFP acceptor can be independently ascertained by using fluorescence.

For some applications, in vitro crosslinked or otherwise in vitro modified versions of the native proteins is contemplated. The genetically encoded fusion proteins have many great advantages: A) In vivo use—unlike chemistry-based luminescence or radioactivity-based assays, fusion proteins can be genetically incorporated into living cells or whole organisms. This greatly increases the range of possible applications; B) Flexible and precise modification—many different response modifying elements can be reproducibly and quantitatively incorporated into a given luciferase-GFP pair; C) Simple purification—only one reagent would need to be purified, and its purification could be monitored via the fluorescent protein moiety. Ligand-binding motifs can be incorporated to facilitate affinity purification methods.

1. Design of Sensors Based on BRET

Resonance energy transfer between two chromophores is a quantum mechanical process that is exquisitely sensitive to the distance between the donor and acceptor chromophores and their relative orientation in space (Wu & Brand (1994) *Anal. Biochem.* 218:1–13). Efficiency of energy transfer is inversely proportional to the $6^{th}$ power of chromophore separation. In practice, the useful distance range is about 10 to 100 A°, which has made resonance energy transfer a very useful technique for studying the interactions of biological macromolecules. A variety of fluorescence-based FRET biosensors have been constructed, initially employing chemical fluors conjugated to proteins or membrane components, and more recently, using pairs of spectrally distinct GFP mutants (Giuliano & Taylor (1998) *Trends Biotech.* 16:99–146; Tsien (1998) *Annu. Rev. Biochem.* 67:509–44).

Although these genetically encoded GFP bioluminescence-based biosensors have advantages over less convenient and less precise chemical conjugate-based biosensors, all share a limitation in their design: it is generally difficult to construct a biosensor in which energy transfer is quantitative when the chromophores are in closest apposition. It is almost impossible to arbitrarily manipulate the complex stereochemistry of proteins so that conjugated or intrinsic chromophores are stably positioned with minimal separation and optimal orientation. The efficiency of such biosensors are also often limited by stoichiometric imbalances between resonance energy donor and acceptor; the donor and acceptor macromolecules must be quantitatively complexed to avoid background signal emanating from uncomplexed chromophores. These limitations in general design become important when biosensors must be robust, convenient and cheap. Developing technologies such as high throughput screening for candidate drugs (using high throughput screening (HTS) protocols), biochips and environmental monitoring systems would benefit greatly from modular biosensors where the signal of a rare target "hit" (e.g., complex formation between two polypeptides) is unambiguously (statistically) distinguishable from the huge excess of "non-hits"). Current genetically encoded FRET and bioluminescence-based biosensors display hit signals that very often are less than two-fold greater than non-hit signals, and are at best a few-fold greater (Xu et al. (1999) *Proc. Natl. Acad. Sci USA* 96: 151–156; Miyawaki et al. (1997) *Nature* 388:882–7).

To solve these problems, the anthozoan GFPs, particularly the *Renilla* GFPs, provided herein can be used in combination with its cognate luciferases. Anthozoan luciferases-GFP complexes provide a "scaffold" upon which protein domains that confer the biological properties specific to a given biosensor can be linked. Although one can construct many useful two component biosensors based on this scaffold, in a biosensor contemplated herein, independent protein domains that potentially complex with one another are respectively fused to the luciferase and the GFP.

There are many possible variations on this theme. For example, in a three component system either the luciferase or GFP can be fused to a ligand-binding domain from a protein of interest or other target peptide or other moiety of interest. If the design of the fusion protein is correct, binding of a small molecule or protein ligand then prevents the luciferase-GFP association. The resulting combination of elements is a BRET-based biosensor; the change in spectral properties in the presence and absence of the ligand serves as sensor. More complex protein fusions can be designed to create two component and even single component BRET biosensors for a multitude of uses.

The nucleic acids, and the constructs and plasmids herein, permit preparation of a variety of configurations of fusion proteins that include an anthozan GFP, in this case *Renilla reniformis*, preferably with a *Renilla* luciferase, more preferably with the *Renilla reniformis* luciferase. The nucleic acid encoding the GFP can be fused adjacent to the nucleic acid encoding the luciferase or separated therefrom by insertion of nucleic acid encoding, for example, a ligand-binding domain of a protein of interest. The GFP and luciferase will be bound. Upon interaction of the ligand-binding domain with the a test compound or other moiety, the interaction of the GFP and luciferase will be altered thereby changing the emission signal of the complex. If necessary the GFP and luciferase can be modified to fine tune the interaction to make it more sensitive to conformational changes or to temperature or other parameters.

2. BRET Sensor Architectures

Figure 3:
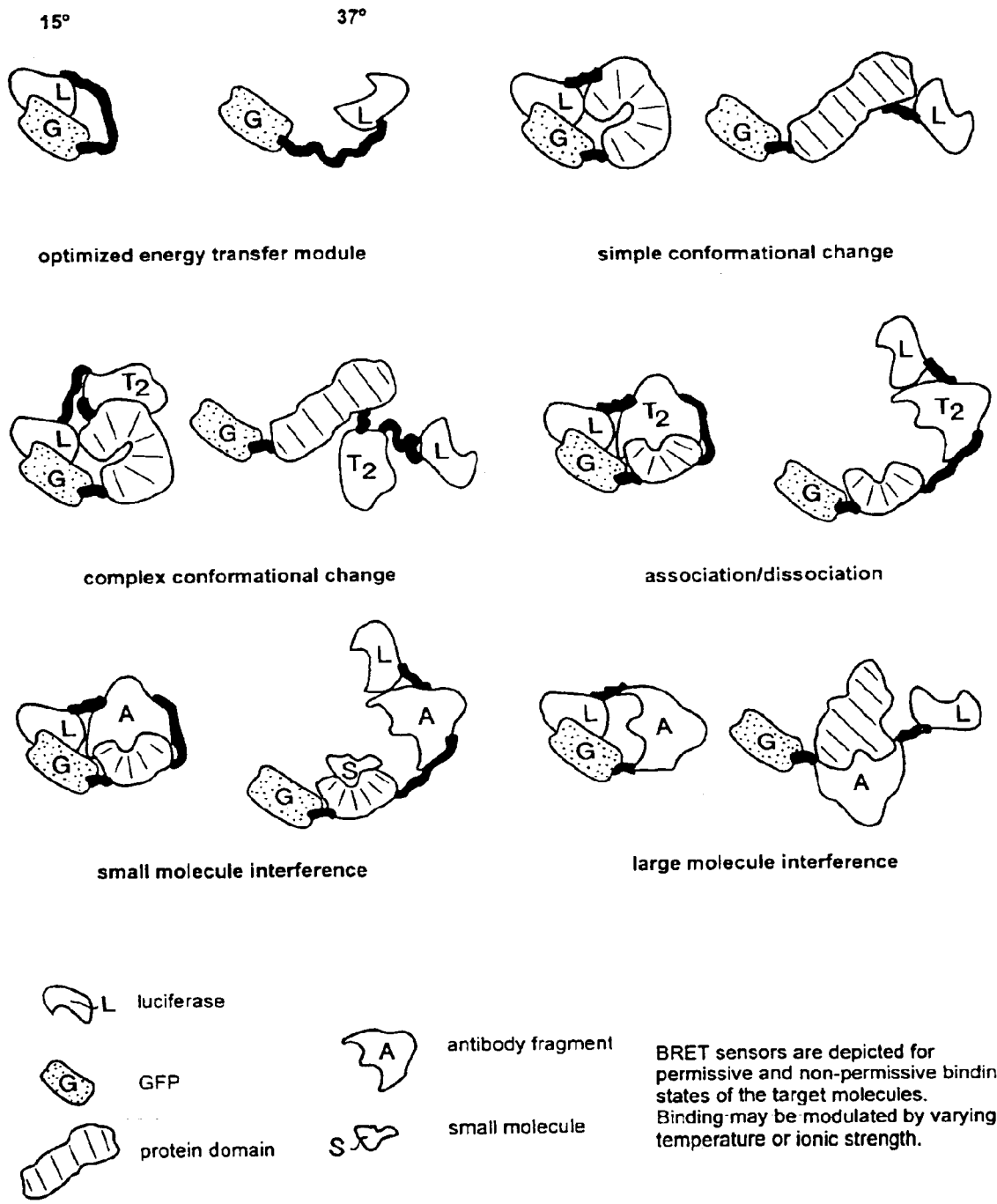
FIG. 3 illustrates exemplary BRET sensor architecture.

FIG. 3 depicts some exemplary BRET sensor architectures. The upper left panel depicts the luciferase-GFP scaffold, the basis for the representative BRET sensor architectures shown here. The depicted single polypeptide fusion constructs place the luciferase and GFP at the polypeptide termini, bracketing interacting protein domains of choice. The luciferase and GFP can alternatively be placed centrally within the polypeptide, between interacting protein domains (not shown). This alternative arrangement is advantageous for one step protein interaction-based cloning schemes, where cDNA fragments encoding potential protein targets can be ligated onto one end of the construct.

Single polypeptide sensors that detect conformational changes within protein targets or the association-dissociation of protein targets are well-suited for the detection of physiological signals, such as those mediated by phosphorylation or other modification of targets, or by binding of regulatory ligands, such as hormones, to targets. Sensors based on interference are best suited to assaying the presence of small molecules or proteins independent of any regulatory context. Quantitative assays of metabolites, such as a sugar and allergens, are among those contemplated.

Since in vivo and in vitro luciferase-to-GFP energy transfer can be nearly 100% efficient, binding interactions between the luciferase and GFP must be sufficient to establish an optimal spatial relationship between donor and acceptor chromophores. Optimization of the luciferase-GFP energy transfer module is important in building effective BRET sensors. In a single polypeptide sensor it is crucial that the luciferase-GFP interaction be weak relative to interactions between target domains, thus the need for an optimized energy transfer module. In practice, either the luciferase or GFP surface can be randomly mutagenized, and an optimized luciferase-GFP scaffold then selected by screening for either blue or green emission at two near physiological temperatures (thermal endpoint-selection) using current robotic systems. This disruption of BRET is readily achievable because loss-of-function mutants (weakened luciferase-GFP binding) are orders of magnitude more frequent than gain-of-function mutants.

With an optimized energy transfer scaffold in hand, thermal endpoint-selection can then be used, if necessary, to optimize the interactions between the target domains incorporated into a sensor. This second round of thermal endpoint-selection may be especially important for the construction of interference sensors because it is essential that such sensors be able to "open and close" at near physiological temperatures to sense interference. Thermal endpoint-selection can also be used to weaken the binding affinity of the analyte to the interference sensor, making it possible to thermally wash off the analyte and reuse the sensor, a great advantage for biochip-based applications.

3. Advantages of BRET Sensors

There are many advantages to the BRET sensors provided herein. For example, BRET sensors are self-ratioing. The reporter and target are integrated into single polypeptide. This ensures 1:1:1 stoichiometry among luciferase, GFP and target (or a 1:N:1 stoichiometry if more than one, typically a homodimer, GFP can be bound to a luciferase). GFP fluorescence allows absolute quantitation of sensor. The null state gives signal that verifies sensor functionality. Quantifiable null state facilitates disruption-of-BRET sensors (DBRET). BRET sensors have better signal-to-noise ratio than GFP FRET sensors because there is no cellular autofluorescence, no excitation of the acceptor from the primary exciting light, the quantum yield of luciferase greatly enhanced by non-radiative energy transfer to GFP, and there is minimal signal overlap between emission of the luciferase and emission of the GFP. Also, anthozoan GFPs have 6-fold higher extinction coefficients than *Aequorea* GFP.

The BRET sensors can be used for hit identification and downstream evaluation in in vitro screening assays in in vitro or in vivo or in situ, including in cultured cells and tissues and animals. The BRET sensors can be created by thermal endpoint-selection, which is suited to DBRET (Disruption-of-BRET) and reduces need for knowledge of target 3D structure and functional dynamics. Existing screening robotics can be used to optimize biosensors. BRET sensors benefit from vast genetic diversity, anthozoans have evolved efficient luciferase-GFP energy transfer systems and the components can be mixed and matched. Highly efficient heterologous luciferases may be substituted for less active luciferases. For example, a copepod luciferase active site can be fused to an anthozoan luciferase GFP-binding domain. There are many diverse coelenterazine-using luciferases.

BRET sensors are modular so that an optimized sensor scaffold may be used with different targets. Also the BRET acceptor may be varied to give shifted emissions, facilitating multiple simultaneous readouts. The anthozoan GFPs can be mutated, GFPs or other proteins can be modified with different chemical fluors, high throughput screening (HTS) fluor-modified FRET acceptors can be adapted, and the BRET donor (luciferase) may be varied, such as by using an Aequorin (Ca++ activated) photoprotein, or a firefly luciferse (requires ATP and a firefly luciferin) to give conditional activation. The sensor scaffold can be incorporated into a variety of immobilization motifs, including free format plates, which can reduce reagent volumes, reusable microtiter plates, miniature columns and biochips. Finally, BRET sensors are inexpensive and reproducible reagents because they can be produced by standardized protein production and can incorporate purification tags. Genetically encoded reporters more reproducible than chemically modified reporters. Linear translation of BRET modules ensures sensor integrity.

The following example is included for illustrative purposes only and is not intended to limit the scope of the invention.

EXAMPLE

Specimens of the sea pansy *Renilla reniformis* were collected from inshore waters off the coast of Georgia. To prepare the sea pansies for isolation of mRNA, about 25 or so at time were placed on a large bed of dry ice. They were flipped with a spatula to flip them over to prevent them from freezing. Oddly, the entire animal illuminated when it came in contact with the dry ice. The brightest and greenest were culled, placed in a bag and back into sea water at about 65–70° C. for two hours. This process of dry ice, culling and sea water treatment was repeated three times over a 6 hour period. In addition, the process was performed at night. After they were exhausted with the last chilling, the culled animals were frozen solid. A cDNA library was prepared from the frozen animals.

The animals that were selected this way were frozen in liquid nitrogen, and shipped to Stratagene, Inc. (La Jolla, Calif.), a commercial vendor whose business includes the construction of custom cDNA libraries under contract to prepare the library. Purified polyA-mRNA was prepared, and a cDNA synthesis reaction was performed, appending a 3' XhoI site and a 5' EcoRI restriction site to the cDNA. The cDNA was inserted by ligation between the EcoRI and XhoI sites of the Uni-ZAP Lambda phage cDNA cloning vector.

The resulting unamplified library contained approximately $1.6 \times 10^8$ primary plaques, which after amplification gave a titer of 3.5–7.5 pfb (plaque forming units)/ml. Insert sizes ranged from 0.9 to 3.0 kb, with an average size around 1.5 kb. Two mass excisions were performed to give pBluescript phagemid containing the cDNA inserts; each excision from about $8 \times 10$ plaques gave rise to about $4.8 \times 10^9$ cfu (colony forming units)/ml. Phagemids were transfected into the SOLR strain of *E. coli*.

Screening was performed by plating (using an artist's airbrush) approximately 200,000 colonies to each of 40 cafeteria trays containing LB agar medium incorporating 0.4% carbon black to absorb background fluorescence. After 24 hours growth at 30° C. in a humidified incubator, GFP expressing colonies were identified by illuminating the plates using a 250 Watt quartz halogen fiber optics light (Cuda Products Corp) with an EGFP bandpass excitation filter (Chroma), and viewing colonies through a GFP bandpass emission filter. Approximately 10 fluorescent colonies were picked, DNA isolated from minipreps, and the DNA transformed into the XL-10 Gold *E. coli* strain (Stratagene). Analysis by restriction digestion resolved three distinguishable sizes of insert. DNA was prepared from a clone of each size class and sent to SeqWright LLB (Houston, Tex.) for sequencing. Sequencing data were reported to Prolume on Jan. 1, 1999.

Three independent cDNA clones of *Renilla reniformis* GFP were isolated (SEQ ID NOs. 23–25). Each cDNA is full length as judged by identical 5' termini and each encodes an identical protein of 233 amino acids (see SEQ ID NO. 27). Compared to the primary clone (Clone 1), the coding sequence of Clone 2 differs by 4 silent mutations. Clones 2 and 3 also contain small differences in the 5' and 3' untranslated regions of the cDNA. This nucleic acid has been inserted into expression vector, and the encoded protein produced.

Since modifications may be apparent to those of skill in the art, it is intended that the invention be limited only by the appended claims.

What is claimed is:

1. An isolated nucleic acid molecule encoding a *Renilla reniformis* green fluorescent protein, comprising a nucleotide sequence that encodes the protein of SEQ ID NO. 27 or a green fluorescent protein encoded by a nucleic acid molecule of *Renilla reniformis* having at least 80% sequence identity thereto.

2. An isolated nucleic acid molecule of claim 1 that encodes a protein having at least 90% sequence identity to the protein of SEQ ID NO. 27.

3. The isolated nucleic acid molecule of claim 1, comprising a nucleotide sequence selected from the group consisting of:

(a) the coding portion of the nucleotide sequence set forth in any of SEQ ID NOs. 23–25;

(b) a nucleotide sequence that hybridizes under conditions of 0.1× standard saline phosphate EDTA buffer, 0.1% SDS at 65° C. to the nucleotide sequence of (a); and (c) a nucleotide sequence comprising degenerate codons of (a) or (b).

4. The isolated nucleic acid molecule of claim 1, wherein the nucleic acid is DNA.

5. The isolated nucleic acid molecule of claim 1, wherein the nucleic acid is RNA.

6. A nucleic acid probe or primer, comprising at least 14 contiguous nucleotides selected from the nucleotide sequence set of claim 1.

7. The probe or primer of claim 6, comprising at least 16 contiguous nucleotides selected from the nucleotide sequence in claim 1.

8. The probe or primer of claim 7, comprising at least 30 contiguous nucleotides.

9. A plasmid, comprising the nucleotide sequence of claim 1.

10. A cell comprising the plasmid of claim 9, wherein the cell is selected from the group consisting of a bacterial cell, a yeast cell, a fungal cell, a plant cell, an insect cell and an animal cell.

11. The plasmid of claim 9 that is an expression vector, further comprising:
a promoter element;
a cloning site for the introduction of the nucleic acid molecule; and
a marker gene;
wherein the nucleic acid comprising the cloning site is positioned between nucleic acids encoding the promoter element and the green fluorescent protein and wherein the nucleic acid encoding the green fluorescent protein is operatively linked to the promoter element.

12. The plasmid of claim 11, wherein the marker gene comprises a nucleotide sequence encoding a luciferase.

13. A recombinant host cell, comprising the plasmid of claim 9.

14. The cell of claim 13, wherein the cell is selected from the group consisting of a bacterial cell, a yeast cell, a fungal cell, a plant cell, an insect cell and an animal cell.

15. A reporter gene construct, comprising the nucleic acid molecule of claim 1.

16. A nucleic acid construct, comprising the nucleotide sequence encoding a luciferase and a nucleotide sequence of claim 1 that encodes a *Renilla reniformis* fluorescent protein (GFP).

17. The nucleic acid construct of claim 16, wherein the luciferase is a *Renilla mulleri* luciferase, a *Gaussia* luciferase or a *Pleuromamma* luciferase.

18. The nucleic acid construct of claim 17, wherein the *Gaussia* luciferase is a *Gaussia princeps* luciferase.

19. The nucleic acid construct of claim 16, wherein the luciferase is encoded by:
a nucleotide sequence set forth in SEQ ID NO. 17, SEQ ID NO. 19, or SEQ ID NO. 28;
a nucleotide sequence encoding the amino acid sequence set forth in SEQ ID NO. 18, SEQ ID NO. 20 or SEQ ID NO. 29; and
a nucleotide sequence that hybridizes under the condition of claim 3 to the nucleotide sequence set forth in SEQ ID NO. 17, SEQ ID NO. 19 or SEQ ID NO. 28.

20. The nucleic acid construct of claim 16, that is DNA.

21. The nucleic acid construct of claim 16, that is RNA.

22. A plasmid, comprising the nucleic acid construct of claim 16.

23. The plasmid of claim 22, further comprising a nucleotide sequence encoding:
a promoter element; and
a selectable marker;
wherein, the nucleotide sequence encoding the luciferase and *Renilla reniformis* GFP is operatively linked to the promoter element, whereby the luciferase and *Renilla reniformis* GFP are expressed.

24. The construct of claim 16, wherein the luciferase and the GFP are encoded by a polycistronic message.

25. The construct of claim 16, wherein the encoded luciferase and *Renilla reniformis* GFP comprise a fusion protein.

26. The nucleic acid construct of claim 25, wherein the nucleotide sequence that encoding the luciferase and GFP are not contiguous.

27. The nucleic acid construct of claim 26, comprising a nucleotide sequence that encodes a ligand binding domain of a target protein.

28. The construct of claim 16, wherein the luciferase is *Renilla reniformis* luciferase.

29. A recombinant host cell, comprising the plasmid of claim 22.

* * * * *

SEQUENCE LISTING

```
<160> NUMBER OF SEQ ID NOS: 33
<210> SEQ ID NO 1
<211> LENGTH: 1196
```

-continued

```
<212> TYPE: DNA
<213> ORGANISM: Renilla reniformis
<220> FEATURE:
<221> NAME/KEY: CDS
<222> LOCATION: (1)...(942)
<223> OTHER INFORMATION: Renilla reniformas luciferase

<400> SEQUENCE: 1 agc tta aag atg act tcg aaa gtt tat gat cca gaa caa agg aaa cgg        48
Ser Leu Lys Met Thr Ser Lys Val Tyr Asp Pro Glu Gln Arg Lys Arg
  1               5                  10                  15 atg ata act ggt ccg cag tgg tgg gcc aga tgt aaa caa atg aat gtt        96
Met Ile Thr Gly Pro Gln Trp Trp Ala Arg Cys Lys Gln Met Asn Val
             20                  25                  30 ctt gat tca ttt att aat tat tat gat tca gaa aaa cat gca gaa aat       144
Leu Asp Ser Phe Ile Asn Tyr Tyr Asp Ser Glu Lys His Ala Glu Asn
         35                  40                  45 gct gtt att ttt tta cat ggt aac gcg gcc tct tct tat tta tgg cga       192
Ala Val Ile Phe Leu His Gly Asn Ala Ala Ser Ser Tyr Leu Trp Arg
     50                  55                  60 cat gtt gtg cca cat att gag cca gta gcg cgg tgt att ata cca gat       240
His Val Val Pro His Ile Glu Pro Val Ala Arg Cys Ile Ile Pro Asp
 65                  70                  75                  80 ctt att ggt atg ggc aaa tca ggc aaa tct ggt aat ggt tct tat agg       288
Leu Ile Gly Met Gly Lys Ser Gly Lys Ser Gly Asn Gly Ser Tyr Arg
                 85                  90                  95 tta ctt gat cat tac aaa tat ctt act gca tgg ttg aac ttc tta att       336
Leu Leu Asp His Tyr Lys Tyr Leu Thr Ala Trp Leu Asn Phe Leu Ile
            100                 105                 110 tac caa aga aga tca ttt ttt gtc ggc cat gat tgg ggt gct tgt ttg       384
Tyr Gln Arg Arg Ser Phe Phe Val Gly His Asp Trp Gly Ala Cys Leu
        115                 120                 125 gca ttt cat tat agc tat gag cat caa gat aag atc aaa gca ata gtt       432
Ala Phe His Tyr Ser Tyr Glu His Gln Asp Lys Ile Lys Ala Ile Val
    130                 135                 140 cac gct gaa agt gta gta gat gtg att gaa tca tgg gat gaa tgg cct       480
His Ala Glu Ser Val Val Asp Val Ile Glu Ser Trp Asp Glu Trp Pro
145                 150                 155                 160 gat att gaa gaa gat att gcg ttg atc aaa tct gaa gaa gga gaa aaa       528
Asp Ile Glu Glu Asp Ile Ala Leu Ile Lys Ser Glu Glu Gly Glu Lys
                165                 170                 175 atg gtt ttg gag aat aac ttc ttc gtg gaa acc atg ttg cca tca aaa       576
Met Val Leu Glu Asn Asn Phe Phe Val Glu Thr Met Leu Pro Ser Lys
            180                 185                 190 atc atg aga aag tta gaa cca gaa gaa ttt gca gca tat ctt gaa cca       624
Ile Met Arg Lys Leu Glu Pro Glu Glu Phe Ala Ala Tyr Leu Glu Pro
        195                 200                 205 ttc aaa gag aaa ggt gaa gtt cgt cgt cca aca tta tca tgg cct cgt       672
Phe Lys Glu Lys Gly Glu Val Arg Arg Pro Thr Leu Ser Trp Pro Arg
    210                 215                 220 gaa atc ccg tta gta aaa ggt ggt aaa cct gac gtt gta caa att gtt       720
Glu Ile Pro Leu Val Lys Gly Gly Lys Pro Asp Val Val Gln Ile Val
225                 230                 235                 240 agg aat tat aat gct tat cta cgt gca agt gat gat tta cca aaa atg       768
Arg Asn Tyr Asn Ala Tyr Leu Arg Ala Ser Asp Asp Leu Pro Lys Met
                245                 250                 255 ttt att gaa tcg gat cca gga ttc ttt tcc aat gct att gtt gaa ggc       816
Phe Ile Glu Ser Asp Pro Gly Phe Phe Ser Asn Ala Ile Val Glu Gly
            260                 265                 270 gcc aag aag ttt cct aat act gaa ttt gtc aaa gta aaa ggt ctt cat       864
Ala Lys Lys Phe Pro Asn Thr Glu Phe Val Lys Val Lys Gly Leu His
```

```
                275                 280                 285
ttt tcg caa gaa gat gca cct gat gaa atg gga aaa tat atc aaa tcg      912
Phe Ser Gln Glu Asp Ala Pro Asp Glu Met Gly Lys Tyr Ile Lys Ser
    290                 295                 300 ttc gtt gag cga gtt ctc aaa aat gaa caa taattacttt ggttttttat        962
Phe Val Glu Arg Val Leu Lys Asn Glu Gln
305                 310 ttacattttt cccgggttta ataatataaa tgtcattttc aacaattttta ttttaactga  1022 atatttcaca gggaacattc atatatgttg attaatttag ctcgaactttt actctgtcat  1082 atcattttgg aatattacct ctttcaatga aactttata acagtggttc aattaattaa   1142
tatatattat aattacattt gttatgtaat aaactcggtt ttattataaa aaaa         1196

<210> SEQ ID NO 2
<211> LENGTH: 1822
<212> TYPE: DNA
<213> ORGANISM: Cypridina hilagendorfii luciferase
<220> FEATURE:
<221> NAME/KEY: CDS
<222> LOCATION: (1)...(1665)
<223> OTHER INFORMATION: Cypridina hilgendorfii luciferase

<400> SEQUENCE: 2 atg aag cta ata att ctg tct att ata ttg gcc tac tgt gtc aca gtc       48
Met Lys Leu Ile Ile Leu Ser Ile Ile Leu Ala Tyr Cys Val Thr Val
1               5                   10                  15 aac tgc cag gat gca tgt cct gta gaa gct gaa gca ccg tca agt aca       96
Asn Cys Gln Asp Ala Cys Pro Val Glu Ala Glu Ala Pro Ser Ser Thr
            20                  25                  30 cca aca gtc cca aca tct tgt gaa gct aaa gaa gga gaa tgt atc gat      144
Pro Thr Val Pro Thr Ser Cys Glu Ala Lys Glu Gly Glu Cys Ile Asp
        35                  40                  45 acc aga tgc gca aca tgt aaa cga gac ata cta tca gac gga ctg tgt      192
Thr Arg Cys Ala Thr Cys Lys Arg Asp Ile Leu Ser Asp Gly Leu Cys
    50                  55                  60 gaa aat aaa cca ggg aag aca tgc tgt aga atg tgc cag tat gta att      240
Glu Asn Lys Pro Gly Lys Thr Cys Cys Arg Met Cys Gln Tyr Val Ile
65                  70                  75                  80 gaa tcc aga gta gaa gct gct gga tat ttt aga acg ttt tac gcc aaa      288
Glu Ser Arg Val Glu Ala Ala Gly Tyr Phe Arg Thr Phe Tyr Ala Lys
                85                  90                  95 aga ttt aat ttt cag gaa cct ggt aaa tat gtg ctg gct cga gga acc      336
Arg Phe Asn Phe Gln Glu Pro Gly Lys Tyr Val Leu Ala Arg Gly Thr
            100                 105                 110 aag ggt ggc gac tgg tct gta acc ctc acc atg gag aat cta gat gga      384
Lys Gly Gly Asp Trp Ser Val Thr Leu Thr Met Glu Asn Leu Asp Gly
        115                 120                 125 cag aag gga gct gta ctg act aag aca aca ctg gag gta gta gga gac      432
Gln Lys Gly Ala Val Leu Thr Lys Thr Thr Leu Glu Val Val Gly Asp
    130                 135                 140 gta ata gac att act caa gct act gca gat cct atc aca gtt aac gga      480
Val Ile Asp Ile Thr Gln Ala Thr Ala Asp Pro Ile Thr Val Asn Gly
145                 150                 155                 160 gga gct gac cca gtt atc gct aac ccg ttc aca att ggt gag gtg acc      528
Gly Ala Asp Pro Val Ile Ala Asn Pro Phe Thr Ile Gly Glu Val Thr
                165                 170                 175 att gct gtt gtc gaa ata ccc ggc ttc aat att aca gtc atc gaa ttc      576
Ile Ala Val Val Glu Ile Pro Gly Phe Asn Ile Thr Val Ile Glu Phe
            180                 185                 190 ttt aaa cta atc gtg ata gat att ctg gga gga aga tct gtg aga att      624
```

```
                Phe Lys Leu Ile Val Ile Asp Ile Leu Gly Gly Arg Ser Val Arg Ile
                    195                 200                 205 gct cca gac aca gca aac aaa gga ctg ata tct ggt atc tgt ggt aat        672
Ala Pro Asp Thr Ala Asn Lys Gly Leu Ile Ser Gly Ile Cys Gly Asn
210                 215                 220 ctg gag atg aat gac gct gat gac ttt act aca gac gca gat cag ctg        720
Leu Glu Met Asn Asp Ala Asp Asp Phe Thr Thr Asp Ala Asp Gln Leu
225                 230                 235                 240 gcg atc caa ccc aac ata aac aaa gag ttc gac ggc tgc cca ttc tac        768
Ala Ile Gln Pro Asn Ile Asn Lys Glu Phe Asp Gly Cys Pro Phe Tyr
                245                 250                 255 ggg aat cct tct gat atc gaa tac tgc aaa ggt ctc atg gag cca tac        816
Gly Asn Pro Ser Asp Ile Glu Tyr Cys Lys Gly Leu Met Glu Pro Tyr
                260                 265                 270 aga gct gta tgt cgt aac aat atc aac ttc tat tac act ctg tcc            864
Arg Ala Val Cys Arg Asn Asn Ile Asn Phe Tyr Tyr Tyr Thr Leu Ser
                275                 280                 285 tgc gcc ttc gct tac tgt atg gga gga gaa gaa aga gct aaa cac gtc        912
Cys Ala Phe Ala Tyr Cys Met Gly Gly Glu Glu Arg Ala Lys His Val
        290                 295                 300 ctt ttc gac tat gtt gag aca tgc gct gca ccg gaa acg aga gga acg        960
Leu Phe Asp Tyr Val Glu Thr Cys Ala Ala Pro Glu Thr Arg Gly Thr
305                 310                 315                 320 tgt gtt tta tca gga cat act ttc tat gac aca ttc gac aaa gcc aga       1008
Cys Val Leu Ser Gly His Thr Phe Tyr Asp Thr Phe Asp Lys Ala Arg
                325                 330                 335 tat caa ttc cag ggc cca tgc aaa gag ctt ctg atg gcc gca gac tgt       1056
Tyr Gln Phe Gln Gly Pro Cys Lys Glu Leu Leu Met Ala Ala Asp Cys
                340                 345                 350 tac tgg aac aca tgg gat gta aag gtt tca cat aga gat gtt gag tca       1104
Tyr Trp Asn Thr Trp Asp Val Lys Val Ser His Arg Asp Val Glu Ser
                355                 360                 365 tac act gag gta gag aaa gta aca atc agg aaa cag tca act gta gta       1152
Tyr Thr Glu Val Glu Lys Val Thr Ile Arg Lys Gln Ser Thr Val Val
370                 375                 380 gat ttg att gtg gat ggc aag cag gtc aag gtt gga gga gtg gat gta       1200
Asp Leu Ile Val Asp Gly Lys Gln Val Lys Val Gly Gly Val Asp Val
385                 390                 395                 400 tct atc ccg tac agt tct gag aac aca tcc ata tac tgg cag gat gga       1248
Ser Ile Pro Tyr Ser Ser Glu Asn Thr Ser Ile Tyr Trp Gln Asp Gly
                405                 410                 415 gac atc ctg acg acg gcc atc cta cct gaa gct ctt gtc gtt aag ttc       1296
Asp Ile Leu Thr Thr Ala Ile Leu Pro Glu Ala Leu Val Val Lys Phe
                420                 425                 430 aac ttt aag cag ctc ctt gta gtt cat atc aga gat cca ttc gat gga       1344
Asn Phe Lys Gln Leu Leu Val Val His Ile Arg Asp Pro Phe Asp Gly
                435                 440                 445 aag aca tgc ggc ata tgt ggt aac tat aat caa gat tca act gat gat       1392
Lys Thr Cys Gly Ile Cys Gly Asn Tyr Asn Gln Asp Ser Thr Asp Asp
                450                 455                 460 ttc ttt gac gca gaa gga gca tgc gct ctg acc ccc aat ccc cca gga       1440
Phe Phe Asp Ala Glu Gly Ala Cys Ala Leu Thr Pro Asn Pro Pro Gly
465                 470                 475                 480 tgt aca gag gag cag aaa cca gaa gct gag cga ctc tgc aat agt cta       1488
Cys Thr Glu Glu Gln Lys Pro Glu Ala Glu Arg Leu Cys Asn Ser Leu
                485                 490                 495 ttt gat agt tct atc gac gag aaa tgt aat gtc tgc tac aag cct gac       1536
Phe Asp Ser Ser Ile Asp Glu Lys Cys Asn Val Cys Tyr Lys Pro Asp
                500                 505                 510
```

```
cgt att gca cga tgt atg tac gag tat tgc ctg agg gga cag caa gga        1584
Arg Ile Ala Arg Cys Met Tyr Glu Tyr Cys Leu Arg Gly Gln Gln Gly
        515                 520                 525 ttc tgt gac cat gct tgg gag ttc aaa aaa gaa tgc tac ata aag cat        1632
Phe Cys Asp His Ala Trp Glu Phe Lys Lys Glu Cys Tyr Ile Lys His
530                 535                 540 gga gac act cta gaa gta cca cct gaa tgc caa taaatgaaca aagatacaga      1685
Gly Asp Thr Leu Glu Val Pro Pro Glu Cys Gln
545                 550                 555 agctaagact actacagcag aagataaaag agaagctgta gttcttcaaa aacagtatat      1745
tttgatgtac tcattgttta cttacataaa ataaattgt tattatcata acgtaaagaa       1805
aaaaaaaaaa aaaaaaa                                                     1822

<210> SEQ ID NO 3
<211> LENGTH: 1644
<212> TYPE: DNA
<213> ORGANISM: Luciola cruciata
<220> FEATURE:
<221> NAME/KEY: CDS
<222> LOCATION: (1)...(1644)
<223> OTHER INFORMATION: Luciola cruciata luciferase

<400> SEQUENCE: 3 atg gaa aac atg gaa aac gat gaa aat att gta gtt gga cct aaa ccg          48
Met Glu Asn Met Glu Asn Asp Glu Asn Ile Val Val Gly Pro Lys Pro
1               5                  10                  15 ttt tac cct atc gaa gag gga tct gct gga aca caa tta cgc aaa tac          96
Phe Tyr Pro Ile Glu Glu Gly Ser Ala Gly Thr Gln Leu Arg Lys Tyr
                20                  25                  30 atg gag cga tat gca aaa ctt ggc gca att gct ttt aca aat gca gtt         144
Met Glu Arg Tyr Ala Lys Leu Gly Ala Ile Ala Phe Thr Asn Ala Val
            35                  40                  45 act ggt gtt gat tat tct tac gcc gaa tac ttg gag aaa tca tgt tgt         192
Thr Gly Val Asp Tyr Ser Tyr Ala Glu Tyr Leu Glu Lys Ser Cys Cys
        50                  55                  60 cta gga aaa gct ttg caa aat tat ggt ttg gtt gtt gat ggc aga att         240
Leu Gly Lys Ala Leu Gln Asn Tyr Gly Leu Val Val Asp Gly Arg Ile
65                  70                  75                  80 gcg tta tgc agt gaa aac tgt gaa gaa ttt ttt att cct gta ata gcc         288
Ala Leu Cys Ser Glu Asn Cys Glu Glu Phe Phe Ile Pro Val Ile Ala
                85                  90                  95 gga ctg ttt ata ggt gta ggt gtt gca ccc act aat gag att tac act         336
Gly Leu Phe Ile Gly Val Gly Val Ala Pro Thr Asn Glu Ile Tyr Thr
                100                 105                 110 tta cgt gaa ctg gtt cac agt tta ggt atc tct aaa cca aca att gta         384
Leu Arg Glu Leu Val His Ser Leu Gly Ile Ser Lys Pro Thr Ile Val
            115                 120                 125 ttt agt tct aaa aaa ggc tta gat aaa gtt ata aca gta cag aaa aca         432
Phe Ser Ser Lys Lys Gly Leu Asp Lys Val Ile Thr Val Gln Lys Thr
        130                 135                 140 gta act act att aaa acc att gtt ata cta gat agc aaa gtt gat tat         480
Val Thr Thr Ile Lys Thr Ile Val Ile Leu Asp Ser Lys Val Asp Tyr
145                 150                 155                 160 cga gga tat caa tgt ctg gac acc ttt ata aaa aga aac act cca cca         528
Arg Gly Tyr Gln Cys Leu Asp Thr Phe Ile Lys Arg Asn Thr Pro Pro
                165                 170                 175 ggt ttt caa gca tcc agt ttc aaa act gtg gaa gtt gac cgt aaa gaa         576
Gly Phe Gln Ala Ser Ser Phe Lys Thr Val Glu Val Asp Arg Lys Glu
                180                 185                 190 caa gtt gct ctt ata atg aac tct tcg ggt tct acc ggt ttg cca aaa         624
Gln Val Ala Leu Ile Met Asn Ser Ser Gly Ser Thr Gly Leu Pro Lys
```

```
                Gln Val Ala Ile Met Asn Ser Ser Gly Ser Thr Gly Leu Pro Lys
                    195                 200                 205 ggc gta caa ctt act cac gaa aat aca gtc act aga ttt tct cat gct       672
Gly Val Gln Leu Thr His Glu Asn Thr Val Thr Arg Phe Ser His Ala
210                 215                 220 aga gat ccg att tat ggt aac caa gtt tca cca ggc acc gct gtt tta       720
Arg Asp Pro Ile Tyr Gly Asn Gln Val Ser Pro Gly Thr Ala Val Leu
225                 230                 235                 240 act gtc gtt cca ttc cat cat ggt ttt ggt atg ttc act act cta ggg       768
Thr Val Val Pro Phe His His Gly Phe Gly Met Phe Thr Thr Leu Gly
                245                 250                 255 tat tta att tgt ggt ttt cgt gtt gta atg tta aca aaa ttc gat gaa       816
Tyr Leu Ile Cys Gly Phe Arg Val Val Met Leu Thr Lys Phe Asp Glu
                260                 265                 270 gaa aca ttt tta aaa act cta caa gat tat aaa tgt aca agt gtt att       864
Glu Thr Phe Leu Lys Thr Leu Gln Asp Tyr Lys Cys Thr Ser Val Ile
            275                 280                 285 ctt gta ccg acc ttg ttt gca att ctc aac aaa agt gaa tta ctc aat       912
Leu Val Pro Thr Leu Phe Ala Ile Leu Asn Lys Ser Glu Leu Leu Asn
        290                 295                 300 aaa tac gat ttg tca aat tta gtt gag att gca tct ggc gga gca cct       960
Lys Tyr Asp Leu Ser Asn Leu Val Glu Ile Ala Ser Gly Gly Ala Pro
305                 310                 315                 320 tta tca aaa gaa gtt ggt gaa gct gtt gct aga cgc ttt aat ctt ccc       1008
Leu Ser Lys Glu Val Gly Glu Ala Val Ala Arg Arg Phe Asn Leu Pro
                325                 330                 335 ggt gtt cgt caa ggt tat ggt tta aca gaa aca aca tct gcc att att       1056
Gly Val Arg Gln Gly Tyr Gly Leu Thr Glu Thr Thr Ser Ala Ile Ile
                340                 345                 350 att aca cca gaa gga gac gat aaa cca gga gct tct gga aaa gtc gtg       1104
Ile Thr Pro Glu Gly Asp Asp Lys Pro Gly Ala Ser Gly Lys Val Val
            355                 360                 365 ccg ttg ttt aaa gca aaa gtt att gat ctt gat acc aaa aaa tct tta       1152
Pro Leu Phe Lys Ala Lys Val Ile Asp Leu Asp Thr Lys Lys Ser Leu
        370                 375                 380 ggt cct aac aga cgt gga gaa gtt tgt gtt aaa gga cct atg ctt atg       1200
Gly Pro Asn Arg Arg Gly Glu Val Cys Val Lys Gly Pro Met Leu Met
385                 390                 395                 400 aaa ggt tat gta aat aat cca gaa gca aca aaa gaa ctt att gac gaa       1248
Lys Gly Tyr Val Asn Asn Pro Glu Ala Thr Lys Glu Leu Ile Asp Glu
                405                 410                 415 gaa ggt tgg ctg cac acc gga gat att gga tat tat gat gaa gaa aaa       1296
Glu Gly Trp Leu His Thr Gly Asp Ile Gly Tyr Tyr Asp Glu Glu Lys
                420                 425                 430 cat ttc ttt att gtc gat cgt ttg aag tct tta atc aaa tac aaa gga       1344
His Phe Phe Ile Val Asp Arg Leu Lys Ser Leu Ile Lys Tyr Lys Gly
            435                 440                 445 tac caa gta cca cct gcc gaa tta gaa tcc gtt ctt ttg caa cat cca       1392
Tyr Gln Val Pro Pro Ala Glu Leu Glu Ser Val Leu Leu Gln His Pro
        450                 455                 460 tct atc ttt gat gct ggt gtt gcc ggc gtt cct gat cct gta gct ggc       1440
Ser Ile Phe Asp Ala Gly Val Ala Gly Val Pro Asp Pro Val Ala Gly
465                 470                 475                 480 gag ctt cca gga gcc gtt gtt gta ctg gaa agc gga aaa aat atg acc       1488
Glu Leu Pro Gly Ala Val Val Val Leu Glu Ser Gly Lys Asn Met Thr
                485                 490                 495 gaa aaa gaa gta atg gat tat gtt gca agt caa gtt tca aat gca aaa       1536
Glu Lys Glu Val Met Asp Tyr Val Ala Ser Gln Val Ser Asn Ala Lys
                500                 505                 510
```

```
cgt tta cgt ggt ggt gtt cgt ttt gtg gat gaa gta cct aaa ggt ctt    1584
Arg Leu Arg Gly Gly Val Arg Phe Val Asp Glu Val Pro Lys Gly Leu
    515                 520                 525 act gga aaa att gac ggc aga gca att aga gaa atc ctt aag aaa cca    1632
Thr Gly Lys Ile Asp Gly Arg Ala Ile Arg Glu Ile Leu Lys Lys Pro
530                 535                 540 gtt gct aag atg                                                    1644
Val Ala Lys Met
545
```

<210> SEQ ID NO 4
<211> LENGTH: 1820
<212> TYPE: DNA
<213> ORGANISM: Vargula (cypridina)
<220> FEATURE:
<221> NAME/KEY: CDS
<222> LOCATION: (1)...(1665)
<223> OTHER INFORMATION: Vargula (cypridina) luciferase

<400> SEQUENCE: 4

```
atg aag ata ata att ctg tct gtt ata ttg gcc tac tgt gtc acc gac     48
Met Lys Ile Ile Ile Leu Ser Val Ile Leu Ala Tyr Cys Val Thr Asp
1               5                   10                  15 aac tgt caa gat gca tgt cct gta gaa gcg gaa ccg cca tca agt aca     96
Asn Cys Gln Asp Ala Cys Pro Val Glu Ala Glu Pro Pro Ser Ser Thr
                20                  25                  30 cca aca gtt cca act tct tgt gaa gct aaa gaa gga gaa tgt ata gat    144
Pro Thr Val Pro Thr Ser Cys Glu Ala Lys Glu Gly Glu Cys Ile Asp
            35                  40                  45 acc aga tgc gca aca tgt aaa cga gat ata cta tca gat gga ctg tgt    192
Thr Arg Cys Ala Thr Cys Lys Arg Asp Ile Leu Ser Asp Gly Leu Cys
        50                  55                  60 gaa aat aaa cca ggg aag aca tgc tgt aga atg tgc cag tat gtg att    240
Glu Asn Lys Pro Gly Lys Thr Cys Cys Arg Met Cys Gln Tyr Val Ile
65                  70                  75                  80 gaa tgc aga gta gaa gca gct ggt tat ttt aga acg ttt tac ggc aaa    288
Glu Cys Arg Val Glu Ala Ala Gly Tyr Phe Arg Thr Phe Tyr Gly Lys
                85                  90                  95 aga ttt aat ttt cag gaa cct ggt aaa tat gtg ctg gct agg gga acc    336
Arg Phe Asn Phe Gln Glu Pro Gly Lys Tyr Val Leu Ala Arg Gly Thr
                100                 105                 110 aag ggt ggc gat tgg tct gta acc ctc acc atg gag aat cta gat gga    384
Lys Gly Gly Asp Trp Ser Val Thr Leu Thr Met Glu Asn Leu Asp Gly
            115                 120                 125 cag aag gga gct gtg ctg act aag aca aca ctg gag gtt gca gga gac    432
Gln Lys Gly Ala Val Leu Thr Lys Thr Thr Leu Glu Val Ala Gly Asp
        130                 135                 140 gta ata gac att act caa gct act gca gat cct atc aca gtt aac gga    480
Val Ile Asp Ile Thr Gln Ala Thr Ala Asp Pro Ile Thr Val Asn Gly
145                 150                 155                 160 gga gct gac cca gtt atc gct aac ccg ttc aca att ggt gag gtg acc    528
Gly Ala Asp Pro Val Ile Ala Asn Pro Phe Thr Ile Gly Glu Val Thr
                165                 170                 175 att gct gtt gtt gaa ata ccg ggc ttc aat atc aca gtc atc gaa ttc    576
Ile Ala Val Val Glu Ile Pro Gly Phe Asn Ile Thr Val Ile Glu Phe
                180                 185                 190 ttt aaa cta atc gtg att gat att ctg gga gga aga tct gtc aga att    624
Phe Lys Leu Ile Val Ile Asp Ile Leu Gly Gly Arg Ser Val Arg Ile
            195                 200                 205 gct cca gac aca gca aac aaa gga ctg ata tct ggt atc tgt ggt aat    672
Ala Pro Asp Thr Ala Asn Lys Gly Leu Ile Ser Gly Ile Cys Gly Asn
        210                 215                 220
```

```
ctg gag atg aat gac gct gat gac ttt act aca gat gca gat cag ctg      720
Leu Glu Met Asn Asp Ala Asp Asp Phe Thr Thr Asp Ala Asp Gln Leu
225                 230                 235                 240 gcg atc caa ccc aac ata aac aaa gag ttc gac ggc tgc cca ttc tat      768
Ala Ile Gln Pro Asn Ile Asn Lys Glu Phe Asp Gly Cys Pro Phe Tyr
            245                 250                 255 ggc aat cct tct gat atc gaa tac tgc aaa ggt ctg atg gag cca tac      816
Gly Asn Pro Ser Asp Ile Glu Tyr Cys Lys Gly Leu Met Glu Pro Tyr
        260                 265                 270 aga gct gta tgt cgt aac aat atc aac ttc tac tat tac act cta tcc      864
Arg Ala Val Cys Arg Asn Asn Ile Asn Phe Tyr Tyr Tyr Thr Leu Ser
    275                 280                 285 tgt gcc ttc gct tac tgt atg gga gga gaa gaa aga gct aaa cac gtc      912
Cys Ala Phe Ala Tyr Cys Met Gly Gly Glu Glu Arg Ala Lys His Val
290                 295                 300 ctt ttc gac tat gtt gag aca tgc gct gcg ccg gaa acg aga gga acg      960
Leu Phe Asp Tyr Val Glu Thr Cys Ala Ala Pro Glu Thr Arg Gly Thr
305                 310                 315                 320 tgt gtt tta tca gga cat act ttc tat gac aca ttc gac aaa gca aga     1008
Cys Val Leu Ser Gly His Thr Phe Tyr Asp Thr Phe Asp Lys Ala Arg
            325                 330                 335 tat caa ttc cag ggc cca tgc aag gag att ctg atg gcc gca gac tgt     1056
Tyr Gln Phe Gln Gly Pro Cys Lys Glu Ile Leu Met Ala Ala Asp Cys
        340                 345                 350 tac tgg aac aca tgg gat gta aag gtt tca cat aga gac gtc gaa tca     1104
Tyr Trp Asn Thr Trp Asp Val Lys Val Ser His Arg Asp Val Glu Ser
    355                 360                 365 tac act gag gta gag aaa gta aca atc agg aaa cag tca act gta gta     1152
Tyr Thr Glu Val Glu Lys Val Thr Ile Arg Lys Gln Ser Thr Val Val
370                 375                 380 gat ctc att gtg gat ggc aag cag gtc aag gtt gga gga gtg gat gta     1200
Asp Leu Ile Val Asp Gly Lys Gln Val Lys Val Gly Gly Val Asp Val
385                 390                 395                 400 tct atc ccg tac agc tct gag aac act tcc ata tac tgg cag gat gga     1248
Ser Ile Pro Tyr Ser Ser Glu Asn Thr Ser Ile Tyr Trp Gln Asp Gly
            405                 410                 415 gac atc ctg acg acg gcc atc cta cct gaa gct ctt gtc gtt aag ttc     1296
Asp Ile Leu Thr Thr Ala Ile Leu Pro Glu Ala Leu Val Val Lys Phe
        420                 425                 430 aac ttt aag cag ctc ctt gta gtt cat atc aga gat cca ttc gat gca     1344
Asn Phe Lys Gln Leu Leu Val Val His Ile Arg Asp Pro Phe Asp Ala
    435                 440                 445 aag aca tgc ggc ata tgt ggt aac tat aat caa gat tca act gat gat     1392
Lys Thr Cys Gly Ile Cys Gly Asn Tyr Asn Gln Asp Ser Thr Asp Asp
450                 455                 460 ttc ttt gac gca gaa gga gca tgc gct cta acc ccc aac ccc cca gga     1440
Phe Phe Asp Ala Glu Gly Ala Cys Ala Leu Thr Pro Asn Pro Pro Gly
465                 470                 475                 480 tgt aca gag gaa cag aaa cca gaa gct gag cga ctt tgc aat aat ctc     1488
Cys Thr Glu Glu Gln Lys Pro Glu Ala Glu Arg Leu Cys Asn Asn Leu
            485                 490                 495 ttt gat tct tct atc gac gag aaa tgt aat gtc tgc tac aag cct gac     1536
Phe Asp Ser Ser Ile Asp Glu Lys Cys Asn Val Cys Tyr Lys Pro Asp
        500                 505                 510 cgg att gcc cga tgt atg tac gag tat tgc ctg agg gga caa caa gga     1584
Arg Ile Ala Arg Cys Met Tyr Glu Tyr Cys Leu Arg Gly Gln Gln Gly
    515                 520                 525 ttt tgt gac cat gct tgg gag ttc aag aaa gaa tgc tac ata aaa cat     1632
Phe Cys Asp His Ala Trp Glu Phe Lys Lys Glu Cys Tyr Ile Lys His
```

-continued

```
       530                 535                 540
gga gac act cta gaa gta cca cct gaa tgt caa taaacgtaca aagatacaga       1685
Gly Asp Thr Leu Glu Val Pro Pro Glu Cys Gln
545                 550                 555 agctaaggct actacagcag aagataaaaa agaaactgta gttccttcaa aaaccgtgta      1745
ttttatgtac tcattgttta attagagcaa aataaattgt tattatcata acttaaacta      1805
aaaaaaaaaa aaaaa                                                       1820

<210> SEQ ID NO 5
<211> LENGTH: 958
<212> TYPE: DNA
<213> ORGANISM: Aequorea victoria
<220> FEATURE:
<221> NAME/KEY: CDS
<222> LOCATION: (115)...(702)
<223> OTHER INFORMATION: Apoequorin-encoding gene

<400> SEQUENCE: 5
gggggggggg gggggggggg gggggggggg gggaatgcaa ttcatctttg catcaaagaa        60
ttacatcaaa tctctagttg atcaactaaa ttgtctcgac aacaacaagc aaac atg        117
                                                              Met
                                                                1 aca agc aaa caa tac tca gtc aag ctt aca tca gac ttc gac aac cca        165
Thr Ser Lys Gln Tyr Ser Val Lys Leu Thr Ser Asp Phe Asp Asn Pro
              5                  10                  15 aga tgg att gga cga cac aag cat atg ttc aat ttc ctt gat gtc aac        213
Arg Trp Ile Gly Arg His Lys His Met Phe Asn Phe Leu Asp Val Asn
         20                  25                  30 cac aat gga aaa atc tct ctt gac gag atg gtc tac aag gca tct gat        261
His Asn Gly Lys Ile Ser Leu Asp Glu Met Val Tyr Lys Ala Ser Asp
     35                  40                  45 att gtc atc aat aac ctt gga gca aca cct gag caa gcc aaa cga cac        309
Ile Val Ile Asn Asn Leu Gly Ala Thr Pro Glu Gln Ala Lys Arg His
 50                  55                  60                  65 aaa gat gct gta gaa gcc ttc ttc gga gga gct gga atg aaa tat ggt        357
Lys Asp Ala Val Glu Ala Phe Phe Gly Gly Ala Gly Met Lys Tyr Gly
                 70                  75                  80 gtg gaa act gat tgg cct gca tat att gaa gga tgg aaa aaa ttg gct        405
Val Glu Thr Asp Trp Pro Ala Tyr Ile Glu Gly Trp Lys Lys Leu Ala
             85                  90                  95 act gat gaa ttg gag aaa tac gcc aaa aac gaa cca acg ctc atc cgt        453
Thr Asp Glu Leu Glu Lys Tyr Ala Lys Asn Glu Pro Thr Leu Ile Arg
        100                 105                 110 ata tgg ggt gat gct ttg ttt gat atc gtt gac aaa gat caa aat gga        501
Ile Trp Gly Asp Ala Leu Phe Asp Ile Val Asp Lys Asp Gln Asn Gly
    115                 120                 125 gcc att aca ctg gat gaa tgg aaa gca tac acc aaa gct gct ggt atc        549
Ala Ile Thr Leu Asp Glu Trp Lys Ala Tyr Thr Lys Ala Ala Gly Ile
130                 135                 140                 145 atc caa tca tca gaa gat tgc gag gaa aca ttc aga gtg tgc gat att        597
Ile Gln Ser Ser Glu Asp Cys Glu Glu Thr Phe Arg Val Cys Asp Ile
                150                 155                 160 gat gaa agt gga caa ctc gat gtt gat gag atg aca aga caa cat tta        645
Asp Glu Ser Gly Gln Leu Asp Val Asp Glu Met Thr Arg Gln His Leu
            165                 170                 175 gga ttt tgg tac acc atg gat cct gct tgc gaa aag ctc tac ggt gga        693
Gly Phe Trp Tyr Thr Met Asp Pro Ala Cys Glu Lys Leu Tyr Gly Gly
        180                 185                 190 gct gtc ccc taagaagctc tacggtggtg atgcacccta ggaagatgat                 742
```

-continued

```
Ala Val Pro
    195 gtgattttga ataaaacact gatgaattca atcaaaattt tccaaatttt tgaacgattt    802 caatcgtttg tgttgatttt tgtaattagg aacagattaa atcgaatgat tagttgtttt    862 tttaatcaac agaacttaca aatcgaaaaa gtaaaaaaaa aaaaaaaaaa aaaaaaaaaa    922 aaaaaaaaaa aaaaaaaaaa aaaaaaaaaa aaaaa                               958

<210> SEQ ID NO 6
<211> LENGTH: 591
<212> TYPE: DNA
<213> ORGANISM: Aequorea victoria
<220> FEATURE:
<221> NAME/KEY: CDS
<222> LOCATION: (1)...(588)
<223> OTHER INFORMATION: Recombinant Aequorin AEQ1

<400> SEQUENCE: 6 atg acc agc gaa caa tac tca gtc aag ctt aca cca gac ttc gac aac     48
Met Thr Ser Glu Gln Tyr Ser Val Lys Leu Thr Pro Asp Phe Asp Asn
 1               5                  10                  15 cca aaa tgg att gga cga cac aag cac atg ttt aat ttt ctt gat gtc     96
Pro Lys Trp Ile Gly Arg His Lys His Met Phe Asn Phe Leu Asp Val
            20                  25                  30 aac cac aat gga agg atc tct ctt gac gag atg gtc tac aag gcg tcc    144
Asn His Asn Gly Arg Ile Ser Leu Asp Glu Met Val Tyr Lys Ala Ser
        35                  40                  45 gat att gtt ata aac aat ctt gga gca aca cct gaa caa gcc aaa cgt    192
Asp Ile Val Ile Asn Asn Leu Gly Ala Thr Pro Glu Gln Ala Lys Arg
    50                  55                  60 cac aaa gat gct gta gaa gcc ttc ttc gga gga gct gga atg aaa tat    240
His Lys Asp Ala Val Glu Ala Phe Phe Gly Gly Ala Gly Met Lys Tyr
65                  70                  75                  80 ggt gta gaa act gaa tgg cct gaa tac atc gaa gga tgg aaa aga ctg    288
Gly Val Glu Thr Glu Trp Pro Glu Tyr Ile Glu Gly Trp Lys Arg Leu
                85                  90                  95 gct tcc gag gaa ttg aaa agg tat tca aaa aac caa atc aca ctt att    336
Ala Ser Glu Glu Leu Lys Arg Tyr Ser Lys Asn Gln Ile Thr Leu Ile
            100                 105                 110 cgt tta tgg ggt gat gca ttg ttc gat atc att gac aaa gac caa aat    384
Arg Leu Trp Gly Asp Ala Leu Phe Asp Ile Ile Asp Lys Asp Gln Asn
        115                 120                 125 gga gct att tca ctg gat gaa tgg aaa gca tac acc aaa tct gat ggc    432
Gly Ala Ile Ser Leu Asp Glu Trp Lys Ala Tyr Thr Lys Ser Asp Gly
    130                 135                 140 atc atc caa tcg tca gaa gat tgc gag gaa aca ttc aga gtg tgc gat    480
Ile Ile Gln Ser Ser Glu Asp Cys Glu Glu Thr Phe Arg Val Cys Asp
145                 150                 155                 160 att gat gaa agt gga cag ctc gat gtt gat gag atg aca aga caa cat    528
Ile Asp Glu Ser Gly Gln Leu Asp Val Asp Glu Met Thr Arg Gln His
                165                 170                 175 tta gga ttt tgg tac acc atg gat cct gct tgc gaa aag ctc tac ggt    576
Leu Gly Phe Trp Tyr Thr Met Asp Pro Ala Cys Glu Lys Leu Tyr Gly
            180                 185                 190 gga gct gtc ccc taa                                                  591
Gly Ala Val Pro
        195

<210> SEQ ID NO 7
<211> LENGTH: 591
<212> TYPE: DNA
```

```
<213> ORGANISM: Aequoria victoria
<220> FEATURE:
<221> NAME/KEY: CDS
<222> LOCATION: (1)...(588)
<223> OTHER INFORMATION: Recombinant Aequorin AEQ2

<400> SEQUENCE: 7 atg acc agc gaa caa tac tca gtc aag ctt aca tca gac ttc gac aac      48
Met Thr Ser Glu Gln Tyr Ser Val Lys Leu Thr Ser Asp Phe Asp Asn
 1               5                  10                  15 cca aga tgg att gga cga cac aag cat atg ttc aat ttc ctt gat gtc      96
Pro Arg Trp Ile Gly Arg His Lys His Met Phe Asn Phe Leu Asp Val
             20                  25                  30 aac cac aat gga aaa atc tct ctt gac gag atg gtc tac aag gca tct     144
Asn His Asn Gly Lys Ile Ser Leu Asp Glu Met Val Tyr Lys Ala Ser
         35                  40                  45 gat att gtc atc aat aac ctt gga gca aca cct gag caa gcc aaa cga     192
Asp Ile Val Ile Asn Asn Leu Gly Ala Thr Pro Glu Gln Ala Lys Arg
     50                  55                  60 cac aaa gat gct gta gaa gcc ttc ttc gga gga gct gga atg aaa tat     240
His Lys Asp Ala Val Glu Ala Phe Phe Gly Gly Ala Gly Met Lys Tyr
 65                  70                  75                  80 ggt gtg gaa act gat tgg cct gca tat att gaa gga tgg aaa aaa ttg     288
Gly Val Glu Thr Asp Trp Pro Ala Tyr Ile Glu Gly Trp Lys Lys Leu
                 85                  90                  95 gct act gat gaa ttg gag aaa tac gcc aaa aac gaa cca acg ctc atc     336
Ala Thr Asp Glu Leu Glu Lys Tyr Ala Lys Asn Glu Pro Thr Leu Ile
            100                 105                 110 cgt ata tgg ggt gat gct ttg ttc gat atc gtt gac aaa gat caa aat     384
Arg Ile Trp Gly Asp Ala Leu Phe Asp Ile Val Asp Lys Asp Gln Asn
        115                 120                 125 gga gcc att aca ctg gat gaa tgg aaa gca tac acc aaa gct gct ggt     432
Gly Ala Ile Thr Leu Asp Glu Trp Lys Ala Tyr Thr Lys Ala Ala Gly
    130                 135                 140 atc atc caa tca tca gaa gat tgc gag gaa aca ttc aga gtg tgc gat     480
Ile Ile Gln Ser Ser Glu Asp Cys Glu Glu Thr Phe Arg Val Cys Asp
145                 150                 155                 160 att gat gaa agt gga caa ctc gat gtt gat gag atg aca aga caa cat     528
Ile Asp Glu Ser Gly Gln Leu Asp Val Asp Glu Met Thr Arg Gln His
                165                 170                 175 tta gga ttt tgg tac acc atg gat cct gct tgc gaa aag ctc tac ggt     576
Leu Gly Phe Trp Tyr Thr Met Asp Pro Ala Cys Glu Lys Leu Tyr Gly
            180                 185                 190 gga gct gtc ccc taa                                                 591
Gly Ala Val Pro
        195

<210> SEQ ID NO 8
<211> LENGTH: 591
<212> TYPE: DNA
<213> ORGANISM: Aequoria victoria
<220> FEATURE:
<221> NAME/KEY: CDS
<222> LOCATION: (1)...(588)
<223> OTHER INFORMATION: Recombinant Aequorin AEQ3

<400> SEQUENCE: 8 atg acc agc gaa caa tac tca gtc aag ctt aca tca gac ttc gac aac      48
Met Thr Ser Glu Gln Tyr Ser Val Lys Leu Thr Ser Asp Phe Asp Asn
 1               5                  10                  15 cca aga tgg att gga cga cac aag cat atg ttc aat ttc ctt gat gtc      96
Pro Arg Trp Ile Gly Arg His Lys His Met Phe Asn Phe Leu Asp Val
             20                  25                  30
```

```
aac cac aat gga aaa atc tct ctt gac gag atg gtc tac aag gca tct    144
Asn His Asn Gly Lys Ile Ser Leu Asp Glu Met Val Tyr Lys Ala Ser
            35                  40                  45 gat att gtc atc aat aac ctt gga gca aca cct gag caa gcc aaa cga    192
Asp Ile Val Ile Asn Asn Leu Gly Ala Thr Pro Glu Gln Ala Lys Arg
 50                  55                  60 cac aaa gat gct gta gga gac ttc ttc gga gga gct gga atg aaa tat    240
His Lys Asp Ala Val Gly Asp Phe Phe Gly Gly Ala Gly Met Lys Tyr
 65                  70                  75                  80 ggt gtg gaa act gat tgg cct gca tac att gaa gga tgg aaa aaa ttg    288
Gly Val Glu Thr Asp Trp Pro Ala Tyr Ile Glu Gly Trp Lys Lys Leu
                 85                  90                  95 gct act gat gaa ttg gag aaa tac gcc aaa aac gaa cca acg ctc atc    336
Ala Thr Asp Glu Leu Glu Lys Tyr Ala Lys Asn Glu Pro Thr Leu Ile
            100                 105                 110 cgt ata tgg ggt gat gct ttg ttc gat atc gtt gac aaa gat caa aat    384
Arg Ile Trp Gly Asp Ala Leu Phe Asp Ile Val Asp Lys Asp Gln Asn
        115                 120                 125 gga gcc att aca ctg gat gaa tgg aaa gca tac acc aaa gct gct ggt    432
Gly Ala Ile Thr Leu Asp Glu Trp Lys Ala Tyr Thr Lys Ala Ala Gly
130                 135                 140 atc atc caa tca tca gaa gat tgc gag gaa aca ttc aga gtg tgc gat    480
Ile Ile Gln Ser Ser Glu Asp Cys Glu Glu Thr Phe Arg Val Cys Asp
145                 150                 155                 160 att gat gaa aat gga caa ctc gat gtt gat gag atg aca aga caa cat    528
Ile Asp Glu Asn Gly Gln Leu Asp Val Asp Glu Met Thr Arg Gln His
                165                 170                 175 tta gga ttt tgg tac acc atg gat cct gct tgc gaa aag ctc tac ggt    576
Leu Gly Phe Trp Tyr Thr Met Asp Pro Ala Cys Glu Lys Leu Tyr Gly
            180                 185                 190 gga gct gtc ccc taa                                                591
Gly Ala Val Pro
        195

<210> SEQ ID NO 9
<211> LENGTH: 567
<212> TYPE: DNA
<213> ORGANISM: Aequoria victoria
<220> FEATURE:
<221> NAME/KEY: CDS
<222> LOCATION: (1)...(567)
<223> OTHER INFORMATION: Aequorin photoprotein

<400> SEQUENCE: 9 gtc aag ctt aca cca gac ttc gac aac cca aaa tgg att gga cga cac     48
Val Lys Leu Thr Pro Asp Phe Asp Asn Pro Lys Trp Ile Gly Arg His
 1               5                  10                  15 aag cac atg ttt aat ttt ctt gat gtc aac cac aat gga agg atc tct     96
Lys His Met Phe Asn Phe Leu Asp Val Asn His Asn Gly Arg Ile Ser
                 20                  25                  30 ctt gac gag atg gtc tac aag gcg tcc gat att gtt ata aac aat ctt    144
Leu Asp Glu Met Val Tyr Lys Ala Ser Asp Ile Val Ile Asn Asn Leu
            35                  40                  45 gga gca aca cct gaa caa gcc aaa cgt cac aaa gat gct gta gaa gcc    192
Gly Ala Thr Pro Glu Gln Ala Lys Arg His Lys Asp Ala Val Glu Ala
 50                  55                  60 ttc ttc gga gga gct gca atg aaa tat ggt gta gaa act gaa tgg cct    240
Phe Phe Gly Gly Ala Ala Met Lys Tyr Gly Val Glu Thr Glu Trp Pro
 65                  70                  75                  80 gaa tac atc gaa gga tgg aaa aga ctg gct tcc gag gaa ttg aaa agg    288
Glu Tyr Ile Glu Gly Trp Lys Arg Leu Ala Ser Glu Glu Leu Lys Arg
```

-continued

```
                       85                  90                  95
tat tca aaa aac caa atc aca ctt att cgt tta tgg ggt gat gca ttg      336
Tyr Ser Lys Asn Gln Ile Thr Leu Ile Arg Leu Trp Gly Asp Ala Leu
                100                 105                 110 ttc gat atc att gac aaa gac caa aat gga gct att tca ctg gat gaa      384
Phe Asp Ile Ile Asp Lys Asp Gln Asn Gly Ala Ile Ser Leu Asp Glu
            115                 120                 125 tgg aaa gca tac acc aaa tct gct ggc atc atc caa tcg tca gaa gat      432
Trp Lys Ala Tyr Thr Lys Ser Ala Gly Ile Ile Gln Ser Ser Glu Asp
        130                 135                 140 tgc gag gaa aca ttc aga gtg tgc gat att gat gaa agt gga cag ctc      480
Cys Glu Glu Thr Phe Arg Val Cys Asp Ile Asp Glu Ser Gly Gln Leu
145                 150                 155                 160 gat gtt gat gag atg aca aga caa cat tta gga ttt tgg tac acc atg      528
Asp Val Asp Glu Met Thr Arg Gln His Leu Gly Phe Trp Tyr Thr Met
                165                 170                 175 gat cct gct tgc gaa aag ctc tac ggt gga gct gtc ccc                  567
Asp Pro Ala Cys Glu Lys Leu Tyr Gly Gly Ala Val Pro
            180                 185

<210> SEQ ID NO 10
<211> LENGTH: 588
<212> TYPE: DNA
<213> ORGANISM: Aequoria victoria
<220> FEATURE:
<221> NAME/KEY: CDS
<222> LOCATION: (1)...(588)
<223> OTHER INFORMATION: Aequorin mutant w/increased bioluminescence
      activity

<400> SEQUENCE: 10 atg acc agc gaa caa tac tca gtc aag ctt aca cca gac ttc gac aac       48
Met Thr Ser Glu Gln Tyr Ser Val Lys Leu Thr Pro Asp Phe Asp Asn
1               5                   10                  15 cca aaa tgg att gga cga cac aag cac atg ttt aat ttt ctt gat gtc       96
Pro Lys Trp Ile Gly Arg His Lys His Met Phe Asn Phe Leu Asp Val
                20                  25                  30 aac cac aat gga agg atc tct ctt gac gag atg gtc tac aag gcg tcc      144
Asn His Asn Gly Arg Ile Ser Leu Asp Glu Met Val Tyr Lys Ala Ser
            35                  40                  45 gat att gtt ata aac aat ctt gga gca aca cct gaa caa gcc aaa cgt      192
Asp Ile Val Ile Asn Asn Leu Gly Ala Thr Pro Glu Gln Ala Lys Arg
        50                  55                  60 cac aaa gat gct gta gaa gcc ttc ttc gga gga gct gca atg aaa tat      240
His Lys Asp Ala Val Glu Ala Phe Phe Gly Gly Ala Ala Met Lys Tyr
65                  70                  75                  80 ggt gta gaa act gaa tgg cct gaa tac atc gaa gga tgg aaa aga ctg      288
Gly Val Glu Thr Glu Trp Pro Glu Tyr Ile Glu Gly Trp Lys Arg Leu
                85                  90                  95 gct tcc gag gaa ttg aaa agg tat tca aaa aac caa atc aca ctt att      336
Ala Ser Glu Glu Leu Lys Arg Tyr Ser Lys Asn Gln Ile Thr Leu Ile
                100                 105                 110 cgt tta tgg ggt gat gca ttg ttc gat atc att tcc aaa gac caa aat      384
Arg Leu Trp Gly Asp Ala Leu Phe Asp Ile Ile Ser Lys Asp Gln Asn
            115                 120                 125 gga gct att tca ctg gat gaa tgg aaa gca tac acc aaa tct gct ggc      432
Gly Ala Ile Ser Leu Asp Glu Trp Lys Ala Tyr Thr Lys Ser Ala Gly
        130                 135                 140 atc atc caa tcg tca gaa gat tgc gag gaa aca ttc aga gtg tgc gat      480
Ile Ile Gln Ser Ser Glu Asp Cys Glu Glu Thr Phe Arg Val Cys Asp
145                 150                 155                 160
```

```
att gat gaa agt gga cag ctc gat gtt gat gag atg aca aga caa cat    528
Ile Asp Glu Ser Gly Gln Leu Asp Val Asp Glu Met Thr Arg Gln His
            165                 170                 175 tta gga ttt tgg tac acc atg gat cct gct tgc gaa aag ctc tac ggt    576
Leu Gly Phe Trp Tyr Thr Met Asp Pro Ala Cys Glu Lys Leu Tyr Gly
        180                 185                 190 gga gct gtc ccc                                                    588
Gly Ala Val Pro
        195

<210> SEQ ID NO 11
<211> LENGTH: 588
<212> TYPE: DNA
<213> ORGANISM: Aequorea victoria
<220> FEATURE:
<221> NAME/KEY: CDS
<222> LOCATION: (1)...(588)
<223> OTHER INFORMATION: Recombinant site-directed Aequorin mutant

<400> SEQUENCE: 11 atg acc agc gaa caa tac tca gtc aag ctt aca cca gac ttc gac aac     48
Met Thr Ser Glu Gln Tyr Ser Val Lys Leu Thr Pro Asp Phe Asp Asn
1               5                  10                  15 cca aaa tgg att gga cga cac aag cac atg ttt aat ttt ctt gat gtc     96
Pro Lys Trp Ile Gly Arg His Lys His Met Phe Asn Phe Leu Asp Val
            20                  25                  30 aac cac aat gga agg atc tct ctt gac gag atg gtc tac aag gcg tcc    144
Asn His Asn Gly Arg Ile Ser Leu Asp Glu Met Val Tyr Lys Ala Ser
        35                  40                  45 gat att gtt ata aac aat ctt gga gca aca cct gaa caa gcc aaa cgt    192
Asp Ile Val Ile Asn Asn Leu Gly Ala Thr Pro Glu Gln Ala Lys Arg
    50                  55                  60 cac aaa gat gct gta gaa gcc ttc ttc gga gga gct gca atg aaa tat    240
His Lys Asp Ala Val Glu Ala Phe Phe Gly Gly Ala Ala Met Lys Tyr
65                  70                  75                  80 ggt gta gaa act gaa tgg cct gaa tac atc gaa gga tgg aaa aga ctg    288
Gly Val Glu Thr Glu Trp Pro Glu Tyr Ile Glu Gly Trp Lys Arg Leu
                85                  90                  95 gct tcc gag gaa ttg aaa agg tat tca aaa aac caa atc aca ctt att    336
Ala Ser Glu Glu Leu Lys Arg Tyr Ser Lys Asn Gln Ile Thr Leu Ile
            100                 105                 110 cgt tta tgg ggt gat gca ttg ttc gat atc att tcc aaa gac caa aat    384
Arg Leu Trp Gly Asp Ala Leu Phe Asp Ile Ile Ser Lys Asp Gln Asn
        115                 120                 125 gga gct att tca ctg gat tca tgg aaa gca tac acc aaa tct gct ggc    432
Gly Ala Ile Ser Leu Asp Ser Trp Lys Ala Tyr Thr Lys Ser Ala Gly
    130                 135                 140 atc atc caa tcg tca gaa gat tgc gag gaa aca ttc aga gtg tgc gat    480
Ile Ile Gln Ser Ser Glu Asp Cys Glu Glu Thr Phe Arg Val Cys Asp
145                 150                 155                 160 att gat gaa agt gga cag ctc gat gtt gat gag atg aca aga caa cat    528
Ile Asp Glu Ser Gly Gln Leu Asp Val Asp Glu Met Thr Arg Gln His
            165                 170                 175 tta gga ttt tgg tac acc atg gat cct gct tgc gaa aag ctc tac ggt    576
Leu Gly Phe Trp Tyr Thr Met Asp Pro Ala Cys Glu Lys Leu Tyr Gly
        180                 185                 190 gga gct gtc ccc                                                    588
Gly Ala Val Pro
        195

<210> SEQ ID NO 12
<211> LENGTH: 588
```

<212> TYPE: DNA
<213> ORGANISM: Aequorea victoria
<220> FEATURE:
<221> NAME/KEY: CDS
<222> LOCATION: (1)...(588)
<223> OTHER INFORMATION: Aequorin mutant with increased biolumenescence activity

<400> SEQUENCE: 12

```
atg acc agc gaa caa tac tca gtc aag ctt aca cca gac ttc gac aac        48
Met Thr Ser Glu Gln Tyr Ser Val Lys Leu Thr Pro Asp Phe Asp Asn
 1               5                  10                  15 cca aaa tgg att gga cga cac aag cac atg ttt aat ttt ctt gat gtc        96
Pro Lys Trp Ile Gly Arg His Lys His Met Phe Asn Phe Leu Asp Val
             20                  25                  30 aac cac aat gga agg atc tct ctt gac gag atg gtc tac aag gcg tcc       144
Asn His Asn Gly Arg Ile Ser Leu Asp Glu Met Val Tyr Lys Ala Ser
         35                  40                  45 gat att gtt ata aac aat ctt gga gca aca cct gaa caa gcc aaa cgt       192
Asp Ile Val Ile Asn Asn Leu Gly Ala Thr Pro Glu Gln Ala Lys Arg
     50                  55                  60 cac aaa gat gct gta gaa gcc ttc ttc gga gga gct gca atg aaa tat       240
His Lys Asp Ala Val Glu Ala Phe Phe Gly Gly Ala Ala Met Lys Tyr
 65                  70                  75                  80 ggt gta gaa act gaa tgg cct gaa tac atc gaa gga tgg aaa aga ctg       288
Gly Val Glu Thr Glu Trp Pro Glu Tyr Ile Glu Gly Trp Lys Arg Leu
                 85                  90                  95 gct tcc gag gaa ttg aaa agg tat tca aaa aac caa atc aca ctt att       336
Ala Ser Glu Glu Leu Lys Arg Tyr Ser Lys Asn Gln Ile Thr Leu Ile
            100                 105                 110 cgt tta tgg ggt gat gca ttg ttc gat atc att tcc aaa gac caa aat       384
Arg Leu Trp Gly Asp Ala Leu Phe Asp Ile Ile Ser Lys Asp Gln Asn
        115                 120                 125 gca gct att tca ctg gat gaa tgg aaa gca tac acc aaa tct gct ggc       432
Ala Ala Ile Ser Leu Asp Glu Trp Lys Ala Tyr Thr Lys Ser Ala Gly
    130                 135                 140 atc atc caa tcg tca gaa gat tgc gag gaa aca ttc aga gtg tgc gat       480
Ile Ile Gln Ser Ser Glu Asp Cys Glu Glu Thr Phe Arg Val Cys Asp
145                 150                 155                 160 att gat gaa agt gga cag ctc gat gtt gat gag atg aca aga caa cat       528
Ile Asp Glu Ser Gly Gln Leu Asp Val Asp Glu Met Thr Arg Gln His
                165                 170                 175 tta gga ttt tgg tac acc atg gat cct gct tgc gaa aag ctc tac ggt       576
Leu Gly Phe Trp Tyr Thr Met Asp Pro Ala Cys Glu Lys Leu Tyr Gly
            180                 185                 190 gga gct gtc ccc                                                       588
Gly Ala Val Pro
        195
```

<210> SEQ ID NO 13
<211> LENGTH: 567
<212> TYPE: DNA
<213> ORGANISM: Aequorea victoria
<220> FEATURE:
<221> NAME/KEY: CDS
<222> LOCATION: (1)...(567)
<223> OTHER INFORMATION: Recombinant apoaequorin (AQUALITEp)

<400> SEQUENCE: 13

```
gtc aag ctt aca cca gac ttc gac aac cca aaa tgg att gga cga cac        48
Val Lys Leu Thr Pro Asp Phe Asp Asn Pro Lys Trp Ile Gly Arg His
 1               5                  10                  15 aag cac atg ttt aat ttt ctt gat gtc aac cac aat gga agg atc tct        96
```

```
                Lys His Met Phe Asn Phe Leu Asp Val Asn His Asn Gly Arg Ile Ser
                             20                  25                  30 ctt gac gag atg gtc tac aag gcg tcc gat att gtt ata aac aat ctt           144
Leu Asp Glu Met Val Tyr Lys Ala Ser Asp Ile Val Ile Asn Asn Leu
             35                  40                  45 gga gca aca cct gaa caa gcc aaa cgt cac aaa gat gct gta gaa gcc           192
Gly Ala Thr Pro Glu Gln Ala Lys Arg His Lys Asp Ala Val Glu Ala
 50                  55                  60 ttc ttc gga gga gct gga atg aaa tat ggt gta gaa act gaa tgg cct           240
Phe Phe Gly Gly Ala Gly Met Lys Tyr Gly Val Glu Thr Glu Trp Pro
 65                  70                  75                  80 gaa tac atc gaa gga tgg aaa aaa ctg gct tcc gag gaa ttg aaa agg           288
Glu Tyr Ile Glu Gly Trp Lys Lys Leu Ala Ser Glu Glu Leu Lys Arg
                 85                  90                  95 tat tca aaa aac caa atc aca ctt att cgt tta tgg ggt gat gca ttg           336
Tyr Ser Lys Asn Gln Ile Thr Leu Ile Arg Leu Trp Gly Asp Ala Leu
            100                 105                 110 ttc gat atc att gac aaa gac caa aat gga gct att ctg tca gat gaa           384
Phe Asp Ile Ile Asp Lys Asp Gln Asn Gly Ala Ile Leu Ser Asp Glu
        115                 120                 125 tgg aaa gca tac acc aaa tct gat ggc atc atc caa tcg tca gaa gat           432
Trp Lys Ala Tyr Thr Lys Ser Asp Gly Ile Ile Gln Ser Ser Glu Asp
    130                 135                 140 tgc gag gaa aca ttc aga gtg tgc gat att gat gaa agt gga cag ctc           480
Cys Glu Glu Thr Phe Arg Val Cys Asp Ile Asp Glu Ser Gly Gln Leu
145                 150                 155                 160 gat gtt gat gag atg aca aga caa cat tta gga ttt tgg tac acc atg           528
Asp Val Asp Glu Met Thr Arg Gln His Leu Gly Phe Trp Tyr Thr Met
                165                 170                 175 gat cct gct tgc gaa aag ctc tac ggt gga gct gtc ccc                       567
Asp Pro Ala Cys Glu Lys Leu Tyr Gly Gly Ala Val Pro
            180                 185

<210> SEQ ID NO 14
<211> LENGTH: 236
<212> TYPE: PRT
<213> ORGANISM: Vibrio fisheri

<400> SEQUENCE: 14

Met Pro Ile Asn Cys Lys Val Lys Ser Ile Glu Pro Leu Ala Cys Asn
 1               5                  10                  15

Thr Phe Arg Ile Leu His Pro Glu Gln Pro Val Ala Phe Lys Ala
            20                  25                  30

Gly Gln Tyr Leu Thr Val Val Met Gly Glu Lys Asp Lys Arg Pro Phe
        35                  40                  45

Ser Ile Ala Ser Ser Pro Cys Arg His Glu Gly Glu Ile Glu Leu His
    50                  55                  60

Ile Gly Ala Ala Glu His Asn Ala Tyr Ala Gly Glu Val Val Glu Ser
65                  70                  75                  80

Met Lys Ser Ala Leu Glu Thr Gly Gly Asp Ile Leu Ile Asp Ala Pro
                85                  90                  95

His Gly Glu Ala Trp Ile Arg Glu Asp Ser Asp Arg Ser Met Leu Leu
            100                 105                 110

Ile Ala Gly Gly Thr Gly Phe Ser Tyr Val Arg Ser Ile Leu Asp His
        115                 120                 125

Cys Ile Ser Gln Gln Ile Gln Lys Pro Ile Tyr Leu Tyr Trp Gly Gly
    130                 135                 140

Arg Asp Glu Cys Gln Leu Tyr Ala Lys Ala Glu Leu Glu Ser Ile Ala
```

```
                145                 150                 155                 160
Gln Ala His Ser His Ile Thr Phe Val Pro Val Val Glu Lys Ser Glu
                    165                 170                 175

Gly Trp Thr Gly Lys Thr Gly Asn Val Leu Glu Ala Val Lys Ala Asp
                180                 185                 190

Phe Asn Ser Leu Ala Asp Met Asp Ile Tyr Ile Ala Gly Arg Phe Glu
            195                 200                 205

Met Ala Gly Ala Ala Arg Glu Gln Phe Thr Thr Glu Lys Gln Ala Lys
        210                 215                 220

Lys Glu Gln Leu Phe Gly Asp Ala Phe Ala Phe Ile
225                 230                 235

<210> SEQ ID NO 15
<211> LENGTH: 1079
<212> TYPE: DNA
<213> ORGANISM: Renilla mulleri
<220> FEATURE:
<221> NAME/KEY: CDS
<222> LOCATION: (259)...(975)
<223> OTHER INFORMATION: Renilla mulleri GFP

<400> SEQUENCE: 15
ggttatacac aagtgtatcg cgtatctgca gacgcatcta gtgggattat tcgagcggta      60
gtatttacgt cagacctgtc taatcgaaac cacaacaaac tcttaaaata agccacattt     120
acataatatc taagagacgc ctcatttaag agtagtaaaa atataatata tgatagagta     180
tacaactctc gccttagaca gacagtgtgc aacagagtaa ctcttgttaa tgcaatcgaa     240
agcgtcaaga gagataag atg agt aaa caa ata ttg aag aac act tgt tta      291
                    Met Ser Lys Gln Ile Leu Lys Asn Thr Cys Leu
                    1               5                   10 caa gaa gta atg tcg tat aaa gta aat ctg gaa gga att gta aac aac      339
Gln Glu Val Met Ser Tyr Lys Val Asn Leu Glu Gly Ile Val Asn Asn
            15                  20                  25 cat gtt ttt aca atg gag ggt tgc ggc aaa ggg aat att tta ttc ggc      387
His Val Phe Thr Met Glu Gly Cys Gly Lys Gly Asn Ile Leu Phe Gly
        30                  35                  40 aat caa ctg gtt cag att cgt gtc acg aaa ggg gcc cca ctg cct ttt      435
Asn Gln Leu Val Gln Ile Arg Val Thr Lys Gly Ala Pro Leu Pro Phe
    45                  50                  55 gca ttt gat att gtg tca cca gct ttt caa tat ggc aac cgt act ttc      483
Ala Phe Asp Ile Val Ser Pro Ala Phe Gln Tyr Gly Asn Arg Thr Phe
60                  65                  70                  75 acg aaa tat ccg aat gat ata tca gat tat ttt ata caa tca ttt cca      531
Thr Lys Tyr Pro Asn Asp Ile Ser Asp Tyr Phe Ile Gln Ser Phe Pro
                80                  85                  90 gca gga ttt atg tat gaa cga aca tta cgt tac gaa gat ggc gga ctt      579
Ala Gly Phe Met Tyr Glu Arg Thr Leu Arg Tyr Glu Asp Gly Gly Leu
            95                  100                 105 gtt gaa att cgt tca gat ata aat tta ata gaa gac aag ttc gtc tac      627
Val Glu Ile Arg Ser Asp Ile Asn Leu Ile Glu Asp Lys Phe Val Tyr
        110                 115                 120 aga gtg gaa tac aaa ggt agt aac ttc cca gat gat ggt ccc gtc atg      675
Arg Val Glu Tyr Lys Gly Ser Asn Phe Pro Asp Asp Gly Pro Val Met
    125                 130                 135 cag aag act atc tta gga ata gag cct tca ttt gaa gcc atg tac atg      723
Gln Lys Thr Ile Leu Gly Ile Glu Pro Ser Phe Glu Ala Met Tyr Met
140                 145                 150                 155 aat aat ggc gtc ttg gtc ggc gaa gta att ctt gtc tat aaa cta aac      771
Asn Asn Gly Val Leu Val Gly Glu Val Ile Leu Val Tyr Lys Leu Asn
```

```
                      160                 165                 170
tct ggg aaa tat tat tca tgt cac atg aaa aca tta atg aag tcg aaa        819
Ser Gly Lys Tyr Tyr Ser Cys His Met Lys Thr Leu Met Lys Ser Lys
            175                 180                 185 ggt gta gta aag gag ttt cct tcg tat cat ttt att caa cat cgt ttg        867
Gly Val Val Lys Glu Phe Pro Ser Tyr His Phe Ile Gln His Arg Leu
            190                 195                 200 gaa aag act tac gta gaa gac ggg ggg ttc gtt gaa cag cat gag act        915
Glu Lys Thr Tyr Val Glu Asp Gly Gly Phe Val Glu Gln His Glu Thr
            205                 210                 215 gct att gct caa atg aca tct ata gga aaa cca cta gga tcc tta cac        963
Ala Ile Ala Gln Met Thr Ser Ile Gly Lys Pro Leu Gly Ser Leu His
220                 225                 230                 235 gaa tgg gtt taa acacagttac attactttt ccaattcgtg tttcatgtca            1015
Glu Trp Val * aataataatt ttttaaacaa ttatcaatgt tttgtgatat gtttgtaaaa aaaaaaaaaa      1075
aaaa                                                                   1079
```

<210> SEQ ID NO 16
<211> LENGTH: 238
<212> TYPE: PRT
<213> ORGANISM: Renilla mulleri

<400> SEQUENCE: 16

```
Met Ser Lys Gln Ile Leu Lys Asn Thr Cys Leu Gln Glu Val Met Ser
1               5                   10                  15

Tyr Lys Val Asn Leu Glu Gly Ile Val Asn Asn His Val Phe Thr Met
            20                  25                  30

Glu Gly Cys Gly Lys Gly Asn Ile Leu Phe Gly Asn Gln Leu Val Gln
        35                  40                  45

Ile Arg Val Thr Lys Gly Ala Pro Leu Pro Phe Ala Phe Asp Ile Val
    50                  55                  60

Ser Pro Ala Phe Gln Tyr Gly Asn Arg Thr Phe Thr Lys Tyr Pro Asn
65                  70                  75                  80

Asp Ile Ser Asp Tyr Phe Ile Gln Ser Phe Pro Ala Gly Phe Met Tyr
                85                  90                  95

Glu Arg Thr Leu Arg Tyr Glu Asp Gly Gly Leu Val Glu Ile Arg Ser
            100                 105                 110

Asp Ile Asn Leu Ile Glu Asp Lys Phe Val Tyr Arg Val Glu Tyr Lys
        115                 120                 125

Gly Ser Asn Phe Pro Asp Asp Gly Pro Val Met Gln Lys Thr Ile Leu
    130                 135                 140

Gly Ile Glu Pro Ser Phe Glu Ala Met Tyr Met Asn Asn Gly Val Leu
145                 150                 155                 160

Val Gly Glu Val Ile Leu Val Tyr Lys Leu Asn Ser Gly Lys Tyr Tyr
                165                 170                 175

Ser Cys His Met Lys Thr Leu Met Lys Ser Lys Gly Val Val Lys Glu
            180                 185                 190

Phe Pro Ser Tyr His Phe Ile Gln His Arg Leu Glu Lys Thr Tyr Val
        195                 200                 205

Glu Asp Gly Gly Phe Val Glu Gln His Glu Thr Ala Ile Ala Gln Met
    210                 215                 220

Thr Ser Ile Gly Lys Pro Leu Gly Ser Leu His Glu Trp Val
225                 230                 235
```

<210> SEQ ID NO 17
<211> LENGTH: 1217
<212> TYPE: DNA
<213> ORGANISM: Renilla mulleri
<220> FEATURE:
<221> NAME/KEY: CDS
<222> LOCATION: (31)...(963)
<223> OTHER INFORMATION: Renilla mulleri luciferase

<400> SEQUENCE: 17

```
cggcacgagg tttaagaatc aataaaaaaa atg acg tca aaa gtt tac gat cct           54
                                Met Thr Ser Lys Val Tyr Asp Pro
                                  1               5 gaa tta aga aaa cgc atg att act ggt cca caa tgg tgg gca aga tgt          102
Glu Leu Arg Lys Arg Met Ile Thr Gly Pro Gln Trp Trp Ala Arg Cys
         10                  15                  20 aaa caa atg aat gtt ctt gat tca ttt att aat tat tat gat tca gaa          150
Lys Gln Met Asn Val Leu Asp Ser Phe Ile Asn Tyr Tyr Asp Ser Glu
 25                  30                  35                  40 aaa cat gca gaa aat gca gtt ata ttt tta cat ggt aat gca gca tct          198
Lys His Ala Glu Asn Ala Val Ile Phe Leu His Gly Asn Ala Ala Ser
             45                  50                  55 tct tat tta tgg cgt cat gtt gta cca cat gtt gaa cca gtg gcg cga          246
Ser Tyr Leu Trp Arg His Val Val Pro His Val Glu Pro Val Ala Arg
         60                  65                  70 tgt att ata cca gat ctt ata ggt atg ggt aaa tca ggc aag tct ggt          294
Cys Ile Ile Pro Asp Leu Ile Gly Met Gly Lys Ser Gly Lys Ser Gly
 75                  80                  85 aat ggt tcc tat aga tta cta gat cat tac aaa tat ctt act gaa tgg          342
Asn Gly Ser Tyr Arg Leu Leu Asp His Tyr Lys Tyr Leu Thr Glu Trp
         90                  95                 100 ttc aaa cat ctt aat tta cca aag aag atc att ttt gtc ggt cat gat          390
Phe Lys His Leu Asn Leu Pro Lys Lys Ile Ile Phe Val Gly His Asp
105                 110                 115                 120 tgg ggt gct tgt tta gca ttt cat tat tgc tat gaa cat cag gat cgc          438
Trp Gly Ala Cys Leu Ala Phe His Tyr Cys Tyr Glu His Gln Asp Arg
            125                 130                 135 atc aaa gca gtt gtt cat gct gaa agt gta gta gat gtg att gaa tcg          486
Ile Lys Ala Val Val His Ala Glu Ser Val Val Asp Val Ile Glu Ser
        140                 145                 150 tgg gac gaa tgg cct gat att gaa gaa gat att gct ttg att aaa tct          534
Trp Asp Glu Trp Pro Asp Ile Glu Glu Asp Ile Ala Leu Ile Lys Ser
    155                 160                 165 gaa gaa gga gaa aaa atg gtt tta gag aat aac ttc ttc gtg gaa acc          582
Glu Glu Gly Glu Lys Met Val Leu Glu Asn Asn Phe Phe Val Glu Thr
170                 175                 180 atg ttg cca tca aaa atc atg aga aag ttg gaa cca gag gaa ttt gct          630
Met Leu Pro Ser Lys Ile Met Arg Lys Leu Glu Pro Glu Glu Phe Ala
185                 190                 195                 200 gct tat ctt gaa cca ttt aaa gag aaa ggt gaa gtt cgt cgt cca aca          678
Ala Tyr Leu Glu Pro Phe Lys Glu Lys Gly Glu Val Arg Arg Pro Thr
            205                 210                 215 tta tca tgg cct cgt gaa atc cct ttg gta aaa ggt ggt aaa ccg gat          726
Leu Ser Trp Pro Arg Glu Ile Pro Leu Val Lys Gly Gly Lys Pro Asp
        220                 225                 230 gta gta gaa att gtc agg aat tat aat gct tat ctt cgt gca agt cat          774
Val Val Glu Ile Val Arg Asn Tyr Asn Ala Tyr Leu Arg Ala Ser His
    235                 240                 245 gat tta cca aaa atg ttt att gaa tct gat cca gga ttc ttt tcc aat          822
Asp Leu Pro Lys Met Phe Ile Glu Ser Asp Pro Gly Phe Phe Ser Asn
250                 255                 260
```

```
gct att gtt gaa ggt gct aag aaa ttc cct aat act gaa ttt gtt aaa      870
Ala Ile Val Glu Gly Ala Lys Lys Phe Pro Asn Thr Glu Phe Val Lys
265                 270                 275                 280 gtc aaa ggt ctt cat ttt tca caa gaa gat gca cct gat gaa atg gga      918
Val Lys Gly Leu His Phe Ser Gln Glu Asp Ala Pro Asp Glu Met Gly
                285                 290                 295 aat tat ata aaa tcg ttt gtt gag cgt gtt ctt aaa aat gaa caa          963
Asn Tyr Ile Lys Ser Phe Val Glu Arg Val Leu Lys Asn Glu Gln
            300                 305                 310 taaactacca ggtttccatg ttgccacttt agctgggttt aataaatttc actatcaatt   1023
tgaacaattt cacattaatt ttaactatta aaaaattatg gacacaggga ttatatcaga   1083
tgattaattt agttgggaac aatgaatacc gaatattatg aattctcttt agctatttat   1143
aataatcaca ttcttatgta ataaaacttt gttttaataa attaatgatt cagaaaaaaa   1203
aaaaaaaaaa aaaa                                                     1217
```

<210> SEQ ID NO 18
<211> LENGTH: 311
<212> TYPE: PRT
<213> ORGANISM: Renilla mulleri

<400> SEQUENCE: 18

```
Met Thr Ser Lys Val Tyr Asp Pro Glu Leu Arg Lys Arg Met Ile Thr
  1               5                  10                  15

Gly Pro Gln Trp Trp Ala Arg Cys Lys Gln Met Asn Val Leu Asp Ser
             20                  25                  30

Phe Ile Asn Tyr Tyr Asp Ser Glu Lys His Ala Glu Asn Ala Val Ile
         35                  40                  45

Phe Leu His Gly Asn Ala Ala Ser Ser Tyr Leu Trp Arg His Val Val
     50                  55                  60

Pro His Val Glu Pro Val Ala Arg Cys Ile Ile Pro Asp Leu Ile Gly
 65                  70                  75                  80

Met Gly Lys Ser Gly Lys Ser Gly Asn Gly Ser Tyr Arg Leu Leu Asp
                 85                  90                  95

His Tyr Lys Tyr Leu Thr Glu Trp Phe Lys His Leu Asn Leu Pro Lys
            100                 105                 110

Lys Ile Ile Phe Val Gly His Asp Trp Gly Ala Cys Leu Ala Phe His
        115                 120                 125

Tyr Cys Tyr Glu His Gln Asp Arg Ile Lys Ala Val His Ala Glu
    130                 135                 140

Ser Val Val Asp Val Ile Glu Ser Trp Asp Glu Trp Pro Asp Ile Glu
145                 150                 155                 160

Glu Asp Ile Ala Leu Ile Lys Ser Glu Glu Gly Glu Lys Met Val Leu
                165                 170                 175

Glu Asn Asn Phe Phe Val Glu Thr Met Leu Pro Ser Lys Ile Met Arg
            180                 185                 190

Lys Leu Glu Pro Glu Glu Phe Ala Ala Tyr Leu Glu Pro Phe Lys Glu
        195                 200                 205

Lys Gly Glu Val Arg Arg Pro Thr Leu Ser Trp Pro Arg Glu Ile Pro
    210                 215                 220

Leu Val Lys Gly Gly Lys Pro Asp Val Val Glu Ile Val Arg Asn Tyr
225                 230                 235                 240

Asn Ala Tyr Leu Arg Ala Ser His Asp Leu Pro Lys Met Phe Ile Glu
                245                 250                 255

Ser Asp Pro Gly Phe Phe Ser Asn Ala Ile Val Glu Gly Ala Lys Lys
```

```
                    260                 265                 270
Phe Pro Asn Thr Glu Phe Val Lys Val Lys Gly Leu His Phe Ser Gln
        275                 280                 285

Glu Asp Ala Pro Asp Glu Met Gly Asn Tyr Ile Lys Ser Phe Val Glu
    290                 295                 300

Arg Val Leu Lys Asn Glu Gln
305                 310

<210> SEQ ID NO 19
<211> LENGTH: 765
<212> TYPE: DNA
<213> ORGANISM: Gaussia
<220> FEATURE:
<221> NAME/KEY: CDS
<222> LOCATION: (37)...(594)

<400> SEQUENCE: 19
gcacgagggt actcaaagta tcttctggca gggaaa atg gga gtg aaa gtt ctt        54
                                        Met Gly Val Lys Val Leu
                                          1               5 ttt gcc ctt att tgt att gct gtg gcc gag gcc aaa cca act gaa aac       102
Phe Ala Leu Ile Cys Ile Ala Val Ala Glu Ala Lys Pro Thr Glu Asn
             10                  15                  20 aat gaa gat ttc aac att gta gct gta gct agc aac ttt gct aca acg       150
Asn Glu Asp Phe Asn Ile Val Ala Val Ala Ser Asn Phe Ala Thr Thr
                 25                  30                  35 gat ctc gat gct gac cgt ggt aaa ttg ccc gga aaa aaa tta cca ctt       198
Asp Leu Asp Ala Asp Arg Gly Lys Leu Pro Gly Lys Lys Leu Pro Leu
     40                  45                  50 gag gta ctc aaa gaa atg gaa gcc aat gct agg aaa gct ggc tgc act       246
Glu Val Leu Lys Glu Met Glu Ala Asn Ala Arg Lys Ala Gly Cys Thr
 55                  60                  65                  70 agg gga tgt ctg ata tgc ctg tca cac atc aag tgt aca ccc aaa atg       294
Arg Gly Cys Leu Ile Cys Leu Ser His Ile Lys Cys Thr Pro Lys Met
                 75                  80                  85 aag aag ttt atc cca gga aga tgc cac acc tat gaa gga gac aaa gaa       342
Lys Lys Phe Ile Pro Gly Arg Cys His Thr Tyr Glu Gly Asp Lys Glu
                 90                  95                 100 agt gca cag gga gga ata gga gag gct att gtt gac att cct gaa att       390
Ser Ala Gln Gly Gly Ile Gly Glu Ala Ile Val Asp Ile Pro Glu Ile
            105                 110                 115 cct ggg ttt aag gat ttg gaa ccc atg gaa caa ttc att gca caa gtt       438
Pro Gly Phe Lys Asp Leu Glu Pro Met Glu Gln Phe Ile Ala Gln Val
        120                 125                 130 gac cta tgt gta gac tgc aca act gga tgc ctc aaa ggt ctt gcc aat       486
Asp Leu Cys Val Asp Cys Thr Thr Gly Cys Leu Lys Gly Leu Ala Asn
135                 140                 145                 150 gtg caa tgt tct gat tta ctc aag aaa tgg ctg cca caa aga tgt gca       534
Val Gln Cys Ser Asp Leu Leu Lys Lys Trp Leu Pro Gln Arg Cys Ala
                155                 160                 165 act ttt gct agc aaa att caa ggc caa gtg gac aaa ata aag ggt gcc       582
Thr Phe Ala Ser Lys Ile Gln Gly Gln Val Asp Lys Ile Lys Gly Ala
            170                 175                 180 ggt ggt gat taa tcctaataga atactgcata actggatgat gatatactag           634
Gly Gly Asp *
        185 cttattgctc ataaaatggc cattttttgt aacaaatcga gtctatgtaa ttcaaaatac     694 ctaattaatt gttaatacat atgtaattcc tataaatata atttatgcaa tccaaaaaaa     754 aaaaaaaaaa a                                                          765
```

```
<210> SEQ ID NO 20
<211> LENGTH: 185
<212> TYPE: PRT
<213> ORGANISM: Renilla mulleri

<400> SEQUENCE: 20

Met Gly Val Lys Val Leu Phe Ala Leu Ile Cys Ile Ala Val Ala Glu
 1               5                  10                  15

Ala Lys Pro Thr Glu Asn Asn Glu Asp Phe Asn Ile Val Ala Val Ala
            20                  25                  30

Ser Asn Phe Ala Thr Thr Asp Leu Asp Ala Asp Arg Gly Lys Leu Pro
        35                  40                  45

Gly Lys Lys Leu Pro Leu Glu Val Leu Lys Glu Met Glu Ala Asn Ala
 50                  55                  60

Arg Lys Ala Gly Cys Thr Arg Gly Cys Leu Ile Cys Leu Ser His Ile
65                  70                  75                  80

Lys Cys Thr Pro Lys Met Lys Lys Phe Ile Pro Gly Arg Cys His Thr
                85                  90                  95

Tyr Glu Gly Asp Lys Glu Ser Ala Gln Gly Ile Gly Glu Ala Ile
            100                 105                 110

Val Asp Ile Pro Glu Ile Pro Gly Phe Lys Asp Leu Glu Pro Met Glu
        115                 120                 125

Gln Phe Ile Ala Gln Val Asp Leu Cys Val Asp Cys Thr Thr Gly Cys
130                 135                 140

Leu Lys Gly Leu Ala Asn Val Gln Cys Ser Asp Leu Leu Lys Lys Trp
145                 150                 155                 160

Leu Pro Gln Arg Cys Ala Thr Phe Ala Ser Lys Ile Gln Gly Gln Val
                165                 170                 175

Asp Lys Ile Lys Gly Ala Gly Gly Asp
            180                 185

<210> SEQ ID NO 21
<211> LENGTH: 1146
<212> TYPE: DNA
<213> ORGANISM: Gaussia
<220> FEATURE:
<221> NAME/KEY: CDS
<222> LOCATION: (1)...(1146)
<223> OTHER INFORMATION: Nucleotide sequence encoding a CBD-Gaussia
      luciferase fusion protein

<400> SEQUENCE: 21 atg tca gtt gaa ttt tac aac tct aac aaa tca gca caa aca aac tca       48
Met Ser Val Glu Phe Tyr Asn Ser Asn Lys Ser Ala Gln Thr Asn Ser
 1               5                  10                  15 att aca cca ata atc aaa att act aac aca tct gac agt gat tta aat       96
Ile Thr Pro Ile Ile Lys Ile Thr Asn Thr Ser Asp Ser Asp Leu Asn
            20                  25                  30 tta aat gac gta aaa gtt aga tat tat tac aca agt gat ggt aca caa      144
Leu Asn Asp Val Lys Val Arg Tyr Tyr Tyr Thr Ser Asp Gly Thr Gln
        35                  40                  45 gga caa act ttc tgg tgt gac cat gct ggt gca tta tta gga aat agc      192
Gly Gln Thr Phe Trp Cys Asp His Ala Gly Ala Leu Leu Gly Asn Ser
 50                  55                  60 tat gtt gat aac act agc aaa gtg aca gca aac ttc gtt aaa gaa aca      240
Tyr Val Asp Asn Thr Ser Lys Val Thr Ala Asn Phe Val Lys Glu Thr
65                  70                  75                  80 gca agc cca aca tca acc tat gat aca tat gtt gaa ttt gga ttt gca      288
```

| | | | | | | | | | | | | |
|---|---|---|---|---|---|---|---|---|---|---|---|---|
| Ala | Ser | Pro | Thr | Ser | Thr | Tyr | Asp | Thr | Tyr | Val | Glu | Phe | Gly | Phe | Ala |
| | | | | 85 | | | | 90 | | | | 95 | |

```
agc gga gca gct act ctt aaa aaa gga caa ttt ata act att caa gga       336
Ser Gly Ala Ala Thr Leu Lys Lys Gly Gln Phe Ile Thr Ile Gln Gly
            100                 105                 110 aga ata aca aaa tca gac tgg tca aac tac act caa aca aat gac tat       384
Arg Ile Thr Lys Ser Asp Trp Ser Asn Tyr Thr Gln Thr Asn Asp Tyr
            115                 120                 125 tca ttt gat gca agt agt tca aca cca gtt gta aat cca aaa gtt aca       432
Ser Phe Asp Ala Ser Ser Ser Thr Pro Val Val Asn Pro Lys Val Thr
            130                 135                 140 gga tat ata ggt gga gct aaa gtt ctt ggt aca gca cca ggt tcc gcg       480
Gly Tyr Ile Gly Gly Ala Lys Val Leu Gly Thr Ala Pro Gly Ser Ala
145                 150                 155                 160 ggt ctg gtg cca cgc ggt agt act gca att ggt atg aaa gaa acc gct       528
Gly Leu Val Pro Arg Gly Ser Thr Ala Ile Gly Met Lys Glu Thr Ala
                165                 170                 175 gct gct aaa ttc gaa cgc cag cac atg gac agc cca gat ctg ggt acc       576
Ala Ala Lys Phe Glu Arg Gln His Met Asp Ser Pro Asp Leu Gly Thr
            180                 185                 190 gat gac gac gac aag atg gga gtg aaa gtt ctt ttt gcc ctt att tgt       624
Asp Asp Asp Asp Lys Met Gly Val Lys Val Leu Phe Ala Leu Ile Cys
            195                 200                 205 att gct gtg gcc gag gcc aaa cca act gaa aac aat gaa gat ttc aac       672
Ile Ala Val Ala Glu Ala Lys Pro Thr Glu Asn Asn Glu Asp Phe Asn
            210                 215                 220 att gta gct gta gct agc aac ttt gct aca acg gat ctc gat gct gac       720
Ile Val Ala Val Ala Ser Asn Phe Ala Thr Thr Asp Leu Asp Ala Asp
225                 230                 235                 240 cgt ggt aaa ttg ccc gga aaa aaa tta cca ctt gag gta ctc aaa gaa       768
Arg Gly Lys Leu Pro Gly Lys Lys Leu Pro Leu Glu Val Leu Lys Glu
                245                 250                 255 atg gaa gcc aat gct agg aaa gct ggc tgc act agg gga tgt ctg ata       816
Met Glu Ala Asn Ala Arg Lys Ala Gly Cys Thr Arg Gly Cys Leu Ile
            260                 265                 270 tgc ctg tca cac atc aag tgt aca ccc aaa atg aag aag ttt atc cca       864
Cys Leu Ser His Ile Lys Cys Thr Pro Lys Met Lys Lys Phe Ile Pro
            275                 280                 285 gga aga tgc cac acc tat gaa gga gac aaa gaa agt gca cag gga gga       912
Gly Arg Cys His Thr Tyr Glu Gly Asp Lys Glu Ser Ala Gln Gly Gly
            290                 295                 300 ata gga gag gct att gtt gac att cct gaa att cct ggg ttt aag gat       960
Ile Gly Glu Ala Ile Val Asp Ile Pro Glu Ile Pro Gly Phe Lys Asp
305                 310                 315                 320 ttg gaa ccc atg gaa caa ttc att gca caa gtt gac cta tgt gta gac      1008
Leu Glu Pro Met Glu Gln Phe Ile Ala Gln Val Asp Leu Cys Val Asp
                325                 330                 335 tgc aca act gga tgc ctc aaa ggt ctt gcc aat gtg caa tgt tct gat      1056
Cys Thr Thr Gly Cys Leu Lys Gly Leu Ala Asn Val Gln Cys Ser Asp
            340                 345                 350 tta ctc aag aaa tgg ctg cca caa aga tgt gca act ttt gct agc aaa      1104
Leu Leu Lys Lys Trp Leu Pro Gln Arg Cys Ala Thr Phe Ala Ser Lys
            355                 360                 365 att caa ggc caa gtg gac aaa ata aag ggt gcc ggt ggt gat            1146
Ile Gln Gly Gln Val Asp Lys Ile Lys Gly Ala Gly Gly Asp
            370                 375                 380

<210> SEQ ID NO 22
<211> LENGTH: 382
<212> TYPE: PRT
```

<213> ORGANISM: Gaussia

<400> SEQUENCE: 22

```
Met Ser Val Glu Phe Tyr Asn Ser Asn Lys Ser Ala Gln Thr Asn Ser
1               5                   10                  15
Ile Thr Pro Ile Ile Lys Ile Thr Asn Thr Ser Asp Ser Asp Leu Asn
            20                  25                  30
Leu Asn Asp Val Lys Val Arg Tyr Tyr Tyr Thr Ser Asp Gly Thr Gln
        35                  40                  45
Gly Gln Thr Phe Trp Cys Asp His Ala Gly Ala Leu Leu Gly Asn Ser
    50                  55                  60
Tyr Val Asp Asn Thr Ser Lys Val Thr Ala Asn Phe Val Lys Glu Thr
65                  70                  75                  80
Ala Ser Pro Thr Ser Thr Tyr Asp Thr Tyr Val Glu Phe Gly Phe Ala
                85                  90                  95
Ser Gly Ala Ala Thr Leu Lys Lys Gly Gln Phe Ile Thr Ile Gln Gly
            100                 105                 110
Arg Ile Thr Lys Ser Asp Trp Ser Asn Tyr Thr Gln Thr Asn Asp Tyr
        115                 120                 125
Ser Phe Asp Ala Ser Ser Thr Pro Val Val Asn Pro Lys Val Thr
    130                 135                 140
Gly Tyr Ile Gly Gly Ala Lys Val Leu Gly Thr Ala Pro Gly Ser Ala
145                 150                 155                 160
Gly Leu Val Pro Arg Gly Ser Thr Ala Ile Gly Met Lys Glu Thr Ala
                165                 170                 175
Ala Ala Lys Phe Glu Arg Gln His Met Asp Ser Pro Asp Leu Gly Thr
            180                 185                 190
Asp Asp Asp Asp Lys Met Gly Val Lys Val Leu Phe Ala Leu Ile Cys
        195                 200                 205
Ile Ala Val Ala Glu Ala Lys Pro Thr Glu Asn Asn Glu Asp Phe Asn
    210                 215                 220
Ile Val Ala Val Ala Ser Asn Phe Ala Thr Thr Asp Leu Asp Ala Asp
225                 230                 235                 240
Arg Gly Lys Leu Pro Gly Lys Lys Leu Pro Leu Glu Val Leu Lys Glu
                245                 250                 255
Met Glu Ala Asn Ala Arg Lys Ala Gly Cys Thr Arg Gly Cys Leu Ile
            260                 265                 270
Cys Leu Ser His Ile Lys Cys Thr Pro Lys Met Lys Lys Phe Ile Pro
        275                 280                 285
Gly Arg Cys His Thr Tyr Glu Gly Asp Lys Glu Ser Ala Gln Gly Gly
    290                 295                 300
Ile Gly Glu Ala Ile Val Asp Ile Pro Glu Ile Pro Gly Phe Lys Asp
305                 310                 315                 320
Leu Glu Pro Met Glu Gln Phe Ile Ala Gln Val Asp Leu Cys Val Asp
                325                 330                 335
Cys Thr Thr Gly Cys Leu Lys Gly Leu Ala Asn Val Gln Cys Ser Asp
            340                 345                 350
Leu Leu Lys Lys Trp Leu Pro Gln Arg Cys Ala Thr Phe Ala Ser Lys
        355                 360                 365
Ile Gln Gly Gln Val Asp Lys Ile Lys Gly Ala Gly Gly Asp
    370                 375                 380
```

<210> SEQ ID NO 23
<211> LENGTH: 864

<212> TYPE: DNA
<213> ORGANISM: Renilla renifomis
<220> FEATURE:
<221> NAME/KEY: CDS
<222> LOCATION: (61)...(762)
<223> OTHER INFORMATION: GFP Clone-1

<400> SEQUENCE: 23

```
ggcacgaggg tttcctgaca caataaaaac ctttcaaatt gtttctctgt agcagtaagt    60 atg gat ctc gca aaa ctt ggt ttg aag gaa gtg atg cct act aaa atc    108
Met Asp Leu Ala Lys Leu Gly Leu Lys Glu Val Met Pro Thr Lys Ile
 1               5                  10                  15 aac tta gaa gga ctg gtt ggc gac cac gct ttc tca atg gaa gga gtt    156
Asn Leu Glu Gly Leu Val Gly Asp His Ala Phe Ser Met Glu Gly Val
             20                  25                  30 ggc gaa ggc aac ata ttg gaa gga act caa gag gtg aag ata tcg gta    204
Gly Glu Gly Asn Ile Leu Glu Gly Thr Gln Glu Val Lys Ile Ser Val
         35                  40                  45 aca aaa ggc gca cca ctc cca ttc gca ttt gat atc gta tct gtg gct    252
Thr Lys Gly Ala Pro Leu Pro Phe Ala Phe Asp Ile Val Ser Val Ala
     50                  55                  60 ttt tca tat ggg aac aga gct tat acc ggt tac cca gaa gaa att tcc    300
Phe Ser Tyr Gly Asn Arg Ala Tyr Thr Gly Tyr Pro Glu Glu Ile Ser
 65                  70                  75                  80 gac tac ttc ctc cag tcg ttt cca gaa ggc ttt act tac gag aga aac    348
Asp Tyr Phe Leu Gln Ser Phe Pro Glu Gly Phe Thr Tyr Glu Arg Asn
                 85                  90                  95 att cgt tat caa gat gga gga act gca att gtt aaa tct gat ata agc    396
Ile Arg Tyr Gln Asp Gly Gly Thr Ala Ile Val Lys Ser Asp Ile Ser
            100                 105                 110 ttg gaa gat ggt aaa ttc ata gtg aat gta gac ttc aaa gcg aag gat    444
Leu Glu Asp Gly Lys Phe Ile Val Asn Val Asp Phe Lys Ala Lys Asp
        115                 120                 125 cta cgt cgc atg gga cca gtc atg cag caa gac atc gtg ggt atg cag    492
Leu Arg Arg Met Gly Pro Val Met Gln Gln Asp Ile Val Gly Met Gln
    130                 135                 140 cca tcg tat gag tca atg tac acc aat gtc act tca gtt ata ggg gaa    540
Pro Ser Tyr Glu Ser Met Tyr Thr Asn Val Thr Ser Val Ile Gly Glu
145                 150                 155                 160 tgt ata ata gca ttc aaa ctt caa act ggc aag cat ttc act tac cac    588
Cys Ile Ile Ala Phe Lys Leu Gln Thr Gly Lys His Phe Thr Tyr His
                165                 170                 175 atg agg aca gtt tac aaa tca aag aag cca gtg gaa act atg cca ttg    636
Met Arg Thr Val Tyr Lys Ser Lys Lys Pro Val Glu Thr Met Pro Leu
            180                 185                 190 tat cat ttc atc cag cat cgc ctc gtt aag acc aat gtg gac aca gcc    684
Tyr His Phe Ile Gln His Arg Leu Val Lys Thr Asn Val Asp Thr Ala
        195                 200                 205 agt ggt tac gtt gtg caa cac gag aca gca att gca gcg cat tct aca    732
Ser Gly Tyr Val Val Gln His Glu Thr Ala Ile Ala Ala His Ser Thr
    210                 215                 220 atc aaa aaa att gaa ggc tct tta cca tag atacctgtac acaattattc      782
Ile Lys Lys Ile Glu Gly Ser Leu Pro  *
225                 230 tatgcacgta gcattttttt ggaaatataa gtggtattgt tcaataaaat attaaatata   842
aaaaaaaaaa aaaaaaaaa aa                                              864
```

<210> SEQ ID NO 24
<211> LENGTH: 860
<212> TYPE: DNA

<213> ORGANISM: Renilla renifromis
<220> FEATURE:
<221> NAME/KEY: CDS
<222> LOCATION: (57)...(758)
<223> OTHER INFORMATION: GFP Clone-2

<400> SEQUENCE: 24

```
ggcacgaggc tgacacaata aaaaaccttt caaattgttt ctctgtagca ggaagt atg       59
                                                               Met
                                                                 1 gat ctc gca aaa ctt ggt ttg aag gaa gtg atg cct act aaa atc aac       107
Asp Leu Ala Lys Leu Gly Leu Lys Glu Val Met Pro Thr Lys Ile Asn
          5                  10                  15 tta gaa gga ctg gtt ggc gac cac gct ttc tca atg gaa gga gtt ggc       155
Leu Glu Gly Leu Val Gly Asp His Ala Phe Ser Met Glu Gly Val Gly
             20                  25                  30 gaa ggc aac ata ttg gaa gga act caa gag gtg aag ata tcg gta aca       203
Glu Gly Asn Ile Leu Glu Gly Thr Gln Glu Val Lys Ile Ser Val Thr
 35                  40                  45 aaa ggc gca cca ctc cca ttc gca ttt gat atc gta tct gtt gct ttc       251
Lys Gly Ala Pro Leu Pro Phe Ala Phe Asp Ile Val Ser Val Ala Phe
 50                  55                  60                  65 tca tat ggg aac aga gct tat act ggt tac cca gaa gaa att tcc gac       299
Ser Tyr Gly Asn Arg Ala Tyr Thr Gly Tyr Pro Glu Glu Ile Ser Asp
              70                  75                  80 tac ttc ctc cag tcg ttt cca gaa ggc ttt act tac gag aga aac att       347
Tyr Phe Leu Gln Ser Phe Pro Glu Gly Phe Thr Tyr Glu Arg Asn Ile
             85                  90                  95 cgt tat caa gat gga gga act gca att gtt aaa tct gat ata agc ttg       395
Arg Tyr Gln Asp Gly Gly Thr Ala Ile Val Lys Ser Asp Ile Ser Leu
         100                 105                 110 gaa gat ggt aaa ttc ata gtg aat gta gac ttc aaa gcg aag gat cta       443
Glu Asp Gly Lys Phe Ile Val Asn Val Asp Phe Lys Ala Lys Asp Leu
     115                 120                 125 cgt cgc atg gga cca gtc atg cag caa gac atc gtg ggt atg cag cca       491
Arg Arg Met Gly Pro Val Met Gln Gln Asp Ile Val Gly Met Gln Pro
130                 135                 140                 145 tcg tat gag tca atg tac acc aat gtc act tca gtt ata ggg gaa tgt       539
Ser Tyr Glu Ser Met Tyr Thr Asn Val Thr Ser Val Ile Gly Glu Cys
                 150                 155                 160 ata ata gca ttc aaa ctt caa act ggc aaa cat ttc act tac cac atg       587
Ile Ile Ala Phe Lys Leu Gln Thr Gly Lys His Phe Thr Tyr His Met
             165                 170                 175 agg aca gtt tac aaa tca aag aag cca gtg gaa act atg cca ttg tat       635
Arg Thr Val Tyr Lys Ser Lys Lys Pro Val Glu Thr Met Pro Leu Tyr
         180                 185                 190 cat ttc atc cag cat cgc ctc gtt aag acc aat gtg gac aca gcc agt       683
His Phe Ile Gln His Arg Leu Val Lys Thr Asn Val Asp Thr Ala Ser
     195                 200                 205 ggt tac gtt gtg caa cac gag aca gca att gca gcg cat tct aca atc       731
Gly Tyr Val Val Gln His Glu Thr Ala Ile Ala Ala His Ser Thr Ile
210                 215                 220                 225 aaa aaa att gaa ggc tct tta cca tag atatctatac acaattattc              778
Lys Lys Ile Glu Gly Ser Leu Pro *
                 230 tatgcacgta gcatttttttt ggaaatataa gtggtattgt tcaataaaat attaaatata    838 aaaaaaaaaa aaaaaaaaaa aa                                              860
```

<210> SEQ ID NO 25
<211> LENGTH: 873

```
<212> TYPE: DNA
<213> ORGANISM: Renilla reniformis
<220> FEATURE:
<221> NAME/KEY: CDS
<222> LOCATION: (61)...(762)
<223> OTHER INFORMATION: GFP Clone-3

<400> SEQUENCE: 25
ggcacgaggg tttcctgaca caataaaaac ctttcaaatt gtttctctgt agcagtaagt     60 atg gat ctc gca aaa ctt ggt ttg aag gaa gtg atg cct act aaa atc    108
Met Asp Leu Ala Lys Leu Gly Leu Lys Glu Val Met Pro Thr Lys Ile
 1               5                  10                  15 aac tta gaa gga ctg gtt ggc gac cac gct ttc tca atg gaa gga gtt    156
Asn Leu Glu Gly Leu Val Gly Asp His Ala Phe Ser Met Glu Gly Val
                20                  25                  30 ggc gaa ggc aac ata ttg gaa gga act caa gag gtg aag ata tcg gta    204
Gly Glu Gly Asn Ile Leu Glu Gly Thr Gln Glu Val Lys Ile Ser Val
            35                  40                  45 aca aaa ggc gca cca ctc cca ttc gca ttt gat atc gta tct gtg gct    252
Thr Lys Gly Ala Pro Leu Pro Phe Ala Phe Asp Ile Val Ser Val Ala
    50                  55                  60 ttt tca tat ggg aac aga gct tat acc ggt tac cca gaa gaa att tcc    300
Phe Ser Tyr Gly Asn Arg Ala Tyr Thr Gly Tyr Pro Glu Glu Ile Ser
65                  70                  75                  80 gac tac ttc ctc cag tcg ttt cca gaa ggc ttt act tac gag aga aac    348
Asp Tyr Phe Leu Gln Ser Phe Pro Glu Gly Phe Thr Tyr Glu Arg Asn
                85                  90                  95 att cgt tat caa gat gga gga act gca att gtt aaa tct gat ata agc    396
Ile Arg Tyr Gln Asp Gly Gly Thr Ala Ile Val Lys Ser Asp Ile Ser
            100                 105                 110 ttg gaa gat ggt aaa ttc ata gtg aat gta gac ttc aaa gcg aag gat    444
Leu Glu Asp Gly Lys Phe Ile Val Asn Val Asp Phe Lys Ala Lys Asp
        115                 120                 125 cta cgt cgc atg gga cca gtc atg cag caa gac atc gtg ggt atg cag    492
Leu Arg Arg Met Gly Pro Val Met Gln Gln Asp Ile Val Gly Met Gln
    130                 135                 140 cca tcg tat gag tca atg tac acc aat gtc act tca gtt ata ggg gaa    540
Pro Ser Tyr Glu Ser Met Tyr Thr Asn Val Thr Ser Val Ile Gly Glu
145                 150                 155                 160 tgt ata ata gca ttc aaa ctt caa act ggc aag cat ttc act tac cac    588
Cys Ile Ile Ala Phe Lys Leu Gln Thr Gly Lys His Phe Thr Tyr His
                165                 170                 175 atg agg aca gtt tac aaa tca aag aag cca gtg gaa act atg cca ttg    636
Met Arg Thr Val Tyr Lys Ser Lys Lys Pro Val Glu Thr Met Pro Leu
            180                 185                 190 tat cat ttc atc cag cat cgc ctc gtt aag acc aat gtg gac aca gcc    684
Tyr His Phe Ile Gln His Arg Leu Val Lys Thr Asn Val Asp Thr Ala
        195                 200                 205 agt ggt tac gtt gtg caa cac gag aca gca att gca gcg cat tct aca    732
Ser Gly Tyr Val Val Gln His Glu Thr Ala Ile Ala Ala His Ser Thr
    210                 215                 220 atc aaa aaa att gaa ggc tct tta cca tag atacctgtac acaattattc      782
Ile Lys Lys Ile Glu Gly Ser Leu Pro *
225                 230 tatgcacgta gcattttttt ggaaatataa gtggtattgt tcaataaaat attaaatata   842
tgcttttgca aaaaaaaaaa aaaaaaaaaa a                                  873

<210> SEQ ID NO 26
<211> LENGTH: 864
<212> TYPE: DNA
```

```
<213> ORGANISM: Renilla reniformis
<220> FEATURE:
<221> NAME/KEY: CDS
<222> LOCATION: (61)...(759)
<223> OTHER INFORMATION: Human codon optimized Renilla reniformis GFP

<400> SEQUENCE: 26
ggcacgaggg tttcctgaca caataaaaac ctttcaaatt gtttctctgt agcagtaagt      60 atg gac ctg gcc aag ctg ggc ctg aag gag gtg atg ccc acc aag atc     108
Met Asp Leu Ala Lys Leu Gly Leu Lys Glu Val Met Pro Thr Lys Ile
  1               5                  10                  15 aac ctg gag ggc ctg gtg ggc gac cac gcc ttc tcg atg gag ggc gtg     156
Asn Leu Glu Gly Leu Val Gly Asp His Ala Phe Ser Met Glu Gly Val
             20                  25                  30 ggc gag ggc aac atc ttg gag ggc acc cag gag gtg aag atc agc gtg     204
Gly Glu Gly Asn Ile Leu Glu Gly Thr Gln Glu Val Lys Ile Ser Val
         35                  40                  45 acc aag ggc gcc ccc ctg ccc ttc gcc ttc gac atc gtg agc gtg gcc     252
Thr Lys Gly Ala Pro Leu Pro Phe Ala Phe Asp Ile Val Ser Val Ala
     50                  55                  60 ttc agc tac ggc aac cgg gcc tac acc ggc tac ccc gag gag atc agc     300
Phe Ser Tyr Gly Asn Arg Ala Tyr Thr Gly Tyr Pro Glu Glu Ile Ser
 65                  70                  75                  80 gac tac ttc ctg cag agc ttc ccc gag ggc ttc acc tac gag cgg aac     348
Asp Tyr Phe Leu Gln Ser Phe Pro Glu Gly Phe Thr Tyr Glu Arg Asn
                 85                  90                  95 atc cgg tac cag gac ggc ggc acc gcc atc gtg aag agc gac atc agc     396
Ile Arg Tyr Gln Asp Gly Gly Thr Ala Ile Val Lys Ser Asp Ile Ser
            100                 105                 110 ctg gag gac ggc aag ttc atc gtg aac gtg gac ttc aag gcc aag gac     444
Leu Glu Asp Gly Lys Phe Ile Val Asn Val Asp Phe Lys Ala Lys Asp
        115                 120                 125 ctg cgg cgg atg ggc ccc gtg atg cag cag gac atc gtg ggc atg cag     492
Leu Arg Arg Met Gly Pro Val Met Gln Gln Asp Ile Val Gly Met Gln
    130                 135                 140 ccc agc tac gag agc atg tac acc aac gtg acc agc gtg atc ggc gag     540
Pro Ser Tyr Glu Ser Met Tyr Thr Asn Val Thr Ser Val Ile Gly Glu
145                 150                 155                 160 tgc atc atc gcc ttc aag ctg cag acc ggc aag cac ttc acc tac cac     588
Cys Ile Ile Ala Phe Lys Leu Gln Thr Gly Lys His Phe Thr Tyr His
                165                 170                 175 atg cgg acc gtg tac aag agc aag aag ccc gtg gag acc atg ccc ctg     636
Met Arg Thr Val Tyr Lys Ser Lys Lys Pro Val Glu Thr Met Pro Leu
            180                 185                 190 tac cac ttc atc cag cac cgg ctg gtg aag acc aac gtg gac acc gcc     684
Tyr His Phe Ile Gln His Arg Leu Val Lys Thr Asn Val Asp Thr Ala
        195                 200                 205 agc ggc tac gtg gtg cag cac gag aca gcc atc gcc gcc cac agc acc     732
Ser Gly Tyr Val Val Gln His Glu Thr Ala Ile Ala Ala His Ser Thr
    210                 215                 220 atc aag aag atc gag ggc agc ctg ccc tagatacctg tacacaatta           779
Ile Lys Lys Ile Glu Gly Ser Leu Pro
225                 230 ttctatgcac gtagcatttt tttggaaata taagtggtat tgttcaataa aatattaaat   839
ataaaaaaaa aaaaaaaaaa aaaaa                                         864

<210> SEQ ID NO 27
<211> LENGTH: 233
<212> TYPE: PRT
<213> ORGANISM: Renilla reniformis
```

<400> SEQUENCE: 27

```
Met Asp Leu Ala Lys Leu Gly Leu Lys Glu Val Met Pro Thr Lys Ile
 1               5                  10                  15
Asn Leu Glu Gly Leu Val Gly Asp His Ala Phe Ser Met Glu Gly Val
             20                  25                  30
Gly Glu Gly Asn Ile Leu Glu Gly Thr Gln Glu Val Lys Ile Ser Val
         35                  40                  45
Thr Lys Gly Ala Pro Leu Pro Phe Ala Phe Asp Ile Val Ser Val Ala
     50                  55                  60
Phe Ser Tyr Gly Asn Arg Ala Tyr Thr Gly Tyr Pro Glu Glu Ile Ser
65                  70                  75                  80
Asp Tyr Phe Leu Gln Ser Phe Pro Glu Gly Phe Thr Tyr Glu Arg Asn
                 85                  90                  95
Ile Arg Tyr Gln Asp Gly Gly Thr Ala Ile Val Lys Ser Asp Ile Ser
            100                 105                 110
Leu Glu Asp Gly Lys Phe Ile Val Asn Val Asp Phe Lys Ala Lys Asp
        115                 120                 125
Leu Arg Arg Met Gly Pro Val Met Gln Gln Asp Ile Val Gly Met Gln
    130                 135                 140
Pro Ser Tyr Glu Ser Met Tyr Thr Asn Val Thr Ser Val Ile Gly Glu
145                 150                 155                 160
Cys Ile Ile Ala Phe Lys Leu Gln Thr Gly Lys His Phe Thr Tyr His
                165                 170                 175
Met Arg Thr Val Tyr Lys Ser Lys Lys Pro Val Glu Thr Met Pro Leu
            180                 185                 190
Tyr His Phe Ile Gln His Arg Leu Val Lys Thr Asn Val Asp Thr Ala
        195                 200                 205
Ser Gly Tyr Val Val Gln His Glu Thr Ala Ile Ala Ala His Ser Thr
    210                 215                 220
Ile Lys Lys Ile Glu Gly Ser Leu Pro
225                 230
```

<210> SEQ ID NO 28
<211> LENGTH: 861
<212> TYPE: DNA
<213> ORGANISM: Pleuromamma
<220> FEATURE:
<221> NAME/KEY: CDS
<222> LOCATION: (148)...(741)
<223> OTHER INFORMATION: Pleurormamma luciferase

<400> SEQUENCE: 28

```
cggcacgaga ttttgtctgt ggtgattggg attgtctgtc tctcaggtca agcagaaagt      60
tcgctgaaag gtgatttctg tagtgatgtt tccttctggg atgtgatcaa gtacaacact     120
gagagtcgac aatgctgtga cacaaaa atg ctt aga aat tgc gct agg aag caa     174
                               Met Leu Arg Asn Cys Ala Arg Lys Gln
                                1               5 gag caa gtt tgc gcc gat gtg acc gag atg aaa tgc caa gca gtt gct       222
Glu Gln Val Cys Ala Asp Val Thr Glu Met Lys Cys Gln Ala Val Ala
 10                  15                  20                  25 tgg gcc gac tgt gga ccc aga ttt gat tcc act ggc agg aat aga tgc       270
Trp Ala Asp Cys Gly Pro Arg Phe Asp Ser Thr Gly Arg Asn Arg Cys
                 30                  35                  40 caa gtt caa tac aag gac tac gcg tac aag tcc tgc gtg gaa gtt gat       318
Gln Val Gln Tyr Lys Asp Tyr Ala Tyr Lys Ser Cys Val Glu Val Asp
             45                  50                  55
```

```
tac act gta ccg cac agg aag caa gtt cca gag tgc aaa caa gtc act      366
Tyr Thr Val Pro His Arg Lys Gln Val Pro Glu Cys Lys Gln Val Thr
            60                  65                  70 aaa gat aac tgc gtt act gat tgg gaa gtt gac gcc aat ggc aac aag      414
Lys Asp Asn Cys Val Thr Asp Trp Glu Val Asp Ala Asn Gly Asn Lys
 75                  80                  85 gtt tgg ggt ggt acc gag aaa tgc act cct gtc act tgg gaa gaa tgt      462
Val Trp Gly Gly Thr Glu Lys Cys Thr Pro Val Thr Trp Glu Glu Cys
 90                  95                 100                 105 aat atc gtg gag aaa gat gta gat ttt cca act gtc aag acg gaa tgc      510
Asn Ile Val Glu Lys Asp Val Asp Phe Pro Thr Val Lys Thr Glu Cys
                110                 115                 120 ggc atc ctg tct cac ctt aag tat gca gac ttc ata gag gga cct tcc      558
Gly Ile Leu Ser His Leu Lys Tyr Ala Asp Phe Ile Glu Gly Pro Ser
            125                 130                 135 cac tct ttg tct atg aga acc aat tgt cag gtc aag agt tca ttg gac      606
His Ser Leu Ser Met Arg Thr Asn Cys Gln Val Lys Ser Ser Leu Asp
        140                 145                 150 tgc cgg cct gtt aag acc agg aag tgt gca acg gtc gag tac cac gaa      654
Cys Arg Pro Val Lys Thr Arg Lys Cys Ala Thr Val Glu Tyr His Glu
155                 160                 165 tgc agc atg aag ccc caa gaa gac tgc agc cca gtc act gtt cat att      702
Cys Ser Met Lys Pro Gln Glu Asp Cys Ser Pro Val Thr Val His Ile
170                 175                 180                 185 cct gac cag gag aaa gtt cac cag aag aag tgc ctc aca taaatgttat      751
Pro Asp Gln Glu Lys Val His Gln Lys Lys Cys Leu Thr
                190                 195 caattttagc tcttactaat ttaaacataa taaatatcac atcgaagccc tttattttat    811
agaagtgtaa tgcttgaata aatctagtga ataaaaaaaa aaaaaaaaaa                861

<210> SEQ ID NO 29
<211> LENGTH: 198
<212> TYPE: PRT
<213> ORGANISM: Pleuromamma

<400> SEQUENCE: 29

Met Leu Arg Asn Cys Ala Arg Lys Gln Glu Gln Val Cys Ala Asp Val
 1               5                  10                  15

Thr Glu Met Lys Cys Gln Ala Val Ala Trp Ala Asp Cys Gly Pro Arg
                20                  25                  30

Phe Asp Ser Thr Gly Arg Asn Arg Cys Gln Val Gln Tyr Lys Asp Tyr
            35                  40                  45

Ala Tyr Lys Ser Cys Val Glu Val Asp Tyr Thr Val Pro His Arg Lys
 50                  55                  60

Gln Val Pro Glu Cys Lys Gln Val Thr Lys Asp Asn Cys Val Thr Asp
65                  70                  75                  80

Trp Glu Val Asp Ala Asn Gly Asn Lys Val Trp Gly Gly Thr Glu Lys
                85                  90                  95

Cys Thr Pro Val Thr Trp Glu Glu Cys Asn Ile Val Glu Lys Asp Val
            100                 105                 110

Asp Phe Pro Thr Val Lys Thr Glu Cys Gly Ile Leu Ser His Leu Lys
        115                 120                 125

Tyr Ala Asp Phe Ile Glu Gly Pro Ser His Ser Leu Ser Met Arg Thr
    130                 135                 140

Asn Cys Gln Val Lys Ser Ser Leu Asp Cys Arg Pro Val Lys Thr Arg
145                 150                 155                 160
```

-continued

```
Lys Cys Ala Thr Val Glu Tyr His Glu Cys Ser Met Lys Pro Gln Glu
            165                 170                 175

Asp Cys Ser Pro Val Thr Val His Ile Pro Asp Gln Glu Lys Val His
        180                 185                 190

Gln Lys Lys Cys Leu Thr
    195
```

<210> SEQ ID NO 30
<211> LENGTH: 1104
<212> TYPE: DNA
<213> ORGANISM: Ptilosarcus gurneyi
<220> FEATURE:
<221> NAME/KEY: CDS
<222> LOCATION: (34)...(747)
<223> OTHER INFORMATION: Ptilosarcus Green Flourescent Protein

<400> SEQUENCE: 30

```
tcggcacgag ctggcctcca cactttagac aaa atg aac cgc aac gta tta aag      54
                                    Met Asn Arg Asn Val Leu Lys
                                      1               5 aac act gga ctg aaa gag att atg tcg gca aaa gct agc gtt gaa gga     102
Asn Thr Gly Leu Lys Glu Ile Met Ser Ala Lys Ala Ser Val Glu Gly
         10                  15                  20 atc gtg aac aat cac gtt ttt tcc atg gaa gga ttt gga aaa ggc aat     150
Ile Val Asn Asn His Val Phe Ser Met Glu Gly Phe Gly Lys Gly Asn
     25                  30                  35 gta tta ttt gga aac caa ttg atg caa atc cgg gtt aca aag gga ggt     198
Val Leu Phe Gly Asn Gln Leu Met Gln Ile Arg Val Thr Lys Gly Gly
 40                  45                  50                  55 ccg ttg cca ttc gct ttc gat att gtt tcc ata gct ttc caa tac ggg     246
Pro Leu Pro Phe Ala Phe Asp Ile Val Ser Ile Ala Phe Gln Tyr Gly
                 60                  65                  70 aat cgc act ttc acg aaa tac cca gac gac att gcg gac tac ttt gtt     294
Asn Arg Thr Phe Thr Lys Tyr Pro Asp Asp Ile Ala Asp Tyr Phe Val
             75                  80                  85 caa tca ttc ccg gct gga ttt ttc tac gaa aga aat cta cgc ttt gaa     342
Gln Ser Phe Pro Ala Gly Phe Phe Tyr Glu Arg Asn Leu Arg Phe Glu
         90                  95                 100 gat ggc gcc att gtt gac att cgt tca gat ata agt tta gaa gat gat     390
Asp Gly Ala Ile Val Asp Ile Arg Ser Asp Ile Ser Leu Glu Asp Asp
     105                 110                 115 aag ttc cac tac aaa gtg gag tat aga ggc aac ggt ttc cct agt aac     438
Lys Phe His Tyr Lys Val Glu Tyr Arg Gly Asn Gly Phe Pro Ser Asn
120                 125                 130                 135 gga ccc gtg atg caa aaa gcc atc ctc ggc atg gag cca tcg ttt gag     486
Gly Pro Val Met Gln Lys Ala Ile Leu Gly Met Glu Pro Ser Phe Glu
                140                 145                 150 gtg gtc tac atg aac agc ggc gtt ctg gtg ggc gaa gta gat ctc gtt     534
Val Val Tyr Met Asn Ser Gly Val Leu Val Gly Glu Val Asp Leu Val
            155                 160                 165 tac aaa ctc gag tca ggg aac tat tac tcg tgc cac atg aaa acg ttt     582
Tyr Lys Leu Glu Ser Gly Asn Tyr Tyr Ser Cys His Met Lys Thr Phe
        170                 175                 180 tac aga tcc aaa ggt gga gtg aaa gaa ttc ccg gaa tat cac ttt atc     630
Tyr Arg Ser Lys Gly Gly Val Lys Glu Phe Pro Glu Tyr His Phe Ile
    185                 190                 195 cat cat cgt ctg gag aaa acc tac gtg gaa gaa gga agc ttc gtg gaa     678
His His Arg Leu Glu Lys Thr Tyr Val Glu Glu Gly Ser Phe Val Glu
200                 205                 210                 215 caa cac gag acg gcc att gca caa ctg acc aca att gga aaa cct ctg     726
Gln His Glu Thr Ala Ile Ala Gln Leu Thr Thr Ile Gly Lys Pro Leu
```

-continued

```
                   220                 225                 230
ggc tcc ctt cat gaa tgg gtg tagaaaatga ccaatatact ggggaaaccg     777
Gly Ser Leu His Glu Trp Val
                235 ataaccgttt ggaagcttgt gtatacaaat tatttggggt cattttgtaa tgtgtatgtg    837 tgttgtatga tcaatagacg tcgtcattca tagcttgaat ccttcagcaa aagaaacctc    897 gaagcatatt gaaacctcga agcatattga aacctcgacg gagagcgtaa agagaccgca    957 caaattaacg cgtttcaacc agcagttgga atctttaaac cgatcaaaac tattaatata   1017 aatatatata ccctgtataa cttatatata tctatatagt ttgatattga ttaaatctgt   1077 tcttgatcaa aaaaaaaaaa aaaaaaa                                       1104
```

<210> SEQ ID NO 31
<211> LENGTH: 1279
<212> TYPE: DNA
<213> ORGANISM: Ptilosarcus gurneyi
<220> FEATURE:
<221> NAME/KEY: CDS
<222> LOCATION: (7)...(720)
<223> OTHER INFORMATION: Ptilosarcus Green Flourescent Protein (GFP)

<400> SEQUENCE: 31

```
gacaaa atg aac cgc aac gta tta aag aac act gga ctg aaa gag att      48
       Met Asn Arg Asn Val Leu Lys Asn Thr Gly Leu Lys Glu Ile
         1               5                  10 atg tcg gca aaa gct agc gtt gaa gga atc gtg aac aat cac gtt ttt     96
Met Ser Ala Lys Ala Ser Val Glu Gly Ile Val Asn Asn His Val Phe
 15                  20                  25                  30 tcc atg gaa gga ttt gga aaa ggc aat gta tta ttt gga aac caa ttg    144
Ser Met Glu Gly Phe Gly Lys Gly Asn Val Leu Phe Gly Asn Gln Leu
                 35                  40                  45 atg caa atc cgg gtt aca aag gga ggt ccg ttg cca ttc gct ttc gac    192
Met Gln Ile Arg Val Thr Lys Gly Gly Pro Leu Pro Phe Ala Phe Asp
             50                  55                  60 att gtt tcc ata gct ttc caa tac ggg aat cgc act ttc acg aaa tac    240
Ile Val Ser Ile Ala Phe Gln Tyr Gly Asn Arg Thr Phe Thr Lys Tyr
         65                  70                  75 cca gac gac att gcg gac tac ttt gtt caa tca ttt ccg gct gga ttt    288
Pro Asp Asp Ile Ala Asp Tyr Phe Val Gln Ser Phe Pro Ala Gly Phe
     80                  85                  90 ttc tac gaa aga aat cta cgc ttt gaa gat ggc gcc att gtt gac att    336
Phe Tyr Glu Arg Asn Leu Arg Phe Glu Asp Gly Ala Ile Val Asp Ile
 95                 100                 105                 110 cgt tca gat ata agt tta gaa gat gat aag ttc cac tac aaa gtg gag    384
Arg Ser Asp Ile Ser Leu Glu Asp Asp Lys Phe His Tyr Lys Val Glu
                115                 120                 125 tat aga ggc aac ggt ttc cct agt aac gga ccc gtg atg caa aaa gcc    432
Tyr Arg Gly Asn Gly Phe Pro Ser Asn Gly Pro Val Met Gln Lys Ala
            130                 135                 140 atc ctc ggc atg gag cca tcg ttt gag gtg gtc tac atg aac agc ggc    480
Ile Leu Gly Met Glu Pro Ser Phe Glu Val Val Tyr Met Asn Ser Gly
        145                 150                 155 gtt ctg gtg ggc gaa gta gat ctc gtt tac aaa ctc gag tca ggg aac    528
Val Leu Val Gly Glu Val Asp Leu Val Tyr Lys Leu Glu Ser Gly Asn
    160                 165                 170 tat tac tcg tgc cac atg aaa acg ttt tac aga tcc aaa ggt gga gtg    576
Tyr Tyr Ser Cys His Met Lys Thr Phe Tyr Arg Ser Lys Gly Gly Val
175                 180                 185                 190 aaa gaa ttc ccg gaa tat cac ttt atc cat cat cgt ctg gag aaa acc    624
```

-continued

| | | |
|---|---|---|
| Lys Glu Phe Pro Glu Tyr His Phe Ile His His Arg Leu Glu Lys Thr<br>               195                     200                 205 | | |
| tac gtg gaa gaa gga agc ttc gtg gaa caa cac gag acg gcc att gca<br>Tyr Val Glu Glu Gly Ser Phe Val Glu Gln His Glu Thr Ala Ile Ala<br>          210                     215                     220 | 672 |
| caa ctg acc aca att gga aaa cct ctg ggc tcc ctt cat gaa tgg gtg<br>Gln Leu Thr Thr Ile Gly Lys Pro Leu Gly Ser Leu His Glu Trp Val<br>          225                     230                     235 | 720 |
| tagaaaatga ccaatatact ggggaaaatc accaatatac tggggaaaat gaccaattta | 780 |
| ctggggaaaa tgaccaatat actgtagaaa atcaccaata tactgggaa atgaccaat | 840 |
| ttactgggga aatgaccaat ttactgtaga aaatcaccaa tactgtgg aaaatgacca | 900 |
| aaatactgta gaaatgttca cactggggtg ataaccgttt cgataaccgt ttggaagctt | 960 |
| gtgtatacaa gttatttggg gtcattttgt aatgtgtatg tgtgttgtat gatctataga | 1020 |
| cgtcgtcatt catagcttga atccttcagc aaaagaaacc tcgaagcata ttgaaacctc | 1080 |
| gacggagagc ataaagagac cgcacgtaca caattataa taccagcagt tggaatcttt | 1140 |
| aaaccgatca aactattaa tatatatata caccctgtat aacatatata tatatata | 1200 |
| tctacatagt ttgatattga ttaaatctgt tcttgatcac taaaaaaaaa aaaaaaaaaa | 1260 |
| aaaaaaaaaa aaaaaaaa | 1279 |

<210> SEQ ID NO 32
<211> LENGTH: 238
<212> TYPE: PRT
<213> ORGANISM: Ptilosarcus gurneyi

<400> SEQUENCE: 32

Met Asn Arg Asn Val Leu Lys Asn Thr Gly Leu Lys Glu Ile Met Ser
 1               5                  10                  15

Ala Lys Ala Ser Val Glu Gly Ile Val Asn Asn His Val Phe Ser Met
             20                  25                  30

Glu Gly Phe Gly Lys Gly Asn Val Leu Phe Gly Asn Gln Leu Met Gln
         35                  40                  45

Ile Arg Val Thr Lys Gly Gly Pro Leu Pro Phe Ala Phe Asp Ile Val
     50                  55                  60

Ser Ile Ala Phe Gln Tyr Gly Asn Arg Thr Phe Thr Lys Tyr Pro Asp
 65                  70                  75                  80

Asp Ile Ala Asp Tyr Phe Val Gln Ser Phe Pro Ala Gly Phe Phe Tyr
                 85                  90                  95

Glu Arg Asn Leu Arg Phe Glu Asp Gly Ala Ile Val Asp Ile Arg Ser
            100                 105                 110

Asp Ile Ser Leu Glu Asp Asp Lys Phe His Tyr Lys Val Glu Tyr Arg
        115                 120                 125

Gly Asn Gly Phe Pro Ser Asn Gly Pro Val Met Gln Lys Ala Ile Leu
    130                 135                 140

Gly Met Glu Pro Ser Phe Glu Val Val Tyr Met Asn Ser Gly Val Leu
145                 150                 155                 160

Val Gly Glu Val Asp Leu Val Tyr Lys Leu Glu Ser Gly Asn Tyr Tyr
                165                 170                 175

Ser Cys His Met Lys Thr Phe Tyr Arg Ser Lys Gly Gly Val Lys Glu
            180                 185                 190

Phe Pro Glu Tyr His Phe Ile His His Arg Leu Glu Lys Thr Tyr Val
        195                 200                 205

Glu Glu Gly Ser Phe Val Glu Gln His Glu Thr Ala Ile Ala Gln Leu

```
                  210                 215                 220
Thr Thr Ile Gly Lys Pro Leu Gly Ser Leu His Glu Trp Val
225                 230                 235

<210> SEQ ID NO 33
<211> LENGTH: 233
<212> TYPE: PRT
<213> ORGANISM: Renilla Reniformis mutein

<400> SEQUENCE: 33

Met Asp Leu Ala Lys Leu Gly Leu Lys Glu Val Met Pro Thr Lys Ile
1               5                   10                  15

Asn Leu Glu Gly Leu Val Gly Asp His Ala Phe Ser Met Glu Gly Val
                20                  25                  30

Gly Glu Gly Asn Ile Leu Glu Gly Thr Gln Glu Val Lys Ile Ser Val
            35                  40                  45

Thr Lys Gly Ala Pro Leu Pro Phe Ala Phe Asp Ile Val Ser Val Ala
    50                  55                  60

Phe Ser Tyr Gly Asn Arg Ala Tyr Thr Gly Tyr Pro Glu Glu Ile Ser
65                  70                  75                  80

Asp Tyr Phe Leu Gln Ser Phe Pro Glu Gly Phe Thr Tyr Glu Arg Asn
                85                  90                  95

Ile Arg Tyr Gln Asp Gly Gly Thr Ala Ile Val Asp Ser Asp Ile Ser
            100                 105                 110

Leu Glu Asp Gly Lys Phe Ile Val Asn Val Asp Phe Lys Ala Asp Asp
        115                 120                 125

Leu Arg Asp Met Gly Pro Val Met Gln Gln Asp Ile Val Gly Met Gln
    130                 135                 140

Pro Ser Tyr Glu Ser Met Tyr Thr Asn Val Thr Ser Val Ile Gly Glu
145                 150                 155                 160

Cys Ile Ile Ala Phe Lys Leu Gln Thr Gly Lys Asp Phe Thr Tyr His
                165                 170                 175

Met Arg Thr Val Tyr Lys Ser Lys Lys Pro Val Glu Thr Met Pro Leu
            180                 185                 190

Tyr His Phe Ile Gln His Asp Leu Val Lys Thr Asn Val Asp Thr Ala
        195                 200                 205

Ser Gly Tyr Val Val Gln His Glu Thr Ala Ile Ala Ala His Ser Thr
    210                 215                 220

Ile Asp Lys Ile Glu Gly Ser Leu Pro
225                 230
```